US012577579B2

(12) United States Patent
Haketa et al.

(10) Patent No.: US 12,577,579 B2
(45) Date of Patent: Mar. 17, 2026

(54) **CYTOPLASMIC MALE-STERILE *RUDBECKIA* PLANTS AND A METHOD OF PRODUCTION**

(71) Applicant: TAKII & Co., Ltd., Kyoto (JP)

(72) Inventors: Tomoaki Haketa, Kyoto (JP); Makoto Endo, Kyoto (JP); Shun Koyama, Kyoto (JP); Kenta Shirasawa, Chiba (JP); Sachiko Isobe, Chiba (JP)

(73) Assignee: TAKII & Co., Ltd., Kyoto (JP)

( * ) Notice: Subject to any disclaimer, the term of this patent is extended or adjusted under 35 U.S.C. 154(b) by 326 days.

(21) Appl. No.: 18/065,814

(22) Filed: Dec. 14, 2022

(65) Prior Publication Data

US 2023/0348931 A1       Nov. 2, 2023

(30) Foreign Application Priority Data

Dec. 17, 2021       (JP) ................................. 2021-205015

(51) Int. Cl.
C12N 15/82       (2006.01)
C12Q 1/6895      (2018.01)

(52) U.S. Cl.
CPC ....... C12N 15/8289 (2013.01); C12Q 1/6895 (2013.01); C12Q 2600/13 (2013.01); C12Q 2600/158 (2013.01)

(58) Field of Classification Search
None
See application file for complete search history.

(56) References Cited

FOREIGN PATENT DOCUMENTS

| | | | |
|---|---|---|---|
| JP | 2018-530323 A | 10/2018 | |
| WO | 2017/058023 A1 | 4/2017 | |

OTHER PUBLICATIONS

Islam et al., Genetics and biology of cytoplasmic male sterility and its applications in forage and turf grass breeding, 2014, Plant Breeding, vol. 133(3), pp. 299-312 (Year: 2014).*

Spassova et al., Characterisation and expression of the mitochondrial genome of a new type of cytoplasmic male-sterile sunflower, 1994, Plant Molecular Biology, vol. 26, pp. 1819-1831 (Year: 1994).*

Jourdan P., Genetic Resources of Herbaceous Ornamentals in North America, Chapter 18, 2019, North American Crop Wild Relatives, vol. 2, pp. 607-643 (Year: 2019).*

Howard et al., "Cell type-specific loss of atp6 RNA editing in cytoplasmic male sterile Sorghum bicolor," PNAS, 94: 11090-11095 (1997).

Palmer et al., "Crossability, Cytogenetics, and Reproductive Pathways in Rudbeckia Subgenus Rudbeckia," Hortscience, 44 (1): 44-48 (2009).

Smith et al., "Increased Flower Longevity in Petunia with Male Sterility," Hortscience, 39 (4): 822B-822 (2004).

Garcia-Sogo et al., "Production of engineered long-life and male sterile Pelargonium plants," BMC Plant Biology, 12: 156 (2012).

Szarvas et al., "Biotechnology of Annual Flower Plants: Micropropagation of *Rudbeckia* sp." Acta Hort. 725: 527-534 (2006).

Oates et al., "Influence of Induced Polyploidy on Fertility and Morphology of *Rudbeckia* Species and Hybrids", HortScience, vol. 47, No. 9, 2012, pp. 1217-1221.

* cited by examiner

*Primary Examiner* — Bratislav Stankovic
*Assistant Examiner* — Christina L Meadows
(74) *Attorney, Agent, or Firm* — Morgan, Lewis & Bockius LLP

(57)       ABSTRACT

The present disclosure provides a cytoplasmic male sterile *Rudbeckia* plant. The present disclosure also provides a method for conferring cytoplasmic male sterility to a *Rudbeckia* plan. The method may comprise introducing, as a cytoplasmic male sterility gene, at least one polynucleotide into a *Rudbeckia* plant of interest.

20 Claims, 6 Drawing Sheets

Specification includes a Sequence Listing.

RdCMS

RdMF

RdCMS HGAP4

RdCMS
Organelle_PBA

RdMF
Organelle_PBA

RdMF HGAP4

M:RdMF, C:RdCMS, 1:Prairie Sun, 2:Roland Orange,

3:Roland Yellow, 4:Roland Orange Bicolor,

5:Toto Golden, 6:Toto Lemon, 7:Toto Rustic,

8:Tiger Eye, 1-8: Commercially available fertile varieties

CYTOPLASMIC MALE-STERILE *RUDBECKIA* PLANTS AND A METHOD OF PRODUCTION

SEQUENCE LISTING SUBMISSION VIA EFS-WEB

The contents of the electronic sequence listing (sequence-listing.xml; Size: 131,346 bytes; and Date of Creation: Mar. 8, 2023) is herein incorporated by reference in its entirety.

TECHNICAL FIELD

The present disclosure relates to a cytoplasmic male sterile *Rudbeckia* plant and a method for producing the same.

BACKGROUND ART

Plants belonging to the genus *Rudbeckia* (referred to as "*Rudbeckia* plants" hereinafter) are plants made up of about 30 species native to North America. It is known that the *Rudbeckia* plants have annual species, biennial species, and perennial species (perennial plants). Among these *Rudbeckia* plants, *Rudbeckia hirta*, which is annual, has a diverse range of flower colors, flower forms, etc. and thus had undergone selective breeding for ornamental purposes. As a result, various varieties of *Rudbeckia hirta* are now commercially available (Non-Patent Document 1).

Commercially available varieties of garden crops, including flowering plants and ornamental plants, are mostly F1 varieties that are produced utilizing a phenomenon called heterosis. Heterosis refers to the tendency of a first filial generation (F1) to have a trait superior to the corresponding trait of either parent. In order to produce an F1 variety, it is necessary to grow two lines as parental lines of the F1 variety, cross them with each other, and collect seeds produced between these lines. In addition, seed production for the F1 variety involves artificial removal of stamens, utilization of self-incompatibility, utilization of male sterility (MS), or the like in order to prevent contamination of selfed seeds of the parental lines.

In flowering plants, male sterility is not only utilized for efficient seed production for F1 varieties but also can bring about ornamental merits. Specifically, male sterile varieties do not shed pollen from their anthers. Thus, the male sterile varieties can prevent adhesion of pollen onto petals and the like, thereby preventing the appearance traits from being deteriorated. In addition, the male sterile varieties can also prevent contamination of clothing due to the adhesion of pollen. Moreover, it has been reported that, in some flowering plants and ornamental plants such as petunias and pelargoniums, conferring male sterility delays the aging of blooming flowers and thus allows for a long-lasting ornamental period (Non-Patent Documents 2 and 3).

Male sterility (MS) is classified into cytoplasmic male sterility (CMS) and genetic male sterility (GMS). In plants with cytoplasmic male sterility, male sterility genes are present in cytoplasmic genomes, i.e., mitochondrial genomes. On the other hand, in plants with genetic male sterility, male sterility genes are present in genomic DNAs.

CITATION LIST

Non-Patent Documents

[Non-Patent Document 1] Irene E. Palmer et al., "Cross-ability, Cytogenetics, and Reproductive Pathways in *Rud-*

*beckia* Subgenus *Rudbeckia*", HORTSCIENCE, 2009, Vol. 44, Issue 1 pages 44-48

[Non-Patent Document 2] Aran G. Smith et al., "Increased Flower Longevity in *Petunia* with Male Sterility", HORTSCIENCE, 2004, Vol. 39, Issue 4, pages 822B-822

[Non-Patent Document 3] Begona Garcia-Sogo et al., "Production of engineered long-life and male sterile *Pelargonium* plants", BMC Plant Biology, 2012, Vol. 12, Article number: 156

SUMMARY OF INVENTION

Technical Problem

In *Rudbeckia* plants, male sterility genes have not yet been identified, and there are no *Rudbeckia* plant varieties that exhibit male sterility. In light of the above foregoing, it is an object of the present disclosure to provide a *Rudbeckia* plant with cytoplasmic male sterility.

Solution to Problem

In order to achieve the above object, the present disclosure provides a *Rudbeckia* plant with cytoplasmic male sterility.

The present disclosure also provides a progeny line of the *Rudbeckia* plant of the present disclosure, wherein the progeny line is cytoplasmic male sterile.

The present disclosure also provides a method for producing a cytoplasmic male sterile *Rudbeckia* plant (also referred to as "first production method" hereinafter), including the step of: (a) crossing the *Rudbeckia* plant of the present disclosure or the progeny line of the present disclosure with another *Rudbeckia* plant.

The present disclosure also provides a method for conferring cytoplasmic male sterility to a *Rudbeckia* plant (also referred to simply as "conferring method" hereinafter), including the step of: introducing, as a cytoplasmic male sterility gene, at least one polynucleotide selected from the group consisting of polynucleotides of (ca) to (ce) and (cf) below into a *Rudbeckia* plant of interest:

(ca) a polynucleotide of any of (ca1) to (ca7) below:
  (ca1) a polynucleotide that consists of a base sequence of SEQ ID NO: 1;
  (ca2) a polynucleotide that consists of the base sequence of (ca1) with deletion, substitution, insertion, and/or addition of 1 to 67 bases and causes expression of cytoplasmic male sterility;
  (ca3) a polynucleotide that consists of a base sequence having at least 90% sequence identity to the base sequence of (ca1) and causes expression of cytoplasmic male sterility;
  (ca4) a polynucleotide that consists of a base sequence complementary to a polynucleotide hybridizing to the polynucleotide consisting of the base sequence of (ca1) under stringent conditions and causes expression of cytoplasmic male sterility;
  (ca5) a polynucleotide encoding a polypeptide that consists of an amino acid sequence of SEQ ID NO: 2;
  (ca6) a polynucleotide that consists of the amino acid sequence of SEQ ID NO: 2 with deletion, substitution, insertion, and/or addition of 1 to 22 amino acids and causes expression of cytoplasmic male sterility; and
  (ca7) a polynucleotide that consists of an amino acid sequence having at least 90% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of 1 to 280 bases and causes expression of cytoplasmic male sterility;

(cb3) a polynucleotide that consists of a base sequence having at least 90% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under stringent conditions and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of 1 to 93 amino acids and causes expression of cytoplasmic male sterility; and (cb7) a polynucleotide that consists of an amino acid sequence having at least 90% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of 1 to 126 bases and causes expression of cytoplasmic male sterility;

(cc3) a polynucleotide that consists of a base sequence having at least 90% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under stringent conditions and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of 1 to 42 amino acids and causes expression of cytoplasmic male sterility; and (cc7) a polynucleotide that consists of an amino acid sequence having at least 90% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of 1 to 291 bases and causes expression of cytoplasmic male sterility;

(cd3) a polynucleotide that consists of a base sequence having at least 90% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under stringent conditions and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of 1 to 97 amino acids and causes expression of cytoplasmic male sterility; and (cd7) a polynucleotide that consists of an amino acid sequence having at least 90% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of 1 to 114 bases and causes expression of cytoplasmic male sterility;

(ce3) a polynucleotide that consists of a base sequence having at least 90% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under stringent conditions and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of 1 to 38 amino acids and causes expression of cytoplasmic male sterility; and (ce7) a polynucleotide that consists of an amino acid sequence having at least 90% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of 1 to 46 bases and causes expression of cytoplasmic male sterility;

(cf3) a polynucleotide that consists of a base sequence having at least 90% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under stringent conditions and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of 1 to 15 amino acids and causes expression of cytoplasmic male sterility; and (cf7) a polynucleotide that consists of an amino acid sequence having at least 90% sequence identity to the amino acid sequence of SEQ ID NO: 12 and causes expression of cytoplasmic male sterility.

The present disclosure also provides a method for producing a cytoplasmic male sterile *Rudbeckia* plant (also referred to as "second production method" hereinafter), including the step of: conferring cytoplasmic male sterility to a *Rudbeckia* plant of interest, wherein the conferring step is performed by the conferring method of the present disclosure.

The present disclosure also provides a screening method for a cytoplasmic male sterile *Rudbeckia* plant (also referred to simply as "screening method" hereinafter), including the step of: selecting, from one or more test *Rudbeckia* plants, a test *Rudbeckia* plant that includes, as a cytoplasmic male sterility gene, at least one polynucleotide selected from the group consisting of the above-described polynucleotides of (ca) to (ce) and (cf) as a cytoplasmic male sterile *Rudbeckia* plant (selection step).

The present disclosure also provides a method for producing a cytoplasmic male sterile *Rudbeckia* plant (also referred to as "third production method" hereinafter), including the step of: screening one or more test *Rudbeckia* plants for a test *Rudbeckia* plant that includes a cytoplasmic male sterility gene, wherein the screening step is performed by the screening method of the present disclosure.

The present disclosure also provides a method for detecting cytoplasmic male sterility of a *Rudbeckia* plant (also referred to simply as "detection method" hereinafter), including the step of: detecting, as a cytoplasmic male sterility gene, at least one polynucleotide selected from the group consisting of the above-described polynucleotides of (ca) to (ce) and (cf) in a test *Rudbeckia* plant.

Advantageous Effects of Invention

The present disclosure can provide a *Rudbeckia* plant that exhibits cytoplasmic male sterility.

DESCRIPTION OF EMBODIMENTS

Definition

Figure 1A:
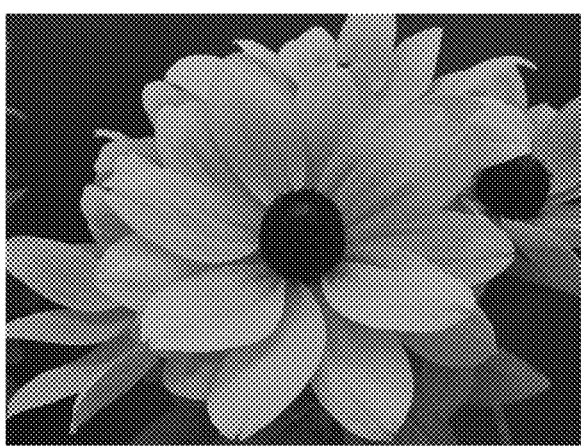
FIGS. 1A and 1B show photographs of flowers of *Rudbeckia* plants in Example 1.

The term "male sterile" or "male sterility" as used herein refers to a trait of being incapable of causing pollen formation or sufficient pollen formation owing to male organ sterility. As specific examples, the term "male sterile" or "male sterility" refers to loss of pollen owing to incomplete formation or insufficient growth of stamens, for example.

The term "cytoplasmic male sterile" or "cytoplasmic male sterility" as used herein refers to a male sterile trait maternally inherited by a gene derived from cytoplasm or from an organ present in the cytoplasm.

The term "genetic male sterile" or "genetic male sterility" as used herein refers to a male sterile trait inherited by a gene derived from a nucleus.

The term "*Rudbeckia* plant" as used herein refers to a plant classified under the genus *Rudbeckia* of the family Asteraceae.

The term "*Rudbeckia* plant for cultivation", "*Rudbeckia* variety for cultivation", or "*Rudbeckia* for cultivation" as used herein refers to a *Rudbeckia* plant that is cultivated by humans and is superior in terms of cultivation or a variety, breeding line, or cultivar of such a *Rudbeckia* plant. The "*Rudbeckia* plant for cultivation", "*Rudbeckia* variety for cultivation", or "*Rudbeckia* for cultivation" may be a hybrid thereof or a hybrid with a related species or wild species.

The term "plant body" or "plant" as used herein refers to a plant individual representing the whole plant.

The term "a part of a plant body" or "a part of a plant" as used herein refers to a part of a plant individual.

The term "polynucleotide" as used herein refers to a polymer of deoxyribonucleotides (DNA) and/or a polymer of ribonucleotides (RNA). The polynucleotide may be a single-stranded polynucleotide or a double-stranded polynucleotide. The "polynucleotide" can also be referred to as, for example, a nucleic acid or a nucleic acid molecule.

The term "polypeptide" as used herein refers to a polymer composed of unmodified amino acids (natural amino acids) and/or modified amino acids. The polypeptide is a peptide having a length of 10 or more amino acids, for example. The "polypeptide" can also be referred to as a protein, for example.

The term "crossing" as used herein refers to crossing of two parental lines. The crossing can also be referred to as crossbreeding, for example.

The term "expression vector" (vector) as used herein refers to a recombinant plasmid or a virus containing a polynucleotide to be delivered to a host cell in vitro or in vivo.

The phrase "causes expression" as used herein means that a desired trait is expressed in a subject or a desired trait is induced in a subject.

The present disclosure will be described below with reference to illustrative examples. It is to be noted, however, that the present disclosure is not limited to the following examples etc., and any changes and modifications may be made therein. In the present disclosure, descriptions regarding one aspect or embodiment can also be applied to another aspect or embodiment, and vice versa, unless otherwise stated. In the present specification, when a numerical range is delimited with the use of "to", numerical values or values representing physical quantities indicated before and after "to" are also included in this numerical range. When a plurality of numerical values are given as examples of the upper limit and/or the lower limit of a certain numerical range in the present specification, these numerical values may be used in any combination as the upper limit and the lower limit of the numerical range. When an expression like "A and/or B" is used in the present specification, it encompasses the cases of "only A", "only B", and "both A and B".

<Cytoplasmic Male Sterile *Rudbeckia* Plant>

In one aspect, the present disclosure provides a *Rudbeckia* plant that exhibits cytoplasmic male sterility. The *Rudbeckia* plant of the present disclosure exhibits cytoplasmic male sterility. The *Rudbeckia* plant according to the present disclosure is characterized in that it exhibits cytoplasmic male sterility, and there is no particular limitation on other structures and conditions.

The inventors of the present disclosure found through in-depth studies novel *Rudbeckia* plant individuals that exhibit cytoplasmic male sterility. As a result of further studies, they also discovered that, in the *Rudbeckia* plant individuals with cytoplasmic male sterility, the cytoplasmic male sterility is a hereditary trait and is caused by novel cytoplasmic male sterility genes. The present disclosure thus can provide a *Rudbeckia* plant that exhibits cytoplasmic male sterility.

In the *Rudbeckia* plant of the present disclosure, the male sterility is cytoplasmic male sterility (CMS). As described above, the types of male sterility include cytoplasmic male sterility and genetic male sterility (GMS). Whether the male sterility is CMS or GMS is determined according to the type of the genome in which the male sterility gene is present (located), for example. Specifically, when the male sterility gene is present in the cytoplasm, i.e., in the mitochondrial genome, a *Rudbeckia* plant including the male sterility gene exhibits cytoplasmic male sterility. On the other hand, when the male sterility gene is present (located) in the nucleus, i.e., in the nuclear genome, a *Rudbeckia* plant including the male sterility gene exhibits genetic male sterility. Accordingly, the type of male sterility can be evaluated by, for example, detecting the genome in which the male sterility gene is present. As a specific example, when the male sterility gene is present in the mitochondrial genome of a test *Rudbeckia* plant, the test *Rudbeckia* plant can be evaluated as being cytoplasmic male sterile. On the other hand, when the male sterility gene is present in the nuclear genome of a test *Rudbeckia* plant, the test *Rudbeckia* plant can be evaluated as being genetic male sterile.

Examples of the *Rudbeckia* plant include *Rudbeckia alpicola*, *Rudbeckia auriculata*, *Rudbeckia californica*, *Rudbeckia flava*, *Rudbeckia fulgida*, *Rudbeckia glaucescens*, *Rudbeckia graminifolia*, *Rudbeckia grandiflor*, *Rudbeckia heliopsidis*, *Rudbeckia hirta*, *Rudbeckia klamathensis*, *Rudbeckia laciniata*, *Rudbeckia missouriensis*, *Rudbeckia mohrii*, *Rudbeckia mollis*, *Rudbeckia montana*, *Rudbeckia newmannii*, *Rudbeckia nitida*, *Rudbeckia occidentalis*, *Rudbeckia scabrifolia*, *Rudbeckia speciosa*, *Rudbeckia subtomentosa*, *Rudbeckia texana*, *Rudbeckia triloba*, *Echinacea atrorubens*, *Echinacea pallida*, and *Echinacea purpurea*. The *Rudbeckia* plant can also be referred to as, for example, a *Rudbeckia* plant for cultivation or a *Rudbeckia* variety for cultivation.

The *Rudbeckia* plant may be a hybrid with a related species or a wild species. Examples of the related species include plants belonging to the genus *Echinacea* and *Rudbeckia* plants of a species different from the *Rudbeckia* plant crossed therewith.

Examples of a part of the plant include plant cells, plant protoplasts, plant cell cultures or tissue cultures from which a plant body can be regenerated, calli (plant calli), plant clumps, plant cells isolated from the plant or a part of the plant, meristematic cells, pollens, flowers, petals, flower buds, corollas, leaves, petioles, pith of leaves, cotyledons, ovaries, embryos, ovules, hypocotyls, egg cells, anthers, pistils, cuttings, scions (grafts), rootstocks, roots, tips of roots (root tips), seeds, fruits, trunks, stems, and seedlings. The part of the plant may be, for example, an organ, tissue, a cell, or a propagule, and any of them may be used. Examples of the organ include petals, corollas, flowers, leaves, seeds, fruits, stems, and roots. The tissue is a part of the organ, for example. The part of the plant may be, for example, cytoplasm, a mitochondrion, or a mitochondrial genome of: a plant individual or a progeny line thereof; or a part of the plant, such as a seed or a callus.

It is preferable that the male sterility of the *Rudbeckia* plant is a hereditary trait. In this case, the male sterility of the *Rudbeckia* plant is caused by a male sterility gene, for example. The male sterility gene may be present in the form of RNA (e.g., mRNA) or DNA (e.g., cDNA, genomic DNA, or mitochondria DNA). DNA may be a double-stranded DNA or a single-stranded DNA. The male sterility gene may include additional sequences such as the sequences of untranslated regions (UTRs).

In the present disclosure, examples of the cytoplasmic sterility gene include ORF3, ORF1, ORF2, ORF6, ORF7, and RPS7.

In the present disclosure, ORF3 includes a polynucleotide of (ca) below:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under stringent conditions and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility.

In (ca1), the base sequence of SEQ ID NO: 1 is the coding sequence encoding the amino acid sequence of SEQ ID NO: 2. The base sequence of SEQ ID NO: 1 can be obtained from a seed of a *Rudbeckia* plant deposited under Accession No. FERM BP-22428 to be described below, for example. The base sequence of SEQ ID NO: 1 shown below is a base sequence including a stop codon (TAA). The nucleotide sequence of SEQ ID NO: 1 is presumed to be the base sequence of a chimeric gene composed of the ATP6 gene of fertile *Rudbeckia* plants and another gene, as will be described below. It is to be noted, however, that the above presumption does not limit the present disclosure by any means.

Base sequence of Cytoplasmic Male Sterility Gene (ORF3) (SEQ ID NO: 1)

```
5'-ATGCTGCTAACTCTCAGTTTGGTCCTACTTCT

GATTCATTTTGTTACTAAAAAAGGAGGAGGAAACT

TAGTACCAAATGCTTGGCAATCCTTGGTAGAGCTT

ATTTATGATTTCGTGCTGAACCTGGTAAACGAACA

AATAGGGGGTCTTTCCGGAAATGTTAAACAAAAGT

TTTTCCCTTGCATCCTGGTCACTTTTACTTTTTTG

TTATTTTGTAATCTTCAGGGTATGATACCTTATAG

CTTCACAGTTACAAGTCATTTTCTCATTACTTTAG

GTCTCTCATTTTCGATTTTTATTGGCATTACTATA

GTGGGATTTCAAAGAAACGGGCTTCATTTTTTAAG

CTTCTTATTACCCGCAGGAGTCCCACTGCCATTAG

CACCTTTTTTAGTACTCCTTGAGCTAATTTCTTAT

TGTTTTCGCGCATTAAGCTTAGGAATACGTTTATT

TGCTAATATGATGGCCGGTCATAGTTTAGTAAAGA

TTTTAAGTGGGTTCGCTTGGACTATGCTATGTATG

AATGATCTTTTGTATTTTATAGGGGATCTTGGTCC

TTTATTTATAGTTCTTGCATTAACCGGTCTGGAAT

TAGGTGTAGCTATATTACAAGCTTATGTTTTTACG

ATCTTAATCTGTATTTACTTGAATGATGCTATAAA

TCTCCATTAA-3'
```

In (ca2), "one or several" need only be, for example, in a range in which the polynucleotide of (ca2) causes expression of cytoplasmic male sterility. The number of "one or several" bases in (ca2) is, for example, 1 to 134, 1 to 100, 1 to 67, 1 to 33, 1 to 26, 1 to 20, 1 to 13, 1 to 6, 1 to 3, 1 or 2, or 1 in the base sequence of (ca1). In the present disclosure, a numerical range regarding the number of bases, amino acids, or the like is intended to disclose all the positive integers falling within that range, for example. That is, for example, the description "one to five" is intended to disclose all of "one, two, three, four, and five" (the same applies hereinafter).

In (ca3), the "sequence identity" need only be, for example, in a range in which the polynucleotide of (ca3) causes expression of cytoplasmic male sterility. The "sequence identity" in (ca3) is, for example, at least 80%, at least 85%, at least 90%, at least 95%, at least 96%, at least 97%, at least 98%, or at least 99% with respect to the base sequence of (ca1). The "sequence identity" can be determined by aligning two base sequences or amino acid sequences (the same applies hereinafter). The sequence identity of the aligned sequences can be calculated, for example, using BLAST or FASTA with default parameters (the same applies hereinafter).

In (ca4), the "polynucleotide hybridizing to" is, for example, a polynucleotide fully or partially complementary to the polynucleotide of (ca1). The "polynucleotide hybridizing to" need only be such that, for example, the polynucleotide of (ca4) causes expression of cytoplasmic male sterility. The hybridization can be detected by various types of hybridization assays, for example. The hybridization assays are not limited to particular types of assays, and for example, a method described in "Molecular Cloning: A Laboratory Manual 2$^{nd}$ Ed." edited by Sambrook et al. (Cold Spring Harbor Laboratory Press (1989)) may be employed.

In (ca4), the "stringent conditions" may be any of low stringency conditions, medium stringency conditions, and high stringency conditions, for example. The "low stringency conditions" are as follows, for example: 5×SSC, 5×Denhardt's solution, 0.5% SDS, 50% formamide, and 32° C. The "moderate stringency conditions" are as follows, for example: 5×SSC, 5×Denhardt's solution, 0.5% SDS, 50% formamide, and 42° C. The "high stringency conditions" are as follows, for example: 5×SSC, 5×Denhardt's solution, 0.5% SDS, 50% formamide, and 50° C. Those skilled in the art can set the degree of stringency by, for example, setting the conditions such as the temperature, the salt concentration, the concentration and length of a probe, the ionic strength, and the time period as appropriate. As the "stringent conditions", it is also possible to employ, for example, conditions described in the above-described "Molecular Cloning: A Laboratory Manual 2$^{nd}$ Ed." edited by Sambrook et al. (Cold Spring Harbor Laboratory Press (1989)).

The polynucleotide of (ca5) need only be such that, for example, the base sequence thereof encodes a protein that causes expression of cytoplasmic male sterility. The base sequence of the polynucleotide of (ca5) can be designed by, for example, substitution to corresponding codons based on the amino acid sequence of SEQ ID NO: 2. The amino acid sequence of SEQ ID NO: 2 can be obtained from a seed of a *Rudbeckia* plant deposited under Accession No. FERM BP-22428 to be described below, for example.

Amino Acid Sequence (SEQ ID NO: 2) Encoded by Cytoplasmic Male Sterility Gene

```
(ORF3)
MLLTLSLVLLLIHFVTKKGGGNLVPNAWQSLVELIYDFVLNLVNEQIGG

LSGNVKQKFFPCILVTFTFLLFCNLQGMIPYSFTVTSHFLITLGLSFSI

FIGITIVGFQRNGLHFLSFLLPAGVPLPLAPFLVLLELISYCFRALSLG

IRLFANMMAGHSLVKILSGFAWTMLCMNDLLYFIGDLGPLFIVLALTGL

ELGVAILQAYVFTILICIYLNDAINLH
```

In (ca6), "one or several" regarding the amino acid sequence need only be, for example, in a range in which the polynucleotide of (ca6) causes expression of cytoplasmic male sterility. The number of "one or several" amino acids in (ca6) is, for example, 1 to 44, 1 to 33, 1 to 22, 1 to 11, 1 to 8, 1 to 6, 1 to 4, 1 to 3, 1 or 2, or 1 in the amino acid sequence of SEQ ID NO: 2.

In (ca7), the "sequence identity" regarding the amino acid sequence need only be, for example, in a range in which the polynucleotide of (ca7) causes expression of cytoplasmic male sterility. The "sequence identity" in (ca7) is, for example, at least 80%, at least 85%, at least 90%, at least 95%, at least 96%, at least 97%, at least 98%, or at least 99% with respect to the amino acid sequence of SEQ ID NO: 2.

The phrase "causes expression of cytoplasmic male sterility" means that, for example, a plant individual that includes the corresponding polynucleotide exhibits cytoplasmic male sterility (the same applies hereinafter).

In the present disclosure, ORF1 includes a polynucleotide of (cb) below:

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under stringent conditions and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility.

In (cb1), the base sequence of SEQ ID NO: 3 is the coding sequence encoding the amino acid sequence of SEQ ID NO: 4. The base sequence of SEQ ID NO: 3 can be obtained from a seed of a *Rudbeckia* plant deposited under Accession No. FERM BP-22428 to be described below, for example. The base sequence of SEQ ID NO: 3 shown below is a base sequence not including a stop codon (TAA). As described below, the base sequence of SEQ ID NO: 3 is presumed to be a DNA-dependent RNA polymerase of a *Rudbeckia* plant. It is to be noted, however, that the above presumption does not limit the present disclosure by any means.

Base Sequence of Cytoplasmic Male Sterility Gene (ORF1) (SEQ ID NO: 3)

5'-

ATGGAACAAACAGTTCGTGAATTCCTATTGAGTACTGTGTCTTTGGATG

ATAACAAGAAAAAAGGTATTGTCGTGGATTTCTGGTCTGAGTTCTATCA

AAAGAACGTCTATACGGAACATCAATCTAATCAGACGAATCGAAGTCTA

TATAAGGAGAAGGTATGTGAGATATTACATGAATTTAAAAGGACACATA

TTACACCTTACTCTAGGGAAGAATTAATAGCATTACAGGCTGAGATTGA

GAGTACTACGATCATTTTCGATGAGGCATCTATTCATGCTAGTAGTGGC

CATATAATGAAATATATGATTGATCCTAAAAAAGAGAGTGCTAAAGATT

TTGTTTATGAACGTCTTACCTCTAGGAAGGAGCAATCCATTATATCGGA

TATGGGTCAATACACACTTGAAGCAATCATAGTTTATGTCATCAGTAAG

TTGTATAGTTCAGAAACAGAAATGATTCGTGTATCGACTTTGATTGATC

AACTCGATAAGCAAGTTAAAGCACAGTCTGTTCTGGTAAATAAACATAA

AAAACCACTTGTGATGAAAGAAGTAGGTCAAAATGTTGCCTTGGGTGAG

-continued

CATTTTCCAATTGGAGCTGCATTAGTTGAATTTATTTCTGATAGGGGGT

TGATGACCATTCAACATATAGATGATAGAAGGTCATCTGTTCCAATTCA

AAAGAAGAAAGGAAAGTATTATATGCCAAAGTTACTCTACGCCTTCTAT

AATTTTGATGTATCTCTACTCCCCGTTAAGCTGAACATACCGATGGTCT

TTCCACCTATAGAATGGAGTAATGCTCGTGAGGATAATCTAGAACCTAA

AACCCTATATGACCTTAGAGGTGGTTACATATCCGGGATGAGCGAGGTA

TCTCGTTACCATCTACTCAGTAGTTGGAATTATAACAACTACTATATTG

ATATAGAATCTGGTCACGAGTCATTATGTGTAGTAATGAACAAGCTGCA

GAAAGTGCCTTTTCGAATAGCTAGTTTCATGCTCACATTTATCAAAGAA

AACTATAATGACTTTGTGAAGGCAGGTTTACTTATGCCAAAAGCTCTCT

GTATTGCAGATATGAAAAAGTTGCGTGATTCCCTCAGAGATTTCTACAT

GAATAATGAAAAGGGAATTAAAACAATCTATAGCTATGACGAAGTCTTA

ACTATTTTATACAAGGATGTGCAGCGTGCTCGTTTTGAGAGAATGACCC

TCATGCTTTCAGAGGCATTAGAAGGTTTTAAACTCTACTTACCAGCCTT

TCTTGACTTTAGGGGTAGAATCTACAGAAGCGGTATTTTACACTTACAT

GAACGAGATTTTGTCAGAAGCCTGCTCATCTTTGACAATTTATATGATT

ATAAAAATCAGGATGAAATTATACATATCAATAAATGTCTTTCAATCCT

AGGGCGAGCTATACCCTACTATTGGAAGTCATTTTCTTCTTATACTGAT

TCAGAAGAATGGGGTCGAAAACTAATTGAAATCAAAGATAATATATGTA

ATTCAGAATTGATCAAGTTTTCAGTTAGTGCAAAAAAACCCTTTCAGTT

CCTTGCATCTGTATGTGCATTGAAGATTGAGGATGAAACTACTCGTAAT

CATTATCTCAATTATCTTCCTATCACCCAAGATGCTTCGTCTAGTGCCT

ATCAAATTATGAGTTTTCTATTGTTAGATACTCAAATAGCAAAACAAAC

TAATCTGATTTCTGAGCATAAAGGTGAGATTCATGATATATATAACCAT

ATGAAAGAATTACTATTGGAATACATAGAATCTTGCTCGGGTGAGTACG

ATTTGAGTGAGAATTTGAAAGAACTAGTTATCAAATCCATTGACCGTAA

GTTAGTTAAGGCTCTTTTTATGCCAATAATCTATGGAAAGACTGTGATT

AGCACTGCAACAGATCTAAGAACAACTCTCTCCAAGTTCGTGACAAAGG

GTGAGAGCATGATCCTGGCTAAGATCTGCTTTTCTTTCTGGAAAGAAAC

CTATAGGGGTATGGATTGTTTGATCACTCTGATCAAGAGTATTGGATGG

ATGGTCTCAGCCAGGGGGAGCCATGTCCGATATCAAAATCAAATTTATA

CCACAGTTCAAAAATACATGAAGATGGATGCAGTCAAGATATGGATCTA

TGATCGAGAAAATAAAAAGAAGCGTCAAGTCACTCTTAGAGTCTCAACA

GAGAAAAATGATAAACGGAAGAGTGAAATCGCTACCTTCGTGAACTTCA

TCCATCAGTTTGATGCTTTCATTGCAATGAGTGTGATTTATGAAATGCC

TAGCTATGCTTCACATATCTACACAGTTCACGACAACTTTATCACTATT

CCAAGTAGTTGTGATGATCTGCCATATCTGTATAAGAAAGCCTTCAGTT

GTAATAATCCTCTCGCAATCATCAACCGTTACATCTACACTAATGTGAT

GGAACATCTTGGTATGATAGAAGGGCTAACTCCTGTTGAAAGTGATCAC

TTTCGGAGATTAAGGAAGAAAGATGGATACGATACCTTAATCATTCACG

AGAATATACTCTTGAAATACTTAATTTGTAATATGCCTATCAATCTCAA

-continued

AAGAAAGAATGAGACTCAGATGTGGGAAGGAAAGATCAATACAATAATA

ACATCATACAAAGAGTATGTTAGAACTATATGCATGTGCGAAGATCCCG

GGAAAGATTATGACATAAATAAACTTGAAAAATGCCGTGATGAGTATAC

CGAAAATGATCAAAATTTCATTAGGCGTATGATGCGAGGTTCCACCAAT

TATAGCATACATCAT-3'

In (cb2), "one or several" need only be, for example, in a range in which the polynucleotide of (cb2) causes expression of cytoplasmic male sterility. The number of "one or several" bases in (cb2) is, for example, 1 to 561, 1 to 421, 1 to 280, 1 to 140, 1 to 112, 1 to 84, 1 to 56, 1 to 28, 1 to 26, 1 to 20, 1 to 13, 1 to 6, 1 to 3, 1 or 2, or 1 in the base sequence of (cb1).

In (cb3), the "sequence identity" need only be, for example, in a range in which the polynucleotide of (cb3) causes expression of cytoplasmic male sterility. The "sequence identity" in (cb3) is, for example, at least 80%, at least 85%, at least 90%, at least 95%, at least 96%, at least 97%, at least 98%, or at least 99% with respect to the base sequence of (cb1).

In (cb4), the "polynucleotide hybridizing to" is, for example, a polynucleotide fully or partially complementary to the polynucleotide of (cb1). The "polynucleotide hybridizing to" need only be such that, for example, the polynucleotide of (cb4) causes expression of cytoplasmic male sterility. Regarding the hybridization, reference can be made to the above description on the hybridization in (ca4).

The polynucleotide of (cb5) need only be such that, for example, the base sequence thereof encodes a protein that causes expression of cytoplasmic male sterility. The base sequence of the polynucleotide of (cb5) can be designed by, for example, substitution to corresponding codons based on the amino acid sequence of SEQ ID NO: 4. The amino acid sequence of SEQ ID NO: 4 can be obtained from a seed of a *Rudbeckia* plant deposited under Accession No. FERM BP-22428 to be described below, for example.
Amino Acid Sequence (SEQ ID NO: 4) Encoded by Cytoplasmic Male Sterility Gene (ORF1)
MEQTVREFLLSTVSLDDNKKKGIVVDFWSEFYQKNVYTEHQSNQTNRSL

YKEKVCEILHEFKRTHITPYSREELIALQAEIESTTIIFDEASIHASSG

HIMKYMIDPKKESAKDFVYERLTSRKEQSIISDMGQYTLEAIIVYVISK

LYSSETEMIRVSTLIDQLDKQVKAQSVLVNKHKKPLVMKEVGQNVALGE

HFPIGAALVEFISDRGLMTIQHIDDRRSSVPIQKKKGKYYMPKLLYAFY

NFDVSLLPVKLNIPMVFPPIEWSNAREDNLEPKTLYDLRGGYISGMSEV

SRYHLLSSWNYNNYYIDIESGHESLCVVMNKLQKVPFRIASFMLTFIKE

NYNDFVKAGLLMPKALCIADMKKLRDSLRDFYMNNEKGIKTIYSYDEVL

TILYKDVQRARFERMTLMLSEALEGFKLYLPAFLDFRGRIYRSGILHLH

ERDFVRSLLIFDNLYDYKNQDEIIHINKCLSILGRAIPYYWKSFSSYTD

SEEWGRKLIEIKDNICNSELIKFSVSAKKPFQFLASVCALKIEDETTRN

HYLNYLPITQDASSSAYQIMSFLLLDTQIAKQTNLISEHKGEIHDIYNH

MKELLLEYIESCSGEYDLSENLKELVIKSIDRKLVKALFMPIIYGKTVI

-continued
STATDLRTTLSKFVTKGESMILAKICFSFWKETYRGMDCLITLIKSIGW

MVSARGSHVRYQNQIYTTVQKYMKMDAVKIWIYDRENKKKRQVTLRVST

EKNDKRKSEIATFVNFIHQFDAFIAMSVIYEMPSYASHIYTVHDNFITI

PSSCDDLPYLYKKAFSCNNPLAIINRYIYTNVMEHLGMIEGLTPVESDH

FRRLRKKDGYDTLIIHENILLKYLICNMPINLKRKNETQMWEGKINTII

TSYKEYVRTICMCEDPGKDYDINKLEKCRDEYTENDQNFIRRMMRGSTN

YSIHH

In (cb6), "one or several" regarding the amino acid sequence need only be, for example, in a range in which the polynucleotide of (cb6) causes expression of cytoplasmic male sterility. The number of "one or several" amino acids in (cb6) is, for example, 1 to 187, 1 to 140, 1 to 93, 1 to 46, 1 to 35, 1 to 28, 1 to 18, 1 to 9, 1 to 8, 1 to 6, 1 to 4, 1 to 3, 1 or 2, or 1 in the amino acid sequence of SEQ ID NO: 4.

In (cb7), the "sequence identity" regarding the amino acid sequence need only be, for example, in a range in which the polynucleotide of (cb7) causes expression of cytoplasmic male sterility. The "sequence identity" in (cb7) is, for example, at least 80%, at least 85%, at least 90%, at least 95%, at least 96%, at least 97%, at least 98%, or at least 99% with respect to the amino acid sequence of SEQ ID NO: 4.

In the present disclosure, ORF2 includes a polynucleotide of (cc) below:
  (cc) a polynucleotide of any of (cc1) to (cc7) below:
    (cc1) a polynucleotide that consists of a base sequence of SEQ ID NO: 5;
    (cc2) a polynucleotide that consists of the base sequence of (cc1) with deletion, substitution, insertion, and/or addition of one or several bases and causes expression of cytoplasmic male sterility;
    (cc3) a polynucleotide that consists of a base sequence having at least 80% sequence identity to the base sequence of (cc1) and causes expression of cytoplasmic male sterility;
    (cc4) a polynucleotide that consists of a base sequence complementary to a polynucleotide hybridizing to the polynucleotide consisting of the base sequence of (cc1) under stringent conditions and causes expression of cytoplasmic male sterility;
    (cc5) a polynucleotide encoding a polypeptide that consists of an amino acid sequence of SEQ ID NO: 6;
    (cc6) a polynucleotide that consists of the amino acid sequence of SEQ ID NO: 6 with deletion, substitution, insertion, and/or addition of one or several amino acids and causes expression of cytoplasmic male sterility; and
    (cc7) a polynucleotide that consists of an amino acid sequence having at least 80% sequence identity to the amino acid sequence of SEQ ID NO: 6 and causes expression of cytoplasmic male sterility.

In (cc1), the base sequence of SEQ ID NO: 5 is the coding sequence encoding the amino acid sequence of SEQ ID NO: 6. The base sequence of SEQ ID NO: 5 can be obtained from a seed of a *Rudbeckia* plant deposited under Accession No. FERM BP-22428 to be described below, for example. The base sequence of SEQ ID NO: 5 shown below is a base sequence not including a stop codon (TAA). As described below, the base sequence of SEQ ID NO: 5 is presumed to be a DNA polymerase of a *Rudbeckia* plant. It is to be noted, however, that the above presumption does not limit the present disclosure by any means.

Base Sequence of Cytoplasmic Male Sterility Gene (ORF2) (SEQ ID NO: 5)

```
5'-

ATGTTAGGCTTTATTGAGGCATATGTGGTATGTCCGAAAACGATCAAGA

AGCCATTTCTACCCTATCGAGAGAAGGAGGGGACTCTCCTCTTTCCAAC

TGGAGAATTTGTAGGTGTATACTTTAGCGAAGAATTGAAGTATGCTAGA

GAGATTGGCTACACAGTGATTCCAATCTCAGGCTACCTCTTTGAGAAGA

AGGAAAGCCCATTCAGGGAGTTTGTAAGCGATCTCTTTGAAAGCAGGTT

AGAAGCTAAAAAGTCTGGGAATGATGCGTTGTCTTATGTGTACAAGATC

CTTATGAATTCGCTATACGGTAGATTTGGCATTAACCCTATGGGCACAA

TAACTGAGATCTGCGATTCCAAAAGACATAAACTGTTAATAAGAAAGAC

TGAGTTGATCTCAACTGATGAGCTTACCGATTCCAAATACATCGTGACC

TACCGTAGCAATACAGAGACTGATTATTGGGATCCACCGAAGAACTCTG

CTGTCCAAATTGCTGCTGCAATCACTGCCTATGCTAGGATCTATATGTA

TCCTTATATCTCAAGGGAGGACAGTTACTACACTGACACTGACTCAGTA

GTGCTAGGACAGCCACTCTCAGATGAATTGATTTCATCTTCTATCTTAG

GTAAGTTTAAGCTTGAGGACAAAATAGTTGAAGGGTACTTTTTAGCTCC

GAAGTCCTATTACTACAGGAATGATAAAGGAGAGGATATACTGAAGTAC

AAAGGGCTTGCGAAAACAGAAATCACTCCTGAATGGTTTCGTTCACAGT

ACGCTAACCCTGATCGTACGCTAGAAGTAGAGGTGGAAGCCAACTTCCG

GATTGACTGGTCCTCACTTAACATCTTCAAGAAAGATAAGAATGTGAAG

GTTGGGCTTAATCAAAATCCAAAGAGGATCAAAGTCTATGAAGGGAAGT

ACTGGGTTGATACTATGCCAGTTGATGTCAAAGACCTGTCTAGACTAGA

TAACATTAGCAGAAAACTAGTCACGTGGCTAAAGGCTGATGTAACACAT

CTTAAGAACGAGAATCTATCTCTCAATGAGAAATTATCAGAGAAGGAAA

GAGAGATAACCGAGAAGAAAAGGATGGACGAGAGAGACAATGAGATGAA

AGAAGAACCTACAGAGGTCACTAACCCTACAATAGATATAGACGAGATA

CCTAAGATAGATATAGACGAGATACCTAAGATGAAACCTAAGAAGAAAG

CCAAGACTGACAAGAAAACAACGACAAAGAAGAAGAAACCCCCA-3'
```

In (cc2), "one or several" need only be, for example, in a range in which the polynucleotide of (cc2) causes expression of cytoplasmic male sterility. The number of "one or several" bases in (cc2) is, for example, 1 to 253, 1 to 190, 1 to 126, 1 to 63, 1 to 50, 1 to 38, 1 to 25, 1 to 12, 1 to 6, 1 to 3, 1 or 2, or 1 in the base sequence of (cc1).

In (cc3), the "sequence identity" need only be, for example, in a range in which the polynucleotide of (cc3) causes expression of cytoplasmic male sterility. The "sequence identity" in (cc3) is, for example, at least 80%, at least 85%, at least 90%, at least 95%, at least 96%, at least 97%, at least 98%, or at least 99% with respect to the base sequence of (cc1).

In (cc4), the "polynucleotide hybridizing to" is, for example, a polynucleotide fully or partially complementary to the polynucleotide of (cc1). The "polynucleotide hybridizing to" need only be such that, for example, the polynucleotide of (cc4) causes expression of cytoplasmic male sterility. Regarding the hybridization, reference can be made to the above description on the hybridization in (ca4).

The polynucleotide of (cc5) need only be such that, for example, the base sequence thereof encodes a protein that causes expression of cytoplasmic male sterility. The base sequence of the polynucleotide of (cc5) can be designed by, for example, substitution to corresponding codons based on the amino acid sequence of SEQ ID NO: 6. The amino acid sequence of SEQ ID NO: 6 can be obtained from a seed of a *Rudbeckia* plant deposited under Accession No. FERM BP-22428 to be described below, for example.

Amino Acid Sequence (SEQ ID NO: 6) Encoded by Cytoplasmic Male Sterility Gene

```
(ORF2)
MLGFIEAYVVCPKTIKKPFLPYREKEGTLLFPTGEFVGVYFSEELKYAR

EIGYTVIPISGYLFEKKESPFREFVSDLFESRLEAKKSGNDALSYVYKI

LMNSLYGRFGINPMGTITEICDSKRHKLLIRKTELISTDELTDSKYIVT

YRSNTETDYWDPPKNSAVQIAAAITAYARIYMYPYISREDSYYTDTDSV

VLGQPLSDELISSSILGKFKLEDKIVEGYFLAPKSYYYRNDKGEDILKY

KGLAKTEITPEWFRSQYANPDRTLEVEVEANFRIDWSSLNIFKKDKNVK

VGLNQNPKRIKVYEGKYWVDTMPVDVKDLSRLDNISRKLVTWLKADVTH

LKNENLSLNEKLSEKEREITEKKRMDERDNEMKEEPTEVTNPTIDIDEI

PKIDIDEIPKMKPKKKAKTDKKTTTKKKKPP
```

In (cc6), "one or several" regarding the amino acid sequence need only be, for example, in a range in which the polynucleotide of (cc6) causes expression of cytoplasmic male sterility. The number of "one or several" amino acids in (cc6) is, for example, 1 to 86, 1 to 63, 1 to 42, 1 to 21, 1 to 16, 1 to 12, 1 to 8, 1 to 6, 1 to 4, 1 to 3, 1 or 2, or 1 in the amino acid sequence of SEQ ID NO: 6.

In (cc7), the "sequence identity" regarding the amino acid sequence need only be, for example, in a range in which the polynucleotide of (cc7) causes expression of cytoplasmic male sterility. The "sequence identity" in (cc7) is, for example, at least 80%, at least 85%, at least 90%, at least 95%, at least 96%, at least 97%, at least 98%, or at least 99% with respect to the amino acid sequence of SEQ ID NO: 6.

In the present disclosure, ORF6 includes a polynucleotide of (cd) below:

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under stringent conditions and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility.

In (cd1), the base sequence of SEQ ID NO: 7 is the coding sequence encoding the amino acid sequence of SEQ ID NO: 8. The base sequence of SEQ ID NO: 7 can be obtained from a seed of a *Rudbeckia* plant deposited under Accession No. FERM BP-22428 to be described below, for example. The base sequence of SEQ ID NO: 7 shown below is a base sequence not including a stop codon (TAA). As described below, the base sequence of SEQ ID NO: 7 is presumed to be a DNA polymerase of a *Rudbeckia* plant. It is to be noted, however, that the above presumption does not limit the present disclosure by any means.

Base Sequence of Cytoplasmic Male Sterility Gene (ORF6) (SEQ ID NO: 7)

```
5'-

ATGAATAAAATGAATATGAAAATGAAAAGAATAATGCCTATGTGTTCTA

GAACCTTACATACGAGTGTACGTCCAGAACTAGAATTTGTATTCAATCG

TTATCAATCGGTGGTAGAGCAGACAAGAGTACAGGATCCGCACCCAGGG

TTAATCATTGCAACACTAAACTTCAAGAAACCAGGTCTAGGTGTAGATG

ATATAGAACTCATCAGCATTGCGCAATGGATCTCTTAAACCAGTATGT

TTACCCATCTATCTCAGGTTACGGGAAGTTCACAATCTCCTTGAGGATG

ATCCAATCTATCGAAGAAGAGATCACATATACAATAGGATGTGCAATAC

CCTTGACCTCGAATGATGGGACTCTCCTACCAAAGAATGAGATCTACGC

TCGGATAAAAGAAGCCTATCAGAAGAATGCTGAACTCTACAACGGATGC

TCTCTTGTTCAACTCATAATCAGAGCATATCTGGACAAGGTAGAACGGC

TGGATCGCCCGGAGCTCACAGTCTCAGATAGATATGAGGAACTGCTCTC

AATTCAGTCAGATAAATTGAGTGAGATCGAAGCAATCAGTGCTAGAAAG

ATTCAACATTCAAAGCGTCAGTATCGAGAGTATATAACAAGAATCAAAA

GAGTGAGCAGTGGTAAGAAAGCATTCATTGTCTCTGATCTCGAGACGAT

TCAGATTGATTATAAACATAGACCTTATGCCGCTGGTCTCATGTTGGTT

CGAGAAGGGAAAGACATCAAGGATAGTCTAATTTATACCTACTTCAGTG

AAGACTACTCAGTATACATCAAAAGTTTTGAGAAAAGGAGTCAAAAGGT

CCTCTTTGACCTGGTCAGGAAGATCATAGCTCTATCAAAGATAGAGAGA

AGTGCAATGACCGTTTATTTTCACAACTTCTCTAGATTTGATGGAATTA

TCTTGTTAAAGCACCTAGCATGTCATCATGACTACAAGCTGAAACAACT

ATTTAGGAATAACAGGCTTTACGAGTTAAAAGTCTATTCTGGCAGGAAG

CTATTATTCAAAATGAGAGATTCATTGAATCTACTTCCGGGTAAACTCG

ACAACCTGGCTAAGAGTCTATGCCCATCTCTAGGTGGTAAAGGAAGTCT

TAATTATGATGATGTGAGAGCTGATAACCTTGTGAGTAAGAAAGATCAA

TTGATTTCATATATGAAACAGGACATCCTGTTACTTGGTGGTATAATGA

AGAAGGCACAAGAGATCTATTATGATCTCTATCAATTGGATATTGTGAG

CAAAATTACCCTATCCTCACTAGCTCTAAGCATCTATCGTATGAGATAT
```

```
TATGATGAGGAAAACTGGCCAATCTACATCCCTAACATGAATCAAGACC

ACTTTATTAGAAAAGCATACTACGGAGGGCATACTGATGTATACAAGCC

TTATGGTGAGAACCTATACTACTACGATGTTAACTCACTCTATCCTTTT

GTCATGAAGAACTTTCAAATGCCTGGTGGTCAACCAGTCTGGCATGGAA

ATCTGCTTGATAAGGACCTCGATAGCTTGTATGGCTTTATAGAGGCTTA

TGTAGTCTGTCCTAAGACAATCAATAAACCCTTTCTACCCTATCGAAAC

AAGAATAACACTCTCATCTTTCCAACAGGGGAATTTGCAGGTGTCTACT

ACAGCGAGGAGTTAAAGTTTGCTAGAGACCTTGGTTACACCGTGCTCCC

GCTCTCTGGCTACCTCTATGAGAGAATGGAAAGCCCATTCAAAGAATTT

GTTAACACGCAATCTTCAAAGAGGATAGAAGCAAAGAAAGAAGGAAATG

ATGCTTTATCCTATGTTTACAAGATCCTAATGAACTCGCTATACGGTAG

ATTTGGTATTAACCCTAAAAGCACAACATCCGAGATCTGTGATCATGAT

CGATACGTAAAAATGCTCAAAGACGATTCATTTTTACAAGGTTCACTGC

TTGATAAGAACAAATACATAGTCATATACCATGTCAATACCGGTAGTAA

CCCAGAATCATGGAACCCACCAAAGAACGGTGCTGTACAGCTTGCTGCT

GCTATCACAGCCTGTGCAAGGATCTATATGTACCCATTGATCTCGAGAG

AGGATTGTTACTATACTGACACTGACTCGGTTGTGCTAGGACAGCCACT

CTCAGATGAATTGATTTCTGCTTCGGAGTTAGGTATGTTAAAGCTAGAA

GCAAGAATCTTAAAGGGCTACTTTTTAGCCCCTAAATCTTATGCATACA

TACAGTATGACGAGAATAAAGAGATCGTTATCAAGCACAAAGGTGCGGC

TAAAAACTTAGTGACCATGGAATGGTTTCAGTCACAGTACGATGACCCA

TCCCGGACACAACTGGTCTCGGTCACATCCAACTTTAAAATCAATTGGA

ATGAACTGGAAATCCATAAGCAAGAAACTTTATACAGGTTAGGTATTAG

CCAGGATTCTAAAAGGTTACCAGTATACTGCGAGAAGAAATGGATTGAT

ACTGAACCTATTGATATCAGAGATCTGTCTAACCATAGTCCTCAGATGT

TAGATAGAATCTTAGCCTATCTCAGGGATGAAGTGAATCGTCATCAGAC

TAATAGTGAGATTCTCCGTAAAGAACTCTCTAAAAAGGATAGTGAGATG

ATCAGCATCATTTCAGATAAGGATAGAGTGATCTCCGAGATGAAAAGTC

GGATTGAATCTCTTCAAGAGATGCGGAAAATCACTAACCCAACTGATAA

GACTGAGAAGAAAACTCATACAGCCAAGAAGACTAAGACTGAGAAGAAA

ACTCATACAGCCAAGAAGACTAAGACTGACAAGAAGAAAACCACCAATC

AAACTCTGAAGAAACATCAGAATCAAAGAAAACAAAGGCCTCCAAGAAA

CCATCATACTACCAAGAAACCTCCG-3'
```

In (cd2), "one or several" need only be, for example, in a range in which the polynucleotide of (cd2) causes expression of cytoplasmic male sterility. The number of "one or several" bases in (cd2) is, for example, 1 to 583, 1 to 437, 1 to 291, 1 to 145, 1 to 116, 1 to 87, 1 to 58, 1 to 50, 1 to 38, 1 to 29, 1 to 25, 1 to 12, 1 to 6, 1 to 3, 1 or 2, or 1 in the base sequence of (cd1).

In (cd3), the "sequence identity" need only be, for example, in a range in which the polynucleotide of (cd3) causes expression of cytoplasmic male sterility. The "sequence identity" in (cd3) is, for example, at least 80%, at least 85%, at least 90%, at least 95%, at least 96%, at least 97%, at least 98%, or at least 99% with respect to the base sequence of (cd1).

In (cd4), the "polynucleotide hybridizing to" is, for example, a polynucleotide fully or partially complementary to the polynucleotide of (cd1). The "polynucleotide hybridizing to" need only be such that, for example, the polynucleotide of (cd4) causes expression of cytoplasmic male sterility. Regarding the hybridization, reference can be made to the above description on the hybridization in (ca4).

The polynucleotide of (cd5) need only be such that, for example, the base sequence thereof encodes a protein that causes expression of cytoplasmic male sterility. The base sequence of the polynucleotide of (cd5) can be designed by, for example, substitution to corresponding codons based on the amino acid sequence of SEQ ID NO: 8. The amino acid sequence of SEQ ID NO: 8 can be obtained from a seed of a *Rudbeckia* plant deposited under Accession No. FERM BP-22428 to be described below, for example.

Amino Acid Sequence (SEQ ID NO: 8) Encoded by Cytoplasmic Male Sterility Gene

```
(ORF6)
MNKMNMKMKRIMPMCSRTLHTSVRPELEFVFNRYQSVVEQTRVQDPHPG

LIIATLNFKKPGLGVDDIELISIATMDLLNQYVYPSISGYGKFTISLRM

IQSIEEEITYTIGCAIPLTSNDGTLLPKNEIYARIKEAYQKNAELYNGC

SLVQLIIRAYLDKVERLDRPELTVSDRYEELLSIQSDKLSEIEAISARK

IQHSKRQYREYITRIKRVSSGKKAFIVSDLETIQIDYKHRPYAAGLMLV

REGKDIKDSLIYTYFSEDYSVYIKSFEKRSQKVLFDLVRKIIALSKIER

SAMTVYFHNFSRFDGIILLKHLACHHDYKLKQLFRNNRLYELKVYSGRK

LLFKMRDSLNLLPGKLDNLAKSLCPSLGGKGSLNYDDVRADNLVSKKDQ

LISYMKQDILLLGGIMKKAQEIYYDLYQLDIVSKITLSSLALSIYRMRY

YDEENWPIYIPNMNQDHFIRKAYYGGHTDVYKPYGENLYYYDVNSLYPF

VMKNFQMPGGQPVWHGNLLDKDLDSLYGFIEAYVVCPKTINKPFLPYRN

KNNTLIFPTGEFAGVYYSEELKFARDLGYTVLPLSGYLYERMESPFKEF

VNTQSSKRIEAKKEGNDALSYVYKILMNSLYGRFGINPKSTTSEICDHD

RYVKMLKDDSFLQGSLLDKNKYIVIYHVNTGSNPESWNPPKNGAVQLAA

AITACARIYMYPLISREDCYYTDTDSVVLGQPLSDELISASELGMLKLE

ARILKGYFLAPKSYAYIQYDENKEIVIKHKGAAKNLVTMEWFQSQYDDP

SRTQLVSVTSNFKINWNELEIHKQETLYRLGISQDSKRLPVYCEKKWID

TEPIDIRDLSNHSPQMLDRILAYLRDEVNRHQTNSEILRKELSKKDSEM

ISIISDKDRVISEMKSRIESLQEMRKITNPTDKTEKKTHTAKKTKTEKK

THTAKKTKTDKKKTTNQTLKKHQNQRKQRPPRNHHTTKKPP
```

In (cd6), "one or several" regarding the amino acid sequence need only be, for example, in a range in which the polynucleotide of (cd6) causes expression of cytoplasmic male sterility. The number of "one or several" amino acids in (cd6) is, for example, 1 to 194, 1 to 145, 1 to 97, 1 to 48, 1 to 38, 1 to 29, 1 to 18, to 16, 1 to 12, 1 to 9, 1 to 8, 1 to 6, 1 to 4, 1 to 3, 1 or 2, or 1 in the amino acid sequence of SEQ ID NO: 8.

In (cd7), the "sequence identity" regarding the amino acid sequence need only be, for example, in a range in which the polynucleotide of (cd7) causes expression of cytoplasmic male sterility. The "sequence identity" in (cd7) is, for example, at least 80%, at least 85%, at least 90%, at least 95%, at least 96%, at least 97%, at least 98%, or at least 99% with respect to the amino acid sequence of SEQ ID NO: 8.

In the present disclosure, ORF7 includes a polynucleotide of (ce) below:

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under stringent conditions and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility.

In (ce1), the base sequence of SEQ ID NO: 9 is the coding sequence encoding the amino acid sequence of SEQ ID NO: 10. The base sequence of SEQ ID NO: 9 can be obtained from a seed of a *Rudbeckia* plant deposited under Accession No. FERM BP-22428 to be described below, for example. The base sequence of SEQ ID NO: 9 shown below is a base sequence not including a stop codon (TAA).

Base Sequence of Cytoplasmic Male Sterility Gene (ORF7) (SEQ ID NO: 9)

```
5'-

ATGACAAATCCGGTTCAACGCGATCAATCTAAGTTTCTTAACAATACTG

TTGTGATGAATGATCAAAAGAAGAAGGATGTGGTGGTAGAGTTTTGGAA

GAGCTTCTATGGTATTCTTTTCGTTTCTTTCACAAATTTTGTTCTGATT

CTTCTAACTTGTATACTTGTTGAACCTGAGACGGTTCAGATGATTGCTA

GGTTCATTGGTGGTTCTTCAGCCATTTACTTTCTTTTTTTAGCCAGAGC

ACGATTTTCTAAGCTCTTCAACCTCTTTTCCTTTCTGGTAACCACCTGT

TATCTATTCGTTCTGAATCATCTTAATGCCCCAGATATAGGTTTAGTTC

CTATTTGCGTCTGTGGTTGCTTTATCTTTTCTTATTATTTTACGGAAAA

ACACACTGGCTGGCACTTTGATCTATGTTTTATGATTATTCTCACTTGT

AGATTGATCGTGTCACCGGACATATGGGCTATTAGCCTTGTCTTTGAAC

TTTTAGTCTTATTTTGCTTACTTGATCATGATATGGATCAAGATCGGAT

GAGATTGTGTTGTTTATATTTCATTCTCCTTCTCTTTTCTGTGCTGTAAC

TATCTCTACGGAAGTAGTATTCATATTGATACTCTCGTTGTGGTTCTAG
```

-continued

TTTTAGCGGCAGCAGGGGCGGGAGGTATCCAGTTCATGTCTCTCAGTAA

GACTGAACGGGGAGAAACCCTTGGACTGCAGCTTTTTTTGATCAATAAT

GTTATCTTGGGCTTCCTTCTTAGAAAGGATGGCGAGACCTTACCCATGA

TAACAATATTCTTTATCGTTTCCATTCTTTGCTTCTGCATCGGCTTATA

CCTAATAGGAAGGATTAAAGAGCAATCTTTCTATTCAGTTCTGTCTGAA

TTGAAGAGCTCGCTTCGGGGCTTGTTCATCCCGGTATTATTGACCTTGA

ATCACTTCTTTTTAGAAGATCAATATTACCTGTGGATCACAAGCCTAGT

GACTCGTATTATCGTTATTCAGCTCCTGCAATTAATTCTGAAAAAGGAG

GATGAAGATCCAGATCAGGACAAAGCGATAAAGAGTGACGATGTTCGAA

GGTGCGAAATCAATGGGTGCCGGAGCTGCTACAACTATTATTATGCGAG

AAGTCCTCCCGATTGCTAC-3'

In (ce2), "one or several" need only be, for example, in a range in which the polynucleotide of (ce2) causes expression of cytoplasmic male sterility. The number of "one or several" bases in (ce2) is, for example, 1 to 229, 1 to 171, 1 to 114, 1 to 57, 1 to 45, 1 to 34, 1 to 22, 1 to 11, 1 to 6, 1 to 3, 1 or 2, or 1 in the base sequence of (ce1).

In (ce3), the "sequence identity" need only be, for example, in a range in which the polynucleotide of (ce3) causes expression of cytoplasmic male sterility. The "sequence identity" in (ce3) is, for example, at least 80%, at least 85%, at least 90%, at least 95%, at least 96%, at least 97%, at least 98%, or at least 99% with respect to the base sequence of (ce1).

In (ce4), the "polynucleotide hybridizing to" is, for example, a polynucleotide fully or partially complementary to the polynucleotide of (ce1). The "polynucleotide hybridizing to" need only be such that, for example, the polynucleotide of (ce4) causes expression of cytoplasmic male sterility. Regarding the hybridization, reference can be made to the above description on the hybridization in (ca4).

The polynucleotide of (ce5) need only be such that, for example, the base sequence thereof encodes a protein that causes expression of cytoplasmic male sterility. The base sequence of the polynucleotide of (ce5) can be designed by, for example, substitution to corresponding codons based on the amino acid sequence of SEQ ID NO: 10. The amino acid sequence of SEQ ID NO: 10 can be obtained from a seed of a *Rudbeckia* plant deposited under Accession No. FERM BP-22428 to be described below, for example.
Amino Acid Sequence (SEQ ID NO: 10) Encoded by Cytoplasmic Male Sterility Gene (ORF7)
MTNPVQRDQSKFLNNTVVMNDQKKKDVVVEFWKSFYGILFVSFTNFVLI

LLTCILVEPETVQMIARFIGGSSAIYFLFLARARFSKLFNLFSFLVTTC

YLFVLNHLNAPDIGLVPICVCGCFIFSYYFTEKHTGWHFDLCFMIILTC

RLIVSPDIWAISLVFELLVLFCLLDHDMDQDRMRLCCLYFILLLFLCCN

YLYGSSIHIDTLVVVLVLAAAGAGGIQFMSLSKTERGETLGLQLFLINN

VILGFLLRKDGETLPMITIFFIVSILCFCIGLYLIGRIKEQSFYSVLSE

LKSSLRGLFIPVLLTLNHFFLEDQYYLWITSLVTRIIVIQLLQLILKKE

DEDPDQDKAIKSDDVRRCEINGCRSCYNYYYARSPPDCY

In (ce6), "one or several" regarding the amino acid sequence need only be, for example, in a range in which the polynucleotide of (ce6) causes expression of cytoplasmic male sterility. The number of "one or several" amino acids in (ce6) is, for example, 1 to 76, 1 to 57, 1 to 38, 1 to 19, 1 to 15, 1 to 12, 1 to 9, 1 to 8, 1 to 6, 1 to 4, 1 to 3, 1 or 2, or 1 in the amino acid sequence of SEQ ID NO: 10.

In (ce7), the "sequence identity" regarding the amino acid sequence need only be, for example, in a range in which the polynucleotide of (ce7) causes expression of cytoplasmic male sterility. The "sequence identity" in (ce7) is, for example, at least 80%, at least 85%, at least 90%, at least 95%, at least 96%, at least 97%, at least 98%, or at least 99% with respect to the amino acid sequence of SEQ ID NO: 10.

In the present disclosure, RPS7 includes a polynucleotide of (cf) below:

(cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under stringent conditions and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

In (cf1), the base sequence of SEQ ID NO: 11 is the coding sequence encoding the amino acid sequence of SEQ ID NO: 12. The base sequence of SEQ ID NO: 11 can be obtained from a seed of a *Rudbeckia* plant deposited under Accession No. FERM BP-22428 to be described below, for example. The base sequence of SEQ ID NO: 11 shown below is a base sequence including a stop codon (TAA).
Base Sequence of Cytoplasmic Male Sterility Gene (RPS7) (SEQ ID NO: 11)

5'-

ATGTCACGTCGAGGTACTGCAGAAGAAAAAACTGCAAAATCCGATCCAA

TTTATCGTAATCGATTAGTTAACATGTTGGTTAACCGTATTCTGAAACA

CGGAAAAAAATCATTGGCTTATCAAATTATCTATCGAGCCGTGAAAAAG

ATTCAACAAAAGACAGAAACAAATCCACTATCTGTTTTACGTCAAGCAA

TACATGGAGTAACTCCGGGTATAGCAGTAAAAGCAAGACGTGTAGGTGG

ATCGACTCATCAAGTTCCCATTGAAATAGGATCCACACAAGGAAAAGCA

-continued

```
CTTGCCATTCGTTGGTTATTAGCGGCATCCCGAAAACGTCCGGGTCGAA

ATATGGCTTTCAAATTAAGTTCCGAATTAGTGGATGCTGCCAAAGGGAG

TGGCGATGCCATACGCAAAAGGGAAGAGACTCATAGAATGGCAGAGGCA

AATAGAGCTTTTGCACATTTTCGTTAA-3'
```

In (cf2), "one or several" need only be, for example, in a range in which the polynucleotide of (cf2) causes expression of cytoplasmic male sterility. The number of "one or several" bases in (cf2) is, for example, 1 to 93, 1 to 70, 1 to 46, 1 to 23, 1 to 18, 1 to 14, 1 to 9, 1 to 6, 1 to 3, 1 or 2, or 1 in the base sequence of (cf1).

In (cf3), the "sequence identity" need only be, for example, in a range in which the polynucleotide of (cf3) causes expression of cytoplasmic male sterility. The "sequence identity" in (cf3) is, for example, at least 80%, at least 85%, at least 90%, at least 95%, at least 96%, at least 97%, at least 98%, or at least 99% with respect to the base sequence of (cf1).

In (cf4), the "polynucleotide hybridizing to" is, for example, a polynucleotide fully or partially complementary to the polynucleotide of (cf1). The "polynucleotide hybridizing to" need only be such that, for example, the polynucleotide of (cf4) causes expression of cytoplasmic male sterility. Regarding the hybridization, reference can be made to the above description on the hybridization in (ca4).

The polynucleotide of (cf5) need only be such that, for example, the base sequence thereof encodes a protein that causes expression of cytoplasmic male sterility. The base sequence of the polynucleotide of (cf5) can be designed by, for example, substitution to corresponding codons based on the amino acid sequence of SEQ ID NO: 12. The amino acid sequence of SEQ ID NO: 12 can be obtained from a seed of a *Rudbeckia* plant deposited under Accession No. FERM BP-22428 to be described below, for example.

Amino Acid Sequence (SEQ ID NO: 12) Encoded by Cytoplasmic Male Sterility Gene

```
(RPS7)
MSRRGTAEEKTAKSDPIYRNRLVNMLVNRILKHGKKSLAYQIIYRAVKK

IQQKTETNPLSVLRQAIHGVTPGIAVKARRVGGSTHQVPIEIGSTQGKA

LAIRWLLAASRKRPGRNMAFKLSSELVDAAKGSGDAIRKREETHRMAEA

NRAFAHFR
```

In (cf6), "one or several" regarding the amino acid sequence need only be, for example, in a range in which the polynucleotide of (cf6) causes expression of cytoplasmic male sterility. The number of "one or several" amino acids in (cf6) is, for example, 1 to 31, 1 to 23, 1 to 15, 1 to 7, 1 to 6, 1 to 4, 1 to 3, 1 or 2, or 1 in the amino acid sequence of SEQ ID NO: 12.

In (cf7), the "sequence identity" regarding the amino acid sequence need only be, for example, in a range in which the polynucleotide of (cf7) causes expression of cytoplasmic male sterility. The "sequence identity" in (cf7) is, for example, at least 80%, at least 85%, at least 90%, at least 95%, at least 96%, at least 97%, at least 98%, or at least 99% with respect to the amino acid sequence of SEQ ID NO: 12.

In the present disclosure, the *Rudbeckia* plant may include any one of, two or more of, or all of the cytoplasmic male sterility genes. When the *Rudbeckia* plant includes one cytoplasmic male sterility gene, the cytoplasmic male sterility gene is preferably ORF3. When the *Rudbeckia* plant includes two or more cytoplasmic male sterility genes, the combination of the cytoplasmic male sterility genes may be as follows, for example:

polynucleotides of (ca) and (cb);
polynucleotides of (ca) and (cc);
polynucleotides of (ca) and (cd);
polynucleotides of (ca) and (ce);
polynucleotides of (ca) and (cf);
polynucleotides of (cb) and (cc);
polynucleotides of (cb) and (cd);
polynucleotides of (cb) and (ce);
polynucleotides of (cb) and (cf);
polynucleotides of (cc) and (cd);
polynucleotides of (cc) and (ce);
polynucleotides of (cc) and (cf);
polynucleotides of (cd) and (ce);
polynucleotides of (cd) and (cf);
polynucleotides of (ce) and (cf);
polynucleotides of (ca), (cb), and (cc);
polynucleotides of (ca), (cb), and (cd);
polynucleotides of (ca), (cb), and (ce);
polynucleotides of (ca), (cb), and (cf);
polynucleotides of (ca), (cc), and (cd);
polynucleotides of (ca), (cc), and (ce);
polynucleotides of (ca), (cc), and (cf);
polynucleotides of (ca), (cd), and (ce);
polynucleotides of (ca), (cd), and (cf);
polynucleotides of (ca), (ce), and (cf);
polynucleotides of (cb), (cc), and (cd);
polynucleotides of (cb), (cc), and (ce);
polynucleotides of (cb), (cc), and (cf);
polynucleotides of (cb), (cd), and (ce);
polynucleotides of (cb), (cd), and (cf);
polynucleotides of (cb), (ce), and (cf);
polynucleotides of (cc), (cd), and (ce);
polynucleotides of (cc), (cd), and (cf);
polynucleotides of (cc), (ce), and (cf);
polynucleotides of (cd), (ce), and (cf);
polynucleotides of (ca), (cb), (cc), and (cd);
polynucleotides of (ca), (cb), (cc), and (ce);
polynucleotides of (ca), (cb), (cc), and (cf);
polynucleotides of (ca), (cb), (cd), and (ce);
polynucleotides of (ca), (cb), (cd), and (cf);
polynucleotides of (ca), (cb), (ce), and (cf);
polynucleotides of (ca), (cc), (cd), and (ce);
polynucleotides of (ca), (cc), (cd), and (cf);
polynucleotides of (ca), (cc), (ce), and (cf);
polynucleotides of (ca), (cd), (ce), and (cf);
polynucleotides of (cb), (cc), (cd), and (ce);
polynucleotides of (cb), (cc), (cd), and (cf);
polynucleotides of (cb), (cc), (ce), and (cf);
polynucleotides of (cb), (cd), (ce), and (cf);
polynucleotides of (cc), (cd), (ce), and (cf);
polynucleotides of (ca), (cb), (cc), (cd), and (ce);
polynucleotides of (ca), (cb), (cc), (cd), and (cf);
polynucleotides of (ca), (cb), (cc), (ce), and (cf);
polynucleotides of (ca), (cb), (cd), (ce), and (cf);
polynucleotides of (ca), (cc), (cd), (ce), and (cf);
polynucleotides of (cb), (cc), (cd), (ce), and (cf); and
polynucleotides of (ca), (cb), (cc), (cd), (ce), and (cf).

When the *Rudbeckia* plant of the present disclosure includes the cytoplasmic male sterility gene(s), the cytoplasmic male sterility gene(s) is present in the cytoplasm or mitochondrial genome (mitochondrial DNA). In this case, the cytoplasmic male sterility gene(s) may be an endogenous gene(s) or an exogenous gene(s). The endogenous gene is, for example, a gene resulting from mutation or the like in the *Rudbeckia* plant. The exogenous gene is, for example, a gene introduced using a genome-editing technique or the like.

In the *Rudbeckia* plant of the present disclosure, ORF3 is presumed to be a chimeric gene composed of the above-described ATP6 gene and another gene, as described below. Accordingly, when the *Rudbeckia* plant of the present disclosure includes ORF3, the *Rudbeckia* plant of the present disclosure preferably includes the cytoplasmic male sterility gene instead of the ATP6 gene or as the ATP6 gene.

The *Rudbeckia* plant that exhibits cytoplasmic male sterility may be, for example, a *Rudbeckia* plant deposited under Accession No. FERM BP-22428 (deposited line) or a progeny line thereof. Information on the deposit is shown below. Hereafter, the deposited line is also referred to as "*Rudbeckia* variety Takii 22".

Type of deposit: International deposit
  Name of depository institution: National Institute of Technology and Evaluation, International
    Patent Organism Depositary; NITE-IPOD
  Address: 2-5-8-120, Kazusakamatari, Kisarazu-shi, Chiba
    292-0818, Japan
  Accession Number: Accession No. FERM BP-22428
  Identifying designation: Takii 22
  Date of acceptance: Sep. 14, 2021

A plant that is substantially the same as the deposited line may be used as the deposited line, provided that it is cytoplasmic male sterile. The plant that is substantially the same as the deposited line may be, for example, a mutant or a genetically modified plant of the deposited line.

The *Rudbeckia* plant of the present disclosure can be obtained by, for example, selection from test *Rudbeckia* plants based on direct or indirect evaluation of cytoplasmic male sterility.

The direct evaluation of cytoplasmic male sterility can be made based on evaluation of the ability to form the male gametophyte, for example. More specifically, when a test *Rudbeckia* plant does not form stamens, pollen, and/or anthers, preferably when a test *Rudbeckia* plant does not form stamens and/or anthers, the test *Rudbeckia* plant can be evaluated as male sterile. On the other hand, when a test *Rudbeckia* plant forms stamens, pollen, and/or anthers, preferably when a test *Rudbeckia* plant forms stamens and/or anthers, the test *Rudbeckia* plant can be evaluated as not male sterile, i.e., as male fertile.

In the direct evaluation, the type of male sterility, i.e., whether the male sterility is CMS or GMS is further evaluated in the test *Rudbeckia* plant that has been evaluated as male sterile. In this case, the evaluation can be made by performing backcrossing a plurality of times using the test *Rudbeckia* plant and progeny lines thereof as seed parents and a male fertile *Rudbeckia* plant as a pollen parent (backcross parent). The pollen parent may or may not include a restorer of fertility, but preferably does not include a restorer of fertility because it enables more accurate evaluation on whether the male sterility is CMS or GMS. The restorer of fertility may be, for example, a pentatrico-peptide repeat (PPR) gene. When all the individuals of the progeny lines resulting from the backcrossing are male sterile, the test *Rudbeckia* plant can be evaluated as CMS. On the other hand, when the progeny lines resulting from the backcrossing are male sterile and male fertile, the test *Rudbeckia* plant can be evaluated as GMS.

The indirect evaluation of cytoplasmic male sterility can be made based on the presence or absence of the cytoplasmic male sterility gene(s), for example. Specifically, when a test

*Rudbeckia* plant has any of the cytoplasmic male sterility genes, the test *Rudbeckia* plant can be evaluated as cytoplasmic male sterile. On the other hand, when the test *Rudbeckia* plant has none of the cytoplasmic male sterility genes, the test *Rudbeckia* plant can be evaluated as not male sterile, i.e., as male fertile. A method for detecting the cytoplasmic male sterility genes will be described below.

In the indirect evaluation, the type of male sterility, i.e., whether the male sterility is CMS or GMS is further evaluated in the test *Rudbeckia* plant that has been evaluated as male sterile. In this case, the evaluation can be made by detecting the chromosomal location of the cytoplasmic male sterility gene(s) in the test *Rudbeckia* plant. When the cytoplasmic male sterility gene(s) is present in the cytoplasm, mitochondrion, or mitochondrial genome in the test *Rudbeckia* plant, the male sterility can be evaluated as CMS. On the other hand, when the male sterility gene is present in the nucleus or nuclear genome in the test *Rudbeckia* plant, the male sterility can be evaluated as GMS.

The indirect evaluation of cytoplasmic male sterility can be made based on the presence or absence of the cytoplasmic male sterility gene(s) in the cytoplasm, mitochondrion, or mitochondrial genome. In this case, when a test *Rudbeckia* plant has the cytoplasmic male sterility gene(s) in the cytoplasm, mitochondrion, or mitochondrial genome, the test *Rudbeckia* plant can be evaluated as cytoplasmic male sterile. On the other hand, when the test *Rudbeckia* plant does not have the cytoplasmic male sterility gene(s) in the cytoplasm, mitochondrion, or mitochondrial genome, the test *Rudbeckia* plant can be evaluated as not cytoplasmic male sterile, i.e., as genetic male sterility or male fertile. A method for detecting the cytoplasmic male sterility genes will be described below.

In the present disclosure, the male sterile *Rudbeckia* plan can be obtained by selecting the test *Rudbeckia* plant that has been evaluated as male sterile. In the present disclosure, a CMS test *Rudbeckia* plant may be selected as the cytoplasmic male sterile *Rudbeckia* plant.

The *Rudbeckia* plant of the present disclosure may also be produced by introducing the cytoplasmic male sterility gene(s) into a *Rudbeckia* plant of interest. In this case, the *Rudbeckia* plant of the present disclosure may be obtained by producing a transformant according to the present disclosure using a vector according to the present disclosure to be described below. In the production of the transformant, the CMS *Rudbeckia* plant can be produced by introducing the cytoplasmic male sterility gene(s) into the cytoplasm, mitochondrion, or mitochondrial genome. In the introduction of the cytoplasmic male sterility gene(s), for example, the cytoplasmic male sterility gene(s) may be introduced in addition to or instead of the ATP6 gene, or the ATP6 gene may be modified to introduce the cytoplasmic male sterility gene(s).

The *Rudbeckia* plant of the present disclosure may be a progeny line of a *Rudbeckia* plant that exhibits cytoplasmic male sterility. The progeny line may be a plant individual of the progeny line, a part of a plant individual of the progeny line, a seed of the progeny line, a callus of the progeny line, cytoplasm of the progeny line, a mitochondrion of the progeny line, or a mitochondrial genome of the progeny line. The progeny line can also be referred to as, for example, a *Rudbeckia* plant to which the cytoplasmic male sterility gene has been transferred by crossing.

The progeny line may be a plant obtained by crossing the *Rudbeckia* plant of the present disclosure with another *Rudbeckia* plant or with a wild *Rudbeckia* plant. The progeny line may be directly or indirectly obtained, obtainable, or derived from the *Rudbeckia* plant of the present disclosure or a progeny line thereof by cross-pollination, or may be derived from a parental line obtained from the *Rudbeckia* plant of the present disclosure using a conventional breeding method such as cross-pollination. The progeny line may be, for example, a first-generation hybrid F1 (hybrid first-generation line, F1 hybrid) or a backcross progeny. In a process of obtaining the progeny line, the *Rudbeckia* plant of the present disclosure may be used as the female parent and the progeny line can be obtained by cross-pollination.

The crossing may be "cross-pollination" or "self-pollination". Cross-pollination means fertilization by the union of two gametes that are derived from different plants. Self-pollination means transfer of pollen from the anthers to the stigma of the same plant. Self-pollination can also be referred to as self-crossing, for example. The crossing may include backcrossing, which is one of conventional breeding methods.

The backcrossing is one of conventional breeding techniques and is a method in which a breeder introduces a trait into a plant or a variety by repeatedly backcrossing a hybrid progeny line with one of the parental lines. A plant that includes the trait to be introduced may be referred to as a donor plant, for example. A plant into which the trait is to be introduced may be referred to as a recurrent parent, for example. The backcrossing can be performed by crossing a donor plant with a recurrent parent, whereby a first-generation hybrid F1 (hybrid first-generation line, F1 hybrid) can be obtained. Next, the progeny line having the trait is crossed with a recurrent parent. Then, by performing backcrossing and/or selfing over several generations, the trait of the donor plant can be introduced into the recurrent parent.

The *Rudbeckia* plant of the present disclosure may also have a desired trait(s) in addition to the cytoplasmic male sterility.

The *Rudbeckia* plant of the present disclosure does not encompass, for example, plants obtained by essentially biological processes or plants obtained only by essentially biological processes.

Regarding a method for producing a cytoplasmic male sterile *Rudbeckia* plant according to the present disclosure, reference can be made to the following descriptions on a conferring method, a second production method, a screening method, and a third production method.

The *Rudbeckia* plant of the present disclosure exhibits cytoplasmic male sterility. Accordingly, the *Rudbeckia* plant of the present disclosure does not require emasculation of the seed parent when obtaining a hybrid first-generation line and can also provide high-purity seeds. Thus, the *Rudbeckia* plant of the present disclosure can reduce labor in breeding and seed production. Further, by crossing the *Rudbeckia* plant of the present disclosure with a maintainer line having substantially the same traits as the *Rudbeckia* plant of the present disclosure except for the cytoplasmic male sterility, maintenance and propagation of the line can be achieved easily. Moreover, the *Rudbeckia* plant of the present disclosure can prevent deterioration of the appearance traits or contamination of clothing due to pollen, thus allowing for a long-lasting ornamental period as compared with *Rudbeckia* plants having substantially the same traits as the *Rudbeckia* plant of the present disclosure except for the cytoplasmic male sterility.

<First Production Method>

In another aspect, the present disclosure provides a method for producing a *Rudbeckia* plant that exhibits cytoplasmic male sterility. As described above, the cytoplasmic male sterile *Rudbeckia* plant production method of the present disclosure includes the step of: (a) crossing the cytoplasmic male sterile *Rudbeckia* plant of the present disclosure or a progeny line thereof with another *Rudbeckia* plant.

The first production method of the present disclosure is characterized in that the *Rudbeckia* plant of the present disclosure is used in the step (a), and there is no particular limitation on other steps and conditions. The first production method of the present disclosure can produce a *Rudbeckia* plant that exhibits cytoplasmic male sterility.

In the step (a), a plant to be used as the first parent may be the cytoplasmic male sterile *Rudbeckia* plant of the present disclosure or a progeny line thereof. The *Rudbeckia* plant of the present disclosure is cytoplasmic male sterile. Accordingly, in the step (a), the *Rudbeckia* plant of the present disclosure or a progeny line thereof is used as a seed parent (female parent). As described above, the cytoplasmic male sterile *Rudbeckia* plant of the present disclosure can also be obtained by, for example, a conferring method, second production method, screening method, and third production method according to the present disclosure to be described below. Thus, in the first production method of the present disclosure, at least one of the conferring method, second production method, screening method, and third production method of the present disclosure may be performed prior to the step (a), for example. In this case, regarding these methods, reference can be made to the following descriptions on the respective methods.

As a specific example, the first production method of the present disclosure may include the following step (x) or (y):

(x) selecting the *Rudbeckia* plant of the present disclosure or a progeny line thereof from one or more test *Rudbeckia* plants (selection step); or (y) producing the *Rudbeckia* plant of the present disclosure or a progeny line thereof from a *Rudbeckia* plant of interest (production step).

In the step (x), the selection of the cytoplasmic male sterile *Rudbeckia* plant of the present disclosure or a progeny line thereof can be made by, for example, directly or indirectly evaluating the cytoplasmic male sterility of the test *Rudbeckia* plant(s) to select the cytoplasmic male sterile *Rudbeckia* plant of the present disclosure or a progeny line thereof. Regarding the direct evaluation, reference can be made to the above description on the method for evaluating the cytoplasmic male sterility.

When the selection is made based on the indirect evaluation, the selection of the cytoplasmic male sterile *Rudbeckia* plant of the present disclosure or a progeny line thereof can be referred to as selection of a *Rudbeckia* plant having the cytoplasmic male sterility gene. In this case, the step (x) can be performed by, for example, the following steps (x1) and (x2):

(x1) detecting the presence or absence of the cytoplasmic male sterility gene in each of the one or more test *Rudbeckia* plants; and (x2) selecting the test *Rudbeckia* plant as a cytoplasmic male sterile *Rudbeckia* plant when the cytoplasmic male sterility gene is found to be present, i.e., when the cytoplasmic male sterility gene(s) is detected therein.

When the step (x) includes the steps (x1) and (x2), the step (x) can be performed, for example, using the base sequence of the cytoplasmic male sterility gene as a criterion for the selection. In the step (x1), the cytoplasmic male sterility gene may be detected, for example, based on the presence or absence of the base sequence encoding the cytoplasmic male sterility gene. Also, in the step (x1), the cytoplasmic male sterility gene may be detected using a reagent(s) for detecting the cytoplasmic male sterility gene, such as a primer set and/or probe capable of identifying the cytoplasmic male sterility gene.

In the case where the cytoplasmic male sterility gene is detected based on the presence or absence of the base sequence encoding the cytoplasmic male sterility gene, the base sequence of, for example, the mitochondrial genome (mitochondrial DNA) of the test *Rudbeckia* plant is decoded in the step (x1). Next, in the step (x1), the presence or absence of the base sequence encoding the cytoplasmic male sterility gene can be detected by comparing the obtained base sequence with the base sequence of the polynucleotide of (ca) to determine whether these base sequences match each other. The decoding of the base sequence can be performed, for example, using a sample containing the mitochondrial genome (mitochondrial DNA), a reagent for sequencing, and a sequencer. The comparison of the base sequences can be performed, for example, using base sequence analysis software (e.g., the above-described BLAST). In the obtained base sequence, intron regions of the mitochondrial genome (mitochondrial DNA), exon regions of the mitochondrial genome (mitochondrial DNA), or both the intron regions and the exon regions may be used in the comparison of the base sequences. In the above-described manner, in the step (x1), a *Rudbeckia* plant having a base sequence that matches the base sequence of the cytoplasmic male sterility gene can be specified (identified or detected) as a test *Rudbeckia* plant including the cyto-plasmic male sterility gene. Then, in the step (x2), for example, a test *Rudbeckia* plant including the cytoplasmic male sterility gene is selected as the *Rudbeckia* plant of the present disclosure or a progeny line thereof, i.e., as a *Rudbeckia* plant that exhibits cytoplasmic male sterility.

In the case where the cytoplasmic male sterility gene is detected using a reagent(s) for detecting the cytoplasmic male sterility gene, the cytoplasmic male sterility gene is detected, for example, using a primer set or probe capable of identifying the cytoplasmic male sterility gene or using such a primer set and a probe in combination. Specifically, in the case where the primer set is used, in the step (x1), for example, PCR is performed using the primer set and a sample containing the mitochondrial genome (mitochondrial DNA), and the cytoplasmic male sterility gene can be detected based on whether amplified fragments indicating the presence of the cytoplasmic male sterility gene are obtained. In the case where the probe is used, in the step (x1), for example, the probe and a sample containing the mitochondrial genome (mitochondrial DNA) are used, and the cytoplasmic male sterility gene can be detected based on whether a probe-derived signal indicating the presence of the cytoplasmic male sterility gene is obtained. In the case where the primer set and the probe are used, in the step (x1), for example, PCR is performed using the primer set and a sample containing the mitochondrial genome (mitochondrial DNA) to obtain amplified fragments indicating the presence of the cytoplasmic male sterility gene. Subsequently, in the step (x1), the amplified fragments and the probe are used, and the cytoplasmic male sterility gene can be detected based on whether a probe-derived signal indicating the presence of the cytoplasmic male sterility gene is obtained. Then, in the step (x2), for example, a test *Rudbeckia* plant including the cytoplasmic male sterility gene is selected as the *Rudbeckia* plant of the present disclosure or a progeny line thereof, i.e., as a *Rudbeckia* plant that exhibits cyto-plasmic male sterility.

In the step (x1), at least one of ORF3, ORF1, ORF2, ORF6, ORF7, and RPS7 may be detected as the cytoplasmic male sterility gene, and two or more of them or all of them may be detected. In the step (x1), ORF3 may be detected as the cytoplasmic male sterility gene, or ORF3, ORF1, ORF2, ORF6, ORF7, and RPS7 may be detected as the cytoplasmic male sterility genes. In the case where a plurality of cyto-plasmic male sterility genes are detected in the step (x1), a test *Rudbeckia* plant in which any one or more, two or more, or all of the cytoplasmic male sterility genes are detected is selected in the step (x2) as the *Rudbeckia* plant of the present disclosure or a progeny line thereof, i.e., a *Rudbeckia* plant that exhibits cytoplasmic male sterility.

ORF3 is presumed to be a chimeric gene composed of the ATP6 gene and another gene. Thus, in the case where ORF3 is to be detected in the step (x1), the above-described primer set and/or probe are designed so as to be capable of, for example, identifying the ORF3 and the ATP6 gene, for example. The primer set may be, for example, a combination of a primer set capable of identifying the ORF3 and a primer set capable of identifying the ATP6 gene. Regarding the base sequence of an ORF (open reading frame) of the ATP6 gene of the *Rudbeckia* plant, reference may be made to the following base sequence (SEQ ID NO: 13, including a stop codon (TAA)), for example. The ATP6 gene may be a functional equivalent thereof, provided that it conserves the functionality of the ATP6 gene. In the base sequence of SEQ ID NO: 13 shown below, the base sequence from position 763 to position 1512 is identical to the base sequence from position 340 to position 1089 in the base sequence of SEQ ID NO: 1 shown above. Thus, in the present disclosure, for example, primers capable of amplifying and/or probes capable of detecting different base sequences in the base sequences of SEQ ID NO: 1 and SEQ ID NO: 13 are designed. Then, in the step (x1), whether the test *Rudbeckia* plant has the ORF3 and/or the ATP6 gene can be detected by using the thus-designed primers and/or probes. Known design methods can be used to design the above-described primer sets and probes, for example. One illustrative example of the primer set capable of identifying the ORF3 and the primer set capable of identifying the ATP6 gene is the combination of a primer set for ORF3 (cytoplasmic male sterility gene) shown below and a primer set for ATP6 shown below. In the above-described manner, in the step (x1), a test *Rudbeckia* plant in which the ORF3 has been identified using the primer set and/or the probe can be specified (identified or detected) as a test *Rudbeckia* plant including the cytoplasmic male sterility gene. Then, in the step (x2), for example, the test *Rudbeckia* plant including the ORF3 (cytoplasmic male sterility gene) is selected as the *Rud-beckia* plant of the present disclosure or a progeny line thereof, i.e., as a *Rudbeckia* plant that exhibits cytoplasmic male sterility.

Base Sequence of ORF of ATP6 gene (SEQ ID NO: 13)

5'-

ATGCAAGTAGAATCTTCGAACTTCAATCAAAATGGGGCTGTCATCCATC

TAAGGAGAAAAGGAGGATGGAAGGGGACGTGTAAGCATGAAGGCGGGTC

AATCTTGGTAGTGAATAGGTCAGCAGTTGGAGAGGAGAATCTTTCTATA

GATAGAAGCAAGCGGGTACGAGATCGAAAAGATCTTTTTCATACCCAGC

CCCAAATTCCCATTTCTTTCTTGGTCGGACCAAGCAAACCAACTATCTA

TTTCCGACAAACAAGCCTTTCCTCTTTTCTTTCAAATTTTGAGAGCAAG

AAGCAGGCGGAACTACAATCAATTTTGACTATGACTATGACTATGAGGG

-continued

```
ACTTTATTCAGTCTTATCGTCAGCATATGCTGACGATAACGGAGAGTGG

GTATCCTAGGGTGACTTCTGCATTTGGATATTCTGTCGAAGAGCTAACA

AAGTTTGGCATCGAAGATTTTACTATTTACATTCCAGGGGAGATTGATG

ACCCCGCAACGGTTACAAGCCTTACAAAGTTAAATAAGCTTTTCATTTT

TATGAAATATGACTTCATCGGTACAGTCAGGCCTCGAGATATTCAAGTA

CTCCAAAAGGAATTTAAAAAAACACCCCCAGAATCACTTTATAGGAAGC

TTGAATCTACGTTTCAAAATGAGTTAACAAGTTTAGAGAATTTTTTAAA

GCCTTTCAAGGCAGATTTCTTGAGTCAAGACTATTTGAATTATTGTGAT

GGGAGACATCGCTCATTTAAAAGCCCACTTGAGCAATTTGAAATTCTCC

CATTGATTCCTATGAAGATAGGAGACTTGTATTTCTCATTCACAAATTC

ATCTTTGTTTATGCTGCTAACTCTCAGTTTGGTCCTACTTCTGATTCAT

TTTGTTACTAAAAAAGGAGGAGGAAACTTAGTACCAAATGCTTGGCAAT

CCTTGGTAGAGCTTATTTATGATTTCGTGCTGAACCTGGTAAACGAACA

AATAGGGGGTCTTTCCGGAAATGTTAAACAAAAGTTTTTCCCTTGCATC

CTGGTCACTTTTACTTTTTTGTTATTTTGTAATCTTCAGGGTATGATAC

CTTATAGCTTCACAGTTACAAGTCATTTTCTCATTACTTTAGGTCTCTC

ATTTTCGATTTTTATTGGCATTACTATAGTGGGATTTCAAAGAAACGGG

CTTCATTTTTTAAGCTTCTTATTACCCGCAGGAGTCCCACTGCCATTAG

CACCTTTTTTAGTACTCCTTGAGCTAATTTCTTATTGTTTTCGCGCATT

AAGCTTAGGAATACGTTTATTTGCTAAATATGATGGCCGGTCATAGTTTA

GTAAAGATTTTAAGTGGGTTCGCTTGGACTATGCTATGTATGAATGATC

TTTTGTATTTTATAGGGGATCTTGGTCCTTTATTTATAGTTCTTGCATT

AACCGGTCTGGAATTAGGTGTAGCTATATTACAAGCTTATGTTTTTACG

ATCTTAATCTGTATTTACTTGAATGATGCTATAAATCTCCATTAA-3'
```

```
          Primer set for ORF3
          Forward primer
                                    (SEQ ID NO: 14)
          5'-ACGTAACACGTATCTATGGTGCAT-3'

Reverse primer
                                    (SEQ ID NO: 15)
          5'-GAGAGTTAGCAGCATAAACAAAGA-3'

Primer set for ATP6
          Forward primer
                                    (SEQ ID NO: 16)
          5'-GAGGGACTTTATTCAGTCTTATCG-3'

Reverse primer
                                    (SEQ ID NO: 17)
          5'-ATCTTCATAGGAATCAATGGGAGA-3'
```

In the case where ORF1, ORF2, ORF6, ORF7, and/or RPS7 are to be detected, primer sets and/or probes for the respective genes can be designed based on the base sequences of the cytoplasmic male sterility genes shown above using methods or software (e.g., Primer-BLAST) commonly used in the technical field to which the present application pertains.

In the step (x1), the chromosomal location of the cytoplasmic male sterility gene may be detected. The chromosomal location may be, for example, in a nucleus, a nuclear genome, cytoplasm, a mitochondrion, or a mitochondrial genome, and preferably in cytoplasm, a mitochondrion, or a mitochondrial genome. In this case, in the step (x2), when a test *Rudbeckia* plant includes the cytoplasmic male sterility gene and the cytoplasmic male sterility gene is present in cytoplasm, a mitochondrion, or a mitochondrial genome, the test *Rudbeckia* plant can be selected as a *Rudbeckia* plant that exhibits cytoplasmic male sterility.

Examples of a sample to be subjected to the detection of the cytoplasmic male sterility gene in the step (x1) include samples containing nuclei, nuclear genomes, cytoplasm, mitochondria, and/or mitochondrial genomes. Each sample can be prepared from the test *Rudbeckia* plant or a part thereof by a method commonly used in the technical field to which the present application pertains. The sample is preferably a sample containing cytoplasm, mitochondria, and/or mitochondrial genomes.

The step (y) can also be referred to as, for example, the step of introducing the cytoplasmic male sterility gene into a *Rudbeckia* plant of interest (introducing step). Regarding the introducing step, reference can be made to the following descriptions on an introducing step in connection with the cytoplasmic male sterility gene, expression vector, transformant, and conferring method according to the present disclosure.

Next, in the step (a), a *Rudbeckia* plant used as the other parent is not limited to particular *Rudbeckia* plants, and need only be a *Rudbeckia* plant that is male fertile, for example.

In the step (a), a method for crossing the cytoplasmic male sterile *Rudbeckia* plant with the other *Rudbeckia* plant is not limited to particular methods, and known methods can be employed.

In a step (b), the *Rudbeckia* plant(s) from which a cytoplasmic male sterile *Rudbeckia* plant is to be selected may be a *Rudbeckia* plant(s) obtained in the step (a) or a progeny line(s) obtained therefrom, for example. Specifically, the *Rudbeckia* plant(s) from which a cytoplasmic male sterile *Rudbeckia* plant is to be selected may be, for example, F1 *Rudbeckia* plant(s) obtained by the crossing in the step (a) or a progeny line(s) thereof. The progeny line may be a backcross progeny of the F1 *Rudbeckia* plant obtained by the crossing in the step (a), or may be a *Rudbeckia* plant obtained by crossing the F1 *Rudbeckia* plant with another *Rudbeckia* plant, for example.

In the step (b), the cytoplasmic male sterile *Rudbeckia* plant can be selected by, for example, directly or indirectly evaluating the cytoplasmic male sterility. Regarding the direct evaluation, reference can be made to the above description on the method for evaluating the cytoplasmic male sterility.

In the step (b), the selection of a cytoplasmic male sterile *Rudbeckia* plant can be made by, for example, directly or indirectly evaluating the cytoplasmic male sterility of the obtained F1 *Rudbeckia* plant(s) or a progeny line(s) thereof to select a cytoplasmic male sterile *Rudbeckia* plant. When the selection is made based on the indirect evaluation, the selection of the cytoplasmic male sterile *Rudbeckia* plant can be referred to as the selection of a *Rudbeckia* plant having the cytoplasmic male sterility gene(s). In this case, the step (b) can be performed by, for example, the following steps (b1) and (b2):

(b1) detecting the presence or absence of at least one cytoplasmic male sterility gene in each of the obtained F1 *Rudbeckia* plant(s) or a progeny line(s) thereof; and (b2) selecting the obtained F1 *Rudbeckia* plant or the progeny line thereof as a cytoplasmic male sterile *Rudbeckia* plant when the cytoplasmic male sterility gene is found to be present, i.e., when the cytoplasmic male sterility gene is detected therein.

The selection of the cytoplasmic male sterile *Rudbeckia* plant in the step (b) is, for example, the same as the selection in the step (x) described above, and the step (b1) can be performed in the same manner as the step (x1) and the step (b2) can performed in the same manner as the step (x2).

Examples of a sample to be subjected to the detection of the cytoplasmic male sterility gene in the step (b1) include samples containing nuclei, nuclear genomes, cytoplasm, mitochondria, and/or mitochondrial genomes. Each sample can be prepared from the test *Rudbeckia* plant or a part thereof by a method commonly used in the technical field to which the present application pertains. The sample is preferably a sample containing cytoplasm, mitochondria, and/or mitochondrial genomes.

The first production method of present disclosure preferably further includes growing the cytoplasmic male sterile *Rudbeckia* plant selected in the step (b). Conditions and a method for growing the *Rudbeckia* plant can be determined as appropriate according to the growth stage and the variety of the *Rudbeckia* plant, for example. In the above-described growing, the *Rudbeckia* plant may be grown to any growth stage, for example.

As described above, in the step (b), the *Rudbeckia* plant or progeny line thereof that has been found to be cytoplasmic male sterile can be selected as a cytoplasmic male sterile *Rudbeckia* plant.

The first production method of the present disclosure may further include the step of collecting seeds from the progeny line obtained by the crossing.

<Cytoplasmic Male Sterility Gene>

In still another aspect, the present disclosure provides a gene capable of conferring cytoplasmic male sterility. The cytoplasmic male sterility gene of the present disclosure includes at least one polynucleotide selected from the group consisting of polynucleotides of (ca) to (ce) and (cf) below:

(ca) a polynucleotide of any of (ca1) to (ca7) below:
  (ca1) a polynucleotide that consists of a base sequence of SEQ ID NO: 1;
  (ca2) a polynucleotide that consists of the base sequence of (ca1) with deletion, substitution, insertion, and/or addition of one or several bases and causes expression of cytoplasmic male sterility;
  (ca3) a polynucleotide that consists of a base sequence having at least 80% sequence identity to the base sequence of (ca1) and causes expression of cytoplasmic male sterility;
  (ca4) a polynucleotide that consists of a base sequence complementary to a polynucleotide hybridizing to the polynucleotide consisting of the base sequence of (ca1) under stringent conditions and causes expression of cytoplasmic male sterility;
  (ca5) a polynucleotide encoding a polypeptide that consists of an amino acid sequence of SEQ ID NO: 2;
  (ca6) a polynucleotide that consists of the amino acid sequence of SEQ ID NO: 2 with deletion, substitution, insertion, and/or addition of one or several amino acids and causes expression of cytoplasmic male sterility; and
  (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:
  (cb1) a polynucleotide that consists of a base sequence of SEQ ID NO: 3;
  (cb2) a polynucleotide that consists of the base sequence of (cb1) with deletion, substitution, insertion, and/or addition of one or several bases and causes expression of cytoplasmic male sterility;
  (cb3) a polynucleotide that consists of a base sequence having at least 80% sequence identity to the base sequence of (cb1) and causes expression of cytoplasmic male sterility;
  (cb4) a polynucleotide that consists of a base sequence complementary to a polynucleotide hybridizing to the polynucleotide consisting of the base sequence of (cb1) under stringent conditions and causes expression of cytoplasmic male sterility;
  (cb5) a polynucleotide encoding a polypeptide that consists of an amino acid sequence of SEQ ID NO: 4;
  (cb6) a polynucleotide that consists of the amino acid sequence of SEQ ID NO: 4 with deletion, substitution, insertion, and/or addition of one or several amino acids and causes expression of cytoplasmic male sterility; and
  (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:
  (cc1) a polynucleotide that consists of a base sequence of SEQ ID NO: 5;
  (cc2) a polynucleotide that consists of the base sequence of (cc1) with deletion, substitution, insertion, and/or addition of one or several bases and causes expression of cytoplasmic male sterility;
  (cc3) a polynucleotide that consists of a base sequence having at least 80% sequence identity to the base sequence of (cc1) and causes expression of cytoplasmic male sterility;
  (cc4) a polynucleotide that consists of a base sequence complementary to a polynucleotide hybridizing to the polynucleotide consisting of the base sequence of (cc1) under stringent conditions and causes expression of cytoplasmic male sterility;
  (cc5) a polynucleotide encoding a polypeptide that consists of an amino acid sequence of SEQ ID NO: 6;
  (cc6) a polynucleotide that consists of the amino acid sequence of SEQ ID NO: 6 with deletion, substitution, insertion, and/or addition of one or several amino acids and causes expression of cytoplasmic male sterility; and
  (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:
  (cd1) a polynucleotide that consists of a base sequence of SEQ ID NO: 7;
  (cd2) a polynucleotide that consists of the base sequence of (cd1) with deletion, substitution, insertion, and/or addition of one or several bases and causes expression of cytoplasmic male sterility;
  (cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under stringent conditions and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under stringent conditions and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under stringent conditions and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

Regarding the polynucleotides of (ca) to (cf), reference can be made to the above descriptions on them in connection with the *Rudbeckia* plant of the present disclosure.

The cytoplasmic male sterility gene of the present disclosure may include any one or more, two or more, or all of the polynucleotides of (ca) to (cf). Regarding the combination of the polynucleotides in the case where two or more of the polynucleotides are included as the cytoplasmic male sterility genes of the present disclosure, reference can be made to the above description on the combination of two or more cytoplasmic male sterility genes in connection with the *Rudbeckia* plant of the present disclosure.

The cytoplasmic male sterility gene of the present disclosure can be suitably used for synthesis (production or breeding) of the cytoplasmic male sterile *Rudbeckia* plant of the present disclosure by a genetic engineering procedure. When the cytoplasmic male sterility gene of the present disclosure is composed of DNA, the cytoplasmic male sterility gene of the present disclosure can also be referred to as a recombinant DNA, for example.

Each of the above-described polynucleotides can be synthesized by, for example, a genetic engineering procedure or an organic synthesis procedure, and can also be referred to as synthetic DNA such as cDNA or as synthetic RNA.

<Cytoplasmic Male Sterility Protein>

In still another aspect, the present disclosure provides a protein that is presumed to induce cytoplasmic male sterility. The cytoplasmic male sterility protein of the present disclosure includes at least one polypeptide selected from the group consisting of polypeptides (CA) to (CE) and (CF) below:

(CA) a polypeptide of any of (CA1) to (CA3) below:

(CA1) a polypeptide that consists of an amino acid sequence of SEQ ID NO: 2;

(CA2) a polypeptide that consists of the amino acid sequence of SEQ ID NO: 2 with deletion, substitution, insertion, and/or addition of one or several amino acids and causes expression of cytoplasmic male sterility; and (CA3) a polypeptide that consists of an amino acid sequence having at least 80% sequence identity to the amino acid sequence of SEQ ID NO: 2 and causes expression of cytoplasmic male sterility;

(CB) a polypeptide of any of (CB1) to (CB3) below:

(CB1) a polypeptide that consists of an amino acid sequence of SEQ ID NO: 4;

(CB2) a polypeptide that consists of the amino acid sequence of SEQ ID NO: 4 with deletion, substitution, insertion, and/or addition of one or several amino acids and causes expression of cytoplasmic male sterility; and (CB3) a polypeptide that consists of an amino acid sequence having at least 80% sequence identity to the amino acid sequence of SEQ ID NO: 4 and causes expression of cytoplasmic male sterility;

(CC) a polypeptide of any of (CC1) to (CC3) below:

(CC1) a polypeptide that consists of an amino acid sequence of SEQ ID NO: 6;

(CC2) a polypeptide that consists of the amino acid sequence of SEQ ID NO: 6 with deletion, substitution, insertion, and/or addition of one or several amino acids and causes expression of cytoplasmic male sterility; and (CC3) a polypeptide that consists of an amino acid sequence having at least 80% sequence identity to the amino acid sequence of SEQ ID NO: 6 and causes expression of cytoplasmic male sterility;

(CD) a polypeptide of any of (CD1) to (CD3) below:

(CD1) a polypeptide that consists of an amino acid sequence of SEQ ID NO: 8;

(CD2) a polypeptide that consists of the amino acid sequence of SEQ ID NO: 8 with deletion, substitution, insertion, and/or addition of one or several amino acids and causes expression of cytoplasmic male sterility; and (CD3) a polypeptide that consists of an amino acid sequence having at least 80% sequence identity to the amino acid sequence of SEQ ID NO: 8 and causes expression of cytoplasmic male sterility;

(CE) a polypeptide of any of (CE1) to (CE3) below:

(CE1) a polypeptide that consists of an amino acid sequence of SEQ ID NO: 10;

(CE2) a polypeptide that consists of the amino acid sequence of SEQ ID NO: 10 with deletion, substitution, insertion, and/or addition of one or several amino acids and causes expression of cytoplasmic male sterility; and (CE3) a polypeptide that consists of an amino acid sequence having at least 80% sequence identity to the amino acid sequence of SEQ ID NO: 10 and causes expression of cytoplasmic male sterility; and (CF) a polypeptide of any of (CF1) to (CF3) below:

(CF1) a polypeptide that consists of an amino acid sequence of SEQ ID NO: 12;

(CF2) a polypeptide that consists of the amino acid sequence of SEQ ID NO: 12 with deletion, substitution, insertion, and/or addition of one or several amino acids and causes expression of cytoplasmic male sterility; and (CF3) a polypeptide that consists of an amino acid sequence having at least 80% sequence identity to the amino acid sequence of SEQ ID NO: 12 and causes expression of cytoplasmic male sterility.

The polypeptide of (CA) is a protein presumed to cause expression of cytoplasmic male sterility and is a polypeptide encoded by the base sequence of SEQ ID NO: 1. The amino acid sequence of SEQ ID NO: 2 can be obtained from a seed of a *Rudbeckia* plant deposited under Accession No. FERM BP-22428 as described above, for example.

In (CA2), "one or several" regarding the amino acid sequence need only be, for example, in a range in which the polypeptide of (CA2) causes expression of cytoplasmic male sterility. The number of "one or several" amino acids in (CA2) is, for example, 1 to 44, 1 to 33, 1 to 22, 1 to 11, 1 to 8, 1 to 6, 1 to 4, 1 to 3, 1 or 2, or 1 in the amino acid sequence of SEQ ID NO: 2.

In (CA3), the "sequence identity" regarding the amino acid sequence need only be, for example, in a range in which the polypeptide of (CA3) causes expression of cytoplasmic male sterility. The "sequence identity" in (CA3) is, for example, at least 80%, at least 85%, at least 90%, at least 95%, at least 96%, at least 97%, at least 98%, or at least 99% with respect to the amino acid sequence of SEQ ID NO: 2.

The polypeptide of (CB1) is a protein presumed to cause expression of cytoplasmic male sterility and is a polypeptide encoded by the base sequence of SEQ ID NO: 3. The amino acid sequence of SEQ ID NO: 4 can be obtained from a seed of a *Rudbeckia* plant deposited under Accession No. FERM BP-22428 as described above, for example.

In (CB2), "one or several" regarding the amino acid sequence need only be, for example, in a range in which the polypeptide of (CB2) causes expression of cytoplasmic male sterility. The number of "one or several" amino acids in (CB2) is, for example, 1 to 187, 1 to 140, 1 to 93, 1 to 46, 1 to 35, 1 to 28, 1 to 18, 1 to 9, 1 to 8, 1 to 6, 1 to 4, 1 to 3, 1 or 2, or 1 in the amino acid sequence of SEQ ID NO: 4.

In (CB3), the "sequence identity" regarding the amino acid sequence need only be, for example, in a range in which the polypeptide of (CB3) causes expression of cytoplasmic male sterility. The "sequence identity" in (CB3) is, for example, at least 80%, at least 85%, at least 90%, at least 95%, at least 96%, at least 97%, at least 98%, or at least 99% with respect to the amino acid sequence of SEQ ID NO: 4.

The polypeptide of (CC1) is a protein presumed to cause expression of cytoplasmic male sterility and is a polypeptide encoded by the base sequence of SEQ ID NO: 5. The amino acid sequence of SEQ ID NO: 6 can be obtained from a seed of a *Rudbeckia* plant deposited under Accession No. FERM BP-22428 as described above, for example.

In (CC2), "one or several" regarding the amino acid sequence need only be, for example, in a range in which the polypeptide of (CC2) causes expression of cytoplasmic male sterility. The number of "one or several" amino acids in (CC2) is, for example, 1 to 86, 1 to 63, 1 to 42, 1 to 21, 1 to 16, 1 to 12, 1 to 8, 1 to 6, 1 to 4, 1 to 3, 1 or 2, or 1 in the amino acid sequence of SEQ ID NO: 6.

In (CC3), the "sequence identity" regarding the amino acid sequence need only be, for example, in a range in which the polypeptide of (CC3) causes expression of cytoplasmic male sterility. The "sequence identity" in (CC3) is, for example, at least 80%, at least 85%, at least 90%, at least 95%, at least 96%, at least 97%, at least 98%, or at least 99% with respect to the amino acid sequence of SEQ ID NO: 6.

The polypeptide of (CD1) is a protein presumed to cause expression of cytoplasmic male sterility and is a polypeptide encoded by the base sequence of SEQ ID NO: 7. The amino acid sequence of SEQ ID NO: 8 can be obtained from a seed of a *Rudbeckia* plant deposited under Accession No. FERM BP-22428 as described above, for example.

In (CD2), "one or several" regarding the amino acid sequence need only be, for example, in a range in which the polypeptide of (CD2) causes expression of cytoplasmic male sterility. The number of "one or several" amino acids in (CD2) is, for example, 1 to 194, 1 to 145, 1 to 97, 1 to 48, 1 to 38, 1 to 29, 1 to 18, 1 to 16, 1 to 12, 1 to 9, 1 to 8, 1 to 6, 1 to 4, 1 to 3, 1 or 2, or 1 in the amino acid sequence of SEQ ID NO: 8.

In (CD3), the "sequence identity" regarding the amino acid sequence need only be, for example, in a range in which the polypeptide of (CD3) causes expression of cytoplasmic male sterility. The "sequence identity" in (CD3) is, for example, at least 80%, at least 85%, at least 90%, at least 95%, at least 96%, at least 97%, at least 98%, or at least 99% with respect to the amino acid sequence of SEQ ID NO: 8.

The polypeptide of (CE1) is a protein presumed to cause expression of cytoplasmic male sterility and is a polypeptide encoded by the base sequence of SEQ ID NO: 9. The amino acid sequence of SEQ ID NO: 10 can be obtained from a seed of a *Rudbeckia* plant deposited under Accession No. FERM BP-22428 as described above, for example.

In (CE2), "one or several" regarding the amino acid sequence need only be, for example, in a range in which the polypeptide of (CE2) causes expression of cytoplasmic male sterility. The number of "one or several" amino acids in (CE2) is, for example, 1 to 76, 1 to 57, 1 to 38, 1 to 19, 1 to 15, 1 to 12, 1 to 9, 1 to 8, 1 to 6, 1 to 4, 1 to 3, 1 or 2, or 1 in the amino acid sequence of SEQ ID NO: 10.

In (CE3), the "sequence identity" regarding the amino acid sequence need only be, for example, in a range in which the polypeptide of (CE3) causes expression of cytoplasmic male sterility. The "sequence identity" in (CE3) is, for example, at least 80%, at least 85%, at least 90%, at least 95%, at least 96%, at least 97%, at least 98%, or at least 99% with respect to the amino acid sequence of SEQ ID NO: 10.

The polypeptide of (CF1) is a protein presumed to cause expression of cytoplasmic male sterility and is a polypeptide encoded by the base sequence of SEQ ID NO: 11. The amino acid sequence of SEQ ID NO: 12 can be obtained from a seed of a *Rudbeckia* plant deposited under Accession No. FERM BP-22428 as described above, for example.

In (CF2), "one or several" regarding the amino acid sequence need only be, for example, in a range in which the polypeptide of (CF2) causes expression of cytoplasmic male sterility. The number of "one or several" amino acids in (CF2) is, for example, 1 to 31, 1 to 23, 1 to 15, 1 to 7, 1 to 6, 1 to 4, 1 to 3, 1 or 2, or 1 in the amino acid sequence of SEQ ID NO: 12.

In (CF3), the "sequence identity" regarding the amino acid sequence need only be, for example, in a range in which the polypeptide of (CF3) causes expression of cytoplasmic male sterility. The "sequence identity" in (CF3) is, for example, at least 80%, at least 85%, at least 90%, at least 95%, at least 96%, at least 97%, at least 98%, or at least 99% with respect to the amino acid sequence of SEQ ID NO: 12.

The cytoplasmic male sterility protein of the present disclosure may include any one or more, two or more, or all of the polypeptides of (CA) to (CF). Regarding the combination of the polypeptides in the case where two or more of the polypeptides are included as the cytoplasmic male sterility proteins of the present disclosure, reference can be made to the above description on the combination of two or more cytoplasmic male sterility genes in connection with the *Rudbeckia* plant of the present disclosure, in which (ca), (cb), (cc), (cd), (ce), (cf), and the term "polynucleotide" should be considered to be replaced with (CA), (CB), (CC), (CD), (CE), (CF), and the term "polypeptide", respectively.

The male sterility protein of the present disclosure can induce cytoplasmic male sterility by, for example, being introduced into a *Rudbeckia* plant. The cytoplasmic male sterility protein of the present disclosure can also be referred to as a recombinant protein, for example.

The cytoplasmic male sterility protein can be synthesized (produced) using a transformant to be described below, for example.

<Expression Vector>

In still another aspect, the present disclosure provides an expression vector capable of expressing a cytoplasmic male sterility protein. The expression vector (vector) of the present disclosure includes the cytoplasmic male sterility gene of the present disclosure. The expression vector of the present disclosure can be used suitably for synthesis (production) of the cytoplasmic male sterile *Rudbeckia* plant of the present disclosure by a genetic engineering procedure.

The expression vector need only include a cytoplasmic male sterility gene such that the expression vector can express the cytoplasmic male sterility protein encoded by the cytoplasmic male sterility gene, and there is no particular limitation on other structures and conditions. It can also be said that the cytoplasmic male sterility gene of the present disclosure is functionally linked in the expression vector of the present disclosure.

The expression vector may include any one or more, two or more, or all of the polynucleotides of (ca) to (cf). Regarding the combination of the polynucleotides in the case where the expression vector includes two or more of the polynucleotides, reference can be made to the above description on the combination of two or more cytoplasmic male sterility genes in connection with the *Rudbeckia* plant of the present disclosure.

The expression vector can be produced by, for example, inserting a polynucleotide encoding a cytoplasmic male sterility protein, i.e., inserting a cytoplasmic male sterility gene, into a vector forming a main structure (also referred to as "basic vector" hereinafter). The vector is not limited to particular types of vectors, and the type of the vector can be determined as appropriate according to the type of a host or cell, for example.

Examples of the host include: non-human hosts such as microorganisms, animal cells, plant cells, insect cells, and cultured cells thereof; isolated human cells and cultured cells thereof; and mammalian cells.

Examples of the vector (basic vector) include viral vectors and non-viral vectors. In the case where the vector is introduced into a host by a heat shock method to transform the host, the vector may be a binary vector, for example. The vector may be a pETDuet-1 vector, a pQE-80L vector, or a pUCP26 Km vector, for example. For transformation of bacteria such as *Escherichia coli*, the vector may be a pETDuet-1 vector (Novagen), pQE-80L (QIAGEN), pBR322, pB325, pAT153, or pUC8, for example. For transformation of yeasts, the vector may be pYepSecl, pMFa, or pYES2, for example. For transformation of insect cells, the vector may be pAc or pVL, for example. For transformation of mammalian cells, the vector may be pCDM8 or pMT2PC, for example. For transformation of plant cells, the vector may be pBI121 or pBI101, for example.

The expression vector preferably includes, for example, regulatory sequences that regulate the expression of the polynucleotide (cytoplasmic male sterility gene) encoding the cytoplasmic male sterility protein and the expression of the cytoplasmic male sterility protein encoded by the cytoplasmic male sterility gene. The regulatory sequences may be, for example, a promoter, a terminator, an enhancer, a polyadenylation signal sequence, and a replication origin sequence (ori). In the expression vector of the present disclosure, there is no particular limitation on the arrangement of the regulatory sequences. In the expression vector of the present disclosure, the regulatory sequences need only be arranged in such a manner that, for example, they can functionally regulate the expression of the polynucleotide of the cytoplasmic male sterility protein and the expression of the male sterility protein encoded by this polynucleotide, and they can be arranged based on known methods. As the regulatory sequence, a sequence originally included in the basic vector may be used, for example. Alternatively, a regulatory sequence may further be inserted into the basic vector, or a regulatory sequence originally included in the basic vector may be replaced with another regulatory sequence.

The expression vector may further include, for example, a coding sequence encoding a selection marker. The selection marker may be, for example, a drug-resistant marker, a fluorescent protein marker, an enzyme marker, or a cell surface receptor marker.

DNA, the regulatory sequences, and/or the coding sequence encoding the selection marker may be inserted into the expression vector, for example, by a method in which a restriction enzyme and ligase are used or using of a commercially available kit or the like.

<Transformant>

In still another aspect, the present disclosure provides a transformant capable of expressing a cytoplasmic male sterility protein. The transformant of the present disclosure includes a nucleic acid of the present disclosure or the expression vector of the present disclosure. The transformant of the present disclosure can also be referred to as a transformant including an exogenous cytoplasmic male sterility gene. The transformant of the present disclosure can be suitably used for synthesis (production) of a *Rudbeckia* plant that exhibits cytoplasmic male sterility or a cytoplasmic male sterility protein.

In the transformant of the present disclosure, the cytoplasmic male sterility gene of the present disclosure is present in the form of an exogenous molecule. Accordingly, the transformant of the present disclosure can be produced by, for example, introducing the cytoplasmic male sterility gene into the host.

The method for introducing the cytoplasmic male sterility gene is not limited to particular methods, and known methods can be employed. The cytoplasmic male sterility gene may be introduced using the expression vector of the present disclosure, for example. The method for introducing the cytoplasmic male sterility gene can be set as appropriate according to the type of the host, for example. The introduction method may be, for example, introduction using a gene gun such as a particle gun, a calcium phosphate method, a polyethylene glycol method, a lipofection method using a liposome, an electroporation method, a nucleic acid introduction using ultrasonic waves, a DEAE-dextran method, direct injection using a minute glass tube or the like, a hydrodynamic method, a cationic liposome method, a method using an introduction aid, or an *agrobacterium*-mediated method. Examples of the liposome include Lipofectamine and cationic liposomes, and examples of the introduction aid include atelocollagen, nano-particles, and polymers. When the host is a plant cell, the introduction method is preferably an *agrobacterium*-mediated method. When the host is a plant cell, a target to which the cytoplasmic male sterility gene is introduced may be a plant cell, a callus, plant tissue, or a plant individual, for example.

The method for introducing the cytoplasmic male sterility gene can be performed by, for example: homologous recombination; or the combination of a donor gene (cytoplasmic male sterility gene) and a genome-editing technique using ZFN, TALEN, CRISPR-CAS9, CRISPR-CPF1, or the like. Introduction of the cytoplasmic male sterility gene using the genome-editing technique can be achieved by introducing, for example: a protein and a nucleic acid used in the genome-editing technique or vectors encoding them; and a polynucleotide encoding the donor gene. The protein may be, for example, a clustered regularly interspaced short palindromic repeat (CRISPR) enzyme, and specific examples thereof include Cas1, Cas1B, Cas2, Cas3, Cas4, Cas5, Cas6, Cas7 Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. The nucleic acid may be, for example: crRNA and tracrRNA; or a single-stranded nucleic acid composed of crRNA and tracrRNA linked via a linker. In this case, the nucleic acid is designed such that, for example, a base sequence that is present in crRNA and anneals to a target sequence is complementary to the base sequence encoding each gene. One type of nucleic acid may be used alone, or two or more types of nucleic acids may be used in combination.

The method for introducing the polynucleotide is not limited to particular methods, and methods that are used in, for example, RNA interference, antisense RNA, and genome-editing techniques can be used to introduce the polynucleotide. An expression cassette such as an expression vector including the polynucleotide can be introduced into a *Rudbeckia* plant of interest by, for example, a polyethylene glycol method, an electroporation method, an *agrobacterium*-mediated method, or a particle gun method. The *Rudbeckia* plant of interest may be any of a plant cell, a callus, plant tissue, or a plant individual, for example.

In the above-described introducing step, the location to which the cytoplasmic male sterility gene is introduced may be in, for example, cytoplasm, a mitochondrion, or a mitochondrial genome.

<Conferring Method>

In still another aspect, the present disclosure provides a method capable of conferring cytoplasmic male sterility to a *Rudbeckia* plant. As described above, the method for conferring cytoplasmic male sterility to a *Rudbeckia* plant according to the present disclosure includes the step of: introducing, as a cytoplasmic male sterility gene, at least one polynucleotide selected from the group consisting of polynucleotides of (ca) to (ce) and (cf) below into a *Rudbeckia* plant of interest (introducing step):

(ca) a polynucleotide of any of (ca1) to (ca7) below:
    (ca1) a polynucleotide that consists of a base sequence of SEQ ID NO: 1;
    (ca2) a polynucleotide that consists of the base sequence of (ca1) with deletion, substitution, insertion, and/or addition of one or several bases and causes expression of cytoplasmic male sterility;
    (ca3) a polynucleotide that consists of a base sequence having at least 80% sequence identity to the base sequence of (ca1) and causes expression of cytoplasmic male sterility;
    (ca4) a polynucleotide that consists of a base sequence complementary to a polynucleotide hybridizing to the polynucleotide consisting of the base sequence of (ca1) under stringent conditions and causes expression of cytoplasmic male sterility;
    (ca5) a polynucleotide encoding a polypeptide that consists of an amino acid sequence of SEQ ID NO: 2;
    (ca6) a polynucleotide that consists of the amino acid sequence of SEQ ID NO: 2 with deletion, substitution, insertion, and/or addition of one or several amino acids and causes expression of cytoplasmic male sterility; and
    (ca7) a polynucleotide that consists of an amino acid sequence having at least 80% sequence identity to the amino acid sequence of SEQ ID NO: 2 and causes expression of cytoplasmic male sterility;
(cb) a polynucleotide of any of (cb1) to (cb7) below:
    (cb1) a polynucleotide that consists of a base sequence of SEQ ID NO: 3;
    (cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under stringent conditions and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under stringent conditions and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under stringent conditions and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under stringent conditions and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under stringent conditions and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

The conferring method of the present disclosure is characterized in that at least one polynucleotide selected from the group consisting of the above-described polynucleotides of (ca) to (ce) and (cf) is introduced as the cytoplasmic male sterility gene into the *Rudbeckia* plant of interest, and there is no particular limitation on other steps and conditions. The conferring method of the present disclosure can confer cytoplasmic male sterility to a *Rudbeckia* plant.

In the introducing step, the method for introducing the cytoplasmic male sterility gene into the *Rudbeckia* plant of interest may be, for example, the same as the method for introducing a cytoplasmic male sterility gene in production of the above-described transformant.

In the introducing step, any one or more, two or more, or all of the polynucleotides of (ca) to (cf) may be introduced. Regarding the combination of the polynucleotides in the case where two or more of the polynucleotides are introduced, reference can be made to the above description on the combination of two or more cytoplasmic male sterility genes in connection with the *Rudbeckia* plant of the present disclosure.

<Second Production Method>

In still another aspect, the present disclosure provides a method for producing a *Rudbeckia* plant that exhibits cytoplasmic male sterility. As described above, the cytoplasmic male sterile *Rudbeckia* plant production method of the present disclosure includes the step of conferring cytoplasmic male sterility to a *Rudbeckia* plant of interest, and the conferring step is performed by the method for conferring cytoplasmic male sterility to a *Rudbeckia* plant according to the present disclosure. The second production method of the present disclosure is characterized in that the conferring step is performed by the method for conferring cytoplasmic male sterility to a *Rudbeckia* plant according to the present disclosure, and there is no particular limitation on other steps and conditions. The second production method of the present disclosure can produce a cytoplasmic male sterile *Rudbeckia* plant.

<Screening Method>

In still another aspect, the present disclosure provides a screening method for a *Rudbeckia* plant that exhibits cytoplasmic male sterility. The screening method for a cytoplasmic male sterile *Rudbeckia* plant according to the present disclosure includes the step of: selecting, from one or more test *Rudbeckia* plants, a test *Rudbeckia* plant that includes, as a cytoplasmic male sterility gene, at least one polynucleotide selected from the group consisting of polynucleotides of (ca) to (ce) and (cf) below as a cytoplasmic male sterile *Rudbeckia* plant:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under stringent conditions and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under stringent conditions and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under stringent conditions and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under stringent conditions and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under stringent conditions and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under stringent conditions and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

The screening method of the present disclosure is characterized in that the cytoplasmic male sterility gene is used as a criterion for the selection in the selection step, and there is no particular limitation on other steps and conditions. According to the screening method of the present disclosure, a cytoplasmic male sterile *Rudbeckia* plant can be selected through screening.

Regarding the selection step in the screening method of the present disclosure, reference can be made to the above description on indirect selection (selection using indirect evaluation) in the step (x) or (x1).

<Third Production Method>

In still another aspect, the present disclosure provides a method for producing a *Rudbeckia* plant that exhibits cytoplasmic male sterility. As described above, the cytoplasmic male sterile *Rudbeckia* plant production method of the present disclosure includes the step of screening one or more test *Rudbeckia* plants for a test *Rudbeckia* plant that includes a cytoplasmic male sterility gene, and the screening step is performed by the screening method of the present disclosure. The third production method of the present disclosure is characterized in that the screening step is performed by the screening method of the present disclosure, and there is no particular limitation on the other steps and conditions.

<Second *Rudbeckia* Plant>

In still another aspect, the present disclosure provides a *Rudbeckia* plant that exhibits cytoplasmic male sterility. The cytoplasmic male sterile *Rudbeckia* plant of the present disclosure (also referred to as "second *Rudbeckia* plant" hereinafter) is obtained by, for example, the first production method, second production method, or third production method of the present disclosure. The second *Rudbeckia* plant of the present disclosure is characterized in that it is obtained by the first production method, second production method, or third production method of the present disclosure, and there is no particular limitation on other structures and conditions.

<Detection Method>

In still another aspect, the present disclosure provides a method capable of detecting cytoplasmic male sterility of a *Rudbeckia* plant. As described above, the method for detecting the cytoplasmic male sterility of a *Rudbeckia* plant according to the present disclosure includes the step of: detecting, as a cytoplasmic male sterility gene, at least one polynucleotide selected from the group consisting of polynucleotides of (ca) to (ce) and (cf) below in a test *Rudbeckia* plant:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under stringent conditions and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under stringent conditions and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under stringent conditions and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under stringent conditions and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under stringent conditions and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under stringent conditions and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

The detection method of the present disclosure is characterized in that the cytoplasmic male sterility gene is detected in the detection step, and there is no particular limitation on the other steps and conditions. The detection method of the present disclosure can detect whether the test Rudbeckia plant has cytoplasmic male sterility.

The detection method of the present disclosure includes, for example, the step of detecting a cytoplasmic male sterility gene of a test Rudbeckia plant. Regarding the detection step, reference can be made to the above description regarding indirect selection (selection using indirect evaluation) in the step (x) or (x1) in the selection step of the first production method of the present disclosure.

In the selection step, the chromosomal location of the cytoplasmic male sterility gene may be detected. The chromosomal location may be in, for example, a nucleus, a nuclear genome, cytoplasm, a mitochondrion, or a mitochondrial genome.

Examples of a sample to be subjected to the detection of the cytoplasmic male sterility gene in the selection step include samples containing nuclei, nuclear genomes, cytoplasm, mitochondria, and/or mitochondrial genomes. Each sample can be prepared from the test Rudbeckia plant or a part thereof by a method commonly used in the technical field to which the present application pertains. The sample is preferably a sample containing cytoplasm, mitochondria, and/or mitochondrial genomes.

<Deposited Line>

The Rudbeckia plant of the present disclosure may be, for example, a Rudbeckia plant identified by (deposited under) Accession No. FERM BP-22428 or a progeny line thereof. Hereafter, Accession No. FERM BP-22428 is also referred to as a Rudbeckia variety Takii 22. Information on the deposit of this variety is shown below.

Type of Deposit: International Deposit

Name of depository institution: National Institute of Technology and Evaluation, International Patent Organism Depositary; NITE-IPOD Address: 2-5-8-120, Kazusakamatari, Kisarazu-shi, Chiba 292-0818, Japan Accession Number: Accession No. FERM BP-22428

Identifying designation: Takii 22

Date of acceptance: Sep. 14, 2021

In the present disclosure, a plant having "essentially all physiological and morphological characteristics of the deposited line" means a plant having major traits of the deposited line when it is grown in the same environment.

<Progeny Line>

The Rudbeckia plant of the present disclosure may be a progeny line of the deposited line. The progeny line may be a plant individual of the progeny line, a part of a plant individual of the progeny line, or a seed of the progeny line.

In the present disclosure, the "progeny line" or "progeny Rudbeckia plant" (collectively referred to as "progeny line" hereinafter) refers to a plant obtained from a Rudbeckia plant of the deposited line or from a progeny line thereof. In the present disclosure, the progeny line may be a plant obtained by crossing the above-described deposited line with another deposited line or with another Rudbeckia plant or by crossing the deposited line with a wild Rudbeckia plant. The progeny line may be directly or indirectly obtained, obtainable, or derived from the deposited line or a progeny line thereof by cross-pollination, or may be derived from a parental line obtained from the deposited line using a conventional breeding method such as cross-pollination. The progeny line may be, for example, a first-generation hybrid F1 (hybrid first-generation line, F1 hybrid) or a backcross progeny line. In a process of obtaining the progeny line, the deposited line is cytoplasmic male sterile, as described above. Thus, the deposited line is used as a female parent.

In the present disclosure, "crossing" refers to crossing of two parental lines. The crossing may be "cross-pollination" or "self-pollination". In the present disclosure, when the crossing is performed using a plant that exhibits cytoplasmic male sterility in combination, the crossing means cross-pollination. Cross-pollination refers to fertilization by the union of two gametes derived from different plants. Self-pollination means transfer of pollen from the anthers to the stigma of the same plant. Self-pollination can also be referred to as self-crossing, for example. The crossing may include backcrossing, which is one of conventional breeding methods.

The "backcrossing" is one of conventional breeding techniques and is a method in which a breeder introduces a trait into a plant or a variety by repeatedly backcrossing a hybrid progeny line with one of the parental lines. A plant that includes the trait to be introduced may be referred to as a donor plant (donor parent), for example. A plant into which the trait is to be introduced may be referred to as a recurrent parent, for example. The backcrossing can be performed by crossing a donor plant with a recurrent parent, whereby a first-generation hybrid F1 (hybrid first-generation line, F1 hybrid) can be obtained. Next, the progeny line having the trait is crossed with a recurrent parent. Then, by performing backcrossing over several generations, the trait of the donor plant can be introduced into the recurrent parent. The *Rudbeckia* plant of the present disclosure may be used as the donor plant.

In the present disclosure, the progeny line may be: regenerated from a cell culture or tissue culture, a protoplast, or a part of a plant individual, each derived from the deposited line; obtained by selfing of the deposited line; or obtained by producing seeds from a plant individual of the deposited line.

In the present disclosure, the "regeneration" refers to the development or vegetative propagation of a plant from a cell culture, a tissue culture, or a protoplast.

The "tissue culture" or "cell culture" may be a composition containing the same type or different types of isolated cells or may be a cell aggregate to be organized into a part of a plant. Tissue cultures of various tissues of *Rudbeckia* plants and methods for regenerating plants from the tissue cultures are well known, and reference can be made to Reference Document 1 below, for example.

Reference Document 1: P. Szarvas et.al., "Biotechnology of annual flower plants: Micropropagation of *Rudbeckia* sp", Acta Horticulturae, 2006, vol. 725, pages 527-548

Cytoplasmic male sterility in the deposited line is a dominantly inherited trait, and crossing the deposited line with a male parent yields a progeny line that inherits the cytoplasm of the female parent, which is cytoplasmic male sterile. Accordingly, the progeny line has cytoplasmic male sterility.

The progeny line may have desired traits. The progeny line may have "essentially all physiological and morphological characteristics of the deposited line" when it is cultivated under the same cultivation conditions, for example.

The progeny line may include cells containing at least one set of chromosomes derived from the corresponding deposited line. At least 6.25%, 12.5%, 25%, 30%, 35%, 40%, 45%, 50%, 55%, 60%, 65%, 70%, 80%, 85%, 90%, 95%, 96%, 97%, 98%, or 99% of alleles of the progeny line may be derived from the corresponding deposited line. That is to say, the progeny line may have at least about 6.25%, 12.5%, 25%, 30%, 35%, 40%, 45%, 50%, 55%, 60%, 65%, 70%, 80%, 85%, 90%, 95%, 96%, 97%, 98%, or 99% genetic complement with the corresponding deposited line.

The "allele(s)" refers to one gene or a plurality of genes, all of which are associated with a characteristic or trait of a *Rudbeckia* plant. In a diploid cell or organism, a pair of alleles of a given gene occupy the corresponding genetic loci on a pair of homologous chromosomes.

The genetic complement can be calculated by, for example, decoding a molecular marker or a base sequence, comparing it with a molecular marker or a base sequence of the deposited line, and calculating the concordance rate. The molecular marker may be, for example, a single nucleotide polymorphism (SNP) marker, an amplified fragment length polymorphism (AFLP) marker, a restriction fragment length polymorphism (RFLP) marker, a microsatellite marker, a sequence-characterized amplified region marker, or a cleaved amplified polymorphic sequence (CAPS) marker. Methods for analyzing genomes using the above-described molecular markers are well known and widely open to the public (e.g., Reference Documents 2 and 3 below). The base sequence can be decoded by, for example, extracting a chromosome from the progeny line and sequencing the chromosome. The percentage of alleles derived from the deposited line and the percentage of genetic complement may each be estimated based on the number of times of crossing, for example. In this case, the percentage can be estimated based on the number of times of crossing from the deposited line. As a specific example, when the number of times of crossing from the deposited line is n, the percentage can be estimated as $(1/2)^n \times 100\%$, for example.

Reference Document 2: Sinchan Adhikari et.al, "Application of molecular markers in plant genome analysis: a review", The Nucleus, 2017, Volume 60, Issue 3, pp. 283-297

Reference Document 3: Elcio P. Guimaraes et.al., "MARKER-ASSISTED SELECTION Current status and future perspectives in crops, livestock, forestry and fish", 2007, Springer, 29-49

Preferably, the percentage of alleles derived from the deposited line and the percentage of genetic complement are each an average value of the percentages determined with respect to a plurality of progeny lines, for example. The "plurality of" refers to, for example, the number of individuals sufficient to enable statistical examination, and specifically refers to, for example, at least 200 individuals and preferably 200 to 1000 individuals.

The progeny line may have SNPs derived from the deposited line. At least 6.25%, 12.5%, 25%, 30%, 35%, 40%, 45%, 50%, 55%, 60%, 65%, 70%, 80%, 85%, 90%, 95%, 96%, 97%, 98%, or 99% of SNPs of the progeny line may be derived from the deposited line, for example. That is to say, at least about 6.25%, 12.5%, 25%, 30%, 35%, 40%, 45%, 50%, 55%, 60%, 65%, 70%, 80%, 85%, 90%, 95%. 96%, 97%. 98%, or 99% of the SNPs of the progeny line may match the SNPs of the deposited line. In the present disclosure, when, for example, at least 50%, 55%, 60%, 65%, 70%, 80%, 85%, 90%, 95%, 96%, 97%, 98%, or 99% of SNPs of a *Rudbeckia* plant of interest match the SNPs of the deposited line, the *Rudbeckia* plant of interest can be determined (discriminated, estimated, appraised, or assessed) as being a progeny line of the deposited line.

The progeny line may have mutation or a transgene, for example. In this case, one or more traits of the progeny line are modified, for example. The progeny line can be produced by, for example, introducing mutation or a transgene into the deposited line or a progeny line thereof. The mutation may be introduced artificially or naturally. The mutation may be, for example, chemical-induced mutation or radiation-induced mutation. Also, the mutation may be introduced by, for example, a molecular biological procedure or a genome-editing technique (e.g., Reference Document 4 below). The transgene can be introduced by a method using *Agrobacterium tumefaciens*, for example (e.g., Reference Document 4 below).

Reference Document 4: Yanfei Mao et.al., "Gene editing in plants: progress and challenges", National Science Review, 2019, vol. 6, pp. 421-437

The above-described transgene refers to, for example, a desired gene introduced into the genome of a plant by a genetic engineering procedure or a conventional breeding method. The transgene may be derived from the same species or a different species, for example. The transgene may include a base sequence that is the same as or different from the base sequence of the species from which it is derived. In the latter case, the different base sequence can be prepared, for example, by codon optimization of the above-described same base sequence or adding a transcriptional regulator such as a promoter to the above-described same base sequence. The transgene may have translated regions and untranslated regions.

<Haploid Plant and Doubled Haploid Plant>

The *Rudbeckia* plant of the present disclosure may be a haploid plant and/or doubled haploid plant that is obtained, obtainable, or induced from the deposited line. The haploid plant and/or doubled haploid plant of the deposited line may be used in a method for producing a parental line of the deposited line. In one embodiment, the present disclosure may provide a haploid plant and/or doubled haploid plant, a part of a haploid plant and/or doubled haploid plant, or a seed of a haploid plant and/or doubled haploid plant.

The doubled haploid plant can be produced by doubling chromosomes in a haploid plant or a cell. As a specific example, haploid cytoplasm is cultured under predetermined conditions, thereby forming plantlets with In chromosomes. Next, the plantlets are treated with, for example, a chemical substance such as colchicine to double the chromosomes. As a result, the cells of the plantlets have 2n chromosomes (doubled haploids). Then, by growing the thus-treated plantlets, the doubled haploid plants and progeny lines thereof can be obtained.

<Method for Producing *Rudbeckia* Plant>

As described above, the method for producing a *Rudbeckia* plant according to the present disclosure includes the step of crossing a first *Rudbeckia* plant with a second *Rudbeckia* plant, and the first *Rudbeckia* plant is the *Rudbeckia* plant of the present disclosure. The production method of the present disclosure is characterized in that the *Rudbeckia* plant of the present disclosure is used as at least one of parents in the crossing step, and there is no particular limitation on other steps and conditions.

*Rudbeckia* plant production method of the present disclosure includes the step of crossing (cross-pollinating) the *Rudbeckia* plant of the present disclosure. The production method of the present disclosure is characterized in that the *Rudbeckia* plant of the present disclosure is used in crossing, and there is no particular limitation on other steps and conditions.

According to the production method of the present disclosure, a progeny line of the deposited line can be produced. Regarding the production method of the present disclosure, reference can be made to the description on the *Rudbeckia* plant of the present disclosure.

In the present disclosure, the crossing between the first *Rudbeckia* plant (first parental line) and the second *Rudbeckia* plant (second parental line) is crossing between different individuals (cross-pollination).

In the present disclosure, the first parental line is the *Rudbeckia* plant of the present disclosure, which is, for example, a *Rudbeckia* plant deposited under Accession No. FERM BP-22428 as described above or a progeny line thereof.

There is no particular limitation on the second parental line, and any *Rudbeckia* plant can be used. The second parental line may be, for example, a *Rudbeckia* plant of a species that is taxonomically the same as or different from the first parental line. The second parental line is, for example, a male fertile *Rudbeckia* plant.

The production method of the present disclosure may further include, after the crossing step, the step of growing a progeny line obtained in the crossing step, for example. Conditions for growing the progeny line in the growing step may be, for example, conditions commonly used for growing *Rudbeckia* plants.

The *Rudbeckia* plant of the present disclosure can be obtained by the production method of the present disclosure, for example.

<Method for Producing Seeds of *Rudbeckia* Plant>

The present disclosure provides a method for producing a *Rudbeckia* seed. The method for producing a *Rudbeckia* seed according to the present disclosure includes the steps of: crossing the *Rudbeckia* plant of the deposited line with another *Rudbeckia* plant; and optionally collecting (gathering or harvesting) the resulting seeds. The seed production method of the present disclosure may provide a plant, a plant part, or a seed by growing a seed of a *Rudbeckia* plant.

The seed production method of the present disclosure may be a method for producing a seed derived from the deposited line. In this case, the seed production method of the present disclosure may include the step of: (a) crossing a plant of the deposited line with another *Rudbeckia* plant to produce a seed. The seed production method of the present disclosure may further include the steps of: (b) cultivating a *Rudbeckia* plant from the seed obtained in the step (a) to produce a *Rudbeckia* plant derived from the deposited line; and (c) crossing the *Rudbeckia* plant obtained in the step (b) with another *Rudbeckia* plant to produce an additional *Rudbeckia* plant derived from the deposited line. The seed production method of the present disclosure may further include the step of: (d) optionally repeating the steps (b) and (c) one or more times to further produce a *Rudbeckia* plant(s) derived from the deposited line. In this case, a *Rudbeckia* plant to be used in a repeated step (b) as the *Rudbeckia* plant cultivated from the seed obtained in the step (a) may be an additional *Rudbeckia* plant obtained in the preceding step (c). The "one or more times" refer to, for example, one to ten times, three to seven times, or three to five times. The seed production method of the present disclosure may further include the step of gathering or harvesting seeds. The seed production method of the present disclosure may provide a seed produced by the above-described method and a plant or a part of a plant individual obtained by growing the seed.

The seed production method of the present disclosure may further include the step of: (e) specifying a progeny line having cytoplasmic male sterility in the production of the *Rudbeckia* plant in the step (b), in the production of the additional *Rudbeckia* plant in the step (c), or in the production of the further *Rudbeckia* plant derived from the deposited line in the step (d). In this case, in the seed production method of the present disclosure, a progeny line having cytoplasmic male sterility is preferably used as a *Rudbeckia* plant used for crossing in subsequent steps. The "specifying" described above can also be referred to as, for example, discriminating, appraising, identifying, selecting, or choosing. The cytoplasmic male sterility of the progeny line is preferably the same as the cytoplasmic male sterility of the deposited line from which it is derived, and regarding the cytoplasmic male sterility of the progeny line, reference can be made to the above description on the cytoplasmic male sterility of the deposited line.

<Production Method of Hybrid *Rudbeckia* Plant>

The present disclosure provides a method for producing a hybrid *Rudbeckia* plant. The hybrid plant production method of the present disclosure includes the step of crossing the *Rudbeckia* plant of the present disclosure with another *Rudbeckia* plant. The hybrid plant production method of the present disclosure may further include the step of gathering or harvesting seeds obtained by crossing. The hybrid plant production method of the present disclosure may provide a seed and a hybrid plant or a part of a hybrid plant individual, produced by the above-described method.

<Method for Introducing New Trait>

The present disclosure provides a method for introducing at least one new characteristic or trait (collectively referred to as "trait" hereinafter) into the deposited line. The trait introduction method of the present disclosure can also be referred to as, for example, a method for producing a *Rudbeckia* plant into which a new trait has been introduced. The trait introduction method of the present disclosure includes, for example, the steps of: (a) crossbreeding a plant of the deposited line with a *Rudbeckia* plant including at least one new trait to produce one or more progeny lines; and (b) selecting a progeny line including the at least one new trait. The trait introduction method of the present disclosure includes, for example, the steps of: (c) crossing the progeny line with a *Rudbeckia* plant having essentially all physiological and morphological characteristics of the deposited line except for cytoplasmic male sterility to produce a seed of a backcross progeny; and (d) selecting a backcross progeny having the at least one new trait and optionally cytoplasmic male sterility. In the steps (b) and (d), selection (choosing) of a progeny line having the new trait may be performed by detecting the trait or by detecting a gene or molecular marker associated (linked) with the trait. The new trait may be, for example, resistance to a pathogen.

In the step (b), it is preferable to select a *Rudbeckia* plant that includes at least one new trait and optionally has cytoplasmic male sterility. As described above, when a *Rudbeckia* plant having cytoplasmic male sterility is used as the female parent, the resulting progeny line exhibits cytoplasmic male sterility. Accordingly, in the selection of the progeny line, the presence or absence of cytoplasmic male sterility may or may not be examined.

In the step (d), a progeny line having at least one new trait, optionally having cytoplasmic male sterility, and having essentially all physiological and morphological characteristics of the deposited line used in the step (a) may be selected.

The trait introduction method of the present disclosure may further include the step of: (e) optionally repeating the steps (c) and (d) one or more times to produce a *Rudbeckia* plant(s) having the at least one new trait. In this case, in the trait introduction method of the present disclosure, a progeny line used in a repeated step (c) may be a backcross progeny selected in a preceding step (d). The *Rudbeckia* plant obtained or obtainable in the step (e) may exhibit cytoplasmic male sterility, and further may have essentially all physiological and morphological characteristics of the deposited line used in the step (a). The "one or more times" refer to, for example, one to ten times, three to seven times, or three to five times. The trait introduction method of the present disclosure may include the step of gathering or harvesting seeds. The trait introduction method of the present disclosure may provide a seed produced by the above-described method and a plant or a part of a plant individual obtained by growing the seed.

<Method for Introducing Transgene>

The present disclosure provides a method for producing a plant that is derived from a deposited line and includes at least one new characteristic or trait. The transgene introduction method of the present disclosure can also be referred to as, for example, a method for producing a *Rudbeckia* plant into which a new trait has been introduced.

The transgene introduction method of the present disclosure includes, for example, the step of introducing mutation or a transgene that confers at least one new trait into a plant of the deposited line or a progeny line thereof. The introduction of mutation or a transgene can be performed, for example, in the same manner as the above-described introduction of mutation or a transgene in the progeny line. The *Rudbeckia* plant obtained or obtainable in the above-described introducing step may exhibit cytoplasmic male sterility, and further may have essentially all physiological and morphological characteristics of the deposited line. The transgene introduction method of the present disclosure may include the step of gathering or harvesting seeds. The transgene introduction method of the present disclosure may provide a seed produced by the above-described method and a plant or a part of a plant individual obtained by growing the seed. The new trait may be, for example, resistance to a pathogen.

<*Rudbeckia* Plant Regenerated Product and Regeneration Method>

The present disclosure provides a *Rudbeckia* plant regenerated from a cell culture, a tissue culture, or a protoplast of the deposited line (the regenerated *Rudbeckia* plant is referred to as "regenerated product" hereinafter). The present disclosure may provide a cell culture or tissue culture of regenerable cells, or a protoplast derived from a *Rudbeckia* plant of the deposited line. The cells, tissue, or protoplast may be derived from tissue including a leaf, an embryo, a cotyledon, a hypocotyl, meristematic cells, a root, a root tip, an anther, a flower, a seed, or a trunk.

The present disclosure provides a method of growth or propagation of a *Rudbeckia* plant of the deposited line. The propagation of the *Rudbeckia* plant of the deposited line may be vegetative propagation of the *Rudbeckia* plant of the deposited line. In this case, a *Rudbeckia* plant regeneration method according to the present disclosure includes, for example, the steps of: (a) collecting propagatable tissue from a plant of the deposited line; (b) culturing the tissue to obtain a grown shoot; and (c) rooting the grown shoot to obtain a rooted plantlet. The *Rudbeckia* plant regeneration method of the present disclosure may further include the step of: (d) optionally growing a plant from the rooted plantlet. Regarding a method for effecting the above-described vegetative propagation, reference can be made to Reference Document 5 below, for example. The regeneration method of the present disclosure may provide, for example, a plantlet, a plant, or a part of a plant individual, each regenerated (produced) by the above-described method. The plant may have essentially all physiological and morphological characteristics of the deposited line. Regarding the "essentially all physiological and morphological characteristics" described above, reference can be made to the above description on the progeny line, in which the term "progeny line" should be considered to be replaced with the term "regenerated plant".

Reference Document 5: Habtamu Gudisa Megersa, "Propagation Methods of Selected Horticultural Crops by Specialized Organs: Review", Journal of Horticulture, 2017, Volume 4, Issue 2, 1000198

<Harvest and Processed Product of *Rudbeckia* Plant>

The present disclosure provides a harvest and/or a processed product of a deposited line or a progeny line. The harvest is a whole plant or a part of a plant individual, and preferably includes: a flower; a flower, leaf, and/or stem; or a seed.

The processed product encompasses any product obtained by treating the deposited line or the progeny line. The treatment is not limited to particular treatments, and examples thereof include cutting, slicing, grinding, pureeing, drying, canning, bottling, washing, packaging, freezing, and/or heating. In the deposited line or the progeny line, a plant or a part of a plant individual used in the processed product is a flower, for example. The processed product may be, for example, a product obtained by washing and packaging the deposited line or the progeny line.

<Method for Determining Genotype>

The present disclosure provides a method for determining or detecting the genotype of a deposited line or a progeny line. The method for determining the genotype according to the present disclosure includes, for example, the steps of: (a) obtaining a nucleic acid sample from a deposited line or a progeny line; and (b) detecting a genome in the nucleic acid sample. In the step (a), as a method for preparing the nucleic acid sample from the deposited line or the progeny line, commonly used methods for preparing a nucleic acid sample from tissue can be used. In the step (b), for example, a polymorphism and/or an allele in the genome in the nucleic acid sample is detected. Detection of the polymorphism and/or allele can be performed using, for example, single nucleotide polymorphism (SNP) genotyping, amplified fragment length polymorphism (AFLP) detection, restriction fragment length polymorphism (RFLP) identification for genomic DNA, sequence-characterized amplified region (SCAR) detection for genomic DNA, cleaved amplified polymorphic sequence (CAPS) detection for genomic DNA, random amplified polymorphic detection (RAPD) for genomic DNA, a polymerase chain reaction (PCR), DNA sequencing, an allele specific oligonucleotide (ASO) probe, or a DNA microarray. Detection of the polymorphism and/or allele may be performed by sequencing the base sequence of the genome or, as described above, with reference to the SNPs of the deposited line, for example. In the step (b), one polymorphism and/or allele or two or more polymorphisms and/or alleles in the genomic DNA may be detected. The genotype determination method of the present disclosure may include the step of storing the result of detecting the polymorphism(s) and/or allele(s) in a computer-readable medium. The present disclosure may provide a computer-readable medium produced by such a method. The genome may be a mitochondrial genome, for example. The genome DNA may be a mitochondrial genome DNA, for example.

The genotype determination method of the present disclosure may be applied to, for example, any *Rudbeckia* plant (*Rudbeckia* plant of interest) instead of the deposited line or the progeny line. In this case, the genotype determination method of the present disclosure may further include, for example, the step of determining whether the *Rudbeckia* plant of interest is the progeny line based on the result obtained in the step (b). The "determining" can also be referred to as, for example, discriminating, estimating, appraising, or assessing. The determination can be made based on, for example, the concordance rate between the result obtained in the step (b) and the genotype of the deposited line.

EXAMPLES

The present disclosure will be described specifically below with reference to examples. It is to be noted, however, that the present disclosure is by no means limited to embodiments described in the following examples.

Example 1

The present example confirmed that novel sterile plants belonging to the genus *Rudbeckia* exhibit male sterility. Also, *Rudbeckia* plants of the deposited line were bred from the above-described male sterile *Rudbeckia* plants, and the causative gene responsible for cytoplasm sterility (SEQ ID NO: 1) were identified from a group of mitochondrial genes of the deposited line.

(1) Growing of Deposited Line and Examination of Cytoplasmic Male Sterility

In order to develop novel male sterile plants belonging to the genus *Rudbeckia*, a large amount of seeds obtained by passage breeding of a group of *Rudbeckia* (*Rudbeckia hirta*) plants in a breeding station of TAKII & CO., LTD. in Konan-shi in Shiga were bred and tested for sterility. This yielded a novel male sterile *Rudbeckia* line (male sterile line) that produced no pollen and thus was presumed to be male sterile. This male sterile line was crossed with pollen from a fertile *Rudbeckia* plant (*Rudbeckia hirta* cv. Roland, fertile line) owned by TAKII & CO., LTD. to obtain seeds. The resulting seeds were bred, and 50 individuals of *Rudbeckia* plants belonging to the genus *Rudbeckia* were tested for male sterility using the presence or absence of pollen production as the criterion for determining the male sterility. As a result, none of the individuals produced pollen and thus they were all found to be male sterile. On the basis of the above results, it was presumed that the male sterility was maternally derived cytoplasmic male sterility.

Figure 1B:

Next, the above-described sterile line was backcrossed three times with the above-described fertile line serving as the backcross parent, whereby the deposited line (RdCMS line) was produced. The deposited line was deposited under Accession No. FERM BP-22428. In the above-described backcrossing, the *Rudbeckia* plants of every generation maintained the male sterility. From the above results, it was found that the male sterility was maternally inherited cytoplasmic male sterility. FIGS. 1A and 1B show photographs of flowers of the RdCMS line and the fertile line (RdMF).

FIGS. 1A and 1B each show a photograph of flowers of a *Rudbeckia* plant. FIG. 1A shows a photograph of flowers of a *Rudbeckia* plant of the deposited line (RdCMS line), and FIG. 1B shows a photograph of flowers of a *Rudbeckia* plant of the fertile line (*R. hiruta*, RdMF line). As can be seen from FIGS. 1A and 1B, it was found that the fertile line produced pollen, whereas the deposited line did not produce pollen.

(2) Breeding of Cytoplasmic Male Sterile Line Using Deposited Line

For breeding of cytoplasmic male sterile lines, fertile lines made up of a plurality of types of *Rudbeckia* plant groups and the above-described deposited line (RdCMS line) were used. Specifically, the above-described male fertile lines of the *Rudbeckia* plant groups were obtained by selecting, from a population of *Rudbeckia* plants with a variety of traits, about 5 to 20 individuals sharing desired cultivation traits, randomly crossing them with each other, and collecting the resulting seeds. Subsequently, selection and crossing were performed in the same manner over several generations, whereby male fertile fixed lines (26 lines) were obtained. Then, the 26 lines were crossed with the deposited line (RdCMS line), whereby F1 generations were obtained. For the F1 generation obtained from each combination, 24 individuals were cultivated. As a result, the individuals obtained from all the combinations were found to be male sterile (BC1 lines). These results demonstrate that the male sterility gene of the RdCMS line can confer male sterility when it is combined with various lines. Out of the above-described 26 lines, a line with high seed production ability (S1 line) was selected. Using the S1 line as a recurrent parent, backcrossing with the above-described male sterile line was performed four times, whereby a backcrossed progeny line (BC5 line) was obtained. After confirming that the BC5 line had the same traits as the S1 line except for the male sterility, the BC5 line was regarded as a male sterile line with fixed traits (SMS1 line). Also, the S1 line was used as the maintainer line (pollen parent) for the SMS1 line.

(3) Breeding of F1 Variety

Figure 2:
FIG. 2 show a photograph of plant bodies of a *Rudbeckia* plant of an F1_MS1 line in Example 1.

Using the SMS1 line produced by the method described in (2) of Example 1 as a female parent and a fertile fixed line (SSS line) as a male parent, a first filial generation (F1_MS1 line) was obtained by artificial crossing. The SSS line was a line different from the S1 line. 100 individuals of the F1_MS1 line were cultivated. As a result, all the individuals exhibited male sterility. FIG. 2 shows a photograph of the F1_MS1 line.

FIG. 2 show a photograph of plant bodies of the *Rudbeckia* plant of the F1_MS1 line. As can be seen from FIG. 2, these individuals have uniform traits, and this indicates that there was no contamination by selfed seeds. These results demonstrate that, by using the SMS1 line as a cross parent, a cytoplasmic male sterile F1 variety can be bred easily.

Further, in order to establish a more efficient seed production method for the F1 line, whether crossing of the SMS1 line and the SSS line can be performed using honeybees was examined. In a plastic greenhouse where the SMS1 line and the SSS line were cultivated, crossing of the SMS1 line and the SSS line was performed using honeybees. After the crossing using the honeybees, seeds were collected only from the female line (SMS1 line), whereby a first filial generation (F1_MSH line) was obtained. The F1_MS1 line and the F1_MSH line were seeded under the same conditions, and 100 individuals of each line were cultivated. As a result, no difference was observed between the individuals of the F1_MSH line and the individuals of the F1_MS1 line. The above result demonstrates that seed production for the F1 line can also be performed using honeybees.

(4) Estimation of Mitochondrial Gene of Deposited Line

Cytoplasmic male sterility is known to be caused by mitochondrial genes of the female parent. Thus, the base sequences of whole mitochondria of the deposited line (RdCMS line) produced by the method described in (1) of Example 1 and the above-described fertile lines (RdMF line, 26 lines) were identified, and by comparing these base sequences, the causative gene responsible for cytoplasmic male sterility was estimated. Specifically, mitochondria were purified from 5 g of fresh leaves of the RdCMS line and the RdMF line. The purification of the mitochondria was performed in the manner described in Reference Document 6 shown below. After the purification, DNA was extracted from the purified mitochondria. The DNA extraction was performed in the manner described in Reference Document 6 shown below. Using the obtained mitochondrial DNA and 10 kb Template Preparation and Sequencing with Low-Input DNA (Pacific Biosciences®), sequencing of the DNA extracted from each of the lines was performed in accordance with the attached protocol. Specifically, a genomic DNA solution containing the extracted DNA (1 μg equivalent, liquid volume: 150 μl) was centrifuged at 6110 rpm for 1 minute using a g-TUBE (Covaris®). After the centrifugation, the DNA was purified using an AMPure PB (Pacific Biosciences® in an amount of about 0.45 times. After the purification, damages in the DNA were repaired and then the ends of the DNA were blunted, and further, SMRTbell adapters were added thereto. Next, the base sequence of the thus-obtained DNA was analyzed using a Sequel system (Pacific Biosciences®). Base sequence data obtained by the analysis were assembled using HGAP4 (Pacific Biosciences®) and Organelle_PBA (see Reference Document 7 shown below). As a result of the sequence assembly using the HGAP4, three pseudo genomes were constructed for both the lines. Also, as a result of the sequence assembly using the Organelle_PBA, one pseudopseudo genome was constructed for both the lines. The base sequences resulting from the above assembly were compared with the base sequences of genomes of mitochondria of sunflowers (Accession Nos. CM007908 and NC_023337). As with *Rudbeckia* plants, the sunflowers are also members of the Asteraceae family. Base sequences found to be homologous to the base sequences of the genomes of the mitochondria of the sunflowers were regarded as the base sequences of pseudo mitochondrial genomes of *Rudbeckia* plants of the respective lines, based on which the pseudo mitochondrial genomes were constructed. The thus-constructed pseudo mitochondrial genomes of the respective lines were compared with each other. The results thereof are shown in FIGS. 3A and 3B.

Reference Document 6: Triboush, et al., "A method for isolation of chloroplast DNA and mitochondrial DNA from sunflower", Plant molecular biology reporter, 16.2 (1998): 183.

Reference Document 7: Soorni, et al. "Organelle_PBA, a pipeline for assembling chloroplast and mitochondrial genomes from Pacaio DNA sequencing data.", BMC genomics (2017): 18: 49

Figure 3A:
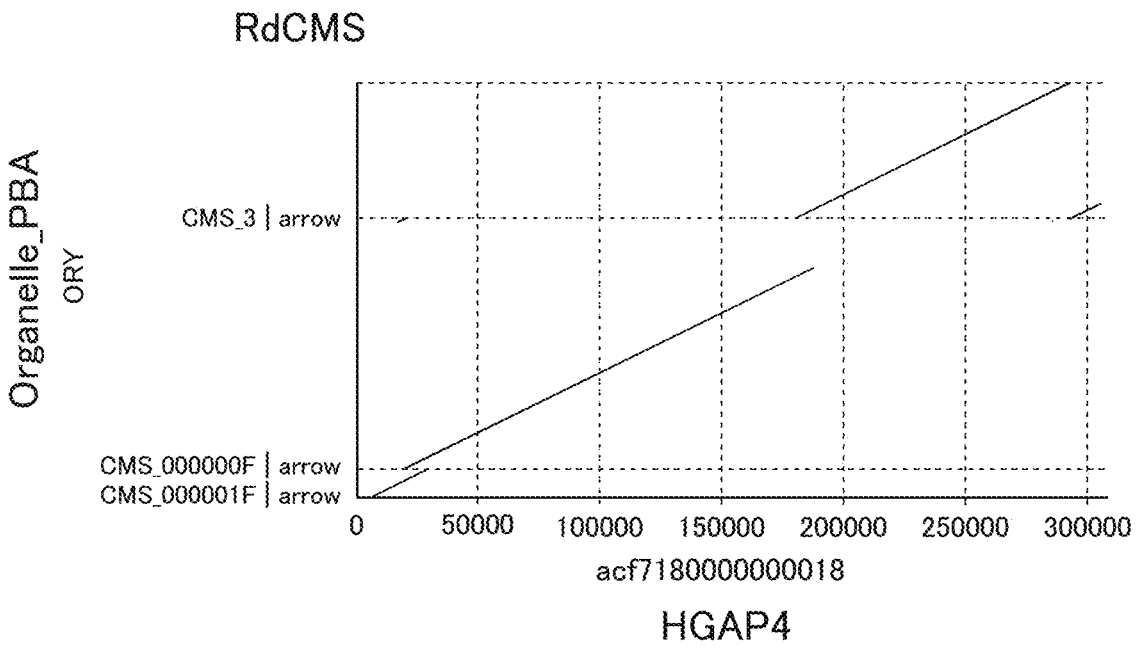
FIGS. 3A and 3B show graphs comparing mitochondrial genomes of respective lines, constructed using two programs in Example 1.
Figure 3B:
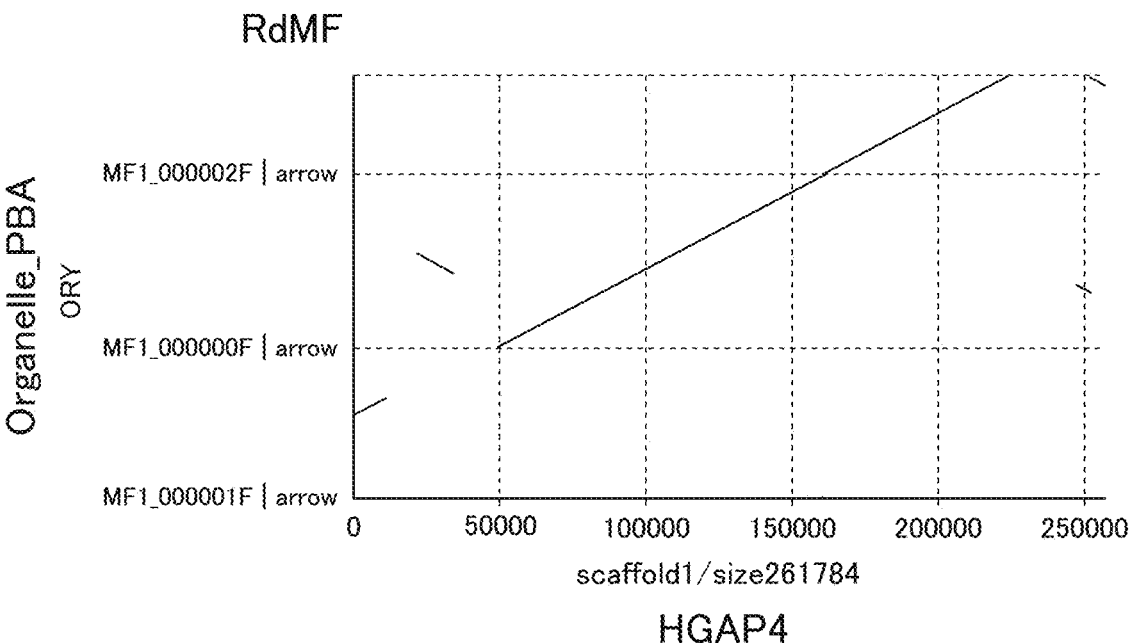

FIGS. 3A and 3B show graphs comparing the mitochondrial genomes of the respective lines constructed using the two programs. FIG. 3A shows the result concerning the pseudo mitochondrial genome of the deposited line (RdCMS line), and FIG. 3B shows the result concerning the pseudo mitochondrial genome of the normal cytoplasm line (RdMF line). In FIGS. 3A and 3B, the vertical axis shows the pseudo mitochondrial genome constructed using the Organelle_PBA, and the horizontal axis shows the pseudo mitochondrial genome constructed using the HGAP4. As can be seen from FIGS. 3A and 3B, in both the RdCMS line and the RdMF line, the pseudo mitochondrial genome constructed using the Organelle_PBA and the pseudo mitochondrial genome constructed using HGAP4 almost fully match each other.

It has been suggested that cytoplasmic male sterility genes are caused by chimeric genes or loss-of-function mutation in genes (Reference Document 8). Thus, in order to identify gene mutation between the RdCMS line and the RdMF line, gene prediction based on information on known mitochondrial genes was performed for the respective pseudo mitochondrial genomes. Mitofy (Reference Document 9) was used for the above-described gene prediction. In addition, gene prediction using getORF (www.bioinformatics.nl/cgi-bin/emboss/getorf) was performed for the respective pseudo mitochondrial genomes. Regarding the genes predicted using Mitofy and the genes predicted based on the respective pseudo genomes using getORF, a set of genes without duplication was constructed based on their amino acid sequences using CD-HIT (github.com/weizhongli/cdhit). Specifically, genes that were at least 90% homologous to each other in at least 50% of the length of their amino acid sequences were defined as duplicate genes identical to each other. As a result, 47 genes in total were predicted from the RdCMS line and the RdMF line. The locations of the set of 47 genes on each of the pseudo mitochondrial genomes were visualized using Simple Synteny (Reference Document 10).

Reference Document 8: Touzet, Pascal, and Etienne H. Meyer. "Cytoplasmic male sterility and mitochondrial metabolism in plants." Mitochondrion 19 (2014): 166-171.

Reference Document 9: Alverson, et al., "Insights into the evolution of mitochondrial genome size from complete sequences of *Citrullus lanatus* and *Cucurbita pepo* (Cucurbitaceae)." Molecular biology and evolution 27.6 (2010): 1436-1448.

Reference Document 10: Veltri, et al., "SimpleSynteny: a web-based tool for visualization of microsynteny across multiple species." Nucleic acids research 44. W1 (2016): W41-W45.

Next, regarding the 47 genes predicted from the RdCMS line and the RdMF line, the amino acid sequences were compared between these two lines using BLAST (blast.ncai.nlm.nih.gov/Blast.cgi). Specifically, a database was constructed for the pseudo mitochondrial genome of each of these lines. Homology analysis was performed using the database as a subject and the 47 genes predicted from the RdCMS line and the RdMF line as queries. Genes that were at least 90% homologous to each other in at least 60% of the length of their amino acid sequences between these lines were defined as genes commonly present in both the lines. Genes other than the commonly present genes were defined as genes specific to one of the lines. The results thereof are shown in FIG. 4.

Figure 4:
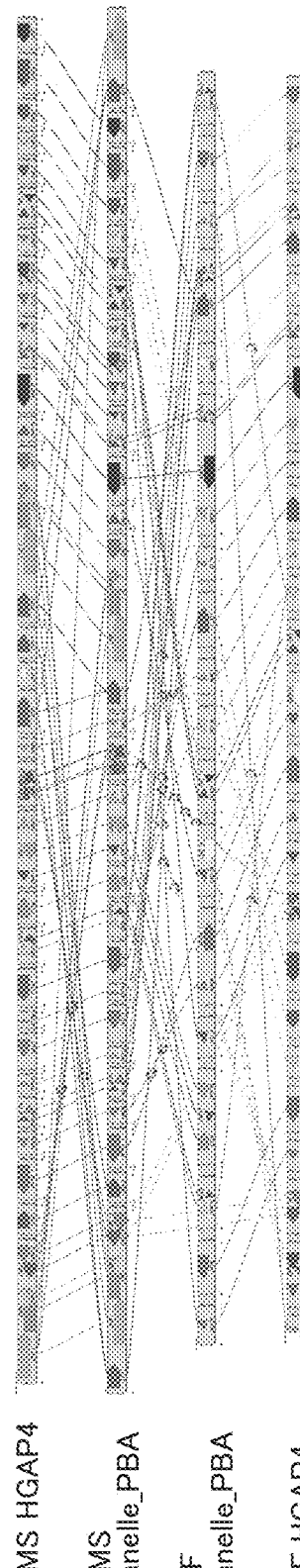
FIG. 4 shows predicted genes on mitochondrial genomes of the respective lines, constructed using Organelle_PBA or HGAP4 in Example 1.

FIG. 4 shows the predicted genes on the mitochondrial genomes of the respective lines, constructed using Organelle_PBA or HGAP4. As can be seen from FIG. 4, a set of 40 genes out of the set of 47 genes was commonly present in both the lines. On the other hand, a set of 7 genes out of the set of 47 genes was not commonly present in both the lines. The arrangements of some of the genes were identical between the RdCMS line and the RdMF line. The arrangements of many of the genes were not conserved between the RdCMS line and the RdMF line.

Out of the seven genes present only in one of the lines, six genes (ORF1, ORF2, ORF3, ORF6, ORF7, and RPS7) were present in the RdCMS line and not present in the RdMF line. The ORF1 was highly homologous to DNA-dependent RNA polymerase. The ORF2 and the ORF6 were highly homologous to DNA polymerase. The ORF3 was found to be a gene homologous to ATP6 having an ATP-synthesizing domain. The ORF7 was a gene whose function is unknown. Out of the seven genes present only in one of the lines, one gene (ATP6) was not present in the RdCMS line and present in the RdMF line.

It is known that ATP6 is responsible for cytoplasmic male sterility (CMS) in several plants. In addition, the genes specific to the RdCMS line include the ORF3 gene, which is homologous to the gene (ATP6) specific to the RdMF line. It is thus considered that ORF3, which is homologous to ATP6, possibly contributes to cytoplasmic male sterility (CMS). On this account, the base sequence of the ATP6 (SEQ ID NO: 3) found in the RdMF line was compared with the base sequence of the ORF3 (SEQ ID NO: 13) found in the RdCMS line. The result of the comparison is shown in FIG. 5.

Figure 5:
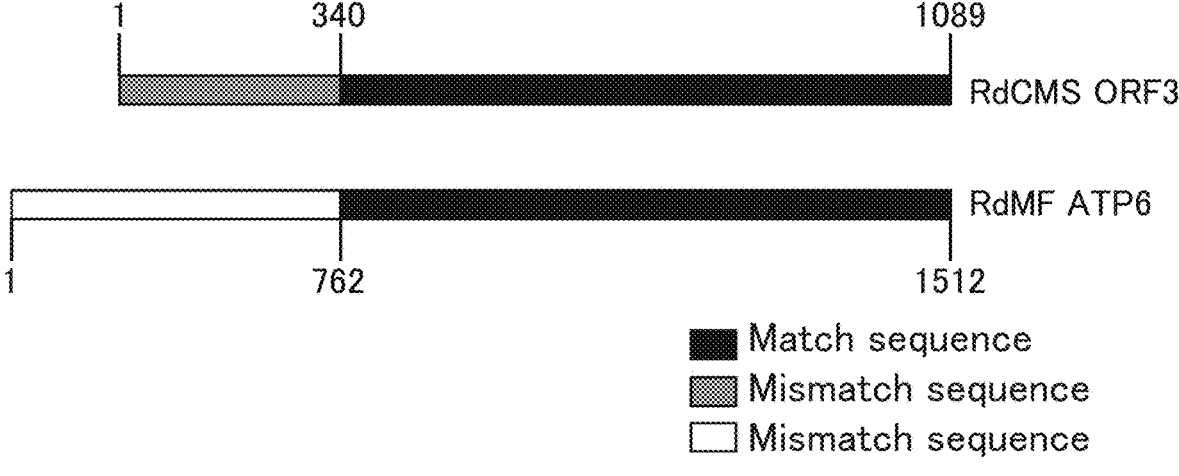
FIG. 5 is a schematic diagram comparing the base sequence of ATP6 of a RdMF line and the base sequence of ORF3 of a RdCMS line in Example 1.

FIG. 5 is a schematic diagram comparing the base sequence of the ATP6 of the RdMF line and the base sequence of the ORF3 of the RdCMS line. As can be seen from FIG. 5, relative to the first amino acid as the translation start point, the base sequence from position 763 to the translation stop codon at position 1512 in the ATP6 fully matched the base sequence from position 340 to the translation stop codon at position 1089 in the ORF3. On the other hand, the base sequence from position 1 to position 762 in the ATP6 and the base sequence from position 1 to position 339 in the ORF3 did not match each other. The base sequence from position 1 to position 339 and the base sequence (SEQ ID NO: 18) from position 1 to position 679 upstream from the translation start point (0th) in the ORF3, neither of which had matching points with the ATP6, were identical to base sequences present in a region from position 24133 to position 24819 in the pseudo mitochondrial genome (contig: MF1_00001F, SEQ ID NO: 19) of the RdMF line, constructed using HGAP4. The above results suggest that the ORF3 in the RdCMS line is a chimeric gene composed of ATP6 fused with a base sequence in another region present in the RdMF line.

Base Sequence Around Translation Start Point in ORF3 (Base Sequence of SEQ ID NO: 18)

5'-

TGCCTATGAAAAGAATGCTTTGGAATTGTATAAGAGCAGGCTGTGAT

GCGAGGACTCTCAGGGACCTACTTAAGTCTGCGATCACTCTAAAAGC

GGATAGGACCAAACCTTTTATTCCCCTAGCAGCGGTTATGTCTCAAA

CCACCGGCAACAGGTTGCGCTCCTACGATCACACCTTCTCTTGCAAA

CATAGCACTGGATGGAAGGTATGCTTCACCGGCCTCGTTTAACACCA

TGCTTCCTCCGAAGCTTTCATCTGAGTAGTCACTACGCCCTACCCTA

TCGCTGAGTCTTTGGAAGTTCACTCCTTTATAGGTCGGAACTCTGGA

ACCTAAAGACTTTCTCAATCAGACAGGATAGATGGATTGAGTGCGCG

TTGCCTTGATTTGAGGTGAACTCCTTTTCCTCTTCTTCCGGACCGGA

CCCTTCCATGTGAGAAGCTGGAAGTCGAGTTATTGATGAATGAGAAT

CTAATGTCTTATTAAACCTTTAGGAGCGATCTGTTCATCCAACTCGA

AATATCGTAAGTAAGAGAAGAAGAAGAATCTGACGCCCAAAACTCCC

GTGTCTTTCTTGGTTGGACCAACCGGCGAAATCAGTCTTCCTGAATT

GGAAGAGCAAGAACAAGTCTCTCCGTTTTTTTGGGGGAGCAGAGCAG

TCAAAGAATGAAACAGATCAAATGAGAGAGTTGATTGAGATGATTTA

TAAGGCGGTTAAGGACAATAAAAGCTTTCCCCTTTTGGTAGTATTGA

CGGTTCTCAGCGGAATAGGCATTGCTATTTACGTAACACGTATCTAT

GGTGCATCCTTTTGGGCGCACCAATCGAGACTTGACGAAGTAGCGCT

TTTCAATAAAAATGCGAAAGAACTGGGTCTCTATTGCGCAAAGGCTT

CTGTGGGGCTCACTGGGACTACCTTAGAATATAACGAACTTTCAAAT

CAAGCGCCTGTTGCTGAAAAAGTGGGTCCCCTTGGAATCCCGCCCGT

AGCCCAGGTTAGTGAAACAGTACCCAGTCCT-3'

Figure 6:
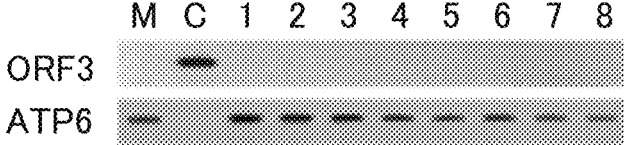
FIG. 6 shows photographs showing the results of electrophoresis performed in Example 1 using individuals of a fertile line (*R. hiruta*, RdMF line), a deposited line (RdCMS line), *R. hiruta* (120 line) owned by TAKII & CO., LTD., and *R. hiruta* growing naturally within the premises of TAKII & CO., LTD.

(5) Identification of Causative Gene Responsible for Cytoplasmic Sterility of Deposited Line Whether the male sterility of the deposited line (RdCMS line) was caused by the difference between ORF3 and ATP6 was examined. Specifically, *Rudbeckia* plants of the RdCMS line and other male fertile *Rudbeckia* plants were subjected to PCR to find out which of ORF3 or ATP6 was detected therein. First, DNA was extracted from about 50 mg of leaves collected from each of individuals (48 individuals) of: the RdCMS line; the RdMF line; male fertile *Rudbeckia* plant lines (120 lines) owned by TAKII & CO., LTD.; and male sterile *Rudbeckia* plants growing naturally within the premises of TAKII & CO., LTD. The DNA extraction was performed using a DNA extraction kit (Puregene® DNA, QIAGEN®) in accordance with the protocol attached thereto. A reaction solution was prepared from 1 μg of the obtained DNA, 0.5 μl of 10 x buffer, 0.25 μl of HsExTaq (TAKARA BIO INC.™), 0.5 μl of a primer mixture solution, and 2.75 μl of pure water, and the DNA in the reaction solution was amplified using a PCR system (Takara™). The primer mixture solution was prepared such that the concentration of each primer of a primer set for ORF3 or primer set for ATP6 shown below was 20 mmol/l. The conditions for the PCR were as follows: after treatment at 95° C. for 10 minutes, a reaction was allowed to proceed at 95° C. for 1 minute, 58° C. for 30 seconds, and 72° C. for 30 seconds, and this cycle was repeated to a total of 35 times. After the DNA amplification, the reaction solution was electrophoresed on a 1% agarose gel in order to examine the amplified DNA. FIG. 6 shows a representative example of the results obtained.

```
        Primer set for ORF3
        Forward primer
                                    (SEQ ID NO: 14)
        5'-ACGTAACACGTATCTATGGTGCAT-3'

Reverse primer
                                    (SEQ ID NO: 15)
        5'-GAGAGTTAGCAGCATAAACAAAGA-3'

Primer set for ATP6
        Forward primer
                                    (SEQ ID NO: 16)
        5'-GAGGGACTTTATTCAGTCTTATCG-3'

Reverse primer
                                    (SEQ ID NO: 17)
        5'-ATCTTCATAGGAATCAATGGGAGA-3'
```

FIG. 6 shows photographs showing the results of the electrophoresis performed using the individuals of the fertile line (*R. hiruta*, RdMF line), the deposited line (RdCMS line), the *R. hiruta* (120 lines) owned by TAKII & CO., LTD., and the *R. hiruta* growing naturally within the premises of TAKII & CO., LTD. Respective samples shown in FIG. 6 indicate, from the left, the RdMF line (M), the RdCMS line (C), and commercially available fertile lines (1 to 8). In FIG. 6, the upper row shows the results concerning ORF3, and the lower row shows the results concerning ATP6. Note here that the lines other than the deposited line (RdCMS line) are fertile lines. As can be seen from FIG. 6, in all the individuals of the RdCMS line, DNA amplification was observed when the primers for ORF3 were used, whereas DNA amplification was not observed when the primers for ATP6 were used. On the other hand, in all the 48 individuals of each of the 120 fertile lines and the naturally growing plants, DNA amplification was not observed when the primers for ORF3 were used, whereas DNA amplification was observed when the primers for ATP6 were used. The same results were obtained for the fertile lines not shown in FIG. 6. From these results, it was found that the presence or absence of ATP6 and ORF3 correlate with the presence or absence of male sterility.

The above results suggest that ORF3 of the deposited line (RdCMS line) is the causative gene responsible for cytoplasmic sterility in *Rudbeckia* plants. The above results also indicate that the primers for ATP6 and the primers for ORF3 used in (5) of Example 1 enable efficient selection of cytoplasmic sterility derived from the RdCMS line.

While the present disclosure has been described above with reference to exemplary embodiments and example, the present disclosure is by no means limited thereto. Various changes and modifications that may become apparent to those skilled in the art may be made in the configuration and specifics of the present disclosure without departing from the scope of the present disclosure.

This application claims priority from Japanese Patent Application No. 2021-205015 filed on Dec. 17, 2021. The entire disclosure of this Japanese patent application is incorporated herein by reference.

Patents, patent applications, and references cited in the present specification are incorporated herein in their entirety by reference, as if fully and specifically set forth herein.

<Supplementary Notes>

The whole or part of the exemplary embodiments and example disclosed above can be described as, but not limited to, the following Supplementary Notes.

<Cytoplasmic Male Sterile *Rudbeckia* Plant>

(Supplementary Note 1)

A *Rudbeckia* plant with cytoplasmic male sterility.

(Supplementary Note 2)

The *Rudbeckia* plant according to Supplementary Note 1, including, as a cytoplasmic male sterility gene, at least one polynucleotide selected from the group consisting of polynucleotides of (ca) to (ce) and (cf) below:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under a stringent condition and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under a stringent condition and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under a stringent condition and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under a stringent condition and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under a stringent condition and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under a stringent condition and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

(Supplementary Note 3)

The *Rudbeckia* plant according to Supplementary Note 2, including the polynucleotide of (ca) as the cytoplasmic male sterility gene.

(Supplementary Note 4)

The *Rudbeckia* plant according to Supplementary Note 2 or 3, including the polynucleotides of (ca) to (ce) and (cf) as the cytoplasmic male sterility genes.

(Supplementary Note 5)

The *Rudbeckia* plant according to any one of Supplementary Notes 2 to 4, which includes the cytoplasmic male sterility gene in a mitochondrial genome.

(Supplementary Note 6)

The *Rudbeckia* plant according to any one of Supplementary Notes 1 to 5, which is grown from a seed deposited under Accession No. FERM BP-22428.

(Supplementary Note 7) A progeny line of the *Rudbeckia* plant according to any one of Supplementary Notes 1 to 6, which is cytoplasmic male sterile.

(Supplementary Note 8)

The progeny line according to Supplementary Note 7, which is a hybrid first-generation line.

(Supplementary Note 9)

A seed of the *Rudbeckia* plant according to any one of Supplementary Notes 1 to 6 or of the progeny line according to Supplementary Note 7 or 8.

(Supplementary Note 10)

A part of the *Rudbeckia* plant according to any one of Supplementary Notes 1 to 6 or of the progeny line according to Supplementary Note 7 or 8.

(Supplementary Note 11)

A callus including:

cells of the *Rudbeckia* plant according to any one of Supplementary Notes 1 to 6 or of the progeny line according to Supplementary Note 7 or 8.

(Supplementary Note 12)

Cytoplasm included in the *Rudbeckia* plant according to any one of Supplementary Notes 1 to 6, the progeny line according to Supplementary Note 7 or 8, the seed according to Supplementary Note 9, the part according to Supplementary Note 10, or the callus according to Supplementary Note 11.

<Method for Producing Male Sterile *Rudbeckia* Plant (First Production Method)>

(Supplementary Note 13)

A method for producing a cytoplasmic male sterile *Rudbeckia* plant, the method including the step of:

(a) crossing the *Rudbeckia* plant according to any one of Supplementary Notes 1 to 6 or the progeny line according to Supplementary Note 7 or 8 with another *Rudbeckia* plant.

(Supplementary Note 14)

The production method according to Supplementary Note 13, further including the following step (x) prior to the step (a):

(x) selecting the *Rudbeckia* plant according to any one of Supplementary Notes 1 to 6 or the progeny line according to Supplementary Note 7 or 8 from one or more test *Rudbeckia* plants.

(Supplementary Note 15)

The production method according to Supplementary Note 14, wherein in the step (x), a *Rudbeckia* plant that includes at least one polynucleotide selected from the group consisting of polynucleotides of (ca) to (ce) and (cf) below as a cytoplasmic male sterility gene is selected:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under a stringent condition and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under a stringent condition and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under a stringent condition and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under a stringent condition and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under a stringent condition and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under a stringent condition and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

(Supplementary Note 16)

The production method according to Supplementary Note 15, wherein in the step (x), a *Rudbeckia* plant that includes the polynucleotide of (ca) as the cytoplasmic male sterility gene is selected.

(Supplementary Note 17)

The production method according to Supplementary Note 15 or 16, wherein in the step (x), a *Rudbeckia* plant that includes the polynucleotides of (ca) to (cf) as the cytoplasmic male sterility genes are selected.

(Supplementary Note 18)

The production method according to any one of Supplementary Notes 15 to 17, wherein in the step (x), the cytoplasmic male sterility gene is detected in the one or more test *Rudbeckia* plants to select a test *Rudbeckia* plant that includes the cytoplasmic male sterility gene.

(Supplementary Note 19)

The production method according to any one of Supplementary Notes 15 to 18, wherein in the step (x), the cytoplasmic male sterility gene is detected in mitochondrial genomes of the one or more test *Rudbeckia* plants to select a test *Rudbeckia* plant that includes the cytoplasmic male sterility gene.

(Supplementary Note 20)

The production method according to any one of Supplementary Notes 13 to 19, further including the following step (b):

(b) selecting a cytoplasmic male sterile *Rudbeckia* plant from one or more *Rudbeckia* plants obtained in the step (a) or one or more progeny lines thereof.

(Supplementary Note 21)

The production method according to Supplementary Note 20, wherein in the step (b), a *Rudbeckia* plant that includes, as a cytoplasmic male sterility gene, at least one polynucleotide selected from the group consisting of polynucleotides of (ca) to (ce) and (cf) below is selected:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under a stringent condition and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under a stringent condition and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under a stringent condition and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under a stringent condition and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under a stringent condition and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under a stringent condition and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

(Supplementary Note 22)

The production method according to Supplementary Note 21, wherein in the step (b), a *Rudbeckia* plant that includes the polynucleotide of (ca) as the cytoplasmic male sterility gene is selected.

(Supplementary Note 23)

The production method according to Supplementary Note 21 or 22, wherein in the step (b), a *Rudbeckia* plant that includes the polynucleotides of (ca) to (cf) as the cytoplasmic male sterility genes is selected.

(Supplementary Note 24)

The production method according to any one of Supplementary Notes 21 to 23, wherein in the step (b), the cytoplasmic male sterility gene is detected in the one or more test *Rudbeckia* plants to select a test *Rudbeckia* plant that includes the cytoplasmic male sterility gene.

(Supplementary Note 25)

The production method according to any one of Supplementary Notes 21 to 24, wherein in the step (b), the cytoplasmic male sterility gene is detected in mitochondrial genomes of the one or more test *Rudbeckia* plants to select a test *Rudbeckia* plant that includes the cytoplasmic male sterility gene.

<Method for Conferring Cytoplasmic Male Sterility to *Rudbeckia* Plant>

(Supplementary Note 26)

A method for conferring cytoplasmic male sterility to a *Rudbeckia* plant, the method including the step of:

introducing, as a cytoplasmic male sterility gene, at least one polynucleotide selected from the group consisting of polynucleotides of (ca) to (ce) and (cf) below into a *Rudbeckia* plant of interest:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under a stringent condition and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under a stringent condition and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under a stringent condition and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under a stringent condition and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under a stringent condition and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under a stringent condition and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

(Supplementary Note 27)

The conferring method according to Supplementary Note 26, wherein in the introducing step, a *Rudbeckia* plant that includes the polynucleotide of (ca) as the cytoplasmic male sterility gene is introduced.

(Supplementary Note 28)

The conferring method according to Supplementary Note 26 or 27, wherein in the introducing step, a *Rudbeckia* plant that includes the polynucleotides of (ca) to (cf) as the cytoplasmic male sterility genes is introduced.

(Supplementary Note 29)

The conferring method according to any one of Supplementary Notes 26 to 28, wherein in the introducing step, the cytoplasmic male sterility gene is introduced into a mitochondrial genome of the *Rudbeckia* plant of interest.

<Method for Producing Male Sterile *Rudbeckia* Plant (Second Production Method)>

(Supplementary Note 30)

A method for producing a cytoplasmic male sterile *Rudbeckia* plant, the method including the step of:

conferring cytoplasmic male sterility to a *Rudbeckia* plant of interest, wherein the conferring step is performed by the conferring method according to any one of Supplementary Notes 26 to 29.

<Screening Method for Male Sterile *Rudbeckia* Plant>

(Supplementary Note 31)

A screening method for a cytoplasmic male sterile *Rudbeckia* plant, the screening method including the step of:

selecting, from one or more test *Rudbeckia* plants, a test *Rudbeckia* plant that includes, as a cytoplasmic male sterility gene, at least one polynucleotide selected from the group consisting of polynucleotides of (ca) to (ce) and (cf) below as a cytoplasmic male sterile *Rudbeckia* plant:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under a stringent condition and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under a stringent condition and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under a stringent condition and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under a stringent condition and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under a stringent condition and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under a stringent condition and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

(Supplementary Note 32)

The screening method according to Supplementary Note 31, wherein in the selection step, a *Rudbeckia* plant that includes the polynucleotide of (ca) as the cytoplasmic male sterility gene is selected.

(Supplementary Note 33)

The screening method according to Supplementary Note 31 or 32, wherein in the selection step, a *Rudbeckia* plant that includes the polynucleotides of (ca) to (cf) as the cytoplasmic male sterility genes is selected.

(Supplementary Note 34)

The screening method according to any one of Supplementary Notes 31 to 33, wherein in the selection step, the cytoplasmic male sterility gene is detected in the one or more test *Rudbeckia* plants to select a test *Rudbeckia* plant that includes the cytoplasmic male sterility gene.

(Supplementary Note 35)

The screening method according to any one of Supplementary Notes 31 to 34, wherein in the selection step, the cytoplasmic male sterility gene is detected in mitochondrial genomes of the one or more test *Rudbeckia* plants to select a test *Rudbeckia* plant that includes the cytoplasmic male sterility gene.

<Method for Producing Male Sterile *Rudbeckia* Plant (Third Production Method)>

(Supplementary Note 36)

A method for producing a cytoplasmic male sterile *Rudbeckia* plant, the method including the step of:

screening one or more test *Rudbeckia* plants for a test *Rudbeckia* plant that includes a cytoplasmic male sterility gene, wherein the screening step is performed by the screening method according to any one of Supplementary Notes 31 to 35.

<Cytoplasmic Male Sterile *Rudbeckia* Plant>

(Supplementary Note 37)

A cytoplasmic male sterile *Rudbeckia* plant obtained by the production method according to any one of Supplementary Notes 13 to 25, the production method according to Supplementary Note 30, or the production method according to Supplementary Note 36.

<Method for Detecting Cytoplasmic Male Sterility in *Rudbeckia* Plant>

(Supplementary Note 38)

A method for detecting cytoplasmic male sterility of a *Rudbeckia* plant, the method including the step of:

detecting, as a cytoplasmic male sterility gene, at least one polynucleotide selected from the group consisting of polynucleotides of (ca) to (ce) and (cf) below in a test *Rudbeckia* plant:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under a stringent condition and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under a stringent condition and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under a stringent condition and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under a stringent condition and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under a stringent condition and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under a stringent condition and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

(Supplementary Note 39)

The detection method according to Supplementary Note 38, wherein in the detection step, the polynucleotide of (ca) is detected as the cytoplasmic male sterility gene.

(Supplementary Note 40)

The detection method according to Supplementary Note 38 or 39, wherein in the selection step, the polynucleotides of (ca) to (cf) are detected as the cytoplasmic male sterility genes.

<First Deposited Line>

(Supplementary Note 41)

A seed of a *Rudbeckia* plant, deposited under Accession No. FERM BP-22428.

(Supplementary Note 42)

A *Rudbeckia* plant grown from a seed of a *Rudbeckia* plant deposited under Accession No. FERM BP-22428.

(Supplementary Note 43)

A progeny line of the *Rudbeckia* plant according to Supplementary Note 41 or 42.

(Supplementary Note 44)

The progeny line according to Supplementary Note 43, which is a hybrid first-generation line.

(Supplementary Note 45)

A seed of the *Rudbeckia* plant according to Supplementary Note 41 or 42 or of the progeny line according to Supplementary Note 43 or 44.

(Supplementary Note 46)

A part of the *Rudbeckia* plant according to Supplementary Note 41 or 42 or of the progeny line according to Supplementary Note 43 or 44.

(Supplementary Note 47)

A callus including:

cells of the *Rudbeckia* plant according to Supplementary Note 41 or 42 or cells of the progeny line according to Supplementary Note 43 or 44.

(Supplementary Note 48)

Cytoplasm included in the *Rudbeckia* plant according to Supplementary Note 41 or 42, the progeny line according to Supplementary Note 43 or 44, the seed according to Supplementary Note 45, the part according to Supplementary Note 46, or the callus according to Supplementary Note 47.

(Supplementary Note 49)

A mitochondrion included in the *Rudbeckia* plant according to Supplementary Note 41 or 42, the progeny line according to Supplementary Note 43 or 44, the seed according to Supplementary Note 45, the part according to Supplementary Note 46, or the callus according to Supplementary Note 47.

(Supplementary Note 50)

A mitochondrial genome included in the *Rudbeckia* plant according to Supplementary Note 41 or 42, the progeny line according to Supplementary Note 43 or 44, the seed according to Supplementary Note 45, the part according to Supplementary Note 46, or the callus according to Supplementary Note 47.

(Supplementary Note 51)

A method for producing a *Rudbeckia* plant, the method including the step of:

crossing the *Rudbeckia* plant according to Supplementary Note 41 or 42 or the progeny line according to Supplementary Note 43 or 44 with another *Rudbeckia* plant.

(Supplementary Note 52)

The production method according to Supplementary Note 51, further including the step of collecting a seed.

<Second Deposited Line>

(Supplementary Note 53)

A seed of a *Rudbeckia* variety Takii 22, wherein a representative sample thereof is a seed of a *Rudbeckia* plant deposited under Accession No. FERM BP-22428.

(Supplementary Note 54)

A *Rudbeckia* plant of a *Rudbeckia* variety Takii 22, wherein a representative sample thereof is a seed of a *Rudbeckia* plant deposited under Accession No. FERM BP-22428.

(Supplementary Note 55)

A *Rudbeckia* plant or a part thereof, wherein the *Rudbeckia* plant or the part thereof has essentially all physiological and morphological characteristics of the *Rudbeckia* plant according to Supplementary Note 54.

(Supplementary Note 56)

A progeny *Rudbeckia* plant of the *Rudbeckia* plant according to Supplementary Note 54, wherein the progeny *Rudbeckia* plant includes at least 50% of alleles of the *Rudbeckia* plant according to Supplementary Note 54, and the progeny *Rudbeckia* plant is cytoplasmic male sterile.

(Supplementary Note 57)

A seed that produces the *Rudbeckia* plant according to Supplementary Note 56.

(Supplementary Note 58)

A part of the *Rudbeckia* plant according to Supplementary Note 54.

(Supplementary Note 59)

The part of the plant according to Supplementary Note 58, wherein the part of the plant includes an ovary, an ovule, an egg cell, a cutting, a root, a trunk, a leaf, a cell, or a protoplast.

(Supplementary Note 60)

A method for producing a *Rudbeckia* seed, the method including:

crossing the *Rudbeckia* plant according to Supplementary Note 54 with another *Rudbeckia* plant; and collecting a resulting seed.

(Supplementary Note 61)

A *Rudbeckia* seed derived from a *Rudbeckia* plant, produced by the method according to Supplementary Note 60.

(Supplementary Note 62)

A *Rudbeckia* plant or a part thereof, produced by growing the *Rudbeckia* seed according to Supplementary Note 61.

(Supplementary Note 63)

The *Rudbeckia* plant or the part thereof according to Supplementary Note 62, wherein the *Rudbeckia* plant or the part thereof includes at least 50% of alleles of a *Rudbeckia* variety Takii 22 whose representative sample is a seed of a *Rudbeckia* plant deposited under Accession No. FERM BP-22428, and the *Rudbeckia* plant or the part thereof has cytoplasmic male sterility.

(Supplementary Note 64)

The *Rudbeckia* plant or the part thereof according to Supplementary Note 63, wherein one or more traits of the *Rudbeckia* plant or the part thereof have been modified.

(Supplementary Note 65)

The *Rudbeckia* plant or the part thereof according to Supplementary Note 64, wherein the modification has been caused by mutagenesis.

(Supplementary Note 66)

A method for producing a seed of a *Rudbeckia* plant derived from the *Rudbeckia* plant according to Supplementary Note 54, the method including the steps of:

(a) crossing a *Rudbeckia* variety Takii 22, which is a seed of a *Rudbeckia* plant deposited under Accession No. FERM BP-22428, with another *Rudbeckia* plant to produce a seed;

(b) growing a *Rudbeckia* plant from the seed obtained in the step (a) to produce a *Rudbeckia* plant derived from the *Rudbeckia* variety Takii 22;

(c) crossing the *Rudbeckia* plant obtained in the step (b) with another *Rudbeckia* plant to produce an additional *Rudbeckia* plant derived from the *Rudbeckia* variety Takii 22; and (d) optionally repeating the steps (b) and (c) one or more times to further produce a *Rudbeckia* plant(s) derived from the *Rudbeckia* variety Takii 22, wherein a *Rudbeckia* plant used in a repeated step (b) is grown from an additional *Rudbeckia* plant obtained in a preceding step (c).

(Supplementary Note 67)

A seed produced by the method according to Supplementary Note 66, wherein the seed includes at least 50% of alleles of the *Rudbeckia* plant according to Supplementary Note 54, and a *Rudbeckia* plant grown from the seed is cytoplasmic male sterile.

(Supplementary Note 68)

A *Rudbeckia* plant produced by growing the seed according to Supplementary Note 67.

(Supplementary Note 69)

A method for introducing at least one new trait into the *Rudbeckia* plant according to Supplementary Note 54, the method including the steps of:

(a) crossing a *Rudbeckia* variety Takii 22, which is a seed of a *Rudbeckia* plant deposited under Accession No. FERM BP-22428, with a *Rudbeckia* plant including at least one new trait to produce one or more progenies;

(b) selecting a progeny including at least one new trait;

(c) crossing the progeny with the *Rudbeckia* variety Takii 22 to produce one or more backcross progenies;

(d) selecting a backcross progeny having at least one new trait and having essentially all physiological and morphological characteristics of the *Rudbeckia* variety Takii 22; and (e) optionally repeating the steps (c) and (d) one or more times to produce a *Rudbeckia* plant(s) having at least one new trait and having essentially all physiological and morphological characteristics of the *Rudbeckia* variety Takii 22, wherein a *Rudbeckia* plant used in a repeated step (c) is a backcross progeny selected in a preceding step (d).

(Supplementary Note 70)

A *Rudbeckia* plant produced by the method according to Supplementary Note 69.

(Supplementary Note 71)

A method for producing a *Rudbeckia* plant derived from a *Rudbeckia* variety Takii 22 and having at least one new trait, the method including the step of:

introducing a mutation or transgene that confers at least one trait into a *Rudbeckia* variety Takii 22, which is a seed of a *Rudbeckia* plant deposited under Accession No. FERM BP-22428.

(Supplementary Note 72)

A *Rudbeckia* plant produced by the method according to Supplementary Note 71.

(Supplementary Note 73)

A method for determining a genotype of the *Rudbeckia* plant according to Supplementary Note 54, the method including the steps of:

(a) obtaining a nucleic acid sample from the *Rudbeckia* plant according to Supplementary Note 54; and (b) detecting a polymorphism in the nucleic acid sample.

(Supplementary Note 74)

A tissue culture of regenerable cells or regenerable protoplasts derived from the *Rudbeckia* plant according to Supplementary Note 54.

(Supplementary Note 75)

The tissue culture according to Supplementary Note 74, wherein the cells or the protoplasts are derived from a leaf, an embryo, a cotyledon, a hypocotyl, a meristematic cell, a root, a root tip, an anther, a flower, a seed, or a stem.

(Supplementary Note 76)

A *Rudbeckia* plant regenerated from the tissue culture according to Supplementary Note 75.

(Supplementary Note 77)

The *Rudbeckia* plant according to Supplementary Note 76, which is cytoplasmic male sterile.

(Supplementary Note 78)

A method for vegetative propagation of the *Rudbeckia* plant according to Supplementary Note 54, the method including the steps of:

(a) collecting propagatable tissue from a *Rudbeckia* plant of a *Rudbeckia* variety Takii 22, which is a seed of a *Rudbeckia* plant deposited under Accession No. FERM BP-22428;

(b) culturing the tissue to obtain a grown shoot;

(c) rooting the grown shoot to obtain a rooted plantlet; and (d) optionally growing a plant from the rooted plantlet.

(Supplementary Note 79)

A *Rudbeckia* plantlet or *Rudbeckia* plant produced by the method according to Supplementary Note 78, wherein the *Rudbeckia* plantlet or *Rudbeckia* plant is cytoplasmic male sterile.

<Male Sterility Gene>

(Supplementary Note 80)

A cytoplasmic male sterility gene including at least one polynucleotide selected from the group consisting of polynucleotides of (ca) to (ce) and (cf) below:

(ca) a polynucleotide of any of (ca1) to (ca7) below:

(ca1) a polynucleotide that consists of a base sequence of SEQ ID NO: 1;

(ca2) a polynucleotide that consists of the base sequence of (ca1) with deletion, substitution, insertion, and/or addition of one or several bases and causes expression of cytoplasmic male sterility;

(ca3) a polynucleotide that consists of a base sequence having at least 80% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under a stringent condition and causes expression of cytoplasmic male sterility;

(ca5) a polynucleotide encoding a polypeptide that consists of an amino acid sequence of SEQ ID NO: 2;

(ca6) a polynucleotide that consists of the amino acid sequence of SEQ ID NO: 2 with deletion, substitution, insertion, and/or addition of one or several amino acids and causes expression of cytoplasmic male sterility; and (ca7) a polynucleotide that consists of an amino acid sequence having at least 80% sequence identity to the amino acid sequence of SEQ ID NO: 2 and causes expression of cytoplasmic male sterility;

(cb) a polynucleotide of any of (cb1) to (cb7) below:

(cb1) a polynucleotide that consists of a base sequence of SEQ ID NO: 3;

(cb2) a polynucleotide that consists of the base sequence of (cb1) with deletion, substitution, insertion, and/or addition of one or several bases and causes expression of cytoplasmic male sterility;

(cb3) a polynucleotide that consists of a base sequence having at least 80% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under a stringent condition and causes expression of cytoplasmic male sterility;

(cb5) a polynucleotide encoding a polypeptide that consists of an amino acid sequence of SEQ ID NO: 4;

(cb6) a polynucleotide that consists of the amino acid sequence of SEQ ID NO: 4 with deletion, substitution, insertion, and/or addition of one or several amino acids and causes expression of cytoplasmic male sterility; and (cb7) a polynucleotide that consists of an amino acid sequence having at least 80% sequence identity to the amino acid sequence of SEQ ID NO: 4 and causes expression of cytoplasmic male sterility;

(cc) a polynucleotide of any of (cc1) to (cc7) below:

(cc1) a polynucleotide that consists of a base sequence of SEQ ID NO: 5;

(cc2) a polynucleotide that consists of the base sequence of (cc1) with deletion, substitution, insertion, and/or addition of one or several bases and causes expression of cytoplasmic male sterility;

(cc3) a polynucleotide that consists of a base sequence having at least 80% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under a stringent condition and causes expression of cytoplasmic male sterility;

(cc5) a polynucleotide encoding a polypeptide that consists of an amino acid sequence of SEQ ID NO: 6;

(cc6) a polynucleotide that consists of the amino acid sequence of SEQ ID NO: 6 with deletion, substitution, insertion, and/or addition of one or several amino acids and causes expression of cytoplasmic male sterility; and (cc7) a polynucleotide that consists of an amino acid sequence having at least 80% sequence identity to the amino acid sequence of SEQ ID NO: 6 and causes expression of cytoplasmic male sterility;

(cd) a polynucleotide of any of (cd1) to (cd7) below:

(cd1) a polynucleotide that consists of a base sequence of SEQ ID NO: 7;

(cd2) a polynucleotide that consists of the base sequence of (cd1) with deletion, substitution, insertion, and/or addition of one or several bases and causes expression of cytoplasmic male sterility;

(cd3) a polynucleotide that consists of a base sequence having at least 80% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under a stringent condition and causes expression of cytoplasmic male sterility;

(cd5) a polynucleotide encoding a polypeptide that consists of an amino acid sequence of SEQ ID NO: 8;

(cd6) a polynucleotide that consists of the amino acid sequence of SEQ ID NO: 8 with deletion, substitution, insertion, and/or addition of one or several amino acids and causes expression of cytoplasmic male sterility; and (cd7) a polynucleotide that consists of an amino acid sequence having at least 80% sequence identity to the amino acid sequence of SEQ ID NO: 8 and causes expression of cytoplasmic male sterility;

(ce) a polynucleotide of any of (ce1) to (ce7) below:

(ce1) a polynucleotide that consists of a base sequence of SEQ ID NO: 9;

(ce2) a polynucleotide that consists of the base sequence of (ce1) with deletion, substitution, insertion, and/or addition of one or several bases and causes expression of cytoplasmic male sterility;

(ce3) a polynucleotide that consists of a base sequence having at least 80% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under a stringent condition and causes expression of cytoplasmic male sterility;

(ce5) a polynucleotide encoding a polypeptide that consists of an amino acid sequence of SEQ ID NO: 10;

(ce6) a polynucleotide that consists of the amino acid sequence of SEQ ID NO: 10 with deletion, substitution, insertion, and/or addition of one or several amino acids and causes expression of cytoplasmic male sterility; and (ce7) a polynucleotide that consists of an amino acid sequence having at least 80% sequence identity to the amino acid sequence of SEQ ID NO: 10 and causes expression of cytoplasmic male sterility; and (cf) a polynucleotide of any of (cf1) to (cf7) below:

(cf1) a polynucleotide that consists of a base sequence of SEQ ID NO: 11;

(cf2) a polynucleotide that consists of the base sequence of (cf1) with deletion, substitution, insertion, and/or addition of one or several bases and causes expression of cytoplasmic male sterility;

(cf3) a polynucleotide that consists of a base sequence having at least 80% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under a stringent condition and causes expression of cytoplasmic male sterility;

(cf5) a polynucleotide encoding a polypeptide that consists of an amino acid sequence of SEQ ID NO: 12;

(cf6) a polynucleotide that consists of the amino acid sequence of SEQ ID NO: 12 with deletion, substitution, insertion, and/or addition of one or several amino acids and causes expression of cytoplasmic male sterility; and (cf7) a polynucleotide that consists of an amino acid sequence having at least 80% sequence identity to the amino acid sequence of SEQ ID NO: 12 and causes expression of cytoplasmic male sterility.

<Male Sterility Protein>

(Supplementary Note 81)

A cytoplasmic male sterility protein including at least one polypeptide selected from the group consisting of polypeptides of (CA) to (CE) and (CF) below:

(CA) a polypeptide of any of (CA1) to (CA3) below:

(CA1) a polypeptide that consists of an amino acid sequence of SEQ ID NO: 2;

(CA2) a polypeptide that consists of the amino acid sequence of SEQ ID NO: 2 with deletion, substitution, insertion, and/or addition of one or several amino acids and causes expression of cytoplasmic male sterility; and (CA3) a polypeptide that consists of an amino acid sequence having at least 80% sequence identity to the amino acid sequence of SEQ ID NO: 2 and causes expression of cytoplasmic male sterility;

(CB) a polypeptide of any of (CB1) to (CB3) below:

(CB1) a polypeptide that consists of an amino acid sequence of SEQ ID NO: 4;

(CB2) a polypeptide that consists of the amino acid sequence of SEQ ID NO: 4 with deletion, substitution, insertion, and/or addition of one or several amino acids and causes expression of cytoplasmic male sterility; and (CB3) a polypeptide that consists of an amino acid sequence having at least 80% sequence identity to the amino acid sequence of SEQ ID NO: 4 and causes expression of cytoplasmic male sterility;

(CC) a polypeptide of any of (CC1) to (CC3) below:

(CC1) a polypeptide that consists of an amino acid sequence of SEQ ID NO: 6;

(CC2) a polypeptide that consists of the amino acid sequence of SEQ ID NO: 6 with deletion, substitution, insertion, and/or addition of one or several amino acids and causes expression of cytoplasmic male sterility; and (CC3) a polypeptide that consists of an amino acid sequence having at least 80% sequence identity to the amino acid sequence of SEQ ID NO: 6 and causes expression of cytoplasmic male sterility;

(CD) a polypeptide of any of (CD1) to (CD3) below:

(CD1) a polypeptide that consists of an amino acid sequence of SEQ ID NO: 8;

(CD2) a polypeptide that consists of the amino acid sequence of SEQ ID NO: 8 with deletion, substitution, insertion, and/or addition of one or several amino acids and causes expression of cytoplasmic male sterility; and (CD3) a polypeptide that consists of an amino acid sequence having at least 80% sequence identity to the amino acid sequence of SEQ ID NO: 8 and causes expression of cytoplasmic male sterility;

(CE) a polypeptide of any of (CE1) to (CE3) below:

(CE1) a polypeptide that consists of an amino acid sequence of SEQ ID NO: 10;

(CE2) a polypeptide that consists of the amino acid sequence of SEQ ID NO: 10 with deletion, substitution, insertion, and/or addition of one or several amino acids and causes expression of cytoplasmic male sterility; and (CE3) a polypeptide that consists of an amino acid sequence having at least 80% sequence identity to the amino acid sequence of SEQ ID NO: 10 and causes expression of cytoplasmic male sterility; and (CF) a polypeptide of any of (CF1) to (CF3) below:

(CF1) a polypeptide that consists of an amino acid sequence of SEQ ID NO: 12;

(CF2) a polypeptide that consists of the amino acid sequence of SEQ ID NO: 12 with deletion, substitution, insertion, and/or addition of one or several amino acids and causes expression of cytoplasmic male sterility; and (CF3) a polypeptide that consists of an amino acid sequence having at least 80% sequence identity to the amino acid sequence of SEQ ID NO: 12 and causes expression of cytoplasmic male sterility.

<Expression Vector>

(Supplementary Note 82)

An expression vector including:

the cytoplasmic male sterility gene according to Supplementary Note 80.

<Transformant>

(Supplementary Note 83)

A transformant including:

the cytoplasmic male sterility gene according to Supplementary Note 80 or the expression vector according to Supplementary Note 82.

INDUSTRIAL APPLICABILITY

As specifically described above, the *Rudbeckia* plant of the present disclosure is cytoplasmic male sterile. Therefore, the present disclosure is very useful in the fields of, for example, breeding and agriculture.

The invention claimed is:

1. A *Rudbeckia* plant with cytoplasmic male sterility, comprising:

a (ca) polynucleotide selected from the group consisting of:

(ca1) a polynucleotide that consists of a base sequence of SEQ ID NO: 1;

(ca2) a polynucleotide that consists of the base sequence of (ca1) with deletion, substitution, insertion, and/or addition of 1 to 67 bases and causes expression of cytoplasmic male sterility;

(ca3) a polynucleotide that consists of a base sequence having at least 90% sequence identity to the base sequence of (ca1) and causes expression of cytoplasmic male sterility;

(ca4) a polynucleotide that consists of a base sequence complementary to a polynucleotide hybridizing to the polynucleotide consisting of the base sequence of (ca1) under a stringent condition and causes expression of cytoplasmic male sterility;

(ca5) a polynucleotide encoding a polypeptide that consists of an amino acid sequence of SEQ ID NO: 2;

(ca6) a polynucleotide encoding a polypeptide that consists of the amino acid sequence of SEQ ID NO: 2 with deletion, substitution, insertion, and/or addition of 1 to 22 amino acids and causes expression of cytoplasmic male sterility; and (ca7) a polynucleotide encoding a polypeptide that consists of an amino acid sequence having at least 90% sequence identity to the amino acid sequence of SEQ ID NO: 2 and causes expression of cytoplasmic male sterility, a (cb) polynucleotide selected from the group consisting of:

(cb1) a polynucleotide that consists of a base sequence of SEQ ID NO: 3;

(cb2) a polynucleotide that consists of the base sequence of (cb1) with deletion, substitution, insertion, and/or addition of 1 to 280 bases and causes expression of cytoplasmic male sterility;

(cb3) a polynucleotide that consists of a base sequence having at least 90% sequence identity to the base sequence of (cb1) and causes expression of cytoplasmic male sterility;

(cb4) a polynucleotide that consists of a base sequence complementary to a polynucleotide hybridizing to the polynucleotide consisting of the base sequence of (cb1) under a stringent condition and causes expression of cytoplasmic male sterility;

(cb5) a polynucleotide encoding a polypeptide that consists of an amino acid sequence of SEQ ID NO: 4;

(cb6) a polynucleotide encoding a polypeptide that consists of the amino acid sequence of SEQ ID NO: 4 with deletion, substitution, insertion, and/or addition of 1 to 93 amino acids and causes expression of cytoplasmic male sterility; and (cb7) a polynucleotide encoding a polypeptide that consists of an amino acid sequence having at least 90% sequence identity to the amino acid sequence of SEQ ID NO: 4 and causes expression of cytoplasmic male sterility, a (cc) polynucleotide selected from the group consisting of:

(cc1) a polynucleotide that consists of a base sequence of SEQ ID NO: 5;

(cc2) a polynucleotide that consists of the base sequence of (cc1) with deletion, substitution, insertion, and/or addition of 1 to 126 bases and causes expression of cytoplasmic male sterility;

(cc3) a polynucleotide that consists of a base sequence having at least 90% sequence identity to the base sequence of (cc1) and causes expression of cytoplasmic male sterility;

(cc4) a polynucleotide that consists of a base sequence complementary to a polynucleotide hybridizing to the polynucleotide consisting of the base sequence of (cc1) under a stringent condition and causes expression of cytoplasmic male sterility;

(cc5) a polynucleotide encoding a polypeptide that consists of an amino acid sequence of SEQ ID NO: 6;

(cc6) a polynucleotide encoding a polypeptide that consists of the amino acid sequence of SEQ ID NO: 6 with deletion, substitution, insertion, and/or addition of 1 to 42 amino acids and causes expression of cytoplasmic male sterility; and (cc7) a polynucleotide encoding a polypeptide that consists of an amino acid sequence having at least 90% sequence identity to the amino acid sequence of SEQ ID NO: 6 and causes expression of cytoplasmic male sterility, a (cd) polynucleotide selected from the group consisting of:

(cd1) a polynucleotide that consists of a base sequence of SEQ ID NO: 7;

(cd2) a polynucleotide that consists of the base sequence of (cd1) with deletion, substitution, insertion, and/or addition of 1 to 291 bases and causes expression of cytoplasmic male sterility;

(cd3) a polynucleotide that consists of a base sequence having at least 90% sequence identity to the base sequence of (cd1) and causes expression of cytoplasmic male sterility;

(cd4) a polynucleotide that consists of a base sequence complementary to a polynucleotide hybridizing to the polynucleotide consisting of the base sequence of (cd1) under a stringent condition and causes expression of cytoplasmic male sterility;

(cd5) a polynucleotide encoding a polypeptide that consists of an amino acid sequence of SEQ ID NO: 8;

(cd6) a polynucleotide encoding a polypeptide that consists of the amino acid sequence of SEQ ID NO: 8 with deletion, substitution, insertion, and/or addition of 1 to 97 amino acids and causes expression of cytoplasmic male sterility; and (cd7) a polynucleotide encoding a polypeptide that consists of an amino acid sequence having at least 90% sequence identity to the amino acid sequence of SEQ ID NO: 8 and causes expression of cytoplasmic male sterility, a (ce) polynucleotide selected from the group consisting of:

(ce1) a polynucleotide that consists of a base sequence of SEQ ID NO: 9;

(ce2) a polynucleotide that consists of the base sequence of (ce1) with deletion, substitution, insertion, and/or addition of 1 to 114 bases and causes expression of cytoplasmic male sterility;

(ce3) a polynucleotide that consists of a base sequence having at least 90% sequence identity to the base sequence of (ce1) and causes expression of cytoplasmic male sterility;

(ce4) a polynucleotide that consists of a base sequence complementary to a polynucleotide hybridizing to the polynucleotide consisting of the base sequence of (ce1) under a stringent condition and causes expression of cytoplasmic male sterility;

(ce5) a polynucleotide encoding a polypeptide that consists of an amino acid sequence of SEQ ID NO: 10;

(ce6) a polynucleotide encoding a polypeptide that consists of the amino acid sequence of SEQ ID NO: 10 with deletion, substitution, insertion, and/or addition of 1 to 38 amino acids and causes expression of cytoplasmic male sterility; and (ce7) a polynucleotide encoding a polypeptide that consists of an amino acid sequence having at least 90% sequence identity to the amino acid sequence of SEQ ID NO: 10 and causes expression of cytoplasmic male sterility, and a (cf) polynucleotide of selected from the group consisting of:

(cf1) a polynucleotide that consists of a base sequence of SEQ ID NO: 11;

(cf2) a polynucleotide that consists of the base sequence of (cf1) with deletion, substitution, insertion, and/or addition of 1 to 46 bases and causes expression of cytoplasmic male sterility;

(cf3) a polynucleotide that consists of a base sequence having at least 90% sequence identity to the base sequence of (cf1) and causes expression of cytoplasmic male sterility;

(cf4) a polynucleotide that consists of a base sequence complementary to a polynucleotide hybridizing to the polynucleotide consisting of the base sequence of (cf1) under a stringent condition and causes expression of cytoplasmic male sterility;

(cf5) a polynucleotide encoding a polypeptide that consists of an amino acid sequence of SEQ ID NO: 12;

(cf6) a polynucleotide encoding a polypeptide that consists of the amino acid sequence of SEQ ID NO: 12 with deletion, substitution, insertion, and/or addition of 1 to 15 amino acids and causes expression of cytoplasmic male sterility; and (cf7) a polynucleotide encoding a polypeptide that consists of an amino acid sequence having at least 90% sequence identity to the amino acid sequence of SEQ ID NO: 12 and causes expression of cytoplasmic male sterility.

2. The *Rudbeckia* plant according to claim 1, wherein the plant comprises (ca1) the polynucleotide of SEQ ID NO: 1.

3. The *Rudbeckia* plant according to claim 1, wherein the plant comprises (ca3) the polynucleotide having at least 90% sequence identity to the base sequence of (ca1).

4. The *Rudbeckia* plant according to claim 1, wherein the plant comprises (ca5) the amino acid sequence of SEQ ID NO: 2.

5. The *Rudbeckia* plant according to claim 1, wherein the plant comprises (cb1) the polynucleotide of SEQ ID NO: 3.

6. The *Rudbeckia* plant according to claim 1, wherein the plant comprises (cb3) the polynucleotide having at least 90% sequence identity to the base sequence of (cb1).

7. The *Rudbeckia* plant according to claim 1, wherein the plant comprises (cb5) the amino acid sequence of SEQ ID NO: 4.

8. The *Rudbeckia* plant according to claim 1, wherein the plant comprises (cc1) the polynucleotide of SEQ ID NO: 5.

9. The *Rudbeckia* plant according to claim 1, wherein the plant comprises (cc3) the polynucleotide having at least 90% sequence identity to the base sequence of (cc1).

10. The *Rudbeckia* plant according to claim 1, wherein the plant comprises (cc5) the amino acid sequence of SEQ ID NO: 6.

11. The *Rudbeckia* plant according to claim 1, wherein the plant comprises (cd1) the polynucleotide of SEQ ID NO: 7.

12. The *Rudbeckia* plant according to claim 1, wherein the plant comprises (cd3) the polynucleotide having at least 90% sequence identity to the base sequence of (cd1).

13. The *Rudbeckia* plant according to claim 1, wherein the plant comprises (cd5) the amino acid sequence of SEQ ID NO: 8.

14. The *Rudbeckia* plant according to claim 1, wherein the plant comprises (ce1) the polynucleotide of SEQ ID NO: 9.

15. The *Rudbeckia* plant according to claim 1, wherein the plant comprises (ce3) the polynucleotide having at least 90% sequence identity to the base sequence of (ce1).

16. The *Rudbeckia* plant according to claim 1, wherein the plant comprises (ce5) the amino acid sequence of SEQ ID NO: 10.

17. The *Rudbeckia* plant according to claim 1, wherein the plant comprises (cf1) the polynucleotide of SEQ ID NO: 11.

18. The *Rudbeckia* plant according to claim 1, wherein the plant comprises (cf3) the polynucleotide having at least 90% sequence identity to the base sequence of (cf1).

19. The *Rudbeckia* plant according to claim 1, wherein the plant comprises (cf5) the amino acid sequence of SEQ ID NO: 12.

20. The *Rudbeckia* plant according to claim 1, wherein the plant comprises (ca1) the polynucleotide of SEQ ID NO: 1, (cb1) the polynucleotide of SEQ ID NO: 3, (cc1) the polynucleotide of SEQ ID NO: 5, (cd1) the polynucleotide of SEQ ID NO: 7, (ce1) the polynucleotide of SEQ ID NO: 9, and (cf1) the polynucleotide of SEQ ID NO: 11.

\*    \*    \*    \*    \*

SEQUENCE LISTING

```
Sequence total quantity: 19
SEQ ID NO: 1              moltype = DNA  length = 672
FEATURE                   Location/Qualifiers
source                    1..672
                          mol_type = genomic DNA
                          organism = Rudbeckia hirta
SEQUENCE: 1
atgctgctaa ctctcagttt ggtcctactt ctgattcatt ttgttactaa aaaaggagga  60
ggaaacttag taccaaatgc ttggcaatcc ttggtagagc ttatttatga tttcgtgctg  120
aacctggtaa acgaacaaat agggggtctt tccggaaatg ttaaacaaaa gttttttccct  180
tgcatcctgg tcacttttac tttttttgtta ttttgtaatc ttcagggtat gatacctat  240
agcttcacag ttacaagtca tttctcatt actttaggtc tctcattttc gatttttatt  300
ggcattacta tagtgggatt tcaaagaaac gggcttcatt ttttaagctt cttattaccc  360
gcaggagtcc cactgccatt agcaccttttt ttagtactcc ttgagctaat ttcttattgt  420
tttcgcgcat taagcttagg aatacgttta tttgctaata tgatggccgg tcatagttta  480
```

-continued

```
gtaaagattt taagtgggtt cgcttggact atgctatgta tgaatgatct tttgtatttt    540
atagggatc  ttggtccttt atttatagtt cttgcattaa ccggtctgga attaggtgta    600
gctatattac aagcttatgt ttttacgatc ttaatctgta tttacttgaa tgatgctata    660
aatctccatt aa                                                        672

SEQ ID NO: 2               moltype = AA  length = 223
FEATURE                    Location/Qualifiers
source                     1..223
                           mol_type = protein
                           organism = Rudbeckia hirta
SEQUENCE: 2
MLLTLSLVLL LIHFVTKKGG GNLVPNAWQS LVELIYDFVL NLVNEQIGGL SGNVKQKFFP    60
CILVTFTFLL FCNLQGMIPY SFTVTSHFLI TLGLSFSIFI GITIVGFQRN GLHFLSFLLP    120
AGVPLPLAPF LVLLELISYC FRALSLGIRL FANMMAGHSL VKILSGFAWT MLCMNDLLYF    180
IGDLGPLFIV LALTGLELGV AILQAYVFTI LICIYLNDAI NLH                      223

SEQ ID NO: 3               moltype = DNA  length = 2808
FEATURE                    Location/Qualifiers
source                     1..2808
                           mol_type = genomic DNA
                           organism = Rudbeckia hirta
SEQUENCE: 3
atggaacaaa cagttcgtga attcctattg agtactgtgt ctttggatga taacaagaaa    60
aaaggtattg tcgtggattt ctggtctgag ttctatcaaa agaacgtcta tacggaacat    120
caatctaatc agacgaatcg aagtctatat aaggagaagg tatgtgagat attacatgaa    180
tttaaaagga cacatattac accttactct agggaagaat taatagcatt acaggctgag    240
attgagagta ctacgatcat tttcgatgag gcatctattc atgctagtag tggccatata    300
atgaaatata tgattgatcc taaaaaagag agtgctaaag attttgttta tgaacgtctt    360
acctctagga aggagcaatc cattatatcg gatatgggtc aatacacact tgaagcaatc    420
atagtttatg tcatcagtaa gttgtatagt tcagaaacag aaatgattcg tgtatcgact    480
ttgattgatc aactcgataa gcaagttaaa gcacagtctg ttctggtaaa taaacataaa    540
aaaccacttg tgatgaaaga agtaggtcaa aatgttgcct tgggtgagca tttttccaatt    600
ggagctgcat tagttgaatt tatttctgat aggggggttga tgaccattca acatatagat    660
gatagaaggt catctgttcc aattcaaaag aagaaaggaa agtattatat gccaaagtta    720
ctctacgcct tctataattt tgatgtatct ctactccccg ttaagctgaa catccgatg    780
gtctttccac ctatagaatg gagtaatgct cgtgaggata atctagaacc taaaacccta    840
tatgaccttta gaggtggtta catatccggg atgagcgagg tatctcgtta ccatctactc    900
agtagttgga attataacaa ctactatatt gatatagaat ctggtcacga gtcattatgt    960
gtagtaatga acaagctgca gaaagtgcct tttcgaatag ctagtttcat gctcacattt    1020
atcaaagaaa actataatga ctttgtgaag gcaggtttac ttatgccaaa agctctctgt    1080
attgcagata tgaaaaagtt gcgtgattcc ctcagagatt tctacatgaa taatgaaaag    1140
ggaattaaaa caatctatag ctatgacgaa gtcttaacta ttttatacaa ggatgtgcag    1200
cgtgctcgtt ttgagagaat gaccctcatg ctttcagagg cattagaagg ttttaaactc    1260
tacttaccag cctttcttga ctttaggggg agaatctaca gaagcggtat tttacactta    1320
catgaacgag attttgtcag aagcctgctc atctttgaca atttatatga ttataaaaat    1380
caggatgaaa ttatacatat caataaatgt ctttcaatcc tagggcgagc tatacctac    1440
tattggaagt cattttcttc ttatactgat tcagaagaat gatgtcgaaa actaattgaa    1500
atcaaagata atatatgtaa ttcagaattg atcaagtttt cagttagtgc aaaaaaaccc    1560
tttcagttcc ttgcatctgt atgtgcattg aagattgagg atgaaactac tcgtaatcat    1620
tatctcaatt atcttcctat cacccaagat gcttcgtcta gtgcctatca aattatgagt    1680
tttctattgt tagatactca aatagcaaaa caaactaatc tgatttctga gcataaaggt    1740
gagattcatg atatatataa ccatatgaaa gaattactat tggaatacat agaatcttgc    1800
tcgggtgagt acgatttgag tgagaatttg aaagaactag ttatcaaatc cattgaccgt    1860
aagttagtta aggctctttt tatgccaata atctatggaa agactgtgat tagcactgca    1920
acagatctaa gaacaactct ctccaagttc gtgacaaagg atggagagcat gatcctggct    1980
aagatctgct tttctttctg gaaagaaacc tataggggta tggattgttt gatcactctg    2040
atcaagagta ttggatggat ggtctcagcc aggggggagcc atgtccgata tcaaaatcaa    2100
atttataccca cagttcaaaa atacatgaag atggatgcag tcaagatatg gatctatgat    2160
cgagaaaata aaaagaagcg tcaagtcact cttagagtct caacagagaa aaatgataaa    2220
cggaagagtg aaatcgctac cttcgtgaac ttcatccatc agtttgatgc tttcattgca    2280
atgagtgtga tttatgaaat gcctagctat gcttcacata tctacacagt tcacgacaac    2340
tttatcacta ttccaagtag ttgtgatgat ctgccatatc tgtataagaa agccttcagt    2400
tgtaataatc ctctcgcaat catcaaccgt tacatctaca ctaatgtgat ggaacatctt    2460
ggtatgatag aagggctaac tcctgttgaa agtgatcact ttcggagatt aaggaagaaa    2520
gatggatacg ataccttaat cattcacgag aatatactct tgaaatactt aatttgtaat    2580
atgcctatca atctcaaaag aaagaatgag actcagatgt gggaaggaaa gatcaataca    2640
ataataacat catacaaaga gtatgttaga actatatgca tgtgcgaaga tcccgggaaa    2700
gattatgaca taaataaact tgaaaaatgc cgtgatgagt ataccgaaaa tgatcaaaat    2760
ttcattaggc gtatgatgcg aggttccacc aattatagca tacatcat             2808

SEQ ID NO: 4               moltype = AA  length = 936
FEATURE                    Location/Qualifiers
source                     1..936
                           mol_type = protein
                           organism = Rudbeckia hirta
SEQUENCE: 4
MEQTVREFLL STVSLDDNKK KGIVVDFWSE FYQKNVYTEH QSNQTNRSLY KEKVCEILHE    60
FKRTHITPYS REELIALQAE IESTTIIFDE ASIHASSGHI MKYMIDPKKE SAKDFVYERL    120
TSRKEQSIIS DMGQYTLEAI IVYVISKLYS SETEMIRVST LIDQLDKQVK AQSVLVNKHK    180
```

```
KPLVMKEVGQ NVALGEHFPI GAALVEFISD RGLMTIQHID DRRSSVPIQK KKGKYYMPKL    240
LYAFYNFDVS LLPVKLNIPM VFPPIEWSNA REDNLEPKTL YDLRGGYISG MSEVSRYHLL    300
SSWNYNNYYI DIESGHESLC VVMNKLQKVP FRIASFMLTF IKENYNDFVK AGLLMPKALC    360
IADMKKLRDS LRDFYMNNEK GIKTIYSYDE VLTILYKDVQ RARFERMTLM LSEALEGFKL    420
YLPAFLDFRG RIYRSGILHL HERDFVRSLL IFDNLYDYKN QDEIIHINKC LSILGRAIPY    480
YWKSFSSYTD SEEWGRKLIE IKDNICNSEL IKFSVSAKKP FQFLASVCAL KIEDETTRNH    540
YLNYLPITQD ASSSAYQIMS FLLLDTQIAK QTNLISEHKG EIHDIYNHMK ELLLEYIESC    600
SGEYDLSENL KELVIKSIDR KLVKALFMPI IYGKTVISTA TDLRTTLSKF VTKGESMILA    660
KICFSFWKET YRGMDCLITL IKSIGWMVSA RGSHVRYQNQ IYTTVQKYMK MDAVKIWIYD    720
RENKKKRQVT LRVSTEKNDK RKSEIATFVN FIHQFDAFIA MSVIYEMPSY ASHIYTVHDN    780
FITIPSSCDD LPYLYKKAFS CNNPLAIINR YIYTNVMEHL GMIEGLTPVE SDHFRRLRKK    840
DGYDTLIIHE NILLKYLICN MPINLKRKNE TQMWEGKINT IITSYKEYVR TICMCEDPGK    900
DYDINKLEKC RDEYTENDQN FIRRMMRGST NYSIHH                              936

SEQ ID NO: 5              moltype = DNA   length = 1269
FEATURE                   Location/Qualifiers
source                    1..1269
                          mol_type = genomic DNA
                          organism = Rudbeckia hirta
SEQUENCE: 5
atgttaggct ttattgaggc atatgtggta tgtccgaaaa cgatcaagaa gccatttcta    60
ccctatcgag agaaggaggg gactctcctc tttccaactg gagaatttgt aggtgtatac    120
tttagcgaag aattgaagta tgctagagag attggctaca cagtgattcc aatctcaggc    180
tacctctttg agaagaagga aagcccattc agggagtttg taagcgatct ctttgaaagc    240
aggttagaag ctaaaaagtc tgggaatgat gcgttgtctt atgtgtacaa gatccttatg    300
aattcgctat acggtagatt tggcattaac cctatgggca caataactga gatctggcat    360
tccaaaagac ataaactgtt aataagaaag actgagttga tctcaactga tgagcttacc    420
gattccaaat acatcgtgac ctaccgtagc aatacagaga ctgattattg ggatccaccg    480
aagaactctg ctgtccaaat tgctgctgca atcactgcct atgctaggat ctatatgtat    540
ccttatatct caagggagga cagttactac actgacactg gctaggacag    600
ccactctcag atgaattgat ttcatcttct atcttaggta agtttaagct tgaggacaaa    660
atagttgaag ggtacttttt agctccgaag tcctattact acaggaatga taaaggagag    720
gatatactga agtacaaagg gcttgcgaaa acagaaatca ctcctgaatg gtttcgttca    780
cagtacgcta accctgatcg tacgctagaa gtagaggtgg aagcaacctt ccggattgac    840
tggtcctcac ttaacatctt caagaaagat aagaatgtga aggttgggct taatcaaaat    900
ccaaagagga tcaaagtcta tgaagggaag tactgggttg atactatgcc agttgatgtc    960
aaagacctgt ctagactaga taacattagc agaaaactag tcacgtggct aaaggctgat    1020
gtaacacatc ttaagaacga gaatctatct ctcaatgaga aattatcaga gaaggaaaga    1080
gagtaaccg agaagaaaag gatggacgag agagacaatg agatgaaaga agaacctaca    1140
gaggtcacta accctacaat agatatagac gagataccta gatagatat agacgagata    1200
cctaagatga aacctaagaa gaaagccaag actgacaaga aacaacgac aaagaagaag    1260
aaaccccca                                                          1269

SEQ ID NO: 6              moltype = AA   length = 423
FEATURE                   Location/Qualifiers
source                    1..423
                          mol_type = protein
                          organism = Rudbeckia hirta
SEQUENCE: 6
MLGFIEAYVV CPKTIKKPFL PYREKEGTLL FPTGEFVGVY FSEELKYARE IGYTVIPISG    60
YLFEKKESPF REFVSDLFES RLEAKKSGND ALSYVYKILM NSLYGRFGIN PMGTITEICD    120
SKRHKLLIRK TELISTDELT DSKYIVTYRS NTETDYWDPP KNSAVQIAAA ITAYARIYMY    180
PYISREDSYY TDTDSVVLGQ PLSDELISSS ILGKFKLEDK IVEGYFLAPK SYYYRNDKGE    240
DILKYKGLAK TEITPEWFRS QYANPDRTLE VEVEANFRID WSSLNIFKKD KNVKVGLNQN    300
PKRIKVYEGK YWVDTMPVDV KDLSRLDNIS RKLVTWLKAD VTHLKNENLS LNEKLSEKER    360
EITEKKRMDE RDNEMKEEPT EVTNPTIDID EIPKIDIDEI PKMKPKKKAK TDKKTTTKKK    420
KPP                                                                423

SEQ ID NO: 7              moltype = DNA   length = 2916
FEATURE                   Location/Qualifiers
source                    1..2916
                          mol_type = genomic DNA
                          organism = Rudbeckia hirta
SEQUENCE: 7
atgaataaaa tgaatatgaa aatgaaaaga ataatgccta tgtgttctag aaccttacat    60
acgagtgtac gtccagaact agaatttgta ttcaatcgtt atcaatcggt ggtagagcag    120
acaagagtac aggatccgca cccagggtta atcattgcaa cactaaactt caagaaacca    180
ggtctaggtg tagatgatat agaactcatc agcattgcga caatggatct cttaaaccag    240
tatgtttacc catctatctc aggttacggg aagttcacaa tctccttgag gatgatccaa    300
tctatcgaag aagagatcac atatacaata ggatgtgcaa tacccttgac ctcgaatgat    360
gggactctcc taccaaagaa tgagatctac gctcggataa agaagcctat cagaagaat    420
gctgaactct acaacggatg ctctcttgtt caactcataa tcagagcata tctggacaag    480
gtagaacggc tggatcgccc ggagctcaca gtctcagata gatatgagga actgctctca    540
attcagtcag ataaattgag tgagatcgaa gcaatcagtg caaagattag tcaacattca    600
aagcgtcagt atcgagagta tataacaaga atcaaaagat gtgagcagtg taagaaagca    660
ttcattgtct ctgatctcga gacgattcag attgattata acatagacc ttatgccgct    720
ggtctcatgt tggttcgaga agggaaagac atcaaggata gtctaattta tacctacttc    780
agtgaagact actcagtata catcaaaagt tttgagaaaa ggagtcaaaa aggtcctctt    840
gacctggtca ggaagatcat agctctatca aagatagaga gaagtgcaat gaccgtttat    900
```

```
tttcacaact tctctagatt tgatggaatt atcttgttaa agcacctagc atgtcatcat   960
gactacaagc tgaaacaact atttaggaat aacaggcttt acgagttaaa agtctattct  1020
ggcaggaagc tattattcaa aatgagagat tcattgaatc tacttccggg taaactcgac  1080
aacctggcta agagtctatg cccatctcta ggtggtaaag gaagtcttaa ttatgatgat  1140
gtgagagctg ataaccttgt gagtaagaaa gatcaattga tttcatatat gaaacaggac  1200
atcctgttac ttggtggtat aatgaagaag gcacaagaga tctattatga tctctatcaa  1260
ttggatattg tgagcaaaat taccctatcc tcactagctc taagcatcta tcgtatgaga  1320
tattatgatg aggaaaactg gccaatctac atccctaaca tgaatcaaga ccactttatt  1380
agaaaagcat actacggagg gcatactgat gtatacaagc cttatggtga gaacctatac  1440
tactacgatg ttaactcact ctatccttt gtcatgaaga actttcaaat gcctggtggt  1500
caaccagtct ggcatggaaa tctgcttgat aaggacctcg atagcttgta tggctttata  1560
gaggcttatg tagtctgtcc taagacaatc aataaaccct ttctaccccta tcgaaacaag  1620
aataacactc tcatctttcc aacaggggaa tttgcaggtg tctactacag cgaggagtta  1680
aagtttgcta gagaccttgg ttacaccgtg ctcccgctct ctggctacct ctatgagaga  1740
atggaaagcc cattcaaaga atttgttaac acgcaatctt caaagaggat agaagcaaag  1800
aaagaaggaa atgatgcttt atcctatgtt tacaagatcc taatgaactc gctatacggt  1860
agatttggta ttaaccctaa aagcacaaca tccgagatct gtgatcatga tcgatacgtt  1920
aaaatgctca aagacgattc attttacaa ggttcactgc ttgataagaa caaatacata  1980
gtcatatacc atgtcaatac cggtagtaac ccagaatcat ggaacccacc aaagaacggt  2040
gctgtacagc ttgctgctgc tatcacagcc tgtgcaagga tctatatgta cccattgatc  2100
tcgagagagg attgttacta tactgacact gactcggttg tgctaggaca gccactctca  2160
gatgaattga tttctgcttc ggagttaggt atgttaaagc tagaagcaag aatcttaaag  2220
ggctactttt tagcccctaa atcttatgca tacatacagt atgacgagaa taaagagatc  2280
gttatcaagc acaaaggtgc ggctaaaaac ttagtgacca tggaatggtt tcagtcacag  2340
tacgatgacc catcccggac acaactggtc tcggtcacat ccaactttaa aatcaattgg  2400
aatgaactgg aaatccataa gcaagaaact ttatacaggt taggtattag ccaggattct  2460
aaaaggttac cagtatactg cgagaagaaa tggattgata ctgaacctat tgatatcaga  2520
gatctgtcta accatagtcc tcagatgtta gatagaatct tagcctatct cagggatgaa  2580
gtgaatcgtc atcagactaa tagtgagatt ctccgtaaag aactctctaa aaaggatagt  2640
gagatgatca gcatcatttc agataaggat agagtgatct ccgagatgaa aagtcggatt  2700
gaatctcttc aagagatgcg gaaaatcact aacccaactg ataagactga gaagaaaact  2760
catacagcca agaagactaa gactgagaag aaaactcata cagccaagaa gactaagact  2820
gacaagaaga aaaccaccaa tcaaactctg aagaaacatc agaatcaaag aaaacaaagg  2880
cctccaagaa accatcatac taccaagaaa cctccg                            2916
```

```
SEQ ID NO: 8          moltype = AA  length = 972
FEATURE               Location/Qualifiers
source                1..972
                      mol_type = protein
                      organism = Rudbeckia hirta
SEQUENCE: 8
MNKMNMKMKR IMPMCSRTLH TSVRPELEFV FNRYQSVVEQ TRVQDPHPGL IIATLNFKKP    60
GLGVDDIELI SIATMDLLNQ YVYPSISGYG KFTISLRMIQ SIEEEITYTI GCAIPLTSND   120
GTLLPKNEIY ARIKEAYQKN AELYNGCSLV QLIIRAYLDK VERLDRPELT VSDRYEELLS   180
IQSDKLSEIE AISARKIQHS KRQYREYITR IKRVSSGKKA FIVSDLETIQ IDYKHRPYAA   240
GLMLVREGKD IKDSLIYTYF SEDYSVYIKS FEKRSQKVLF DLVRKIIALS KIERSAMTVY   300
FHNFSRFDGI ILLKHLACHH DYKLKQLFRN NRLYELKVYS GRKLLFKMRD SLNLLPGKLD   360
NLAKSLCPSL GGKGSLNYDD VRADNLVSKK DQLISYMKQD ILLLGGIMKK AQEIYYDLYQ   420
LDIVSKITLS SLALSIYRMR YYDEENWPIY IPNMNQDHFI RKAYYGGHTD VYKPYGENLY   480
YYDVNSLYPF VMKNFQMPGG QPVWHGNLLD KDLDSLYGFI EAYVVCPKTI NKPFLPYRNK   540
NNTLIFPTGE FAGVYYSEEL KFARDLGYTV LPLSGYLYER MESPFKEFVN TQSSKRIEAK   600
KEGNDALSYV YKILMNSLYG RFGINPKSTT SEICDHDRYV KMLKDDSFLQ GSLLDKNKYI   660
VIYHVNTGSN PESWNPPKNG AVQLAAAITA CARIYMYPLI SREDCYYTDT DSVVLGQPLS   720
DELISASELG MLKLEARILK GYFLAPKSYA YIQYDENKEI VIKHKGAAKN LVTMEWFQSQ   780
YDDPSRTQLV SVTSNFKINW NELEIHKQET LYRLGISGDS KRLPVYCEKK WIDTEPIDIR   840
DLSNHSPQML DRILAYLRDE VNRHQTNSEI LRKELSKKDS EMISIISDKD RVISEMKSRI   900
ESLQEMRKIT NPTDKTEKKT HTAKKTKTEK KTHTAKKTKT DKKKTTNQTL KKHQNQRKQR   960
PPRNHHTTKK PP                                                       972
```

```
SEQ ID NO: 9          moltype = DNA  length = 1146
FEATURE               Location/Qualifiers
source                1..1146
                      mol_type = genomic DNA
                      organism = Rudbeckia hirta
SEQUENCE: 9
atgacaaatc cggttcaacg cgatcaatct aagtttctta acaatactgt tgtgatgaat    60
gatcaaagaa agaaggatgt ggtggtagag ttttggaaga gcttctatgg tattctttc   120
gtttctttca caaattttgt tctgattctt ctaacttgta tacttgttga acctgagacg   180
gttcagatga ttgctaggtt cattggtggt tcttcagcca tttactttct ttttttagcc   240
agagcacgat tttctaagct cttcaacctc ttttcctttc tggtaaccac ctgttatcta   300
ttcgttctga atcatcttaa tgccccagat ataggtttag ttcctatttg cgtctgtggt   360
tgctttatct tttcttatta ttttacggaa aaacacactg gctggcactt tgatctatgt   420
tttatgatta ttctcacttg tagattgatc gtgtcaccgg acatatgggc tattagcctt   480
gtctttgaac ttttagtctt attttgctta cttgatcatg atatggatca agatcggatg   540
agattgtgtt gtttatattt cattctcctt ctctttctgt gctgtaacta tctctacgga   600
agtagtattc atattgatac tctcgttgtg gttctagttt tagcggcagc aggggcggga   660
ggtatccagt tcatgtctct cagtaagact gaacggggag aaacccttgg actgcagctt   720
tttttgatca ataatgttat cttgggcttc cttcttagaa aggatggcga gaccttaccc   780
atgataacaa tattctttat cgtttccatt ctttgcttct gcatcggctt atacctaata   840
```

-continued

```
ggaaggatta aagagcaatc tttctattca gttctgtctg aattgaagag ctcgcttcgg    900
ggcttgttca tcccggtatt attgaccttg aatcacttct ttttagaaga tcaatattac    960
ctgtggatca caagcctagt gactcgtatt atcgttattc agctcctgca attaattctg   1020
aaaaaggagg atgaagatcc agatcaggac aaagcgataa agagtgacga tgttcgaagg   1080
tgcgaaatca atgggtgccg gagctgctac aactattatt atgcgagaag tcctcccgat   1140
tgctac                                                               1146

SEQ ID NO: 10            moltype = AA  length = 382
FEATURE                  Location/Qualifiers
source                   1..382
                         mol_type = protein
                         organism = Rudbeckia hirta
SEQUENCE: 10
MTNPVQRDQS KFLNNTVVMN DQKKKDVVVE FWKSFYGILF VSFTNFVLIL LTCILVEPET    60
VQMIARFIGG SSAIYFLFLA RARFSKLFNL FSFLVTTCYL FVLNHLNAPD IGLVPICVCG   120
CFIFSYYFTE KHTGWHFDLC FMIILTCRLI VSPDIWAISL VFELLVLFCL LDHDMDQDRM   180
RLCCLYFILL LFLCCNYLYG SSIHIDTLVV VLVLAAAGAG GIQFMSLSKT ERGETLGLQL   240
FLINNVILGF LLRKDGETLP MITIFFIVSI LCFCIGLYLI GRIKEQSFYS VLSELKSSLR   300
GLFIPVLLTL NHFFLEDQYY LWITSLVTRI IVIQLLQLIL KKEDEDPDQD KAIKSDDVRR   360
CEINGCRSCY NYYYARSPPD CY                                            382

SEQ ID NO: 11            moltype = DNA  length = 468
FEATURE                  Location/Qualifiers
source                   1..468
                         mol_type = genomic DNA
                         organism = Rudbeckia hirta
SEQUENCE: 11
atgtcacgtc gaggtactgc agaagaaaaa actgcaaaat ccgatccaat ttatcgtaat    60
cgattagtta acatgttggt taaccgtatt ctgaaacacg gaaaaaaatc attggcttat   120
caaattatct atcgagccgt gaaaaagatt caacaaaaga cagaaacaaa tccactatct   180
gttttacgtc aagcaataca tggagtaact ccgggtatag cagtaaaagc aagacgtgta   240
ggtggatcga ctcatcaagt tcccattgaa ataggatcca cacaaggaaa agcacttgcc   300
attcgttggt tattagcggc atcccgaaaa cgtccgggtc gaaatatggc tttcaaatta   360
agttccgaat tagtggatgc tgccaaaggg agtggcgatg ccatacgcaa aagggaagag   420
actcatagaa tggcagaggc aaatagagct tttgcacatt ttcgttaa               468

SEQ ID NO: 12            moltype = AA  length = 155
FEATURE                  Location/Qualifiers
source                   1..155
                         mol_type = protein
                         organism = Rudbeckia hirta
SEQUENCE: 12
MSRRGTAEEK TAKSDPIYRN RLVNMLVNRI LKHGKKSLAY QIIYRAVKKI QQKTETNPLS    60
VLRQAIHGVT PGIAVKARRV GGSTHQVPIE IGSTQGKALA IRWLLAASRK RPGRNMAFKL   120
SSELVDAAKG SGDAIRKREE THRMAEANRA FAHFR                              155

SEQ ID NO: 13            moltype = DNA  length = 1515
FEATURE                  Location/Qualifiers
source                   1..1515
                         mol_type = genomic DNA
                         organism = Rudbeckia hirta
SEQUENCE: 13
atgcaagtag aatcttcgaa cttcaatcaa aatggggctg tcatccatct aaggagaaaa    60
ggaggatgga aggggacgtg taagcatgaa ggcgggtcaa tcttggtagt gaataggtca   120
gcagttggag aggagaatct ttctatagat agaagcaaga gggtacgaga tcgaaaagat   180
ctttttcata cccagcccca aattcccatt tctttcttgg tcggaccaag caaaccaact   240
atctatttcc gacaaacaag cctttcctct tttctttcaa attttgagag caagaagcag   300
gcggaactac aatcaatttt gactatgact atgactatga gggactttat tcagtcttat   360
cgtcagcata tgctgacgat aacggagagt gggtatccta gggtgacttc tgcatttgga   420
tattctgtcg aagagctaac aaagtttggc atcgaagatt ttactattta cattccaggg   480
gagattgatg accccgcaac ggttacaagc cttacaaagt taaataagct tttcattttt   540
atgaaatatg acttcatcgg tacagtcagg cctcgagata ttcaagtact ccaaaaggaa   600
tttaaaaaaa caccccagga atcactttat aggaagcttg aatctacgtt tcaaaatgag   660
ttaacaagtt tagagaattt tttaaagcct ttcaaggcag atttcttgag tcaagactat   720
ttgaattatt gtgatgggag acatcgctca tttaaaagcc cacttgagca atttgaaatt   780
ctcccattga ttcctatgaa gataggagac ttgtatttct cattcacaaa ttcatctttg   840
tttatgctgc taactctcag tttggtccta cttctgattc attttgttac taaaaaagga   900
ggaggaaact tagtaccaaa tgcttggcaa tccttggtag agcttattta tgatttcgtg   960
ctgaacctgg taaacgaaca aatagggggt ctttccggaa atgttaaaca aaagtttttc   1020
ccttgcatcc tggtcacttt tactttttgt ttattttgta atcttcaggg tatgatacct   1080
tatagcttca cagttacaag tcattttctc attactttag gtctctcatt ttcgattttt   1140
attggcatta ctatagtggg atttcaaaga aacgggcttc attttttaag cttcttatta   1200
cccgcaggag tcccactgcc attagcacct tttttagtac tcctgagct aatttcttat    1260
tgttttcgcg cattaagctt aggaatacgt ttatttgcta atatgatggc cgattcatagt   1320
ttagtaaaga ttttaagtgg gttcgcttgg actatgctat gtatgaatga tctttttgtat   1380
tttatagggg atcttggtcc tttatttata gttcttgcat taaccggtct ggaattaggt    1440
gtagctatat tacaagctta tgtttttacg atcttaatct gtatttactt gaatgatgct   1500
ataaatctcc attaa                                                   1515
```

```
SEQ ID NO: 14          moltype = DNA   length = 24
FEATURE                Location/Qualifiers
source                 1..24
                       mol_type = other DNA
                       note = FW primer for ORF3
                       organism = synthetic construct
SEQUENCE: 14
acgtaacacg tatctatggt gcat                                                    24

SEQ ID NO: 15          moltype = DNA   length = 24
FEATURE                Location/Qualifiers
source                 1..24
                       mol_type = other DNA
                       note = RV primer for ORF3
                       organism = synthetic construct
SEQUENCE: 15
gagagttagc agcataaaca aaga                                                    24

SEQ ID NO: 16          moltype = DNA   length = 24
FEATURE                Location/Qualifiers
source                 1..24
                       mol_type = other DNA
                       note = FW primer for ATP6
                       organism = synthetic construct
SEQUENCE: 16
gagggacttt attcagtctt atcg                                                    24

SEQ ID NO: 17          moltype = DNA   length = 24
FEATURE                Location/Qualifiers
source                 1..24
                       mol_type = other DNA
                       note = RV primer for ATP6
                       organism = synthetic construct
SEQUENCE: 17
atcttcatag gaatcaatgg gaga                                                    24

SEQ ID NO: 18          moltype = DNA   length = 1018
FEATURE                Location/Qualifiers
source                 1..1018
                       mol_type = genomic DNA
                       organism = Rudbeckia hirta
SEQUENCE: 18
tgcctatgaa aagaatgctt tggaattgta taagagcagg ctgtgatgcg aggactctca   60
gggacctact taagtctgcg atcactctaa aagcggatag gaccaaacct tttattcccc   120
tagcagcggt tatgtctcaa accaccggca acaggttgcg ctcctacgat cacaccttct   180
cttgcaaaca tagcactgga tggaaggtat gcttcaccgg cctcgtttaa caccatgctt   240
cctccgaagc tttcatctga gtagtcacta cgccctaccc tatcgctgag tctttggaag   300
ttcactcctt tataggtcgg aactctggaa cctaaagact ttctcaatca gacaggatag   360
atggattgag tgcgcgttgc cttgatttga ggtgaactcc ttttcctctt cttccggacc   420
ggacccttcc atgtgagaag ctggaagtcg agttattgat gaatgagaat ctaatgtctt   480
attaaacctt taggagcgat ctgttcatcc aactcgaaat atcgtaagta agagaagaag   540
aagaatctga cgcccaaaac tcccgtgtct ttcttggttg gaccaaccgg cgaaatcagt   600
cttcctgaat tggaagagca agaacaagtc tctccgtttt tttggggggag cagagcagtc   660
aaagaatgaa acagatcaaa tgagagagtt gattgagatg atttataagg cggttaagga   720
caataaaagc tttccccttt tggtagtatt gacggttctc agcggaatag gcattgctat   780
ttacgtaaca cgtatctatg gtgcatcctt ttgggcgcac caatcgagac ttgacgaagt   840
agcgcttttc aataaaaatg cgaaagaact gggtctctat tgcgcaaagg cttctgtggg   900
gctcactggg actaccttag aatataacga actttcaaat caagcgcctg ttgctgaaaa   960
agtgggtccc cttggaatcc cgcccgtagc ccaggttagt gaaacagtac ccagtcct     1018

SEQ ID NO: 19          moltype = DNA   length = 98106
FEATURE                Location/Qualifiers
source                 1..98106
                       mol_type = genomic DNA
                       organism = Rudbeckia hirta
SEQUENCE: 19
ttgatgacga attccacgat aacaagaaat agaaatgaat cgttcgatgt ctgctcgttc   60
tcccctcttc aattcccaat gaacaacatg atcttgacct atcatttgct caatttggtc   120
gatctgatac ttagttaatt cttttatctt tatgttccca ctgataccta atcgataacg   180
aaccagaatg gctttttttag gcccaattcc atctattttt gttgaggcaa ttcttacttg   240
ttcatcggca actgatctag ctcctgaaat atataacatt cttgatcctt ccttttacta   300
gttttctcgg ctggaatcaa aaaagattct ccgctctgct cctactcctt cttctccttt   360
aggatagggt cgtcgttggt cctttttttgc actaaaaaac tagtcagagc aactaactgt   420
ctacgtacga aatttacgga acagggataa gaaagcaggc gggataaaag aagagcgagg   480
tatagtgaga aagctcaccc ctgcctttag acgataaagc cttcttttac atcccatccc   540
ctagacaaat caataggaaa tgctacaagc cattgttgtt cttttgacga tgaaccactc   600
cggtacaaca ggctaaagtg acctctacgc ttcacccccg gtgcgtaggg ccgtgtgcta   660
gagggaggac cagaaagttt gtgttaagca tatagttggt tcttgtcttg tttaggcatt   720
tggtgccctc tctgccggcc tgcttagtgg cagagccacc ttctttgggg tcagtgagga   780
```

-continued

```
ggacaggaca atcccccact ccggcggttt ctttctttcc aaccggattc tacccggccc   840
ggtcctattt caaacaaaag aagcaaagaa gggaaatcct cgtaaaggca gcaagggctg   900
aaagagaaga gcaggggggtg gtaggcttag tagggctcga acctacaata tcaccgttat   960
gagcggtacg tttcaaccaa ttaaactata agcccctacg gatctctaca tgcaattcgc  1020
tcgcttcggg aagagcgaac ggaaagagga ggcctttgct ctatctgctt cttcctctcc  1080
ccaggaatga acaattggaa aaagaaaaag attctatata tctttttttt atagatatag  1140
aattctattt attatatага attctttat aatatagaaa aatgaagtta agcaagcggc  1200
cctttcgcga ctaaaactgc cggtacgctt tccggctcgc aaccgatcaa acgggcgggg  1260
ctctctattt gcttgcaatg ccggctcttc gcctttagtt agaagtagaa gtagagggcg  1320
gcgtttgccc cacacttcat aaaaggtaaa aaagtctgga tgaagtaaga aaaagtacat  1380
aaggaatgat aaagaaaaac ttggttacgg gaaccgaagg ttaggccaat ttagtatagc  1440
tacacctaaa aaagtgtatt cctacccttt ccccttctg tcaatgttgc caattcccag  1500
aagactaatg taccctcgtg tatacagttg tccgactact ttcttcctcc gacttcttta  1560
gccacttccg gcttccccac ttccgcatct gtcgtattcg ggagagcttg cttcgtggcg  1620
gagcatttag caatgctagc agcctggtga gggctggctg tctggggaca ttttaaggta  1680
gggcctgctg ggcttgcttc tcatgagatt gggtaaggga atcggaaatg ggctcataaa  1740
ccgggcggtc gggcttttgg gcacacgaa aagggggaagt ggatggaggg tgcttctcag  1800
ctagagttgg gggtggggtc gctatagtgg ctagggtagg tcttcctaca cggctggacg  1860
cccggctcta gacgaagctg agggggttac caccacatcc tctcccgata gactcgaagc  1920
tcttcatagt caggcgtggt agaaaatctt ctctcaaaaa gagacagacc agagatgaca  1980
gaggaaggta ttcggttcaa aaaagatacg gcagtcagaa cagcttcagt ccaaaattga  2040
ctaaggacag aagcaagcta caagcattag caaccgcttt cgtttaatct tcaaaaaaaa  2100
aatcaataaa aaaaaagaaa aagagaatca aaatagaaag atgaaggaac aaagttgaca  2160
caatcccttt ctttccgttg gtctcaaata aatatagaaa aaaggatagc tggaagccca  2220
cccatactca tccccgaaaa taagatctga gtcaacctca gagtcggaag gtgcgccaaa  2280
tggaaaatgc ccgaacaaaa cgaccgagac cactggccga tatgcctagg atagcgggca  2340
agtaagtaca ggaacagacc tggctcggca tacaaagccc atatggtaag gttctcttcg  2400
aaggtgaaaa acaacagctt gccgacacac gtgcccgctg agaagccttg acttctattc  2460
ggggctatgg agcgcgaact ttcactcatg agcagtggga tatggaaaat gggaagtgtt  2520
ttagccaggt atgaatgaat agattgattg tcggtcgaat ggtctcggtt ctagaatgag  2580
aaatagcctt ctcaccatac ttcgaagtat gaggcagaag taccgaaaca agcacaatat  2640
gcaccacttc caaactctat gcattattca ttccattggt ctggattact cgggttttcg  2700
aaactataaa aaattggatt gtaagtatgc ttttcgtaag gcgtctttca acgctttatt  2760
tctcatctca tctagaaagg gagggtctac ggcataccct aacgaatccg attgcccggt  2820
caccggcctt cttgatcctc tttgtcttct tgcactgttg ggagatgcag cctccataag  2880
tattgagctt gctctcgaga gacatggacc aaaaagtgct cttgacccgg tgtcatgaga  2940
gagggtagcc atagggaaac ctgcggctgg atggaatcct ttataaatag gtagaagaaa  3000
ttatgatgga tgatttggaa gttgtgttct agctaagtaa atggtgagtg atgacagccg  3060
gctccatcct tatctggaaa gcgtagttgc tcacaggtct tatgcctagg caccgacaac  3120
cttcagcgct ggtgaaacat acgccctata cccatttagg gggggtagg atacggcatg  3180
ctttctcagg gcgatagaga gacatatcca tgcaaacaac tattttcctc ccgagaaaaa  3240
gaagaggagt tggaatttac tgttgtaaaa tgtgaaaggg tcctataatt ggttaggtaa  3300
ttctgatcaa ctcgaaacct ctttcgttct tggtttttct gtgttcgttt aagaggcagc  3360
tttcgtcggt ctgattcttg agcaagacca aggggtcacc aaactttgtg aatcacaagg  3420
caacttatag gctgggttat gttccaactg aagaagacaa ggcagccgag gtagatgggc  3480
gaaagagaga agagggtgaa tgtaattcag ctcgactgaa aggagaggaa tgaatacggc  3540
tagccgaaag aataaataga tcgatccggg acttgcatca atgaatgcac caaccacggg  3600
tacaatgggc ataccttta tctacccctgc gcaggaggtc gccttagctg gtgccaaagg  3660
ttttgcatca tccttggctt gggttgtccc aattcctta tctgattatg aaacaagctc  3720
ttctgcgact gccttagctc ttagctgcgg ggtcaactaa agaaatgatt tcagccccag  3780
gaccaacttc tcaatgaaag agctctttc ggcataagaa agaaccataa agcagagcct  3840
caaaaggggc tttttgggcc gtgggaaact cacctgtgaa gctggtgagg cgtcctaaaa  3900
ccgaccgacg agtctgcaat agattggatt gggaggaaac ccaggtaaaa aaaggttact  3960
gggaaactaa gctaatagaa tagggttatt cggcattgat cgaaaagaa agagaaaacg  4020
aactcagcgt gggattataa atcatatata tagattgtgt ggtagagtgg ggctttgcct  4080
ccttcgagac acatcgctct gtatgctact aggcgtacta gcttgcttaa gcccagcata  4140
aggctttctt tactgcgcct tccttgcttg acagttttct ttctttgtag aagaaagaaa  4200
atatagatag atctttgttt gaaggggtct cagatcgtat gctttctagc ctgcctcttt  4260
cttgagctgg ccatggaata aaaagtagat ctctatctga tctgtgaagt gaaagacttt  4320
agccctccca ccatacttgt atagttcctt ggatcaagtc ttttctttga gtaaagccga  4380
agcctttagc gactagcctg accttttcct cctaagagga atcacgacca ccacattccc  4440
ttaaaacctg gtagtgagcc tgtgagtgta aggccctaca gatacccca catccaaatg  4500
agatagaaaa acaggtcaag gagatgctgt taagtggtat tctcagggca agtgtgagtt  4560
cttatgcctc tccagtgttg ctggtgaaaa aaagggacaa tacctggaaa ttttgcgtgg  4620
attatcgagc actccatgcc atcaccatga aagagaaatt ccccattgag gaattcttga  4680
tgaattacat ggtagcagga tattttcgaa gcttcatttg agaagtggtt accatcagat  4740
tcgggtgttt gaagatgata cacacaagac tgcatttcga actcaccagg gccattacga  4800
gttaatagtt atgccctttg gtttaactaa tgctccagcc tcatttcagg ctttcatgaa  4860
tgaggttttc atggattata tgaggaaatt tgtactggtt tttttcgatg acatcttgat  4920
tgacagtgac agcctagata gccacttgca acacttgagg atagtgtttg aaactttaaa  4980
acaacacagg ttgtttgtga agaaatcgaa atgctctttc ggtcaggcaa ggttagagta  5040
tttcgggcat gtggtgagca gtgaaggggt atcgataaaa gcaagattga cagcatgttg  5100
agctggccac aaacccactac tgtcaagggg ttgagaggtt ttctgggtca ggctattacc  5160
gaaaattttg aaaggggtat ggggttatca gcaagccact gaccaattta ctgaataaag  5220
atagcttcac ctggaatgaa gaagcagcaa gggctttcag tcgtgttctg atgcacacca  5280
agtctttgtc acaagttctg agtgaagttg tgctcgttct tgtgcacctc tgcttggata  5340
tgatctacca tgtgacatat gctacttttg tcttgctgca atggagtgat tgctgctcac  5400
gtgcgcgggc atctactgat tcacttgatg actgatgctc ggccactgct gctgctacta  5460
cagagtattc ttctccttgg ttcctcttga agcttgggga tgtagttaca tgctcatgag  5520
```

-continued

```
actactgtag tcgacttaat agtgatgtac tttgtaatat actttttgct accttgctct  5580
cccaaaggag ctttctagct actgatctcc tcgaccatct tccttctggt ataaaggaaa  5640
gagcttcccg agagcccta tgcgaccttc cacttgcaga gagtcctgcc gatgtagctc  5700
ttgttcttct tccttatcga ggtcttccct ttcctctgat caacaatgaa agtttcattc  5760
aagtcgtcac cttagcgaaa gcactaagta agcaaactac cttaatgaaa taggaaagcg  5820
gctgaaaaga aagccatttt tcgatagtga ttcaaggtga agtaaatccc ctatatctga  5880
tagccgtaac aggccttctt cttacagaga aatgcccta ttgcgaatct ctctcataag  5940
aaagaagaga gctagcataa gcagagctac cagctatact accagaagag cagctactat  6000
cagtcctaaa gagccagtat ccgtccttca ctcttaactt aaggaaagga tagaccttag  6060
cgcttcctct tgatcacagt aatgcgggaa gtctggctaa aggaagatag catatcataa  6120
agagatgaaa aaaagaaaaa tgagtcagcg agggacctct ataaagtcat tatctgatag  6180
ctttcacagg gcttcttgct aaagataaat tgacatagag agcgactgat tccaggctta  6240
gtatcttcgg tttcatctta taggctgact tgcatcactc taataggatt ccttgcttgc  6300
atcatatcgt acaaataagg cattagagag ccctttctct tcctttattc gccgcaggaa  6360
gaaattccaa ctatgctgcc ttctaacgat aggactggaa atccgagctc ctaggcaaaa  6420
gcttgaagct tgaagacaga aagagaagag attaacggga tgctttatag tcgaagttgc  6480
gcctaatgct taatctaact atttactata ttagaattag agaaagactc aatctgccca  6540
atactatacg ctaggaagaa cttgattagg gtagtagccc agctcttgaa ggggggaagca 6600
cataactaat agggttcagg tttatacgat tcatgttatc cccccgaagc ccctatcgcc  6660
tgcctggaac tcctgaattc actctttaac tagaggaagc gcctaaaagg gaagcaactg  6720
ggctagactg ctgatcttat ggagtagtct gaccctggga aagagactgt catcgctgcc  6780
gagaataaac atgctgtgcc gggtgactgg aatcctctga ggtcagctga acaggctgac  6840
aatcggcaga agatgctgag caaagctgct tgaagcgcga ggctgatccg taacatcaac  6900
cgcagaagaa tgcggttaga gttgatgaac aggagaaggc cgcaatacat ctccatcatc  6960
attctccccc ggggcttatt aattaggtta aggaaaagat gaagcgcccc cattaaagag  7020
aacattcaag gatacatcga gtctcttgga tttcacgtca tagcgtctat acccggactg  7080
agcatatcca agaaagacac aagtggtttc cttggggaca atttctctct taactgcgca  7140
ggaatatgaa caaaagacgt gcatccaaac actcgaaaat gcctatagta ctgctccagt  7200
aagaagttcg tgaggtgccg ctgcagcttc ttccctctct cttcccccaa aaaaggatag  7260
agacgccccg tcccttcttt atgcacatcc atatacatag ccagacacaa aggtgtacaa  7320
tccggtcaaa atctgcggca ttcactgtag gttctcttac ttgctctagt ggctggcaaa  7380
ggccaaccga gaggggagaa cgaatggctc aggaatcgac tggttccgag cagactcgtg  7440
gagcttgcag tttggattat cgtagaaaga ataagaggag ccgtcttagg aaatgactta  7500
acttaaaaga cagatgacgc cccagcttga ctcgagatca agactcctta cagctcgcac  7560
caatagcgga gcggccggag actgattgaa aaggcgcagc cctgccgccc ccctagccgc  7620
ctacctactc gtgttcgtag ctcgatcgga ggtcaagact gtggtccggt ggaaaaacag  7680
aagtcgtccg tatcaagtga tacgtgaatt gctcagtagt gcttcgccac taccgtagct  7740
ggcggaaata gcttaattgg tagagcatag ccttgccaag gctgaggttg agggttcaag  7800
tccctccttc cgctcccggc ttcgtcgttt agtggtaacg agtgtgcgcc cctttagaga  7860
taggggtgag cagcaagcag ccccttgtat agggttccaa acctatcttc ctaataagaa  7920
gaaaggggca agccaaaacc tagtcctaac aagttgctgg cttttcatca gcccttgcgc  7980
gctagccttt tcccttacta gtaaggggct gctagttgta gcgcgcattg tactagtgaa  8040
taggaaaagc gaattgagat tactaatgac ggatggaggt tgaggataga acatgttcgg  8100
tccctcgccc ttatctcctt cgccggagac tgcaaatgac gggaatccta tcgataaaga  8160
agaggtataa gcatcgcctc tcgatccaat ccgtctcccc ccaaaacact cttgatacga  8220
cgccatagag aagagatcta aagtctgggt ccctcgatc accctccctt gaacctgaac  8280
tggtcgagag agatgaaccc gcaccacatt ttataacctt cgaaccgaaa gccccaacta  8340
gagatggaat tccagaacct aaaccactcc gttgagagct ccgtgactcg ttcaagggaa  8400
ggtccaccaa tgattgccat tctcccccta tctgtctctt gatccctcat tccgctaatc  8460
cgttgttact ttactgattc attcaaggca tagactccct ctttgtctta ttagcgcagg  8520
tgttcgtcaa cgatgaaagc cgcttaagac tcgaagggct aggcccccgg gagggcttcc  8580
agggactggg tagggtggat tatagagcta ggggctaagg tttgtccatt gggattgggc  8640
atggacgact gggccagcat tgatgaaaaa tgaaaaaaga aaaacttctc ccatcgcatc  8700
attaaccggt gtaggattaa agatcaggtc caggattcga gtcaaatcga ccttccctct  8760
catctcaggg tgaggcaagg aattcaagca aatgttcgtt cttcaatctc tcggctgctc  8820
aagaagttgg actagctgct cctccgaccc ggagtggatt ctagtggaag ggcagagcaa  8880
agccttgcag taggaaggtg ttcgttgctg ggacgggttc aaactggact gaagggagga  8940
ggaattcaat agtcctctct tcctggggat tcatcactgg ctaggctttt cgaatcaaag  9000
catgggcatc tgcaactaag agggagcagt agatcgtcga tggaagagcc atgtcagtaa  9060
acttctattg ggacttctat ggattatgga ttcgactaga gggactccta gcagcaaact  9120
agtataaagg gccccagacg caggagccgc cagccgggtc gaccaacaaa tgataggcca  9180
gagggatggg ctcattcgac taatcagcga tccctgggcc tacctaacac agatgtccct  9240
gaaataggg attggttgat cggaaagctc gggcaggagt aggacattcc atacaattcc  9300
gattcgctag cctctcaaat cccattttt catcgggtga aattctaagg ttccttattc  9360
cggttgtaaa gcggaagaag agggagaagg ggcacagccc caccagcagc ccacgtttcc  9420
gacccgaaag gaattgcaaa tgaaagaaga atctgtgtgc actatccatg gagtggagtg  9480
gctattctga atctcctctt ctctatctcc ccctttttg ccttcggcta ttaccggccc  9540
aacattggat ttgtttgaaa acaatacaac caaggtggcg ttcattcaat caaagctttt  9600
atgccctagc actaatgact ctctttggaa agaaaggaat gcagggaaca agtctttcct  9660
ttccactggt tcttgaaagc tctcaatccc cgcttctccc atattgattc tccctctcgc  9720
atcggttctg catcagataa tgagcccatg cgcaaacttt ctcttttatt gtattggcgc  9780
ccgataggta ggctattaga ttgagtcgaa agcctaccgg ttccgattcg agcgagagcc  9840
caaacggggg aggcgagaac atcttgatcg aaagctccac tgttctgaat agcgagaaag  9900
acttttcaa atttgatcaa atcgatcgat cattttgaa tatcttaggt gggccaaccg  9960
accgaccgag ttgggctggg cgtccatgtc acagaacctt tctctaggca agaatcccat  10020
tattgatcga atcgaggcgg atccaattca ttggcaaatg aaaaatctac cgttttcaca  10080
ctcagaaaaa cctagaaaag aggaagagtc actaagacaa gagctaggta agcaagcaag  10140
aaggagaggc tagaaaaggc aggggctctc catctctagg aagattgtgt ccaggatctg  10200
gtaatctaaa gccttgcttc ttctggtcgg ctcgtattag cctgtgcttt attacaggta  10260
```

```
gtcattcccc cgttccttta gtcttttcaa cggtacttga atcttaagtc gcggtcatgt   10320
ctcgcccccc ggtatagtga ccggttccgt gttttccccg aatttcatca gttccaggct   10380
caagtgcctg ttcatccatc ttcattccaa aggcgagcat atccattgag tgactgtaac   10440
tgctatcgtt tacagtcaat agttcttaac caaccctttt tagagcttta taaagcttta   10500
agagagaata gggagtaagg gggaccttcg cttcattaga aattggaccc ggaccttctt   10560
tcttctcctg cggagccctg ataaagtaac cggcggcagg ttagtacagt tctcctgctt   10620
gcggattttt ccctgcgctg attcaggagc cttcttcttt ctaaaaaaca taataaaaat   10680
caaataaaaa aaagagaaga aaggtttggt tacgggaacc aacggtgacg aaggttacct   10740
actttcggtg gacgtggagc caacgagttc agtcgaacag cgtaacgagt ctaaggttac   10800
agaagcgttc gccaactttg ataggcatag cattgcaagc aaatagagca gagagcttac   10860
cctttctttc tattagagtc gtgagcttgt tgtagtcggt cctaaaggga gaacctttct   10920
gcttacttgc tatatccccg cgtccttgcg cggctcggct cgttcttcga gccctgcttc   10980
cccccttcccc ctctcccctt taccgtccaa aacaggccgt atggagtata gccaagtggt   11040
aaggcatcgg ttttttggtac cggcatgcaa aggttcgaat ccttttactc cagattatga   11100
acacccgatc ggatctgtca aaaacgagct gacgactaca gggggaagcgg ctgactgcag   11160
tccctgagcc cagcttgtag caagccaaaa gtttgacttg agcctacttt gctaagagaa   11220
gagagagaag gaaaagacag acggcagaaa gcaatccttc caaccgcgga gttgaacaca   11280
acactgactt cggccagttt ctttcatcaa tctcctggcc cttgcttaac tccttgttcc   11340
gtaaaccggt cgctggttga tctgatcgga ccccggacac gcgagagccc agcccgagag   11400
gaagatttca tttgctttct gtttcgtgga acgaagttga tccatggtca tcgggatgtc   11460
tatgttgaaa gagaacctaa cctgaggagt cattggtttt ccaggtcgga aaatgaagta   11520
aacgactcag gtggacaaga ggcgaaccac tcagctgatg agtcagctat acttttttaa   11580
aatagcctaa tgaggagacg atcgtaacct ctgagctcaa agatggaaag cagattcctt   11640
ttttcaggtt ttgcatagct tcccaagcgc ccggctttct ttttgggttc cgaaaggcag   11700
agtagcttca gcatcgagta gggtatggga tagagttcga gtgaggcatc aaccatagat   11760
tgcggaactt tcgagatgct tccttgcgaa agccaacgga gtctgtactg taactcaacc   11820
ctctcatcca tggaaggatt ccttattcga tgatcaatgt caatcgaggg caccctcatt   11880
tccagagaga gagtcaggct gcacagaagg gggaaagccc tcctactgag caagatcatt   11940
cattaatatt aagaaggaag cacttaactt agggcagcca gtctcacttc acacagcaca   12000
gcgccttgct attagcattc atccttgtaa cttaccgaag cgaggatctc atgctatcat   12060
tgaacggcta ccgaaccgcc atactcaggt aaccggtcta ggttccaagt acatcaacac   12120
cccatagcta cataggggcg caacgcaata aggcttttcg ctctagttgg gcaatgcaag   12180
gaggcctctt tcgccattct ttctaaatga taaactatta ttagttcagt tcggtagaac   12240
atcgatgaga ggatcatttt ttcacagaag catatgattg cccctcaatc gccaggtggc   12300
tcgctccagg tgcatgagta gctttgctgg ctcttataga aagcggcctc tttcagtggt   12360
tcttgcttgc tctttaaagc tgatctggtg ctgtctcgtt ccttcagttt gttctgattc   12420
cgatgaagga tacgcctaca caaccacctt gcttggtggt tcaaaatgga agtctaggta   12480
tctgcttaag tggtctgctc gtaccgttcc aaaaagagct gcgctgacag gcgtatttga   12540
aaatgtgttt ccgggctcac atatctaaat ttcagcgaga tagggtgcgg ataggtggaa   12600
tgggatgggt atcatgctta gttgtcagtt acaggcaagg acgaaggaaa tgagtttaca   12660
gactctggag ttggggctcg ttttcattga tactgaggga aagacttgtg tgatggatgc   12720
tcttgatgcc acttgacttg cttcttcctt cgttaacatc aaaagggagt gtattaaaga   12780
gagtgaaatt gaatggtagt ttaggtcact ctcaaaggat atctgctttg gctgaggtgc   12840
ctgtgaatgg gaatgagccc gcaaccggga ctctacatac agaataaggc aacctatctc   12900
aatcagctag agccattgca agttcatcca ctacaagctt accggactag agatcctatc   12960
cctctctacc ttaccaggac tctacctaag gcctaagtaa ggccgactga gtcaacgagt   13020
taaagaggac aacaagaagc agaagaccaa gaaagagtta ttacgcaaaa aggggcaggc   13080
tatattagct aatgtctctc agcaggatgc cccacacgga accaatcgaa ggagatgaga   13140
aggtctcgta gattggggta gcagtagctg gtcgtagtta ctttatataa aaaatggatt   13200
taagcatcat taaagaatga aattctaata attaaataga agaagaacga ataaagatcg   13260
gatttgctaa atgaaggtgt agaagtggct gtagtcaaac aatagtaagg agaattcgct   13320
tagtcttccg gttcagaagt ctacttagtt tcacaaaatc ttattaatga gatgagttgc   13380
ttaacacagt caagtcgtaa gacaaagaaa agcgtaggta acaatctgat atataagaag   13440
accgtaagta actcagtgct ccatatgtgt aaattgaaag cggtattccc ccttatatcc   13500
aaaaaaagaa atagaatcat ggaattctct ccgagagctg ctgaactaac gactctatta   13560
gaaagtagaa ttagcaactt ttacacgaat tttcaagtgg atgagattgg tcgagtggtc   13620
tcggttggag atgggattgc acgtgtttat gggttgaacg agattcaagc tggggaaatg   13680
gttgaatttg ccagcggtgt gaaaggaata gccttgaatc ttgagaacga gaatgtaggg   13740
attgttgtct ttggtagtga tactgctatt aaagaaggag atcttgtcaa gcgcactggc   13800
tctattgtgg atgtccctgc ggggagagct atagctccag acgaagatta acgacttggc   13860
attaccggtt aaggagaagg tcttgaagct cgactgatta gagagtaggt cttggtaagg   13920
acagtaagca ttacagaccc tggtcctggg gaacaagagt cagagttcaa cctacttgaa   13980
agcggtcttt agccaatgaa atcgggacaa gcctgccgat agaatttctt atagtaaggt   14040
aataggatgg tatggtttcc gcggcagtaa gagttgggtt tagctcacaa ggatgccag   14100
tcccgcgagg ggatccatca acaagaaagt cattcaagag agaagatggt gctatttcct   14160
tagctagctt ggactaggaa gaatgaattg tctctagaac ccttggttgg tctaggcaaa   14220
gcgataaaag aacaggtctt ttcggataag ctgttgcccc tcttctgtta tagctctttta   14280
gtcccatccc taccaaagag gatctcccct aaaaagatgc gtagcgctct tgagagatgg   14340
gattcatacc cggaagcggg gaagacaagg tttagaatct cggtgtcagg tgcagcccag   14400
aggaagctgc ttgataatct agtcccggcc aagcaggaaa taagtgcttt gtcggttgaa   14460
ggtgctctct tgcagcttct ttaatgggaa gccctgagct accgctccct cttaccaggg   14520
atatcactag tgaagcctta ctttcagtta aatattataa aacccttcgc cctatcttgg   14580
attcgttgaa ctttccactcg agcttgatcg gggtactcgt ctatcgcgct tagaatagaa   14640
gataggatac atcccaaagg cgtctgggtt tcggtggtag gaggaatccc cataactgca   14700
atagccctct ctgtccggaa aatcaagata gcttcttccc ttagctaggt acggctcttt   14760
cgagcaatca atctgctaaa agtggagctc ctttttgggg tagactacac gagtcctatg   14820
aaaaagagcg gatgactata taatagcaaa ggctttctgg tcgataagtc aacagatctt   14880
cccaaggggac tcatacaaga ctttcagttt gtatctgatc taatgcctga agcttaaaga   14940
gaaagaaagc cgtatgtata gggtgatcaa ctcatcatac aagagctaac ttcccgactc   15000
```

-continued

```
ccgtttccga caggtggaag tatggatacc agaggagcta accgagaagg gaaggaggat   15060
cggaagtctt gaaagacaga acggtgttcg tagatggatt ggtcttttgg caggagagaa   15120
tactgattga gcacatgctt ctgatttcta tctatatagg atatgctaag ccttttctta   15180
tttatctatc taggaagcag agagagatta ttatcttatt aataggttcc ttcgcttgag   15240
ggaaagagac aaaagaacag acctttccta cgaatgtgaa tctgccaagt aagggggtt    15300
aagggggagg tcttttttctg ttttcacggg aacttctcct ttttggttaa caacctatgt   15360
tgggcttaga acaagaccca tcggtggata agatcacatc ttcataacaa acaaaaggtg   15420
tacacgttcg gcctcactca aggtaatggg ccaaacctaa cgagtccaaa ctggatctta   15480
ttgtatgaca aaaccacaga ttgggcttaa tattcaaggc ccagaaaaga tgggttgaat   15540
ccagaaagcc ttaccgctct tattccgcag cctttagcac atagcagtcg acgcagaaga   15600
gagcagccct acaaaaatagt aaaacttcct tcctgtgatg ttagtattcg tattacatac   15660
actgatgtaa gtggaatcaa tcacctaaat gacatgattc aactgccagt gagattagga   15720
gcttcctgag aagagtaagt tgaatcatgt aaatagcatg attcctcagc tgaagcattg   15780
tttaaacact gaaagagtga tattagaata tacctgagaa ggaagaaagt tgaatcagca   15840
aaatggcatg attcaacaac tgatgaattg tttgttgaat catccaattc gcgctcgctc   15900
taaaaaatac tacagtataa atagagaatc aacaagaact gccatttgcc agaaaactct   15960
tctttcgata ataaatcaat ccttacactc aaagagattc ctaaaacaaa caatggctgg   16020
agaattcaga ctacaccaac tttctctga aatagagaaa gaagaaaaat tgatacagga   16080
gcgcaaggaa ctccttataa ggttctggaa aaaacttcca aaagacgctc cactcaggga   16140
agcagagctc aggctcaaag ccctacggga agagcagaac tctcttgtga gagaaatgac   16200
attaaaacac cgaggtaacg gaagtgaagg caactcaaca ggaggaataa taagaggagc   16260
acagggagaa aattgaagga acaggagaga agaataagaa ttagtttatt ttagccaatt   16320
gttagttata tttgaaatgt agtgcctgtt ctgtaagctc tcttatagga tctccctttg   16380
ttctttttta taaaaatat ataaaaatag gttattccta tgagtaatgt tccgaaatca   16440
tttataaaat gtttatatca aaaaagaact cccaggataa aataaattag agtttctaaa   16500
tgctttgaat caatattcat tggaggttat catggtgtat acacttggta gtgtcgtaaa   16560
tagtgtacaa tcagagtttc ctgctgttcg cctatctact ctggttgagc atcttgattc   16620
cctcattaga acgcatgctc gtttgatgaa agatcgcagg tgtggctcct tcctatggtc   16680
tctactgcca actcgtttca ctccagttta ccgtagcaac tacagcaagc tgactagctc   16740
cctggctcgt atgactagct cgcttacttt actttcactc aacagcctag ctctaacaag   16800
ccaactccgt tcctagtttc gctaccctgc tttagcctcc ccccttataa cgagcaagta   16860
agtatactag ctgagctagc cgcattccta gttactactt agtagcctta tttcacttac   16920
agctatctaa gacattcagg ggctgtgtaa ctgctgttag aacgcggatg tcgaaaagtg   16980
aagattggtt ctgtgccagg tcatggtgat atgctggatt ggataaaggg ttgtttcgtc   17040
gatagcatta tctgatgtgg gatgcgtagt agctgttgtc acagtagggg tccctaaggc   17100
gggaattgtc catagcgttg attgctctcc ttgttctatt gtatgggcga attatcttaa   17160
cgaaagcctt ctttttggcc gggttgccat aacttgtgtc tatccgctgt taaatgactt   17220
cacttaatag agtcctaagg gcagtctctt tgagaagggg ccgtattagt ttttattagc   17280
tgtcccaggg aaaagagtaa gtattggctg ttggcatgtc cgagctaaga tcggttgagg   17340
cgggtaaggt tgcctagctt acttggtaaa ggactccttt ctttagttta gcggtcatgg   17400
atcgattcta ggtggttcac ttgtataccc ctattctcag agttcacgtt ctgatctagc   17460
aaatcgactt ttcagatgag ttccttagtt tttggacagg acaggtggga accaggaggt   17520
aacgcgtctg ttaaagcaat cgggcaaatg cgtgtatact agcttactag ctatagctgt   17580
tactgtgctt tctggatacc ttttccatgct ttaacaagcc agctacgcac cctgctcttc   17640
tcttataagc aagtagcttt gatttgggaa taagctgaaa gtcaagtagt atgagttgaa   17700
gtgaagggcg ctagtaagta ataactagta agtaataata agtagagtgg aacactgttg   17760
gctgaacaaa agacgtatga cttgagaaag taagatctcc gatctgttgt cgggaaaagg   17820
gacctagcta gattctcaag ccacccgcaa cggccttagt cctcccagtt tctcacttcc   17880
ctccggtgcg gtagatactt aagagagagg gagggcaaag cggggaactc aaccaaggaa   17940
aggagattac tcaacaggct ctactacgta gttatagtta gggtttggaa aagtgtgatc   18000
cggatcgatg taattgactt tcgcaaaggt tagctcacta taataaggtg ctgtggcatc   18060
tctatcagct gcttattcct actaattcta agtgggtgtt cttcgaagct tagacgagtt   18120
gaatggaaga caaactgtca caccattctg aggaaggttc gactgtgaaa agagagaagc   18180
tgatgtagag gtattccatt cccctcaaac tcttgtttc tcaggatcag ggtagtgaat   18240
tggcaccggc tgttagaaca gctggcgacc atgcaaggtt acttcataaa agtaatcttg   18300
ctggtcaccg acggtctcac taaggaagac tgcattggat cttacctgct ggcacagagg   18360
atagtgaagt tggctcggcg atcgggactt tagccttcta tttgaaaga gtgtgcttca   18420
tgtctccaac gagtggtgat aaatcacccc atgaggccct tcctgtgtca ctcaattggt   18480
catggtatcc cggcatttca tcgtaagctt attgcgatga gaacgctctg acattttagt   18540
caagctttat ctgtccttct ttgagcccca tagctcaaat attgattata cggaacagct   18600
tttcaaactt aagtaagggt acgtgtgtac atgataacaa gagtacacaa tgaggattcc   18660
ccgcctgaaa aaataggaaa gctcctttcc ttaagggcct ttcatcagag tcccttcttt   18720
taccgggtat ttattctaca tccatttcag gtcacacatg gctaagctcc tgggacaggg   18780
agaggtaaaa aggcatagca tagctttcag ggaaatcct tcagatgtat tggaaatgga   18840
aatacagatc aaataccttc tgaggcggtg ttccctacat acagtcatac agtacggagg   18900
ggaagagaag aagggctagg cacataaggt ggggttaatt gtcttacagg caagctctcg   18960
ggcttctagt accgatttat aagccactgc ttacttcgac gtttttccat ttcccataga   19020
atctccctcc atccaaatgg cacttgttca tgcgtctgtc gccgtagcag ctaaaataac   19080
ggaggaagga ggaggggggaa aggtgggtat gtggctttcc ccttaggaag gtttctttac   19140
atctagtgaa tgatctagtg aatgaaggtc gcatatgcgc tgcaagaatc gtctgttata   19200
gaattcgctg ctattgaacg aaggggagat aaatagcata ttaaaagggc aagcaagacg   19260
cagataagag aagacaagaa agatcagaag caagaaatgc cctggtttca ggaagaattt   19320
gatgtgcaca gaggattcat ctttcaacag catgtcatgt ccgaaaggac gttcattcaa   19380
cggcattagc ggtctaggct cttcggaagc agagcatgag ataggctctt cggaagcaga   19440
agctttagga gttttgatcg atgaaacaag agagggatga aatagctcga ctgttaaaga   19500
gtttagcccc gatgggtatc ccgaacgatc atagctggca tgcgaggtac gaagtagctc   19560
gactgttaaa gagagggatg gtctcacttt atcaccatct gaaatgcgct tcgattggtg   19620
gaagccagtc tatgaagatt ctccctttc ttacgtgcaa ttcccctgag tcttagtaca   19680
gactcctttc aacccttagt cgagaatctt cgatttcctt ataagactag agccctacaa   19740
```

```
aagaaagact tgacaggcct taacctttga actctttata aggtgttgct ttacctactt    19800
acattagtcc ggaaaagaaa attgaatcac cacatcctca tacaagaact tcgccacctc    19860
tctggccatg cctcaccgcc cttgcttcga cccattagtc tcagctgtat tcggtagcgg    19920
ggagtgaatg aacgaaagag cgcacctat gagctgcaag caactaacta gtagcaagta    19980
aaagaacaac gttcaccgaa tacgattaga ctttcagtac ctactcctag tccgaaaaga    20040
ctagcaaaca tgctaccgtt aaccatgcta ccaggcctag ctaccacaga gaaagtgaag    20100
ccggctcttc ctgctctcgt aggagaggaa agcgaacttc attcctaagc ggtcctagtc    20160
tccttttttt cttggtgtga tcgtatcagc atgttaatag ctttgagaga aaggctgcct    20220
tttttcgttg atcaatgaac actaatgaat tgtttggtac ttcaattacc tcttctggca    20280
gctcaacaat aatcagagga agaagcctcc aaagagcaga gcatagcttt aagccgaagt    20340
tcttccttta ctgagctata tctctatcta tttatttttg cttcaagagt ttagactcac    20400
gataccgaga aagcaagccg atcatagacg gaggtttaag cttgaagtgt ccaaccaaag    20460
gtgaatcaga tgttcgaagg agactgttca tgaacatgga ttgttggtat accagctcaa    20520
tagctttctc tacaagccta caagctttgg cttagcttcc aactaaggct aagggcatgt    20580
tcccaagctc actcttgata acctctgttc ccgctcacaa tgttactagc acagctcaac    20640
ttctttccat gctaagtgaa ctaagcacag gagaagccta caggaaagga gatctcgctc    20700
tttccggtcg ggatgtgtat ccgcaacagg atgtttccag cttgggactt agagtaagca    20760
ggaagcctac ttgttaagag tagggcgcag aatgcatttc tacaacaaga agaagcttag    20820
cccgaaatga gcgggtagga gtcatgaata atcaagcaga ctgataccat gctgaattgg    20880
attacggtgt aatacatctg atgacggagt gaagcgggta ggcaacttag ttgctagcta    20940
gttagtcaca atctgacggt atgagaaaga ttctgattgc cgtctttcag cgaatctatg    21000
tggagcaaga agggtctgtg ccaaccaaga acgatggaat aaaagagaaa gagaagatat    21060
gaaggaaaag caaagtcaaa gacagaagaa aggggctgag gaactgagat catggagtag    21120
gaattctcat tcatcaagaa ctttttcttcc atactatcct atgggaaaga aagactgtag    21180
gactgtagcc atcatcgggt tgggttaaca accactgaaa gggatgtgat aggacgagct    21240
aagtcagcag tagagtcgaa ctggctatga aagaactcgt tccagcttca cttcaagcac    21300
ggaacttcaa gtccatgtaa gaaggaccta ggcattgaag gtcatcagat cggtcaacgg    21360
cagagaagga gtagcgaggg tagccctccg atagcacagg ttcctgcttc gagggagttg    21420
aaaaaagcca gtctttgatt caagcagcta tagctctgcc actcaaaacc ttgtgaaatc    21480
gagcagtgga gaagctttta tactagattg agaggggttg cctgagatca tgtcgtaggg    21540
aatggagatc ctgttagtca atcagtggta gctcaacaat aatctgagga agaagctact    21600
atcgattaga caagaaccgg cctttctttt gttcaagaaa gaagacagcc cgcgcaaaag    21660
cagcaataca ggatgaatag aagctcaaac cctcaactca accagagaaa acagctacgg    21720
gtatcgatga cttcgttcta ttcgagtaga gatccttctg tcagtggggc tggagtgaga    21780
tagcactcag gactgtttca ggttctaaga tcaaggcaga atcgatcggg atacccatcg    21840
gggcatccct ctcttgttga ttgaatcgat cgggatgccc atcggggcat ccctctcttg    21900
ttgattgaat cgatcgggat gccccgatgg gtatccctct cttgtctcct gcttttagtt    21960
tgactcgcct gcaggcgagg gcgcctctcc caccctacc ccggagacgc ttgttttaca    22020
tctcctaccg gacatgggta catggttcag cctaaaagg gggttgtaag agcatcctgt    22080
tatttctttc gattgtaggg acagaacaac actactggta taagaaagag agtaggaaag    22140
aagcttgcta taaaaatcac tttactcgga aaggttgcaa aagtcgactt aagagagtac    22200
aggcagataa ttaccgatag aagcccccca gggatcagtc tactgcttta gggagagatc    22260
ctttgagtag ggtttctaac tctacaatca cgaataaaga gagtagaatc tagttactgt    22320
ccggctatta cttgaggagc gcgcatacaa agcagagcga aagtgattgt ctcaatcaaa    22380
accgatatgc aggaagaaat tacacctcca taacagcagt cagtttggaa agaacaagag    22440
agcattgagt tcgaaagaag acagcagtgc cttaataacc taagcagatg tcaacagctt    22500
cttcctttc taaagatttt cagtgcaggt atgggcaccc ctcgtcagct gttcgtttag    22560
cagtcttatt agcttgaaag cacacagttg gagtgtgaat accgtgtact tatgatataa    22620
ggaatgcttt agtgtattct ctaattataa aagcggttta ggcggatgca gtagtttata    22680
cctaccttgg tcttccattg cttagtgtga tgtggactac agaaaggccg gacattaagg    22740
tttatagatt ggtttagtca agcctggaac tagtaaggaa tacaccaaat agaaagggag    22800
tgcggaagtt aggtccaggg aggcattgct tgttctggtt ccgtaccagc acccttacca    22860
acttgcttca tccattcact aaactgaaga cccatactgt aaaccctcct tgatctttag    22920
tgcattcctt cattgatgtg atgtaatctc ggttgaagat gaatcatgtg cgacataact    22980
cattcaatta gctgccgctt tccttcaatc ccactatagg aagtgatgta cccgggctag    23040
gctagtgaat cgggcttgct tctctcctt gtagggtgcg tggtgatatt gtgggttgtt    23100
gaccctggaa actaggaaat agaaaggtta cagccaacga tcagaacggc aatgagagac    23160
ggcaaaatac gcccatccag ataaaagggt caaaaaaatt ccatgcggcg ggaaaagctc    23220
tcggaaaagc taatgaaaaa agccatgggg aacataaaaa tgacaccggt cagatagaag    23280
gagacatgct tcgtcactgg agttctgtgt taggaaactt gctatcttcg gaatcaccca    23340
tctcgaccta gcagacacag caaagaacca cgctaatcga gacaccctac accgtagtag    23400
tataccttaa gccagcagcg aaaaaccaga tcagagacag ccctaccgag aattcgtctc    23460
aattaggcgc ttgtaggaga ctaggagggg ggccagccgt caagtagaaa ggagagagga    23520
gggcacataa gtttaccaaa agtcggctta tacgatttgt aaactagtac ctgaaactta    23580
caatctcgag ctctagggct tactgcttaa taaagactac ttgcaggctt actcctagta    23640
cctgtggcag tttactatag cacccgcccc gggacttcct tactttattc aattcttctt    23700
ctgcccttcc tgacctggaa tgacttgctt agctagtttc cttgctcgcg gggttagact    23760
gatagaggga ttagctggct cctactccta cagggttata aggtttatcc acttccttac    23820
ttcctcaaaa aagggggaga caggtttag aaccagcaaa ccctagaagt caaaataagg    23880
ttaggttcta aagcagctat cccgaagtaa gagctcagtt acatcgaccc ccgttctggt    23940
gcaaggttct cttttaagta attcctgagg atagaactct atttaagtaa gctcatcgct    24000
ctattaagga agttaggagc tagtctgcca agcttaagaa aaagttcaaa gtaagcaagg    24060
ttgtcagcga gtaaggaaaa gaaaaggtag gcttagaacc agtataccct atcttgtatc    24120
agttattag tctgcctatg aaaagaatgc tttggaattg tataagagca ggctgtgatg    24180
cgaggactct cagggaccta cttaagtctg cgatcactct aaaagcggat aggaccaaac    24240
cttttattcc cctagcagcg gttatgtctc aaaccaccgg caacaggttg agctcctacg    24300
atcacacctt ctcttgcaaa catagcactg gatggaaggt atgcttcacc ggcctcgttt    24360
aacaccatgc ttcctccgaa gctttcatct gagtagtcac tacgccctac cctatcgctg    24420
agtctttgga agcggtttca ctcctttata ggtcggaact ctggaaccta aagactttct    24480
```

-continued

```
caatcagaca ggatagatgg attgagtgcg cgttgccttg atttgaggtg aactcctttt  24540
cctcttcttc cggaccggac ccttccatgt gagaagctgg aagtcgagtt attgatgaat  24600
gagaatctaa tgtcttatta aacctttagg agcgatctgt tcatccaact cgaaatatcg  24660
taagtaagag aagaagaaga atctgacgcc caaaactccc gtgtctttct tggttggacc  24720
aaccggcgaa ataagtcttc ctgaattgga agagcaagaa caagtctctc cgtttttttg  24780
ggggagcaga gcagtcaaag aatgaaacag atcaaatgat tgttctagaa tggctatttc  24840
tcacaattgc tccttgtgat gcagcggaac catggcaatt aggatctcaa gacgcagcaa  24900
cacctatgat gcaaggaata atagacttac atcacgatat cttttttttc ctcattctta  24960
ttttggtttt cgtctcacgg atcttggttc gcgctttatg gcatttccaa aaagaaaaaa  25020
atccaatccc gcaaaggatt gttcatggaa ctactatcga gattcttcgg accatatttc  25080
ctagtatcat cccgatgttc attgctatac catcatttgc tctcttatac tcaatggacg  25140
aggtagtagt aaatccagcc attactatca aagctattgg acatcaatgg tatcggagtg  25200
cgcctcttca cgagggtgat ttaagtgcaa cgaaatgcct taagaatatg gttcgcgaag  25260
catctggctt accggtaatc tcccattccc gccgtcgaga gacttaaata actatagcat  25320
gccagaaacg gggagttgag atggttagac ctataccccg aaatgctccc agcatagaag  25380
cctatggttc catcttgttg ttgctggagg tacacatccc tcttctcggt gcggagcgat  25440
atacgagaaa tagatgctca gcctgaaatg tccgataacg gcgctgaagt agtgaatcta  25500
tcggcaccat agctgtgtca tacaactttg gacctaatgg ccggcccagt aacctttcgg  25560
aatgggggat ccccgttggc aacaaccacg gtagtagttg cggaactact gggccgggag  25620
aggacaacct cttgttcctg ctcctctttc ttcgcttcgg ggacggaggt cctacggtag  25680
gtaacagcag gtacaagcaa cttgaccgaa ggggaccagc gcttctactc ttccaccgag  25740
gagccgttcg cagcgagaag caagggatgt cgtgaacggt gggaggtcac agagaattta  25800
cctattcata gagtgatcct atgatcgata caggatatag actatctctt tctttgttta  25860
ttcgattctt tttctgaaaa aaaaaagaag aagggtgact caacttctca gctagagttg  25920
ggggcgggac ttgttggcat aatgcaagct ggaacgtggg aattcgaggt ctcatgaact  25980
actactaaaa acctactttt tcttttttgga caaacgatat caggtcaggt ctatggatgg  26040
atccagatct acgggccggc cggccccggc cgatgagcat agggaatcta tactcgagcg  26100
ttcaactggg cccctgacag gataggtgag gaatcactct tgatcttttt gattggggcc  26160
tacaacttct ccgagccgac tagcatccct ttccactgcg catttatcga acaaagaaga  26220
cgactatagg atcgaattcg ctttccatgg tgaactggtc gtcccatacc ttctgcccgt  26280
ctcatatgtg tggaaccagg tcttttttcgg ttccagcccc ccctcgaata catagggtag  26340
gtaggactgg gtgagaaagg gttccctgtt gccaataaac tttccccggc cttcgattcc  26400
ccttactcat aaagggtctt acggtcggta ctaactaaag aaaaagagtc ttctttctaa  26460
gagttaggcg tggagagctt tttgcgggga aacttgcaag tacagtttgg ggggagacgg  26520
gcgtcgaccc aaccttatga gtattcggac tataacagtt ccgatgaaca gtcactcact  26580
tttgacagtt atacgattcc agaagatgat ctagaattgg gtcaattacg tttattagaa  26640
gtggacaatc gagtggttgt accagccaaa agtcatctac gtattattgt aacatctgct  26700
gatgtacttc atagttgggc tgtaccttcc tcaggtgtaa aatgtgatgc tgtacctggt  26760
cgtttaaatc aaacctctat ttcggtacaa cgagaaggag tttactatgg tcagtgcagt  26820
gagatttgtg gaactaatca tgcctttatg cgtgcgcccg gaaagatagg ccgactgctg  26880
agcccactct ggctcagccg caccacccag ggtgcgagcc acccgagaag caagctatta  26940
cagcgagcgg ctggagcagt atggagccga ggagcaaggc agtagataag atagaagaag  27000
gggtcaagac cccggtggag cagaggatac ggttaggata acgaacttga aacgcggagc  27060
ccgagcgtcc ggcgagcgag cggttagtgg ccaatagcgc cctagttgat ggcattcctc  27120
tctgcggctg gcactcgagg aaccacgggg cactccatac agagcaaaca agtcttaggg  27180
atgagacgcc cgcgcaagga cctcaattct cattaggagg tcgaaccaag gacctatgga  27240
agtcgtgggc agcccgtccc catgggcaac gcaacagtgt cctgagggag gagtttagag  27300
gcctatagt agcacggact tctttttctt tctaggtcat gcgaaggggg ccagtccaag  27360
atcgtactgt tcctctacaa agacaacaga cgctctcaac ggctaggcgc cactctcttt  27420
ctgagttatt ccagcttctt catgattttg tgccgcggtg aacaaacaaa aaaagagggc  27480
catctcagcg gaaggagaag gacctgcaac ggcagagact actgacccta ttcttgttcc  27540
tagccgtctt ttacgagtcc ggaaagccgg atcctcaaaa tagaatagag aagggcgggc  27600
agggcttccg caagagcctc cccctcttc ccggtcaaga tagatgggaa ggagccctat  27660
caaggccata accagtctct ttatttatgt acgtacacct ttgtttcagg gtggggccgc  27720
ccttcctcct gctaatccgg ccatttccga acctgtcttt ctcatcccat tcaatggagg  27780
acttttcaat tcttgcgatt cccagccccc ttagcttatt attttatata tagatagata  27840
tcttattgat aaaggttcca aaccttagct cggctaaata ggctcaatga tctctttctt  27900
cgcttcgata ggcggtacg gcgctccgcg tggttatatt catacatgtt ccgactcgcc  27960
ggtcattatg gatctagtgg catggcgggg caaaagaaa agggggggag caactacgaa  28020
gcttcgtaga ctcgacaagt cgctccgctt atagaataga atgcaagcta gcgactctcc  28080
tagtagcgaa ggaaaggggc attcgggaag cgactagtcg cttctggcga agcttctaga  28140
aggccgatca ctacatagag agatccatat accagtcatg agcgagagcg aagcctagag  28200
aggcgcaggg caggattcaa gagcttagaa agggtcagga aaggagcaga gaaggggttg  28260
gatttcacct atgatcagat cagcgggcaa ccatagttga cttttttcgt agtgttgtta  28320
acgttgttga aagctcatta cttatttaag taggcctcgc ttttcggagc tgctcccagc  28380
tcacactatg gtggaggagg tgccgtgaag atctaggagt gtgagcagta cgagctgaaa  28440
ggctcccata ctgtttggag ggcaggggc atagatgcca aacaaacctg accccctatct  28500
atcgtcgtag aagctgttcc taggaaagat tatggttctc gggtatccaa tcaattaatc  28560
ccccaaaccg gggaagctta agcggaaatg aaagagtagg gtgagggaaa agaaaagggg  28620
ggaagcaact caatttaagg cttcgctccc agatcgcttc gtgagctcat ttagtagaca  28680
gcgagtgtgc gcccctttag agaagagata ggggcgagta ctacacgagc tcgtaagtaa  28740
agtacggaac gagccttgtc tacgaagcag agcgacctcg tcttgcttgc ttctggcgaa  28800
gcttctagca ctggataata ggcatggaag gaatacgact ttttaggtcg accactacac  28860
tacatagaag cgatagcgaa gccaagccgt ataaaggcga gcagccctta tagcaatagc  28920
aaacggccta cttatagccc ttcccaattt ccagtagtaa acttcccaag tttaagcagg  28980
ataacccccc t ctctattctt ctcttcatgt atgtgggctg cctgccccgc cccgaataga  29040
cgaacaggaa caagctgaag aagcgagaga gatttgagat tccgtaagta actcagtgct  29100
ccatacgtga aaatttcccc tcatccggct caagtaggta cactaaataa agaaaggtcg  29160
agaaaactcc caaacaaaca acaaaaggat ctactcctta ctcaagttcc tagtaaggat  29220
```

-continued

```
aaacattcat tccgtctttt tttcttaaca atattcaatt tcaatttcaa tgacgaagtg   29280
taaaattctt gagtagtcta cttcccttct aatgatgaag acctgaattt ttagtaatga   29340
aatgaaggga ctgccttcac attcataaga gattgacttg tctatgtact gttccattcg   29400
atcttttagg tctcgacttc aactcgatgg ttatgccacg cacgatgtcc ctgcagtcta   29460
tatgcgatga atagactcct gcaaccatga catatttact tccttgaaca gactttcttt   29520
ccaaaagaaa gtgataaaaa aatgctttga aaatcgattt caatctcagt ttaggaaggt   29580
accttcatgg cttcgatcaa actatcaact gaccgacagg ctggaccact ggacatacct   29640
acataggact gcagacagat acgaattcta ccctccggct attacacatg accagaggaa   29700
ggaaaggcta acctatacct atatgactcc tactcttatt gatgaatgtg ggtgttgata   29760
cctcttccag tcttcttttt catgcccacc aggccaaaga aaagtcaaat gagcgaggaa   29820
ggttatagca aagcacgaaa tagaatctat atgagcgggc attcattctt tcagcggggg   29880
ttgctaatgc taataccaga ggagagtagt tccccagcga cgataggtga tatctgtgac   29940
cagccccggc cccggatcac atccttcacc cgctcctaac cttgaaagta agagactttc   30000
tccttatcca attcccttgg gcgctacaaa gtatcctact ccaacacttg ggaatggaag   30060
caagactcct tcggaatgat tggctttagc ccttttcccct gggagcacat ccaagactca   30120
aaatatgaac ttcgaatcaa acctaaaatt tcggtcttgc agcagcagca gaagagttcg   30180
cggatcgcct atttaataaa gattcaaata ccttcccgct gctgaaagat ccccatcaaa   30240
tgctacatcc gaagcaacta taagtcgatc tgccaaacaa aactccccctt tatagaaggg   30300
tttcacccca agctccttta gagcaaggct tttccggctt tactgactta gctgaataat   30360
ccgctctagc aactcttggt caagctgttt tcatctactt atacttagct tcggtattgt   30420
acccaagaga atctgaatca gaaaaagtac ctagacctgg atccaagatc acgatatccg   30480
gaataagtgt tggaggtcga ttcggatacc ccacccttat tatagaggag agtttggcac   30540
ttagtagcct ggttaggagg tttaccctca taacataagg cctttcactc gaaaaaagag   30600
gttttaccta tccgactatg tcctttgttt aatacccatt tccaggaagc tcagagcagg   30660
tcaggacaga agaagtctac aaagaaggca gtccaatctg gcgctttcct tgccttaagt   30720
aataccttt gtttaagtgg cttgcggaac ttcgtttcac ttcgttcgtt ccattagaga   30780
cgcgaagttc gtaccttctc ccctgccaag ggttaaaagg cggagaacca ttaggaattt   30840
cattcccctc cgacgcctag aagacaaaga acggggaaag tcaagcctta cttccgattc   30900
cttcccagaa gaggacgctg tgaacaaaaa aaatgggatt gatagcatag aaggagctgc   30960
aattgaatca aataggttct ttgcaagtga agaagaaaga ataagttgtg atagaatcgt   31020
tacagaatag gcagctatag aatcagctcg gtcctttctt cctagatgct tttcatagct   31080
atccgatgat cctgtaacta ccgctgccga tgccgaagtg cttccttcat cgtctcaagt   31140
aggggattag gccctcgaag acactgggaa tccccagagt ctgtcttcga atcaggaagt   31200
accggcagat aatgaagtag gtctggtcac tcgagcagaa ttgacggcca tgttagatag   31260
aaatcaccag gccgtaaacg agtacttcga taaacagatt caagaaatga ccgatagata   31320
taaacgagaa actgaacaaa tacaggagtc atggaggcgt gactgtgaaa ccatactttg   31380
gtacagttaa caaggctggt acctatgtta gcgaaaggac acatcgagag gctgatagag   31440
ttctcttaaa tagaaaccag tccttgtcag ctacagtggc accgatggcc aaacaagtgg   31500
ccagagaagt catagtcacc cttgagccca tagttgctaa gcacaatgag actaaccaag   31560
ccttggttgg cgagatccaa agagtagcct cgaatgcagg ccagagatct gacttagaaa   31620
ggaatcgaat gacccttagc actagggcac ccccacagga ccctaggtac ctctagctaa   31680
tgaattccca agccttaggg agaacccttt gtttgaacaa gggggggcagg gtgccccatt   31740
aggatatcca acacaagtac aaaataggg ttctcctcaa acgaataact taagtctacc   31800
ttcgaatacc cagagtaacc cagtgattgg acagccctaa atcctggaat ggatgcttcg   31860
aatggccaag tgacaggcca gaatcgtcag gaaaaaccac cactgaatgt acaagggggg   31920
tcaatggcca gaattaccaa atcccacagc ctgctgtgcc agtgaaagga agacttgacc   31980
aactacttga tcgaacaaat gtatggccct agatcacatt gaaaaaaaag taataaaatag   32040
gctgaacgtc cattagagtg tttgaaagcc ctgaatcctt actctgtacg gagcagtagg   32100
ctggagttag agtccgtatc cgtaccgtac tacttgcctg gagtaggaaa gagtgttcta   32160
tctgttttt agccagtcac tggtagtgcg ggggggttcgc aatacaatag tgacttaggt   32220
ttatttctct ctgttcgcta tagtccatta gcggtataaa gtctaatcct tcttgtccgg   32280
taagcaagca ggggaacggc ccccttctgg cctttgcttg tttactttcg tccaccttct   32340
cagtcccgg tcggtgccac aggactttt cctcctaatt cactcgaagc atacatagtt   32400
tgatctccaa attcttggaa gttctactta gacggtttca cgggggtaca tcttgactcg   32460
tctagagcga atatgccgct gatgcataag gcagtgtggc acctgctgaa tcatatatca   32520
ttttttagcta ggcctcacgc acacaaagac ctgaacatcg cgttagaccg gttggtcaaa   32580
atagaaaaaa gacgagctgc taacattaac atggaacgag cctctctttc cttgttgcgg   32640
ctggtcgcct tagttcagtc gaatgacttt ttagaggcga aaccaaaccg cctgacatct   32700
atacagcctc acttccaagg ataatcgaaa aatttccta ttgtcctgtc cccacttcta   32760
cttccccgct acacccttcc ctaaagcctg gtccgtccaa cgaaagtcat tctggtcttt   32820
gctccgaata ttccgaagtt gaggatcagg aggttattgg tactgctgct gtggacttct   32880
tttcgaattg attctctaaa ggtaccagca acccttctag tcctttactt gatgctattc   32940
ctgttctagt tgatgccaat atgaatttct ctctatgcac tcttcccacg gagaaggaaa   33000
ttaggcttta tcgaaattct ctaattcatg attctgccat tctcacttt ggaaggggca   33060
gagggcttgg aatgaattct ttgagggcct atatttatat tagatggagg aaaagctcta   33120
cttatacgga gaggggggc tccctaacca gctttatcaa taaagacatt gcttcttcat   33180
ggattggttc ctcaaggtga cttccgcga taagatcaat aatataactc ctgaacgaaa   33240
gctgactcca ccggggcgag aactccttt taccaggcag aaagcatcct ctcttctagt   33300
ttagccctgc tatcgaaagc taaagcttct gttactgact gtacgcctac ttctcttcct   33360
cgctcttcac cggttggaat ggaatagggc tcgaaaggct ttcttccatg gccgtagcct   33420
gctttatcca taatgtttgg gctatatgct tttcatctct cttttcccctt ccgcttactg   33480
aagaactgga taacatgcta aaatccttgc tccggtggct ggaaaggcta cctctctcct   33540
tttgctttg ccatcttccc gttcttgtct acgataatg aatcattct ttcccggtaa   33600
aaaaggcatc aattcatgct actgatactg agtcagagaa atagccctct ttcttgattt   33660
cacacatagg accctctttc ccttctttc tagttgacct ctaaagagat tcaagccaat   33720
cgattcaata gaaggcatta agcagacaga gcgagcgaag aactgctgcc ataaaaggtt   33780
atctcaagtt ttcctcaaaa agacagcttt agagcacaag tcaagttcat aataggcgag   33840
caattacgaa tatggtttag cagtttacta gggtcttctt cttccccaag acctgatgcc   33900
ttatctgctt attgagctta gaacttcttt cacactattt gcgtgaagca tttgtttgct   33960
```

-continued

```
ttcccactgc tatctatgct acctttaaag gtatggcgac tttcccggtt cctgctgaat   34020
gaaactcctt tcctaaagcc aactcaccca actgaccttc ccagaaaaag gcttgcatac   34080
tctgttgaat cttctgtttg tgttcttgcg cctgcttgcc cttttcaaat cctatacctt   34140
ctgaccegtc cctggggcca ctctctagtg gatcatcttc ttatcatagc gagtacttta   34200
tctaaggaga ctaatggcga tcaaatttcc tttcctccgc tagcagatag agctcaccte   34260
gcgtaaggtg ggcgtcttcg ccttgattct ctagtttatt agaaccaaat cttgagatga   34320
gattggcata gaaaattgac tcaactggct tagggctagt tatccccgcg aacgctaacc   34380
cagacgctta tcgcacgttt tttttgcatt gagttcggaa agtcctcctc cgtgctcttg   34440
ttgctggtat tagggaggcc catcttctta cttaacgagt ttgtgtcgcg taatgctgtg   34500
ccaaaggaga aaggaagatt tgtttttttca caatggaatc atgacaacgt ctagttccgc   34560
ttcttgctct tttgcaagaa tgcctttagt agacaaccaa cgatttgaat tcaaaatccc   34620
ggggcagcta taccgatgtg tcaacgtcaa cggtacttct ctgatctgat cgagaatcat   34680
tctccaacct gcttttagtc aggttgaaaa gcctttccca atcctgttcc cagggcagcg   34740
ctcagtagca acctctcttt gcaaccgggg tattgcttc ctatgcaccc attgattttg   34800
ctcgatggga tattaagaat aagcagcagc ctcagatgag gagatggcca aagagagaga   34860
cccagcctgg tgatgccaat aatccttgat aacaagaaca cacgagcaca tgactaagag   34920
ggagaagggc cttaaacaga gaaaatcaag tcggtttcgg atagctagat tcccccttgg   34980
attcctttt cttcccagtt ggcctgcatt ggctagggat ggtacgttat ttaaacagtg   35040
acatttctca tggatttgaa cacataatct tagcaatcct agatcacacc tatatgaagc   35100
cttgcggcat ctctaacttc ctgcctcgtc atcccaccgt gggggggttgg acttgttctc   35160
tctattcact ttcgacgata gggtaagagc cgcttctttc tcgcggggggg acgccccgt   35220
aaccaattta catttccttg gctcaggtta ttctcaactc atcttatgcg ctttttaagt   35280
cattccagtt caaggactcc actccagtca aagacggaga cgaggctgtg tacaaaaaag   35340
gggggggatag tctatttaga tagtgagtat gttggattgg tccctggaga aagagtgaat   35400
actgagccat caaaaaactcg gagggcctca atcccaatga cccagagatt acgatctaca   35460
accttcccca caaggtagcc cccgtgctaa taccatattg gtgctaactg tccggcgcaa   35520
gcccccttagg gaatcataag atcggtcaac aggcaatgcg ggcccgacga accttaaatt   35580
tctagctcca aaactaattg atcctagaga ataaggtttt ggccgtgtgc ccgctcattt   35640
aaaagtcgta taaagcatca actttgattc ctacatcgtt tgtatctccg atttgagata   35700
agggtgagag gagagggccg aaacaattgg atccgagacg gaggagaag ggtagagccc   35760
cgttcctggt aagcaatgaa caattctata aaaaatttga tatctcgctg gctattccat   35820
ttctgagatt tagagttccg aggcttggta gaggctttga cgccgaagcg aaggtagaaa   35880
ggaatggaat gatatcgggt gaacagaatc tctgtctcgg attccgtgga gcttagggat   35940
caatatgatg actggtttgt ttgggtaccc tttttttgtt tggccaattc cctcttctaa   36000
gatcacaaca tattgaaacg acggcaacgg aaaggtgtgg aatcctttct tgtcaccttc   36060
gcttcaacca gggctgaacc cgtaatgtac caacgaggga aagaaagctt cattaaaagt   36120
atgtacttcc ggtttgggaa gattgagtct ttcgagacat tcattaaaaa atatcccaaa   36180
gggcaggaat tcgcttcaaa gaaagaggtg gccatcaggt ggagcaccca taaagcttgg   36240
gaaatacctt ttctgagccg cctacctatc cgctactctc attgattctc tcataaggtg   36300
atcagacagg caagtctagc tcacaagcag ctgtggaacg tcttccccga tctctgctcg   36360
tgtgtaatgc cggtcaaggt atcttcaggg gctcctaaac aagagttttg actaggtaga   36420
tttgcccttc tacgccgttt taggtgagtt cggactcaat cattgaccgg agattgggac   36480
tgaaagatgg caactagctg acttcttcct gtcactcgta tggcaactag ctgacttctt   36540
cctgtcactc gtacagatct gattgaagat attgcattag aaagggatac aaagtcactt   36600
ccgaagattg aaagagaggc ccggttcgat actggtcttg ttgcgcttct tcgagttcat   36660
gacggatagc ccgctaggga ctgcttggct tgttagcgag aaagcgcata aaagaatgcc   36720
attgatcgat caatagatca aatgtttcgt ccgtcactgc cattttgact aggtggattt   36780
tgccttctag ttgacttctt tctgcgggat accctagtta gagcagtgaa acctttaagg   36840
caagagatgc gggcaagaaa actagaaccc taacgatgcg ctagaagggg tagaaagcct   36900
gttcttttgg tacaaatcct cttgattgaa tgaaggctag ctgacttcga tactgaatga   36960
actcgcatgc tggagaaccg atgagagaca tagtcgatgc caatatagct gtaatttcac   37020
acttgagctt ttcccttcga agagctgatc tttcatttca aaagtggtat ctcccccaatg   37080
gagaaatgat gctagccctt tttccttcga tgacagagat tgaaatggat aaagtggatt   37140
ctccctaatg gtgaaatgag actgatttct agatttcact gatttcagtg attgaactga   37200
tggcaactag cgagcaatct tactcaatag gggctttccg tcttaaaagc cttccttctt   37260
gcttgcttgc gagaaggctt tcttgcgttc ttgcttagct tatttcaaag gggaggcagc   37320
ggaccaataa gctagctgtc ccaaccaaga caggagctag cctcttatct taaaggctat   37380
cgatttcctc cttgaggagc aaggaagatc agaggtcacg ctggaaagct atcaactaac   37440
ctgtaagaag actctttctt ggggcttctt cttagtccgt taggtagttg cctagagcta   37500
ttaactagac cgaaagggga ataacgacca gtcttcctag cgatgtacaa ttctttttgt   37560
atatgaaatc tcgatgtcta ggtcaattca atatcgaaca gaaaggtagc aattcttttg   37620
gcacagtctt ttggtatatg caattgagaa gccaaagtca gatagaaggg cttgccttcc   37680
gcactttcgt ataccaaata cgaattgaga agtgactttg tacaaaagta cattgtacca   37740
tcagtcaatc aaatttctcc tatccattta gaactgaatt ttgtaccaac taaacctaag   37800
ccaatagagc gtcttgcctt cgcaatatcg aaggagaaat gtagtcaatg cggtacgcca   37860
tacaaccatc ccttcccctc ctagtccaag aagagcttcc cctccttcca ggccctaaaa   37920
accttgcttc ctaagcatac tgagaaagaa ttagcagagt cgtctccctc ctcctaaaag   37980
agagaagcgg gctaagctgc tataaagagc gagaaccggc taagttgaag atgatgggaa   38040
ttttccaatt cgattgggta cttatcgcgg accctggaga atcttcgtat tctgtctaca   38100
acatctgtat ctagtaaagg attgaaaaac tggggtctac ccttctcccc tacgtactga   38160
ttgaagagga ggggtttgag tggactatct tacgggaatg ggttaagagc tggttacggc   38220
cagtactatg gaacaaaacc gtcgaaaaaa gtctttctaa aatagaccag atatgccgaa   38280
tctgagctga gagatgctag gtctcgtcta agtgcgtctc cgcatgtgga aagttccagt   38340
ttttcttcca gatctatcaa gcctcataca gatcttatta aaatacgagg taaacgacat   38400
cacatacggt attcttgctt atccaaagcc gttcagtggt gaatcggtgg atcagagatg   38460
ccttccgtcg atcgactgta gtcgagaaaa acataggaat gctgtggtgg atgtctagct   38520
gcaatctttg gtttttgtctg gcctcgacta gaaagtctca aatcactacg aaggataaag   38580
taggtaatgc aattcgcact cgaattggca aagttgtggg tatcacaccc tggataaaag   38640
aaagttcgga aggttcatca attcgatcca ccggtcgagc gtaattgtct tctatttaat   38700
```

-continued

```
attccaaact atctcaccgg cctttcatcc ctaccctatc gtaggaaatt gcgtatgaaa 38760
aggagtctaa tttgtttggg gtgaacttac tgttcccggc tttacctcat agaggtagaa 38820
aggctgattt tgagtacaaa gtcgaggtaa acggcttcca ctcggttagc ttcctctgct 38880
ttcagtaaaa atcccaaata tgatcgaggc actctttctc ttatagcgct ctttccttcc 38940
cttcgagcta gccggaagaa atccatttct tttgtctgta agagaaaagg cgcttattcc 39000
atgaaatagg agcgtagcgg agtcatgaac aaacaagaat agccacttcc ttatctacgc 39060
tatttacttt cctcccctcg tgggaagtag caagagcctt tatctaatcg actattgaac 39120
catctcacct gaaagtcagt cgctaccttaa aggcatgcct tgactccaag agctaactcg 39180
atgggacttg ctttcctaaa gagaagacga agaggatgac actggggatc gttctgactt 39240
aaagaaattc ccatgagctg gtaactccaa aatcgatgat tcttggccac tgacttactg 39300
ctttcactca aatgccactg atgcgtaaga cattgagttg gactactttc cttctggtaa 39360
tgcctttccc tgtggtcacc ttgcccttct acttactggc ttggctattt cgaaggattc 39420
gcttcggcgg gtgattgaac taaaaaagaa tttttgaaag tggcactcct tccttgcttc 39480
ttacccgta gtggggagatt ttttgacaat cggtcgtaga ttccctggct tggctaggaa 39540
cctagtccct tcttgtgaca acagaagaga aggaatttcc ttcttgtcca ataccaacta 39600
tgatttccac gaaatgctag tcgaagatcc actatttact tatttctaat aagataggac 39660
catcggaaag aaagtcaagc agaatcccgt gctttcgggt gattccgcat tcaaatgcta 39720
cccacgtgaa tgctagtcga atccgtatgc ccaaaccaca taagataagc taagcagcta 39780
gatcgattcc aaacgtgtga ttagtagctg atgcagaaaa aagaagaaca gcttcttcta 39840
tgatgacatc tgcagcagat tcaatggcct cggtttacac attcttgact tgaaaaaaag 39900
agtttgaagg attctcgtca gaaggtcagg tcagaagtgg attccctttc tggggtacga 39960
tactaggcta tgattcccgg agagagagaa ctcttataag aaaatgggcc ttgagcctga 40020
ttcatcgcct tgacttgatt cgggtaagtc aaagtaagga ctttgctttt tcaaatccca 40080
gacaggaagg aagtcgaaaa aagatctgct tcggttgatc ctgaagcaga agaagagacc 40140
tttttcccctt gggaatgaa aaagatcatc tttctaaaaa tgaaataaga cgtgttcact 40200
ctgtaagagc cttggtctt agtcttaaag agaaggaagc cggcaatagc acgatagcaa 40260
agagcaaaga aagctaagcg cgcagagaga gcagcatata gcgctaaaga gtccaaatac 40320
aagaaaggca gagcgcgaag cttgtggtcc gttcctttcc caactatagg cccgaaggaa 40380
atcttttatc ttcttgccgg gaaatcgttt tattaccagg ttcgattacc ataagtggaa 40440
gttcaaacct tatatctccg atatatagga tagaatgtca gaaaaaaatc aattttggta 40500
gatagtatgg cttgacaatg tcgagctaag actatcgcga agtaaacata gggtctgtct 40560
cagccttgac tatggaatct gatttcctag cgactatgtt ccccttttttt cctgcagtct 40620
ttccagctat ggatcctaca attccctatg aagctccctg acaacccctt caatccatct 40680
tcatcttggc tggcagccta gattgagccc tgggactgat cttcccgttg gctttactgc 40740
agcagtactc acagtgaaag gtcagcgggg ggcatagcga aattcctcac cgagatgacc 40800
ggacaaccta tcgaccagat cgcaccagcg gagcgattaa aagcgtcttt ggagcgaatt 40860
cctttgaagt agttagtgct ctaattgagt gagccgtgga tcataaatga tgagcgtagc 40920
ttaatttagc tgatctcaca ccgaactata aataaatcaa tatgtgagtg gctctttata 40980
gagacttagc ccaatggcta ccaccggaag cgcgctaagt tagtcacagg ggaaccccaa 41040
gttcttccta acctcagact ctataaaatc aacttggatg gcttgcttgt ttagcttgcc 41100
ccttctttga atgtgtacaa ttagagcaag caaatggcta gcagggccga ggaaccacaa 41160
tgaacgggac gacagaagtt ccacaagaat atgaccagag agatatgttc ttcttcgtgc 41220
atgcaggtct ggttcctgag aaaacagatc tctattacg agtttcgccg tacaatatat 41280
aacccgggac tggctgaaat gaatgaattc tcatggtttc cgccggctaa tagggcgagc 41340
agcgtaatgg agtccccggg gcggacgacg tgagtgagag cccagaccat agcggcttta 41400
gaggcttctc tctcggattg aacggcgacg aaaacgttct ccggaggctt tcctttctgc 41460
tttactgtga tttacccata accatcagcg gcaaggatta tggaagaggc caaaccaacc 41520
caggtacacc acaagtagat acggttggag tagcagatcc tatagaaaca aagacaaagc 41580
ccgaggcaga tccagacgcg tacctaggtg gcgcagcatc ccttcgagtt gcttgccacc 41640
cctttctctc tttctcctc ctccggtcgc ctcgttacct tttttgcttt ctcacattga 41700
cttctttccg cttttttcact tcttttcctt tgattcagct gtattagtag ctgatgattc 41760
ctttttttcca agtgtgtccg attggtatca ctcgcataag acttttcctt tatttgtagc 41820
ggccatgtgg catagtccat cttttcctta tctttttccc tcaaaataga atatatactt 41880
gcctttgtac tgatttgaat atatgtagga aggcttagtg gaagggcggc accctcttca 41940
gaggtgcccg aggggcagct aggcgagcag ggtcaagaaa gaaaaaaagt cgtaggcaga 42000
gatgactaag tgaagaaggc ccggcccccaa gctgttcaag aatagtgtcg ttgagtttct 42060
cgacccttttg tcttaggatt agtcagttct atttctcgat gggggcaggg aagggatata 42120
actcagcggt agagtgtcac cttgacgtgg tggaagtcat cagttcgagc ctgattatcc 42180
ctaaacccaa tgtgagtttt tcattttgat ttgctacccc gccgtgattg aatgagaatg 42240
gataagaggc tcgtgggatt gacgtgaggg ggcagggatg gctatatttc tgggagcgaa 42300
ctccgggcga atatgaagcg catggataca agttaggcct tggaatgaaa gacaattccg 42360
aatccgcttt gtctacgaac aaggaagcta taagtaatgc aactatgaat ctcatggaga 42420
gttcgatcca ttaggttctt cgatttgttc agaaaagaaa cgagagacaa gaaaacatct 42480
tttattacga ttaaaaggac caatctcaaa tagaccaaga tccaatttcg ggtcatttct 42540
tggtgaacat gatctgccat aatctcttcg atcccttcat ttatgtgcca gaataaagag 42600
agatttggta ggaaagcgga agagactttt tgtatatgat aatcaaaggg agcgggaaag 42660
ctgcagtaat tctttggaaa agcccgcttc tctttgtctt cgagcttgaa ttcttcaatc 42720
cactgattcg ttccttcata tacctcccca caatagatag gagacaaatg ggaataaccg 42780
aaccacgtct acaaaatgcc agtaccatgc agctgcttca gcaccaacgt gatgctcctt 42840
ggtcagatga ccaagatatt ggcgaatacc acatacgatc gagaaaagag tacctataat 42900
cacatgaaaa ccatgaaagc cagttgctaa gaaaaaggta gaaccataaa tactatccga 42960
aattgtggag ggcgcttgat aatattccat tccttgaaag gcggtgaata ctagagccag 43020
tgaaacggta gctactaaag cgtaaactgc tcgtttttcc ttccccgcga gtatagcatg 43080
atgagcccaa gttacggcag ctccggatga aaggggaata agagattaa gaaaagggat 43140
ttcccgagga tctaaaaccg caatcccttt tgggggccaa ataccctccga tctctaccgt 43200
aggtgccaaa gaagaatgag aagagcccg aaaaagagca aaaaggaaca taacctccga 43260
aacgataaac agaataaacc catatcgagg tcctaattgt acgactttgg tatgatgtcc 43320
ttccaacgtg gattcacgta gaacatcgcg ccaccatacg aacatggtat ataggataaa 43380
gattaggccc aaactgagaa gtgttgcacc cccttgaaat gagtgcatgt acatcacacc 43440
```

```
tcctacggtg gttgccaaag ctccgagtga acccgaaata ggccatggac ttggatctac   43500
caaatgataa gagtgcctct gagattcaat cataaacaac tttgcctcgg ttgcatgtaa   43560
accccccctt caccccgcc ccctaaagtg gtaaagaagg ctctttgggg tccctctttc   43620
tatctgacag gacaaacaaa taggaaggga tggttctttc attgcaagaa gtctaactag   43680
aaaaggatct ccctattact ttgataagtt tcttgttggt ttgaccgacg aactacgtgg   43740
gaaaatggac cttctttctt ttcagaaagc atttttttaaa gtaacaattc cattcagttc   43800
ggtttcggaa aactttccgc cggggcctaa catcaaaggc gcaggttgat ctctctggtt   43860
gaggctgcaa ttcattttga cacgtgggaa gggcttactc tactagtggc tcggcttggt   43920
ctcgctccct tcccgtgcta ttcctcccca ctaaaaaagc gattgagaat ctcgagaacc   43980
tttctgaacg tctgtcttcg cggggcgatt tgaaaaggag tatatctttc ttgtagtgcc   44040
ttccattcca ctattctgat cgagaaagaa tctcttctga acgaccaagt cataatgaga   44100
ttaaaaaccg atgcttcctt ggccgtgtgg aacatggatt agcattatgt cattcctaca   44160
agtgatcccc catccaggat tggaagaagt gctatatgag gacttcgaga tcaaatagaa   44220
tatgttcctt tccattcctc gtgagccact gatttctccg aaacaagaga tcaaagtgat   44280
cttcctcctt tttcccaata agtcgacggc cttacaccat tgggagactt cgaataaact   44340
ggagtacata taggatagac cggtgctaaa acccttctc aagatctctt ccaaactgtt   44400
ggggtccttg ctccggatgt tgttcgtacg gtgtgaaagc agttggttac gtagtttag   44460
aattctgctg atcccaagta gtccatctcc atcattgcat atggcaatat agaaagtaaa   44520
gaggaaaagg catgaccaga agaattgtgt gaaataagtg aatttatcca gttgaggcat   44580
cttgattgag aataaaggat tcccccata cagaaagaga ggccttcctg tacgagtagt   44640
gaagaactaa acgattttgt tttgttggtt gttgaccaac ggaaagaaag ggagaaagaa   44700
atgccagtcg cttagtaaaa aggctctcta agagtttggg gtcctttcta aaagcgagaa   44760
gaaactcctc gtattcagag acagagtcta gctccaaact tttgacaatg ttggaggata   44820
cctccatata gtggtcatgg gtccgtgaga attgccatgg cttccaacct ctttcggtaa   44880
agtgaactaa ttggtccttt acaaaaaggg tcatttccgc ctttttttgtc tccacacgga   44940
gaggatccgt gttaggatca taagccgggg ggccgtcggca tgcctcggca ggggggttgg   45000
gtgccccggc gtttctcgcc tcatctaccg aggggggatga cgaatccggc atgggctcga   45060
gaagcacacg ctcctcgaaa ctgttacatg tgcttgagtc cgatactgga acctgctgtg   45120
atgggcctac cataagattt ttactttccg aatctacttg tcgccttccc gaggaaggac   45180
cgacgtcctc tacgggatca gggcttcggt ctcgtttttct agaagtgggc tccccttcga   45240
tgccctgccc ctgaccttct gaatcagacg gcaggttgag gtatttttcc caaccgccag   45300
agttacccac cgaatccgac cctgcgggca tcatgcgaag aggacccgct agtacttctg   45360
agactccggc ttctgtaatg aggcccttcg taaaaacccc tatggccaag gtaagccca   45420
tcggtaggcc taacttgcct aaagtatagg cgagggctcg accccccaga gctattccta   45480
tttgaaaaag gggggcctga aaatgcccag aaagacaagt acaagtaggc ccagcaacaa   45540
gaatagaata gaaatcctaa aaaccaggga gaaactgatc aaactacgta aactttccag   45600
ggagaaattg atcaaactac gtacactact agatcaaggg tcgaaaaggg cattctatct   45660
tttttttctat tcgctcatga tctggcctgg tcgacccaat catgatattg aaggatggga   45720
cctttctcg aaaaagaaaa atcctgccga catacgggca ttcttttttg taccttagta   45780
cactgaacac caaccccggg aaaaaagaaa acgacaagca atcatgaaac tggcaaagct   45840
tgataaccat tttctcatga cgagcacatt ggatcatttt aacaattttg aggagatcgc   45900
gcatcagctc tgagatattc cttaacccct tttccgctcc aggtaaagaa agaggcagaa   45960
ttcgttatcg gagtatcctc cgccaactaa cctgagcatg ctctctaaca tcacatacga   46020
gattctttgt ctggctttta taactcctta aggaagtgtc tcttccgagt attttctcac   46080
ttgctttcct aagctaagtc agacattcaa atcaaggaaa gcgaatgaga aaccttcttg   46140
gaatcggttc gttcgggagg gtgtgttagt gccagtacgg ggtgtggtac tggttctcat   46200
ttcctggttt ggatttcagt gaaaaagctt tgaagccgat atcaaaggag ttccttgctt   46260
tctgacccca agtgtacctc attggtaggc tttccccaac ggttgcggcc tgctgtagta   46320
tgaagtacgc cccaataaat tgaagaagag tctcattcgt gagcaaagtc gatagccagt   46380
ccatcttgtc ttctccactt caatgaaagc tagctcctac tcctttagga ttcccttttt   46440
cactgttttt acgaaccttc acatagatta cgaggcttac cgaatgagtt gaccctagtg   46500
aaagaggact ttcaagaaaa agtccagtcc ccacccaatc ccgcttgaag gggaaagatc   46560
gtcctcgtaa agcagtactg gttcaagggc ttggtagcga gggtgtcacc tgtatattct   46620
ctccgcaagg ggaaagaaag tgtgccgcca agtcttgctc tggcttgcca aaagcattga   46680
acatagaatg attagcggaa atggtagact atcgatccaa gccggatagg gtttaggata   46740
gcgacgagac acgtggtgat ggaaatctcg cgcagtctag taatactatt cgccattctt   46800
tcctaacccc tgtcattttt acaagccgaa ttgatccctt tagtagatcg tcagccttag   46860
ctttttttct ttcttccttc tcttaaagaa atccagtaat actatcagaa gtgatcgttt   46920
actagaattc gttattgagt attctcaggc ggggacagga ttcgaacctg tagtcttcag   46980
atcatgagcc tgatgagttg accattcctc caccccgctt cttgtccttc tcaatctctc   47040
tttctatagg atggaattga ggcctatccg gctaggtaag ctaaatcggt atatccagcc   47100
caacagctat tcgtagtgac agagaacccc tatatcccta attaagagaa tacatgtatg   47160
agctgaaaga gaggttgaat gtaattcagc tcgactgaaa ggagtggctt agttgaacat   47220
agtgagacta aggtacgatg tcagacagat ttgacccagt cagggattca gaatgacttc   47280
attgactgat caccgaaaga aaactctata agcgtgtcat caagttaggt taagccaacc   47340
tcggtggtca cctttctgtt ctgatctaac accaacctat attatacgtt attctttatt   47400
ctttgacgt tttcttcaat aagtgcgagt ggcttccgct cctcatgaat aagattgaga   47460
aaaagggtga ggaatgtgat tcaagtagta gatgatgtcc tacttgatac tttaggaggg   47520
cttttgctaa acccacaaag aaagcatcgt gggactaatt acggatagaa gactgtttta   47580
gttgccggtg atactgcttg agaagaagta cacctctttt ttatttagta ctcgataaat   47640
atggaactac ttttgattat tgccgcggct tttgctttag ctcattctct tttcgatgaa   47700
gcttttttttg ttcattccga gacttttttat gaaagcagct aattgaagac tcacatttca   47760
gagtcaatag cttcgacata ttgtatatcg aagatgggag aggcaaccat cagactggtt   47820
tatctaacct tctggttccg ggggtaaccc attacacctc cttcttgatt cccatgcggt   47880
gctaacaacc gatgcagcct aacccaatgc cgatagtgca agtctctatc tatataggaa   47940
gtaaaggctc tcgcagtagt tgttctgtaa gggcttccat tacttgcttc aattgcattg   48000
atttatcctt tctggcctca gacttgtacc taatcttcta aagatcaacc gcgagtcaag   48060
tcaaagaact cctctttcgt agtacacttc ttgctgaata ccttttttct tgcttcctcc   48120
aattggcaat aggacatcct ctcctaagct aaggaagtac ttcaatgaag gcatcgagtg   48180
```

-continued

```
atttcacccc ttaagtaagg cgaattgaca aagcctagtc taagagcagg atgaagtagc 48240
aaagggaac  taaatagcct tacagggaat ggggttagag aaggtggtga aagggtatcg 48300
agctagaatg aaactacagg gcaactcttt ataaaggagg gaatccgtat ttgtggacgt 48360
attgccaatg cttgaacaag acagcttaga cctattagag cgataccaga aaaaggacag 48420
aaatcgatct ctttaaagac agaaagaccg gtataaccaa gcaagataga aagaaatgac 48480
cgattgccat acatagaccg atgaaagaga acagactgtt gttggcagga taaatcccct 48540
tattacagaa agagatcgaa cggaagattt tttcttctat tatgagattt cgaatgacat 48600
ctgtaaaaac tagatgattc aacgagtacc gatgctttgc tttggcgtag gtgtctgtta 48660
aatgttgttt gggatggtct aatagttgct ccgttttcat ctacggttga cggaacgcag 48720
agcaaggact tcctgcccga tccgattccg gggttaaaag aaaaggccgt ggacaagaaa 48780
gcggttcaaa ctgcccctta tttatgatga agggagggga gctgcatcga cccttttcagc 48840
ggtttttaggc gctaaatgct ggaaatatag gttagtgcgg gataatcaat ctccacactt 48900
tcttatagct atagccgaga cttctgttga tggaaggggga tagacgaagt gactcgattt 48960
aaagtaagca acgagaggca ataaggtccc gatgtcactc tttatttatt ttgattttct 49020
ttttttcttga ggtagttaat gtgtatccgg atgtggaacc attggtgtat cggctgaggc 49080
ctcttgcttg gcgatttgcc ttatcttttc agtaagccag taagcaatcc tcaagaaagg 49140
aagatctaga cttctacta actctatggc ataactccgg tctaaggtct aagacttcac 49200
ccaaagagtg aagcgaatca atggtctcct cctcggctt  cttgctaatg gaagtactgc 49260
tctgagtcag gtcctatggc tttctatctc cttcatcttg ttggactgat cctctttatc 49320
tatctttctt gtctgagtgc ttttccaagc cttctttctt tcagaacctc cttcgctctt 49380
cttttttttct aaggtaaatg gagtcagagg agaggtaggt agtatgcctt tccccattct 49440
gctaggggtgg cttttcttaa ctgggctagt gtcccctttct gtttaaggtg cgtttttcttt 49500
tcgactggtc ctataagtag ttgtgtgagg gggtgcgcgc ctctttttct tcttccggct 49560
tgagttctta atgcctgaag ggaaagactc ttcgaccaca ttaacggctt gagcaagagc 49620
attggtgctt acacgatgaa agtaatttgg ccaagctaga ggattttcca tcgatcgtga 49680
ctcaagaacg taaggaactg aaatcgctca aaaagagaaa tcattactgg caggaggtac 49740
cacagtctca cagacgtcat ttcctccttt tcatacggaa aaaactatca gacctactac 49800
atatacgggc taagatagag ttggaatgct tgagatgaaa cccttaggac tcagggaaaa 49860
gaagatgaac cttactactg caagactcaa aagatagaac agaaaaagta ctcgctcact 49920
gaaggtgcga aacgaaaaag aggttctttc gtcaagtgaa gagttaccac agtctcaagc 49980
cataaataaa aagcaggcag ctttcctaag cgatagccca atggtgaaag accagaagcc 50040
acattcctcc gctttcactt tatcttcctg ggagtcctct agtcttgcat tcgttctaat 50100
acgacacaat gaagaattcg attcattttc aattaggcct tgctctagcc tctttagggg 50160
ttattgattt cttggtcgct caacacatgt actctttacc cgcttatacg ttcatagcac 50220
aagaactact caagctgctt tatatactct agatggcagc tagctgagaa cccgaatgaa 50280
tccctgcgc  ctctatcatt tagctatcag gctttcaagg tcagtgcttt cgacttccct 50340
tactaatgct accccataatc tataggattg ttatctgtag gattgtacaa gacaacctta 50400
ccatcattgt ccagagcaac catcctatgc ctacactcga tgggctcatc cccaggtcca 50460
atagactcga tgtctaaatc gatcccaaat tcttcaacta gagcccttcc tttatactca 50520
tcgaagatta gatcatcagt actcgcaata aagaccagac ccatgaatct ttcaaatgta 50580
atcccaggat atagattgca taaccgacgg tcgaactcca ttaaggcaag attgaataag 50640
accctagata attctccaag aattggcata gaaccgaagt gtacacgtct accttcttca 50700
tcaatggtag cgagatccat aaactgacta accaggttat aacaaacaga atcagccccc 50760
acaaaggact taacaggatc taaaaccaga ctgctaggca tcgttgcata taatggatcc 50820
aggataatcc tgtgcagttt agtcacctta cccattttttt gaatacctga ataaaagaga 50880
tctacccgat ctactaatct gtatctctcc ttgggtacgc taccataagt atatcgatat 50940
aaatggatac tcaatgccgt gaacactaag acatcttctt tttttgatgg tgaaactaca 51000
atagaagagt atgaactctc ttcgcaagga taaaacgtta aatctggaaa atctggtagc 51060
gtagcatata aatagttttc aagagcatcc caccttattt tcctggctct tagcggtgat 51120
agtgtgtaaa aaccagaaag taacatcagt tgaagattac ataagtccct ctgagacaga 51180
ttatattgaa gacggctttg aaaatcatta tagataaaat tctatatcctc tgatagttga 51240
actagcgaac tgttaattga attataagat ctagcacttg tcatagtcaa cttaaaagta 51300
ttgaatcgtt ttatcaccat catcttcttg ttattaattc ttgaccttga gggagtcgtta 51360
ttaattctaa ctcagctgga gatgaatatg acatcatacc cattgcgaga aagactgcta 51420
ctatgaggcc taaacctaag gccaccctag catttggggt gctaccctca gagttgatac 51480
tattaggatt atcgcttgct atattgattt ccgagaaagg atagacattc tcaatggctg 51540
ataagacttg ctcagtgata tactgactct caacaaaact cattctctta tagggaggat 51600
agaaatgaaa attcacatcc ttgaatgatt catatggaag ctctctcgga actaagattc 51660
ctggaggtgt tacttctggt actccaggta caaagtggta ccagatagaa caaccaaccc 51720
ccaagctaac taaaatcatt aaacgaccat acataccatt gtaatatgta atcaattcta 51780
taagtttttg agtgggtgtg ctggtgattg tgctggtgct ggtgctggcg acatcttcta 51840
ataaatcatg caacccactc ctgatcctgc tatttacaaa caaattagag ttcgaaaaac 51900
gtaccatttt tggtaagccg agagaagtaa agacatgcat taagatttc  ttcgctttttt 51960
tactaattag aaattcatgt cgttggaact gagtatactc tggataaaag cggaaatata 52020
atgccaacat atcatcagta cgagatttag gtgaaatatg actttctagt agttcagtaa 52080
gagggatact atttataggt aatactgttt catgtaaata gtcactagga aaacgattaa 52140
cccttttcatg aggtttcatc gtaataggtg tataaggctg gactggctta cgagcggccc 52200
ttcgcaaatt cagacctgtt cgcagagaga acgtatccct aatagtcaaa cgatatgata 52260
aaggtaggtt tctacaaacc ccactatcat aaatatcact tctggtgtga tgaaccctta 52320
atttctcaaa caaagataac attctgaatt tgttctttac tagtagtaga aatataacaa 52380
gggtttttca atcagctcat gccgggatag cacttaccat aatgaccttc ttattctaga 52440
ataagattat tggaacgtat tgataacaat aactaaaccg tagaatagga gagggcactt 52500
gtaagtatat tcagtaaggc atgctataat gatagtaaaa agatgctgat gtgccattac 52560
ccgtgaatt  tcctagtata caaggctatg agtggttaca gggggcagaga gccttgttac 52620
atcagccttg gaccggcatt atgggggatttg ccctaaaggg ctgccttaac cctaccagta 52680
attcccccca ggatttagat ttctctaccc ggggacagac acctgttata ctctaaagac 52740
catgaacaag tgggatggac ttccgaaaca acctgggaac taaagtcaaa agcggcatcg 52800
ggatcaggag cggacggagc ttcgaatgac tgaactctca tcactgtaag aagaaaggac 52860
tagtagcatc gcagaggagt aatctaggtc ggaatggaat aatgtatggt tttctcgcac 52920
```

-continued

```
agcgcttctg cccttgggca ttgattgggg ccgctagcaa acacttatac tctccccggg   52980
atcccgtgcc tcccctccaa cactttatgg cctggtatcg gaggcgacgg aagtactacc   53040
tgtcgcatga tgctaacgaa accgaaagcc cgggcggcac tctttcttgt gtgctcagag   53100
gaactccaac ttacaactat actttgtctt tcacactcca tagctctagc tctaagacga   53160
ggatttggtt attaacccga agaggtgccc gtgaacggag tccctacgac ttcttatttt   53220
atggagttgg agttagggat cagatacggt ggcttcttcc tgttcctcca atgggcagcc   53280
gataacggat gatgtcgact ataggttcta tgtccaccaa aagcagcgct aaaccgccca   53340
cgaaaacgaa ggaagagcaa ggcacatctg ttacacgaag aagggaatgg ctgaaactga   53400
gcgtgatagt acccagtgca aatataacct gcggtagaga gcgaggccgg gggtcgtctt   53460
agcggtggat ttacatcgtt cagaggcttt gctaaactgg ctatcaggat agagatagag   53520
taagatgaaa tgctttattt aatttaaggc gattccatta gggatttcta ccttagtaga   53580
tggaagacca accaaatctc aatttctaaa gatagaactt acttctttca agcgatcgac   53640
gaaagctttc tttcacaggc ggatcagtgc tctgattcta cttattagat ttttcaaaat   53700
gaaaagcttt acctaaaaaa gagggtcttg cgatgcttct tcaccccagg tcaccaacca   53760
gtggaagagt cgaaagcgga gtagaaacga acctttagcc acgtagggggc ccctagagcg   53820
ttcttttgag gatcttaact taatcagcag aggggaggag taattcagtg ccaagtccag   53880
gtcttcaatt ccattctatt gaggggtcaa caaggaccaa gtgctttctt cgtagtttac   53940
ccatgtaaag cgagatgatg gaaagccgga tgcgctacag gaagaagatg aaatgaatgc   54000
ttcgtttttag ctcttggatt gagtgagaac tgatagttag agcttgctct caatgaatgc   54060
cgagcggggc accagacttt tcgtatttaa gaaataatct gaggaaagac ccccactacc   54120
ggctctacag taaccgtggg gtcctcctct gaccctattt tgtacgtccg gtgcagtcgt   54180
ctccaaatga tccggtgcta attccagggt tggataattg gctgcagcat ggaagactac   54240
gaagagggaa gattcaattc atcattggcc cgctctatat ccccacggag cgataaggag   54300
agtaagttta ctcacccacc cgaccgacca gacaggaaag gcacgaagcg gaactcctgg   54360
aacaaaacaa gcagttcccg tcggaccaaa ccaaaaggaa gagcagctag ctacaccgga   54420
acagcttcaa ctaagacacc ggatcctcac tcagctgcta gaagaaaggg aatcgtcgaa   54480
tgagaacctt tgaggagaag aggggggcac ctgataccga tcggcgagaa tagactgcgt   54540
ctatcggtga ataatggtct gctccttgag atctctgtct ctctcgtctg tagcaagaaa   54600
acccaagcct gctgtataat ataataaggg cctcggcccc atttatcttc ttgcatcgaa   54660
ctagaatagc ccaatatagt atttctattct cgtcacctac gtaatctaat atagcttcac   54720
ctccccctaat aggaagaaca taaccagaac agctgtctgg tctaccatat gtttgttagc   54780
gctcggccgc caattggaac agacagtaca gcaaaaacaa ctggaagagc caacctcgat   54840
gccatccaag cccggcccag aatcacctca accttttaga aagaaaaact gctgaaagaa   54900
aggtcttatt tgatacagaa agactttcag gcagaacttg ggctatactt tggttgggca   54960
atggtaagct gattcgtttc tgggatgatg tttggccatg ccactctact cagagatgca   55020
tgccagaatt gatatcaatt cacaaggttc tcatgatctc aaagtgatag actacattca   55080
atatgaagga gaaaaaagga cttctccctc tattcaacta cccatccaag agcatttggc   55140
ttcagaatac tttttatagg gaggataatc tcttttggcg gctcaatcct cacggtaata   55200
attatgccaa ttccgcctaa aaatctcttc aggtgatcaa gagggccccct ttttcagtag   55260
atgagattag gatgaaaggt attatctcaa cgatgctttt ctctggcttg cttttcaaaa   55320
ttgcattttg gcctgcggta atgtaatcgg tattttcaaa acattttttt ctatgaaagc   55380
aagagatgga aagttttgtt ctaaattctg ccttattcca tgagatctag aagcacttat   55440
gcaactttat ctctctccat ttccctcact tttttttact tctttcaaag gggaatgaag   55500
accttcctta gaagttgtcg ctcgatcgaa aggatataat acatacaaaa ccttaacttc   55560
gcggactttc cgaggtataa ccttcgccac gacattagtg gcttagctct tcgcgcttcc   55620
cgcaggcttt tttataggga gagagtcagg ggggggcggta cggaagattg gtccgctccg   55680
caaagcttag cttttcggtt ccctcccccct atgtggtcgg ccttattacc agtctgcctc   55740
ctttctcttg atggaatatc tcaatacccg agctcctgct ttccttgtgt tcttcaccgg   55800
cgctcgccgg atgtatcact catcccgctc ctaaggtaag gagtcttctg tgtgttagaa   55860
tctttacggg aatgaatcgc atatgttggt tgagaattgc tcgggaattc attgataatg   55920
ataatgactt tgccaggttc tagggggcta ctattctttt ttgtcgatcg agccgctctc   55980
cctcattcca ctcgtccagc cctcttcacg aacttgtaca atcgatgcca cagagatagc   56040
caactctatt atcgaaaaaa tcaggaaagg ggcgacgatt tggcaccaga tatccggagg   56100
tgtgaaaga gcagctgtga gaagcggaaa aaccatcaaa aaacgacgat tgttcgtgga   56160
ggtttccaca gaaagacccc ttggttctgg caaacggatc acaattacag gtacctggga   56220
gcataccgat ggaatgaacg aaatacgaac agttaacata atatggtcat agatcttagg   56280
ttgtaacttg atcatgagcg aatttgttga tgttgcaccc atcaagtatg gaaagtgcca   56340
aacattggga actacccggg gaggagttag gaacaggaac aaggagaagc gagaaccact   56400
taaatggagg aatcgattgt atttcgtcct ttgttcccca tagcaactgg ggatcaaaaa   56460
gcaccaaatt tgatgactta ttaaaggaaa gacgaagtaa gagcatgcta ttgaagacgt   56520
tgcaagatac gtcgggggagg cctccgttga ttgtgtacga acaaaatacg agtccaaagg   56580
caaggtaaga ataagaaagg gtttagctaa tggagatatt aactcttccg ggaaccagta   56640
acgcgtaaac catgtcaaac caagaccgat caatatccga acggaacgga ttcgaacttc   56700
tcctagaata gtttccggtg cgaaatgaaa ttcataggat atatgagtaa ttcaaaggat   56760
aaataaaagc taataaaaag tttcagacct gctcatagag ttcggcatcc tgcggtacag   56820
gggtagaata catacaaaac tgaaccagaa gggactatgt cttttcaaaat cttcctaaaa   56880
acagaactcc tttgcccttt attaactaat gttttaacca tataggcaag ccgttgattc   56940
cggcagcccg gttcttcatt cattaagtct gttagatgga gatccacccc cgagcgtata   57000
tcattctcgg gcactccttg ccccctgtaaa agcaggctca tctgctcaat cagcaactct   57060
tgctttatgc aggctgttct gaaagtaggg cataaagtct catccctccg gagggcttct   57120
atatagggt tgggtgccct aataggattc tccggttcaa gcggaagatt cagatccggg   57180
atctctccca tccggtctgc ctccatagca aaaactgttt cgtgaaaaag ataagtgtag   57240
aaaaccgata aaagaaccat gatgagaaaa ttccagcgta cgagtagagg ttgtagaaaa   57300
cgaaaaaaaa aaggaaagaa ttcgccgagc aaggaaatca aaacgaaaac caaaacagaa   57360
agtatcatag tacgtcgtcc ttccctgttc tagtgcttgc ataccccataa ggatacgctt   57420
atatacccga atttcgccgg attgcaggaa tgataactga tcatttgatc agaaaactaa   57480
gggagcctgg gcataaagaa actggaaaaa ggtttctaag caaagttgct gagtataggt   57540
ctcgtgtgct tgctatagaa agtacatata cgagtcacga gtaagaggaa gcggtaacgg   57600
tcgatggatg ttcatatttg agtatttgct gacggaatgc ctcacatcaa ggtgacagga   57660
```

-continued

```
ttcgaaccta tggccctctg tacccaaaac agatgcgctg accagactgc gctacacctc   57720
gtctcaccac cccggagcat atagatccac ccgatcgatg aacactcaaa ccgaactcac   57780
ccatcctttt gggcacaggg acgcgagaac ctaagaaaca gcttttttat tttctttctt   57840
ttcttttttcc attttgatag attttctatt ttatatatct atttttaaca tgcctccagc   57900
aagatagggc gacgcaaaaa agccgtatag cgcaggacgg ctcacatttt ttggcttact   57960
cttgcgcttt cattgaaaaa tccggccttt ggacccttgg cccgcttaga agtggattcg   58020
aaccactgac acaaggattt tcagtccttt gctctaacca gctgagctac ctgaaccact   58080
ttcctaaaag atgttttctt catcgaatag cgccctacct taccacttga ctagtaaaaa   58140
gcccttgtac taaaaatcga ataagaataa taagaaataa tagaatctat atataggcct   58200
ttttcgcttc ttcgtcaagc tttcgagcag ctctttcaac tgccgcctaa tccccctcaa   58260
gaaccgagag ccgcccagcc cctgacagc cggaggagg gagcttgctt atagaaagaa   58320
gataggccga tcaaacaaaa agaacgcgca aaggtctctc cgctcctagt cactaagtag   58380
tgctattctg gggggctgga ctccaccaag aggttctttc tctcacgtca tttcgcccgc   58440
ccgtttcact tctgttccgg aggaaatggg atttgaaccc atgatacaat cttcttgtat   58500
gtcgatttag caaaccaatg ccttaagcca ctcagccata cctccaagtt gtgttgatcg   58560
gaatggaatt tgatgtgccg ggtttggttg gttgcccgaa gggctatctg acccgatcaa   58620
ctgcgtaagc cgtagcgcgc tagcgcgcgt actattccgg ggactctatc cagatctatg   58680
gatctcccca gcatccaagc gggactccat caaaatctgc cactcgttgg gcgacgcctt   58740
ctttctacg aacacccac cactgaatga tgaactttgc cagttttcgc ctccgacccg   58800
agaacacagg gtcaagccaa gcccttaccc gcctgaatgg aattcatatc tccttcgtct   58860
ggtcgagaag ggagaaagcc cgtggaactg gactgtgact cttctattac attatggaga   58920
agtccattct cgtcatggtc gatccacgtc ctaccgtagt gcccggagaa ccaggcttgc   58980
ttagcttaca aagctagctt actaacgcga atcatttttt attgattgca cgagctagcc   59040
agcaaagccc ccgacgctta atcccttcat ttaggcacct actgacacta aagccgttcc   59100
actcgtgctt ctctaacgag aatcacttcg ttccactctc ctaacaggcc agcaagccat   59160
tcctagcggc ttagcccttg ttaaaggcta aagagcgtac tgaacactca ccctttctcg   59220
ccagcaagct aagctcctag tcctcttagc cggcttacct ttaacctaac tctctagttt   59280
atggcgggaa aacacgactt ttttgatcaa aaaacagaag gccattgaaa agctctttc   59340
ttgtgttctt gagtacacgt taggatatta cttcaggggc tatccaagcc attgaggagc   59400
ctgctcaagc tgctgaggat gatgaatgat cctagaggct cttcttccgt atgagatctt   59460
ataaccggga agcgtaggta gaacttgtgg aaggaagaca ctggcgagta gacctgtgag   59520
agcccccat caaaggtcga tatcttacct ttaaaagcgg gtataagaat cggaagtcgg   59580
gatatcccaa tcttccggct ctcaagcagt tcagaagatt catccctcat tcaatcccct   59640
ttgctcctgc tttcatctac ccctatgttt ctgctttctt cgtctatgcc tatgcctcca   59700
gggatggatc caattccctg tcctttttttg gaatcgttga tacatatgtt atgttacgat   59760
ggcttcggat gagagagggt ggtcgtagat catagttctg tagcgaagct aggctgttga   59820
gtttgagcta tgagttctga cctgagctag tctttcagat taggcaggga acatgaggga   59880
cggttcctca ctaccgaaat tcccttacag ttctagaagg taagagaagc tagggctttt   59940
gagttccagt aatcaagcca aaccggagtt ctggagagaa ggcagtgaac ggagttggcg   60000
gttcgaggac ggatgggacc cagagtgaac aagtagcttg gctcaacctt tgctttcctt   60060
tgacaaggca gccaaggctc cagcttcgct ttctacttcg ctgcctttct ctaacgagac   60120
aagtaaagta ccttaattca cttacagcaa gataaggtat tcaagcgggt gaaagtatag   60180
agctactaac cagagtcaga aaagttggtt ggcattcaag caagagagaa agaagtcccg   60240
atcaggctac aagtgggact agaagcgagg gccgctattc cggtcagctt gttagaaagg   60300
gaactagcac cctaaagaca gctactctcg ctttctaaca gtaaactaaa ctgccttccg   60360
gtcgcctcac caacgccttc tctccctatc ggtcgaactt ttccatcctc tcccgttggg   60420
aaagggatc gattaccttt cttagctagg ataaagtcac tgtcatcgct ctctccttga   60480
atcgctcgga aatcgtacct agcctctcgt ccataaccta gcccgaagct ctcaagcgac   60540
tgatttcaca caagtagtag gaccttcttt cttttatagt ggagttagaa taggctctag   60600
aatagtcgaa tgaatggtca gtctcgctct ccaccctgct gctagatggg atagggcttt   60660
tcacatgctt gagataagac agatctttt taggcattaa ataggccgag agaaaagtat   60720
cattttaca tagatgagca gcaacttag aaatgaatgc tcaagtctgt cacttagaag   60780
ataggatggt atcaacccgg acaaggggc aagatccgct ggcttagggc cccttttagag   60840
ataggggcga gccaaagaga agttgtagca acgagctact aaggagtgac tgtgttgaag   60900
cttcaaacgc agggctcgcg acgacttcga gcgaacccaa cccatttgag gtgactgctg   60960
ctgctttcga tgccgaagac acaacagtcg gtactgctag ggactccttt ttggcaccgg   61020
gataggggtgg cgcaaggcga gttcgaccct agattattat tatacgtaat gataagaaag   61080
gggaaacgaa tctcctcaga ttacacgaaa aacctgattc acctataaaa agaaaagaga   61140
aatcttaaga cttcctaatt aaggggacag agtgaggttc gacgtagttg actgcacacc   61200
aaccgctgtt tcgctagctt ctcatttcga cgagagacct gcggaaagtc gtcacggcct   61260
cagaaggttc ggccgaggga ttggaggggg gggaccccag ccaggttcag tgtcagcagg   61320
actagccttt cttttccttat ttacagaaa atgtcatttg ctcattttca actagatcaa   61380
cgattggaag atcggatatg cccatcgcc ttagtcgact tgttcctgag atgagaaagc   61440
ttgactcgct tatcagagct tggaaacaga ctacgcactt agaagcccta ctccattgtg   61500
gttgcttgcc ttcataacag taggttcggt cagcagaggg ctctccggag agagactgat   61560
gttgcaaatc aaagatctcg tactacgata agagatacta tacctccgta tcctgtgctt   61620
ggccgtagtt tcccgggctg gagtttgctt ggcttgttcc ggagtttgat ccgttgttgg   61680
cttatcgaat agtgattctt ttggtattgt attccctgtt acaccctac tttatccgtg   61740
ggcgagggct agggctctag tgctctgat gaaccaccta catggacgga atgaaatagg   61800
ctagctggcc aggtatgagc gccctctgat ctaccggttg agctcccttc cctctcttcc   61860
gttctgtctg atagtcagtc cccgcgcttc ttctggcttc agtcagtatg gttgcttcct   61920
tggttcagcc tctctttcgg ttaaaaagat ccgtatgccc ctggccttcc tattggttca   61980
ccaacccgcc attcagtacc gtccgcatcc gctgtcacag gtttttgaacc cttagacgag   62040
tctcacctgg agtagtactc tgtactctcc actacttgta atgtccattt actactataa   62100
tgcctacttg caacaatgcc cgcattaacc gccgattctt cccatcgac gtgctccccc   62160
tatatgggtc atcagttcga gtggcatccg tgtagtcagt accacttgtt tctgtctcgg   62220
acgactcttg cctagatagc tcaggccgta ccgccactgg cgcttgcttt ccgtgcgtgg   62280
gcagggtccc ttcggaagac gaagccaatc cagattccag aaacacacaa gctacgactt   62340
tctccttcgg accctcgcaa actatggtta cagctccaga gaccgagtcg atcctagctt   62400
```

-continued

```
ccctccacct cagcctgcct tctttctttg cctctctatt ctatgtccgt tgcttgttcc   62460
cttctctttc accatggaga tgtgattaca agatttggat gccaacaatc tcgataaaac   62520
gcactgttca tgccaataca caagggtgac atgaagaaaa atagactaat ttcctttccc   62580
ggttttgata ccattttatt actgacatga cgaaaaagaa gcgaagtaga ctttgccttg   62640
aacgaacgat tcttcctttg ttgagataga gtcgacaaac taagctaagc gttttgacat   62700
ttaaccagtt ttgacttttt tgaggaccta aagcgggcat tgatcgatag tacacctttc   62760
tattcctatt catattcttt attccaattt ggctggttca cccgcgttga acgtgacgag   62820
aatagccttt tccagcataa ccaccggctt ctacagtcta gctggaatcc ctcccccctt   62880
cggggtcgag ttacttcgtt cccttctttt tttgccaata atctcatttc atgttccaac   62940
ctgggcatta tggtggagac acgagagatc acatctgatc ctatgatcca tcctgcaatg   63000
aaaatgaatt cttggtaggt ttcgcaatca atccttcctg ggcgaaatgg gttgaggaaa   63060
gactcaaccc agcagcagca gattgcgcgg cacctcgcga agctatccat tctaacctgt   63120
ctttgcctag caagatacgt ctagttctcc ctccgcttgc ctatctcagt aggaaattgg   63180
aacagtctcc gatttccaag gcgaagccga ggcaagagct ataccttctg gaaccagagc   63240
aataactgct ataaaggaag cagatgcgca ggaacgatcc ctaaagcaaa tactcggaat   63300
gctccacgac taagtatacc cattcagact cgcttttgtt caattataaa taaatcacca   63360
ctttaatgga gatttatagc atcattcaag taaatacaga ttaagatcgt aaaaacataa   63420
gcttgtaata tagctacacc taattccaga ccggttaatg caagaactat aaataaagga   63480
ccaagatccc ctataaaata caaaagatca ttcatacata gcatagtcca agcgaaccca   63540
cttaaaatct ttactaaact atgaccggcc atcatattag caaataaacg tattcctaag   63600
cttaatgcgc gaaaacaata agaaattagc tcaaggagta ctaaaaaagg tgctaatggc   63660
agtgggactc ctgcgggtaa taagaagctt aaaaaatgaa gcccgtttct ttgaaatccc   63720
actatagtaa tgccaataaa aatcgaaaat gagagaccta aagtaatgag aaaatgactt   63780
gtaactgtga agctataagg tatcataccc tgaagattac aaaataacaa aaaagtaaaa   63840
gtgaccagga tgcaagggaa aaacttttgt ttaacatttc cggaaagacc ccctatttgt   63900
tcgtttacca ggtcagcac gaaatcataa ataagctcta ccaaggattg ccaagcattt   63960
ggtactaagt ttcctcctcc tttttttagta acaaaatgaa tcagaagtag gaccaaactg   64020
agagttagca gcataaacaa agatgaattt gtgaatgaga aatacaagtc tcctatcttc   64080
ataggaatca atgggagaat ttcaaattgc tcaagtgggc tttttaaatga gcgatgtctc   64140
ccatcacaat aattcaaata gtcttgactc aagaaatcct ccttgaaagg cttttaaaaaa   64200
ttctctaaac ttgttaactc attttgaaac gtagattcaa gcttcctata aagtgattct   64260
gggggtgttt ttttaaattc cttttggagt acttgaatat ctcgaggcct gactgtaccg   64320
atgaagtcat atttcataaa aatgaaaagc ttatttaact ttgtaaggct tgtaaccgtt   64380
gcggggtcat caatctcccc tggaatgtaa atagtaaaat cttcgatgcc aaactttgtt   64440
agctcttcga cagaatatcc aaatgcagaa gtcaccctag gatacccact ctccgttatc   64500
gtcagcatat gctgacgata agactgaata aagtccctca tagtcatagt catagtcaaa   64560
attgattgta gttccgcctg cttcttgctc tcaaaatttg aaagaaaaga ggaaaggctt   64620
gtttgtcgga aatagatagt tggtttgctt ggtccgacca agaaagaaat gggaatttgg   64680
ggctgggtat gaaaaagatc ttttcgatct cgtacccgct tgcttctatc tatagaaaga   64740
ttctcctctc caactgctga cctattcact accaagattg acccgccttc atgcttacac   64800
gtcccctcc atcctccttt tctccttaga tggatgacag ccccattttg attgaagttc   64860
gaagattcta cttgcatttg ttaagcatgt gaacaaggat ccccctactg aaggaatgga   64920
ttgtttgcgg cttatcaagc ttgaaatccg ttcttagacc tacggtgac cggcctcgcg   64980
agacctttc gatctacgca tggctaagct ctatcgggcg gtggcttatc gaagcactac   65040
ttgataagat cagtaataaa aagaaagacc tgcccttttcg gtgaagttgc tttcttctct   65100
tacgataaaa ctagttggat tcaaagagcg ctcctaaatg ccttacacaa ttcaagagtt   65160
aagaaaggct cttattcatt ctttttataa tataggaaga aggagatctg acttcttaga   65220
aggaaatgag ctacctagac ctttgttttt tatgtacagg tctcgtgaag agagaagata   65280
ggagacagag gagtacgtga aaggagactg tgaagtagct aggtgataag aagactagct   65340
cgggcttgaa aacttgaacg tataggctgc aggatcacaa taggtggagt ctctaaaagc   65400
cttatagaag catgagactg aagaagtcag gcatcagttg gtgtgaatga ctccggccga   65460
aaggttagcg aatccgactt ccattctttt tgagggaccc aaccaagggg gctgtgcctc   65520
cctaagctgt cttgatccct taagggcttc ggaatggaag ggcagatcat ggaagagtaa   65580
ctgcttcacc gggaatacta aattactgtg aagaagctgt catagcctat tgatctcgcc   65640
tattgatctc ttagtggata agggaatgca actcaataga aagacttgtt ctctcaggaa   65700
cacctgtaac atcctccccc gatagacttc agtccactct tgaggaatag gatgatcaga   65760
taggtaaatc cccgctaact tacaaatcta tcttcctaat aagaagaaag gggcaagcca   65820
aaacctagtc ctaacaagtt gctggattga agtaggacat tctccatccg cccgccagca   65880
gaagagggg cattctagcg atgtggcgaa aaagactgat tcaacgagat agaaagtgca   65940
taaaagaaag aaattgtact ccgtaaacga gattcactca cgtacaaagg aaattgttct   66000
ttctccatcg accatttcac ctgtgtctac gtccgccatt tcgcctgctc cttcgcagga   66060
agccgactca ccggtggatt attctaaagt cttccaatat tattgtccca ccctgccccc   66120
tggaagtacc ggcaccggta ccgcaggatg ccgaactcta tgagcaggtc ttgcaaccac   66180
tcccggatct aatgcaacca ctaccggatc ctctttgatt aagcaaccc ctcttaaatt   66240
ccatagtgga tcccctctgg gatagtatct ccctcaaact ttttgagatt ctcacgaatg   66300
gggaattttc gatacctcag gggacggctg ctcgcttctt gctggatttg ggggaaaagt   66360
gacaacttga agacgtggtc ggcatgtatg ttaccagcat gtttgaaaaa actcccgtga   66420
gtgtcctgca gcatgtatac tttttattgt cttattttgt gggaaatttc cactttttag   66480
accttttat tgattctatt ttataacgga acattcgttt tctattttat tttctattct   66540
ctgcaagact cctcgatata gagtagagca aagcaatcga tttcaacagg cttttctgta   66600
actatcgaat aatggaagtt cacggggaaa gtcactggac ccggagcatt ggttcaaatc   66660
caattcgttt ctccttagcc ttagaaggaa gaaagggact caattcaata aagggtactt   66720
actactaaga tttcatattt gatcttatat atggcattta tctctatact ctaaactgga   66780
agggcatgag accctagtgg aggaaacaaa ggaagagtcg acaagggcta actacatact   66840
gattgcctaa tttccctcgg tgacgtaaga ctgaagaaaa gaccacaata agggacctac   66900
tcttgccgaa agataggaga agatcaagac tttgatttag acaaggaaga ttctgacaac   66960
tcactagatc gggatactaa ggtatagagt ggcatactag aatagaagaa gaggtacact   67020
aaaactacct taggacctgt cttgctgtgg aagcagtggc cggaagcttc actacatcag   67080
ctgtaaaaag cggaatatcg gctggtggcg gaatctcggc caagatacgt cgtgctgttg   67140
```

-continued

```
aaagagctgt caaacaagga ggagtctgtt gttggcgaaa tccgtaccgt tcgctctaga   67200
gaacatcctt ttattcactc ctatgcttgc tttagctaat gcagcatgca actgtaagat   67260
agtcccgata gctaccgttc gccgctacca ctttagctac taaagctcgg aaatcagagc   67320
attagctcgc tcaaactcga aacatcctat acgtgagctc aactcataac tagactactc   67380
ctatgatcat gatcatatgt tgcctcacta gtgcctgcgg tatgaggtag ggattccgga   67440
tctctctata ttaagtcatt aataccgtac cccagcagat agaagtcgga ctaaaacccc   67500
ggaatttagg tatttgagat cccatctgtc cttatagtag aactcagatt agagtttgga   67560
ttcatactga ttcactacgg aactacaggt cccatcttat agactggaac tcacaactag   67620
aactcaaagg cgaactcctg gcttggctca cttacttaca ctcagaagcc ttgcttcccg   67680
atcccactca tgattagaat aatcgaataa gtcaaagctg ttctcaatcc tggctcagga   67740
actcccggat ccttcttccc gctttaggtc acgcggtagg cttgaaacga gactagactt   67800
ctattacagg acttcttcca atagacttgc taccttctaa agtcttgagc ttgagattga   67860
attcttccta acagacggct gtctttcata agaactgcaa acccgccagg aaaagtcttt   67920
acaggaagtg atcgaatcag tacgccttgc cctaatgaat gtctgttgga gagaggtatg   67980
gcgaagagct ttagaacttt tcttcttgga ttgagagtac ccgttatctg ccttagccgc   68040
aggaagaatg aagagaggag gtcttttccg ccctaaagag aagggattga tagatcgctt   68100
ctcacctgta gctagcctgt ctactgtccc atagaaggga atcaagcccg attctatctt   68160
gctttctcct ccgctgtgaa ggcatacaaa aagctcttcc acgcctagca tcgtactttc   68220
ctcaactcgt gtaaggtcag tcctccttct cttaggagaa tcactcgccg caagaatttg   68280
atatgaccta tgaagatttc ggatctcttt cttaaaagaa tgcatctttt cgaaggccag   68340
ttgccacggt gagaaaagaa aactacatga ggcgagagga ggcaactccc tgagatttcc   68400
gggcaaagtc ttcttcggat gatgcttgaa cttcactgtc ttctcgaaag aaagttgagt   68460
catccagtta aagataggag tggagattgc actgcagatg ttgaggttgt agatcaatag   68520
cagcggatcc gtttcccacg cttacttcat gccaaagctt ctcgttcgat cccttttcctt   68580
tcagtcgagt cactagggaa tagggaaaag agattcgttt cactatgttc aactcatttc   68640
gtacctctcc tttcagtcga gtgtatataa taacctctca ctttagctcg agccatttca   68700
tctcctctca ataacaataa aaatagcttt tttcgtttcg cttcatcata agctgtcgct   68760
gaagaggctg atgccgccaa tcggctttc ctgaatgttt acattttttt ttggttcacg   68820
agtgatcaat agtagagtag ttggcgaacg gtgttttagt ttgaatgact tctgggcaca   68880
agtgccattc tcgtctactc ttctatggga ggactgagag gctttccctg agcaaagaag   68940
gtgaaagggg ccaaaggatg ctaaatcatt actgttataa tgagtttttcc agtcgtcggt   69000
gcaaaacgaa actgaagagc tcttccgctc aggtatagtg aaaggtgtct cccttgtgta   69060
tgcgtatcat ttgttagtac ttgcccttttc tttcacataa cacttctttc tttatctca   69120
tatatccagt tattgtctac ccctcgatat gaagatggtt ggactaacta aagccagacg   69180
cgtagcggtc aggaaaaaga aagccttgtt gaagtttttga agtcaaccaa gtaagccaga   69240
aagaccagtt gtaggaagct ttgaccggct gaagcgaagc aaaaaactga acccgaacca   69300
aaccectaag caaagaaggg attgccttag ttcagtctcg aggccggatg gtagcaatac   69360
acttctgacc caagcccttg agcagggagc aattgaagta agtagtcggc tatttctgag   69420
gttaagcgaa cacagtcagt gacaaggtga gtctcaacta agcagtacag gaagcccact   69480
cactcgggca agtaagcgag ccaagcttta aaataaaaag ttcgggagtc aatacagtaa   69540
agtcagggag gaaaagttgc ggttatgaaa taacctagcc tgtttagggc tagatttata   69600
taggagaccc catgaaagaa gagagaagat accttcgccc acccacccga taaatataag   69660
tgatgccgt atatacggca tatgccgtca taagcgggaa taggaagacc ctcctttcaa   69720
ttctcctttt gacctaattc ctagcttttat cctgcattgc tttcaaaggg gataataact   69780
agaaattcct gccttacacg cttaacaata aggacttcca actcacttcc tcaccggttg   69840
gcagagaccc tattcgatcg tatggaccta ttcccattta tgggacagta tcccaagcag   69900
taaggctctg tagagctagt ctcccttgag acctgctgac gcaaaacaaa agctctttct   69960
gctgctcctt cgcctgcgaa ttaagctgta gaaggcaagc aagcaaacct tggcaactga   70020
caatttcaag gatcaggga ggtatgaaat ggttatctcg gctgggaatc aagccccaac   70080
acaaagagct gtggggctag gagtgttatc aatcttagca ttccgagaca aagcctgggt   70140
cgtcgaactc cataaaaacg cgtttgaagg cctgtttctg ggacttatag ggagggactt   70200
tcatttctgc tatctcaacc ttccaaacca aaagggggatt ccgctcctct ccatatcagt   70260
cgagtggctt ccgctcctag cccttagctc gggacgggat gaagtgttca aggttctccc   70320
cagtcattat tattataaca catcaaaatt gtctcgtcaa cgctatgcgc tctcaagatt   70380
tcaataacac ttctgaagta gaattgttag agattcaact cccctccatc ctaccactga   70440
gctcaatcta aataaggccg gggctcgcga ggataggact gcaggcacta cacttatcat   70500
ttcacatatg ctgatcttac tcttccttct cttatgattt ttttttgccaa cgacaaaaaa   70560
agctatctat ttcttggtgc tttgagtaga aatagtgctt gctttcgcac gccgatctaa   70620
ttgatcgcat cgcaagtgaa gatgtcgtcg cgtcaatcaa gtcaagtata attgctgttt   70680
ttttcccttt ctactttaga attagaaact aaatgctatt cgtttcttcc caaaattgct   70740
caaagagcat gtgttaagaa tattcttctg tcagagccgg aggatctttc gcgtaaccct   70800
agttaactcg agtcgaagca cccaagaaag ggaaagacta gaaggatgct acccacgcac   70860
catcaacaat agcataaggt caagagctag gaagagatgg gagggaagtc cccaacctca   70920
aaggtttcgg atgaacatca aatccacctc gaaagaaaac aagtgaacta caaagaaaga   70980
attgaaagga attcctttttt tgtattggta gccacttgca gctcgatttc acttagcgat   71040
ctcgactaag taacctcacc agagatagg tgatttcctt ctattctaat agaggatacc   71100
gtatgagttg aacgattcgt tgaaaatgag ttgataaacg aatccctatt cccttttccc   71160
taatccctat aagagtcttc cgctcctact cgtagttaga attccaaagt tggaggaata   71220
aaaacctaaa ctcgatcaaa gaactgagac gcttatagag ccttttttaag acaaggaagt   71280
tcactcctaa gaaaggcctc cagaaggaag caaaaagagt cgttccgccg catctaatgc   71340
tgagtaaggc gacggaactt cttaaccacg gtcttagaga aagagccaaa gcagggactg   71400
aaatgttgat ggctgggatt gatgcccaca atcggatgct agagaataag ccaataacaa   71460
tcgaaagggc agggacttct tattcttaga cgcccgcttg ataaagggct tgtttgcaag   71520
ctaagggcga cacagatatt caattaatta acagatttca ctttgacttc ttcttacttc   71580
tttgcactag tctcatggca atatatcttt aagcatcccg gcattcctta ttgccctaag   71640
gctagtcacc tcaagtcttt gtatgggcaa tgtctcttgt tgtatagcta ttttatccgg   71700
gttcttcccg aaggggctaa ccgtattaat agctgattta aggtagttgc tacttcgttg   71760
ttgaaaaatg gttttctagc tgttgatggg tgaacccatt agggttgtta tcggtttcga   71820
gttctcgctg ttctctaagg aagttgagtg agaagaagta agaagtcaaa atcattggag   71880
```

-continued

```
caaggcccct caagcttaaa gactagcagt tcctctcttt catgtcatga agcaactggc   71940
caaagaagct cctcggctag ggtttatgat caaaccctaa aaatcaaaag ggttcttgct   72000
aagactgctt tctctcttcc gtatgttcaa ttttcctttc aagcaaccac attcagcagt   72060
gacatcgaaa tgtgtgagat tgaaactttt tccttcgcat ttgcttgtta acaacgagcc   72120
aaccttctga gggttaggtg aaggtctcgt tcctggactg tccatacata ataagagtct   72180
tcttaaccgt agtagcaaca atgatttata cttcttctat aagaatcaat ccggaaaagac  72240
agcattagat acctcagaac taagaagaat ggcagccgat gagatttacc ttctttaggt   72300
aggacaggaa ggaagagagc attacaaatt gccctatttg atctagtctc ttccattatc   72360
gatacccgta catactaaga tctaggtagc aaagtacgag ttggagagac acatttcctt   72420
ccgagctcac attcgttcta tataatatat tcatttatct tcattataag agaacggaaa   72480
gatggggatg aatgcaatac ggagagaggt agaaagccaa gcactgcacg gggcctctct   72540
gatgcctaca cttccctga gggaaggggg gagaggatga ttgctaggtc cgcttacgac     72600
aaagccacat atttaataga acaagtcaag ctagaaggaa agaaagcact ttgagatcgg   72660
tcgtgaacca gaaagaatga gccgcttcaa taccaaaagg aagaaataag cacttgcttc   72720
ttgagctggt acaacaactc cagcaagaag gattagccga ttagaaggca tggccaaggg   72780
tactacaagc ggaaccccag tcccaagcta taggacgaca aatgaattag gcgctgactc   72840
caagactgat acgataggct ttgagtcatc agtttgatct cctagacgag agggctatgg   72900
gtatagaccc gaaagcacct tcactggcca tggactactc aatcaaccgg acaaccgctt   72960
cactacttcc aagacttaaa atccaatgat agaagaatcg actgcagcaa aacttcctaa   73020
actagactag aatagaataa tctttcgtag cagtcaagga tgagttcgat ccattaggtt   73080
cttcgatttg ttcagaggga gtgggaaagc tacagtaatt ctttatcaat agcccaccct   73140
ttctttgaac cttaagagga tgctatcgaa tgtgctcttg gcgcacgtga gggatgtgac   73200
ctatgttagg tccataagat agcacagctt ttggtgttct atgattcacc tccgaataat   73260
gagtagatag ggaagagctt ttgattttc tcttcataga agactgatgg gtggagcaag    73320
aggtcaaatt actatagaaa gaagagttgt aaactatagg acttctttt ctagtagtaa    73380
gatttagggt tttttcgttc cttctcttcg ataagaaat cgatttgaaa tgataaaaat    73440
tcctcttgat tctcttgtgt tcagcgaaag aactgcctaa gcatactttt tcggatccaa   73500
acttctttgt tctttctaag tcttcgtctt gcatagaaga acgcaactct tgcaaaaacg    73560
ggtctttcag tagtaggcgg catcccctct tagttttaag taagcggaac cattccgttt   73620
tggttcttct ccacattctt accgggctat ccagggattt tcctatgatt ttagaaactg   73680
aaatttcgat atagaaggat ctccttattt ctgaatagat tatagcatca ttttctttca   73740
aagatatgaa atcaccttgg gaaacttgaa aagaagtaat gctgactatt acattattca   73800
cacaaagcct tcgatgactt atcggctgcc ttgcttgagg aagagtttca ctaaaatgga   73860
gacgaaccgg aataacgtcc gatcttgtt ctggattgag tggaaaaggg atatatgaag    73920
ttcgttctgt tcctctatgc atctctgtga tgggtaaatc tccatgaaaa aggggcaact   73980
ttcgtgtagt ttgtaattgg atgtaactat tcagatttt tcgagaataa atcattctct    74040
taatagatct cgtcttgttc ctcaatcttc gaagaatgcg gcgttgtatt attgtaagtt   74100
ccctgttcca aacatttcct tcaagtagac gacaagtttt aaatcttaat gcaggcattc   74160
ctccctcaca tgcatttgca acagattctt actaagaccg gtcatcccca tagacacggg   74220
cattctcggc atcttcactg ttgcccctct tctcaaagcc tttcgaaatt tcaacgtgcc   74280
ttttttcttct ttccccggga tactattggc ttactcttct tttccttcgg cgaggatacc   74340
ttagttccaa tcgtttgagg aaagtcggca ttcttagttg aaaggaaagg acttctacca   74400
tgaacggact ctttgccttg gggaaagaac ttccttggct tactaatgac cacttcgaga   74460
agaacctatt tgaagtctaa tgccacatct gactcaacag ctccttcttc ctctgagaac   74520
tctactttga tttctgcctc cactactggt gtgtcttctg ccgttcccag tgcttcccta   74580
gtggcatctt cactcatgac agactcaagc atcgagtctt catcgctgtc acaggctacg   74640
gctttgcagt cctacaccac tgcatctggt tcgttgtcct ttgtgaaccc gaaaccattg   74700
ttgccctctt atcgggttca tggaccgact gcaggacct cggcatctat tccacagccc     74760
tccagtcatg ttttcatgcc ttccccacag gtatatacca cggttccctc tgctgccttc   74820
tcaccgttat acaccatgtc ttccaatgca tctcctcaat ctttcccttc cacctaccag   74880
aacccatcat ccttctcacc tgcgcccctt cttgccgcac ccatctcgta tccataaagc   74940
tagactgacg caactatctt ctctggaaat cgcagtttga acctatactc atcagtaatg   75000
atttaatggg ctatgtgtag gggaccttcc catgttcccc tcaattcatc agtgatgccg   75060
aaggaaggc tcatctcaac cccgcttata gtgcttgggt gagaacggat caaagtgttc    75120
gctcttggtt gaacgcgaca ctctcagtgg acatgttgac ggaagcctac aatagaaat    75180
gaaaacaaaa catatatgga tgtttggatg gctttagagc aaatcttttt ttatcagtcc   75240
acggctaaag aaatgaaatt gaagttcgat attcagaata acaggaaagg taacaagcct   75300
atggatgcct atttacggga actgaagtct atggttgatg ccttggctgc tatcaactct   75360
cttctatgtc cccaaagtcg ttttcactac aaagcccttt gaatatgaag ctttttgttac  75420
aaccatctcc gactctaaga ctgttccatc gtttgaggag ctgcggacta aggtccttaa   75480
ccaagaatcg cgtcttcatc gcatacaagc tgcacaacac agtgagcagc aatcagcctt   75540
tgtgtctcag acttcagctg cttctgataa tcgttcctct cgctccaact acaatggagc   75600
tcgcaacaac aatgggcgaa atcaacaact gattctccgc attgctcttc caagccctta   75660
ttcccaagtc accttaacta gttctccgca cctgtctgta acggaccctc tgcctttagc   75720
tacaaataaa gactctcaag aatgatggga ctgtcttaga ggcctgaatc ctttggatag   75780
tggtcaggaa gataccttta accctgaac acactggcag tgcttggcct ttgatggctt    75840
tgagagtctt gaaacaatg tagtattccg ccaggagcat ttgccacctt gctatccccc    75900
cagagagaga ggctttctcg aatatgtatt tcagtgcgcc catgcgagcg atgagccgag    75960
ttgtgtgata aagcatgtac tgccagagca gcccaagcga atgcgcggat atgccgcttct   76020
agcgctgaat atctgttctc gtaatccgtg aacttctttc tcagttagtt cgtgggatcg   76080
gcatctcctg aatggctttc accttgtcgg gatacatctc actcatcttc tgcacaggct   76140
acaccatgac cgttcccaac gaccggaaca gtgacacatg cacagtttct tgggcgcatt   76200
acccaggaag agtggctggc tgcctcatct cgaaagccat taatgactct tattcctacc   76260
caacggatca accgcagagc tccggggccaa cccttaccag tgattctcgc ctcccctaca  76320
attctgtcct tccaggagga gatggatgaa tggaaagcaa gtaaacagga aagctagact   76380
aaggtcctta accaggggtt ggaagcccga ttttcaaggg gtgatgggcg gtgagttcgg   76440
gtatgacctg ggtatggctt cggtatgatt ctaacaggtc ctactctgat ctcactctca   76500
agctattctc tttatagaca gcgactccct ccctagactg ctattatctc tctacactgc   76560
attgctccta agataccta ttagtaactc aactcaaatg ccataactcc cttcaggttt    76620
```

-continued

```
aaaggcgcaa agaaagaaac ttcttaacaa agccttaact actaacatta tataaaccat   76680
atgcaatact ggaacctaac tcgaaaaacc tggaatataa aactcttctt taaacatcct   76740
aaattcacct ttcaaaaatg tttttcggct aaaaaagata gattaagttt gtgttcagtg   76800
gtaccttttc ccttccatgt taatagtgga aatcaagcaa gaaaatcaat gaaaaaacga   76860
gaaaaaggt atcggattga cgtcggcagg gggttcctat taagtctttc ctccattaac   76920
gaaattgcca acagccaccg atacggatac ccgacttgag gaagcaagca ccggccggag   76980
tgccctcgaa gcttatttat caatatcttc cttatgtgat ggctctcgac atctgtctca   77040
ggtgcctaac tttggacgga ttctattctg tacccatcta tggaaccatc ttggctgact   77100
tcctcgcagc acatcctatc cccgatgatt cacctctggc aacagactta ccagatgaag   77160
aagttatgca gatcgagata aaaagggggct ggaaaatgta ctttgattga gcttcaagga   77220
gtcccgacgg ccaaaaacag gaaaaaaatc gaaaaaaaaa aagattcttt tttctttttt   77280
cgagatttTg agttcttttt agaagagaga aagagtagaa acaaagggta cgctctctag   77340
aagatttgct cggagctgtt cactttcact cggtcgactg gtatcttgaa acctcttcgc   77400
ttgcggggggc aggagtggaa acatctgaga gagcgcttcg cgaaagaatc gtgtggcgcg   77460
gtgaagggtt cccgttgggg tttccggctc tcctggtctc cacctacttg tggaagaggg   77520
gggtgagttg atattaaggt gtcaaggcgc tcgaagaagg ccacaagcgg aagcaaccga   77580
tgctttggtc attcagttga ctccttgctg ccagtccgtg cttgctgtca tgctggcaaa   77640
agcgggggctt tcggtcggtt ttacctacta ttggatttga accaatgact ctcgccgtat   77700
gaaagcgata ctctaaccgc tgagtcaagt aggtcaagct gagtcaagtc agagaaaata   77760
gaccccctata agtataagag aaagccgcgc aaccaaagtt cccttacta tacaaggggg   77820
gggcggagcg ctaagaaaga gaaagcgtta tcactatacg aaatgaagca gcggctagca   77880
cgctaagcta agatcaacca cttggagaac gcggagcctt tctttctcgg tcgtctgtct   77940
taataagtta agcggattcc gattcatgtg gtcgttctct gttgcattgg tgttttcact   78000
ccccactctc caccataaca aaatgtttcc actatatctc aggagtagtc aaaggaagta   78060
cggcgggtcc gagtaggaaa aaatgaacta agaattaggg catagaacaa tggatcaatt   78120
cattcaacaa gatccgttcg gatcagacca ggatgaatgg gattggtttg acctctcgct   78180
cggaattaac ccgccgccga cagatgtccc atgccacgtt ttgtgaacag ctatgcccga   78240
gaatgaatga attgtgatat agcgccgaat aagtcacagc tctattcccg acttgaaatc   78300
cataaaggac tttaagggag ataaaagagg gggccctaaa atgcctcggg acgactgcac   78360
gttacatcat agcagcacga ccaaacggag gcggaaagcc ggttgggcgc tagcgcttta   78420
tattatacta atctaatatg aattaaatta agttaagggc ttttcccctta ttagtaaagt   78480
tgctcgaggc cggaaaatga gaatacaatc tagaagatct ggtcgaatgg tagaagaatc   78540
tatggattcg ttaggaatcg atagtcgttg gctggacata cgagtcacaa ccggccggga   78600
agagagagaa tcaacgacgg agctactagc tactagttgt aaaggaaagg gcaagaccac   78660
ctttcgtaca tttctactgg tccagacatt cgaatagcga acgaaagacc aggagattgg   78720
atctagaaag cacttccagc agggttgacg gctgtgtggc cctcattcag ctggaagtag   78780
gaaatcaatc ccggcacgac cgatgactta gtctccttct ccgcttcgac tcaaccacct   78840
acctaacctc ttagaaaaga tccgatagat agtagctacc taacttttaa gcccttcacc   78900
aagcaaggtc tttcatctag caagtcctgg tactatgttc tccaagcttg actaatagaa   78960
taggcaggcc ctttagagag cagtagaatg ttggggttagc tctgccttta agtgataggg   79020
ggtgagggga actgctcaga aatgtcttag ttggttgagg agtgaccgat ccggtcagta   79080
ggcgtcagtg tctaatcccg ccgtctcgtt tcgtagtaat attgtagttc aaaagtcatt   79140
gctccctaga ggaaccggtc tcggagcttc atgagataga ttctaggget cattcgtcag   79200
aaagtttcct tcttcgctat cgagcccctg caattacagg aaatacctca tcgatacta   79260
aacctaaagt taaggagaaa tccctactgg aatgaatccg tatcggcgcc taatcagaag   79320
aaaggtccct gctggtgagg gttaaatcca cggtctccgg cagcaactag tctcgaacgg   79380
aaggagttgt cttgaaagag cccaaaggcc gatggccaac caaagccctt tcccttttag   79440
cctaagccat catgaaatcc aagccatcgt tcagtgcctc tcttcatttc ccgtagttga   79500
tagagatttc ccttgtcatt cagcaaagcc ctcgtacagc ccacaaccat tgttcggtag   79560
taccttcgcc tcctctccct tcagtcaaat ctgcttcaaa caaaacctt ctcttcttca   79620
ttcgctcggt ggtcttagta aaagccttc atttcctccc aatactcaat ttccggtaag   79680
gcagaccctc caacctcccc atttcatcct cccgtttacc tttcaatcgt cagttattcc   79740
gccagccttg accaaaggag ggggaagcgc ggcgtaagca aagaccttcg aataagaaca   79800
ggggctcctg actccgaatc aagggagtgg aggtaatccg ggcgaaatca gaaagtcatt   79860
caaaatcaac ccctcaaaga ggaatcagta taaagtcac tcatttggtc ccattaacag   79920
aacagccacc ttttttcttc taatattaca taacataaat agaatcgatt tttgtacaac   79980
ataataaaat aagttaaggg ttcgacccct ctccgatagc acgaaagaac cctttccatt   80040
taaaaagctc caattcgaag gtgaaccata tagaggagag ctgcttactg gctttttttt   80100
gggaggttgg tatcctataa tagatcctgg ttacatacaa cattgttcct ggaaactttc   80160
ttcaaagatg agcctcgagg aattgctgcg tttctgcgaa gatgttcatt tgacatttcc   80220
attaggagaa aagctgcatt gggcatttcc accattaaga gaggggctcg ctaatgcgca   80280
aagggtaaca ccgggggtctg gttgggctga tcaaagtagt tgattcagaa taatccagca   80340
ggaaaactag ccctgtcact ttatttctaa gaacaaatag gaaagcgcgc ttaaccgagg   80400
gctgcattcc tgttacaaag tccttgttat ggcctcgatt tcgaaaccaa gatctaagga   80460
attatattct tcgggccaaa tccccccatca accccgagtc actacctta ccattgcatt   80520
ggatctggcg atcccaatta agaaagcgtt ggtcttgggt ttgggtgccc caagcaaaaa   80580
gcggtccaac cccttctttg ataagcgata cctttctctg ttcaagttat aaggctgacg   80640
gaaccaaatg cataccttt tgcttcgtca gcagcagtcc ttactagccg atgacctagc   80700
atgagtacga acaaaggact tcttcgatct gaccctcagt aatcgcggtg gagcattcat   80760
tattctaaat agtcctatct attttttggt ctgactccct ggttcccatc ttttgtccag   80820
agctaaaacg agttataaag ccatatttag gtagcaataa cccctttca accatctgac   80880
gtggtaactg aatacaatcc attttgtggg tatttcagag gagcccaaag gctctctcta   80940
tgaaatccta cggtcatatc tttatcctaa gggctataga actctctttg gcaagcatta   81000
agccgtcgaa ctaccgactc tataataagc ttctacgtac tatattctct tcgcctaaca   81060
cattcaacta cctttttcttg caacaagtcc gactgctgct ctaatacagt ctgtttagag   81120
tctctttttta tgcggctctc cttcctggga ggtcattacc gttagcgtac agcaccctc   81180
gtaagcaact cggctacccc ttaggcctcc ggcgcgcaca acaaccaaac cactttactt   81240
cttcaatcta ttcgtttgga tacgcggtaa gtaaggcgaa agaagcgcag ctcaataggg   81300
ctcctaaaac gcctatgagc tatcgagaca ccgggaatgt gtatcgctat tagtgcccca   81360
```

-continued

```
tcaggttaaa acttggacct cccctcttcg gcctaaaaga aaagacagac aaccagtaag   81420
gatactagga ggagggaagc cggccatctg ctttcttcct ttgaattact aggtctgtga   81480
actgagtcat cggatgcaaa aggcgcatag ccgacatcaa cgtgaagtgc agcccttccg   81540
tttttcaggtc tagtgctaga ccctgaccgg ttaaaccgcg acgatcaaat gctttctatt   81600
ggttggctgc cttcgataga aacgaaaggg tgttaatccg cacgggacca gataggccga   81660
gggttagaag gccgccttaa cgccttatcc aaaaagttgt ccttctgagg ctaacccctc   81720
ataccctgc gcaaaagaac gaaaacgggg atgaaaagaa gcaggcaaat ttctctcaaa   81780
gaacgactct ctaaagtcgg ggatttcgat gaaagcaagg tatacgccat ctttgacatg   81840
ttgatcgcta acggtcagct gactctacct ccgtgtaagc gacccgccaa gatcgagaaa   81900
gttgatgatt ccaactactt actgtcggtc ccacaggtcg tgggacaatt tacttgaatg   81960
atgctataaa tctccattaa agtggtgatt tatttataat tgaacaaaag cgaggaggcg   82020
aagccgcttt accgaattgt agaggtgaag gaacgagaac ttcccccgaa tcgacaaaaa   82080
gattccgagc acgtctggtc aaagtatatc ttgtctttgc cagagcggct aacaaaagaa   82140
tttcagtttt gcacatatcc gcgggttctt caatttgatt tcttcctcat agacgaaaga   82200
agtaaggtgg tatactatat ttatccgctg attggaactc cttaccatga cctatgcatt   82260
ctgctatcat ttccagttgt tcgatccatt gtgatttggt tccttggtgt ggagagatct   82320
ctgccataaa agaaaagaga gagctcgtag gccttattct gcagatcaaa gagcgactta   82380
attccccatt catccgaaat agtcttttag tatagaacag aggcattgtg ggccgactac   82440
tatgactaca tgcgcatcta gcgcagtggc ttggaagcca gctaccttga ccatcttccg   82500
aagttctaaa taatctactg atcaaaggct gtaagggcgg gctgctctac attcagccac   82560
atcacagtga cccccgaagc gatcttattc tagttgcggg acgaaatccg acagccaatt   82620
gctggctctg aataaccagc ccagcaagaa gctcaattct tctataacat aacggggcgg   82680
ggttgcgcgc gagccgagtg acgtaggtgc acaagagtac ttcgcgccac aaccatctct   82740
tttttatagg ttctacggac cgatgcctgc tgcttcatct gggagaaaat catcatagat   82800
atgccggtca ttagaaggaa gaaccaccat aaaaagattc ctcgtgtatc atctgtagca   82860
aaattatgca cgggagctag caatccggac cgtattgaag aggttcctga gacacagcat   82920
ggaagagtca caatattcag aaacgaggtc caagaatgaa gaaggggtag aattactgaa   82980
tgaatacgag ctgtagctaa tacccgaggc ataaaagaag cattttccac gggatcccga   83040
aaccaccagc caccccaacc taattcatga tgagcccacc aacttcctgg caaaatgcct   83100
acggttaaaa accaccgaca tgtcaagatc aaaattcgaa ttggttcctg gtcctggtca   83160
gagaccactg tgttcgcgcc ggcgatccaa caaaaaagcg aggtagtggt ctctttcttt   83220
ccattacgaa cgacacgctt cgcctgctcc ctccccgtgt ccgctagcgc tcctgtccag   83280
agcgaagaga aggcgaaacg ccgccgaagc aacataagca ggcttctatt gctacgtaac   83340
aatagacag gatagccttt tgcgcccaca tgtttgaatt tgagggtaaa gagcttgctt   83400
cttatacggg atccgacgca tccagcagag cgaaagagcc ttccattctt ttcggcgtca   83460
tccttccgca ttggcggcga gtggagtgcc acaatcccat tcatcatttt tgatctacat   83520
aagccaaagc ccatagcact ggcgacgtct ccggcataaa tgcaaggagg atgtatagct   83580
gatataggat cttgtggaac aggatttgat tctgcaagcg gttcggtacg aacgaagaaa   83640
tttcgaacaa aagggtcgga actcgccgat aggaaaggag agaaaaacaa agcaatgcca   83700
agagctccgt caatccgctg ttcatcgata gacgaagctc tctctttatc atctcgcgcc   83760
agatgcaaca aaggatgagt cctttttcct tctcgcgaac cacggaagcg cctagcaccc   83820
agaggagcaa agcttctttg ggaaaacggc gcataaaaaa gggctggccc gtcaaaagtc   83880
cggtgccttc gcgaacgaag ttcagaatca acaagggttc gtagaacgaa gggagtgtac   83940
aactgggtcg tagccccagt tttttgttcg taactaggga gagatagaat ggagttcttc   84000
acgaagttcg agacaaagga ataaaaaaga ctttctctac ggcctcctcg ttttgagaca   84060
ttatggcttt ggggtcgacc ccggtaacaa agaaggaatc cataaaaact taggatccga   84120
caccatgata aaatactacc ctcatgatta gaccatgtcc ctgagatttg ataaaagaaa   84180
ggtgcgtttg cggttaattc gttgtcattg gataagttat taggaatatg acggaacgga   84240
agaccaagga aagaaagaag aatgcaccaa aatgcaggtg ctgcaccaaa cactggtggt   84300
tctttcttgt tgtaagtgaa tgcaacgaaa agacccggaa ataacgaata atgaaacaat   84360
tcatatattg acgtgctcat ttcaaaattg atgctttgtt attcccatca tcctgtggtt   84420
tcaggatgat ccacaagaaa ggtggcagga ttcgaaccta cactctgacc atgcctcacc   84480
gccttcaacc cattagtctc cgtgacaagg tagggcgggg gtgaggaaag gcagaaatga   84540
gttcatgcca caacgatccc tatggaaggg aaattgatca agattttttgg ctcgcaataa   84600
agctagggtc ctgttcgggc aagctattga ttccattacc gaaccaaaca agattattcc   84660
cttagtccta tctatccacc tctccagaca caatatcttg agtacctatg atggtgacca   84720
catctgctgg catgtgatgt ttggacatag aatcgagtcc ttgtgaatgc gcagagccag   84780
gtgctcttat tttacgacgg tagggacgat tgcttccatt actgaccaga aagacaccaa   84840
attctccttt aggtgcttca actgcggtat aggtagaagg agctggtacg gaaaaacctt   84900
ctgtataagc ttcgaaatgg tgaattgagg tagagtagac cgatgatcct gtagtcattt   84960
ggccggctat tgaaagaaaa agcttgcatc tgcccccccc ctattatata accggtccta   85020
tctctctcca aacctaacgt ggtagtttcc catcataggg ctttctatct atagattaag   85080
ccattaccaa accaaggagc gaattcgttc agaagtcagt tgactgcttc tatagataag   85140
gcggagcctc cttggctcag cattatagcc cttcttagta aggcttcggc cctactacag   85200
cgcttcgcta actcgaagcg cctcgcatg agaatctagc ttcgctaacg ttcggctaag   85260
tcttgaacct tcgcgctgac cgttcgcttt ctcagtagca aaagcgcttc tctttgcccc   85320
ttaagtagaa ggacaagaaa gagattcttg gttttcttgc tcccgcttcc tcatctgcgc   85380
tcatcaagcc aactttgctc tttgggaggt gaaagagcgc ttgaagcgga cagaccgcat   85440
tgaagatcga tttatatata tacacggtta cggttatctc ggatgcgctt cgggaaaaag   85500
tagcctactt gagaaagaag gggcgggcac tcttgtcttt caaccccact atactattca   85560
tagttgtagg gcactgtgta cttacagcct ctacgataag caagtgaatg gggcggtgc   85620
gtggcgaacg gaacggttca tcaagccatt tttagccttc actccctaaa taggaatcga   85680
gctactttac aaataggggct aattacttcg cacctgactg tgatagccct ctcgatacct   85740
tattggagct ttgtaaccag tggccggttt cccgtcgcta ggacctttc ccagtgcacg   85800
gagccccaac gaggaaggcg ttagtggttt atggtccata atgctaatcc ctcttttgt   85860
gctactccta ctcctagggc gggaagaaga taagaaaagg ccaagcgttc tcttggtttc   85920
ccaacctgtt gcttctaaag actgccctct ctcggttgga tgttggtcca gcctactacg   85980
aggatcccgt atccagcaac ccaacctata caaagggcat ccatcaaagc cccttracta   86040
gattggagct atgaagctta ccttcttttt attaaaaaag ggaaagggcc ttttcagctg   86100
```

-continued

```
gtgcgcagta gcgcacttcc gtttcccctt tactagtagg ggtcccgtgg ttcctatgcc   86160
gccgcctttc ccggtccttt tcttttagtg cttcgacccg aagcgatagc ttctagctag   86220
ttcagtggat aagatggctg cgctccagct cactcaagaa tgggacggca gtggtccgcc   86280
ggcaagctcg ttctgatctt ggacgcagta cattggaatc ctgaagcacc accacgaacg   86340
ctaccgcgcg tccgcctgcg gtgcggtaag gcaccaccct gttgtgccag cagccaactc   86400
cggcgtgtca gcttagttat cctcatcaag ccacttactt gatgtctagc ttcccaactg   86460
gtagacggtt cctttccccc ccagatcaat gaagaaggga gaacttgatt cttccgaaga   86520
accggaagcg aagcgctatg ccggggcggg gggacgggaa aagaaacggc tccgaagaaa   86580
gaaattgggg ttcccaatgc ttctccacgc tcaacgagat gcgccaacct cgggatgctt   86640
tactcctaac cccacaaggt tccgagacgg agcttaacct gagtctcggt taagaacggc   86700
gatgacctat gtttcacacg gcgcacgatt ccatggatag tttcattcga gatcgtgatg   86760
gaggacatag cttacgatca tcggctttga tcattccact aggcatttga ttaggacatt   86820
gcacaatgat ccgaacactt tgtcgcatct cttcgatacg aatacagtaa cgatcatagc   86880
gatctcctct ggtacctact ggtacgtcag gatccgattg gtcatgaaca tcgtaaggtg   86940
ctgctcttcg cgaatcccag catacccctg gttgggatgg gtaggcccac cacttcactt   87000
tcacttaggc ccgggccaag tcagtggggg gaccctgtcg ggctccttcc cccccaaaaa   87060
aagaaactgt acgtgagagt ttcccttcat acggctcgaa tcattctcag atgccccgag   87120
aggcatcctt tccttgtttg ttggggttggt tcacgcgcgc gcaaacgagc accggccgca   87180
acagcaggaa actatgacca atagagtcag cacttagct acatccgcac gcaaaaggaa   87240
tgtggttctg gttgaggctt tcttttcctt attagtaaag ggggctaggg acgttcgcgg   87300
agtccgtgcc ttccgtacca ccgaaaggtc gttcttgggc ggatcccgct cctaaacata   87360
agggataggg gtcctggggc ctaccatatc aaaagggtcg tagaaaaaga acccggccac   87420
ctatttcatt cgacgttccg gggcaggggc ccgaccgatt cgaccgactt ttgcttttgg   87480
ataacaagaa ggcgagcttc tctgctttga tcaaataaaa agcccagtca gccaccaact   87540
cggtgcaggt cacgtgacct acagctcggc cttcgctttt tgaggcttcc tctacccaca   87600
tctctatgtg cccgcagcac ttccatatgg agaaagatag gcttaccatg ttccatcaat   87660
agcacctaac ctatgccgat tttggcggac cgtgctccac cccggtgaac tcatgcggtt   87720
ccgacgtgcc cagaggccag aggcgaatcc gttcacagtc cgtaggacca acaccgttcg   87780
aaggtgggcg gcccacccccg cctagaacag ttatgtttga ctgggcttac acacattcgc   87840
tcacttacgc tgtccccct cagctcaccc tagcccccgg ccttttgctc ttctaacgta   87900
agctccaagg cttcacacca agtcttcact gacataatat gcatgcttaa gtagggtcag   87960
gcagaaccgt tgttgcctga tgggaacttc ccccatattg ctatcaatgt cttcatgtcg   88020
cacgacctct taacattaca ccactgaatc cccaatcctt tgcttgctgt gcagtgacag   88080
taccaatatc cactaatcgt tgtttccaga tacggttgcc ggttgacatc tcttctaatt   88140
cgtcgatacg agaagcaaat tgttgtgtgg aggaatcaat atctcgacat aagccaagag   88200
gcagatcttg tgccactcca cctggtcgta tgaaactggc atgcatcctg gctcccgaga   88260
ctctttcata gaattccaac aattttttccc gctcctcaaa agcccacagg aacggagttg   88320
atgctcccac atccatagca tgagtagtta aagcaagtga atgatttgaa attcgagtga   88380
tttcacggaa taacactcgt atatattgag ctcgtaatgg tacctcgcaa ttcaaaagtc   88440
tctctacggc tgaagaatga gcgtgttctt gggccatcgt agaaacatag ataggtcga   88500
cgacggaacg aacaacgaaa ctttacgaca gcttttttcgt acacgttcac ttgcatcaca   88560
tacacaagtg ctctctgaac cgtgcaataa ggtcacccat aacacggctc tcccatttga   88620
gttatcttag ccccccagcca tgctattcaa gaatattaga aaaatggcag cgtaaggtaa   88680
caactagtat tgaaagctgg tcgcctttgg aagcgttcgc tggtaaccaa agcgtatcgt   88740
tcccgcaacc acttttgtac tttgtttata gcttttttag gttatgcaat agaaggggc   88800
ttgcgcttga attgaagtag cgcttttgga atatgagtag ggctcctagg tggcgcgttc   88860
gtggaggcaa cccgaaggaa gagcaaaaag aaggttgggt caaggccacc   88920
cggcctcgaa taggaggggg cttagctctg gatcctccct gcttgcagaa atgaatggat   88980
cagaaggggg ctggattctc tatttccggg ccgggcggga ggtgaaggcc ataagagaaa   89040
attgccctcc cgctaaggaa gaggggaaaa aggcgctgtc atctatctcg accagtttcc   89100
cgaggcgttg gaaatccaga ccggcgagaa tcactggtga tatttagccc ttcgtttcga   89160
caacaaagaa gtcatctttg acgattcccc attccttccc tgccgagccg gctctcttcg   89220
ccattcgatg cctctgcctt ccctttctat aacataggca ggcgccctcc tttacaatca   89280
ctaagaaaaa atcaatacca atcaaagccc tatcgtatca gtacgtctct gttattttc   89340
cggcaggga ctttactcga cccattcccc ggtctcccgc actgctcaag taagcgcgcg   89400
actccgtatg aggacctcct tcccttctgc ccactctccg ttcacacggt tctcaaagca   89460
gaggaggaag ggtgggcagc aggtaccacg agccctctgt cccacacatc tatccagaag   89520
caagtgtagt tcaccggttc caccgaatgc tcctatctgt cggcaaagat cgtgtgagtg   89580
tgcagttatg cttcggatgc ttcgacatag aatagatcga cccagttccc gttctttcc   89640
ggtgcactcg ctttatatct ccgacacaca aggaaggacg cggcgggaag gaaggagccc   89700
tagcctctgt ccggccgatc attccgctgg catctcgcat tcacgccccc gtttgactgc   89760
cgctcgggga tgtagttgta gatacgttag tcttagtggg tcgttggctc cacttgttat   89820
ctccttctac gacatgctgt tgtcgtcgcc atattccata tgtcacttag tcatctctgc   89880
ctcgctgcgg gtcagcacct ccgaaagaaa cggaggactt cattcagtga cctcgacgatc   89940
gccctctgaa cgatcagaat aaggtaaagc ttgaagataa gtttttgtact ctattaattt   90000
ctcggtccct ctagtcgggt gggcgccggc cggtctttcg accagatccc cctaaaaacc   90060
gtacgtgcg gtctccccgc atgcggctca cgccattcga ggtggcccag cccagcattc   90120
attctaaaat cctgtagtga aattgagact gctcgacttc ggaagcaaat tcgcgtgtag   90180
gcagcgctgt ctgtcgtacc gttgactcta tctattcatt gaatttgctt gattccattt   90240
ttatataggc tcgctccctc ttttttccaag aattcatgca cttcccttta ctccataggg   90300
ccttctttaa taggttcata gtccaaagcc ttccattttcc gtcaaatgac ccggcctccc   90360
ctggctcttc caccgtccgg gctcccttttc ctccctatgc tcccccggcg caggcctacc   90420
acgcttcgcg cctgcggcgt tttcgccaga cggtctttgc cagtagtgcc atcctccccg   90480
ctggctgtat gggcgggttg tccctcgctg ctgcgttctg ttaggctatg gattacagga   90540
acaaatgtag ttgaatggaa tagcaggcgg gttacacgtt ccactgtgcc gagatttgag   90600
gtgcaggtgg tgatgatcac cccggggtat gcgctagcgc ccttgacagg cactccagaa   90660
cccgccaacg ctcgtgaaaa cccgggtcgg tcggtcctcc attcatccga ccggaggtgt   90720
ggataacgag gccaccttca caaccttctc ccttctgtcc ttatgttgta gtaaggtagg   90780
gcggttcgct tgagttgctc aaccgcccct tagcccggtg ctcatgacgc gctacggaac   90840
```

-continued

```
ctccaccgtg ccggggggacc aagcagggca tagctagcgg cataggagcc gactcggcat   90900
cagcggcttc gtgccgcact ggagtgatcc aatatgtggt tccgcacgtt ccaccacttc   90960
tccgttcatt tccaatactg atcgtgaaac accatgagca gcaggatgtt gaggtccgaa   91020
attcgaagtg aaatttttga tttgcccgtt cctagtcgtc atgggaaaga aaggcagaaa   91080
gaagaaagaa atgattccct tttttcttgt ccaataccac cagtaccaga aatgcatctc   91140
cttcgcccgc gcgagagact tattgaaccc gaaaagaaag aagggagaaa gatgcccact   91200
atgattatcg attccttctt gataaaacaa tatcatagcc tagtattcat gtcctagtct   91260
taatgtttta atatgggcac atactagaaa ccgagccagg cacatccctg ttttcttgtc   91320
ttagcacttc aaattagccg cacccttcct tagtccaggg ggacctctca gatgcaggtc   91380
ttttcaaagt gcattcagtg atcacttatg caattgtgag ttgtgtgttt tgctgttttt   91440
cgggcaagac ttttagggaa gggagcgtgc cccgtatccc gggtagggta cgtctccctc   91500
aggtcgacgg ggtatgctcc ctccatcaag aatgagtcag gatcagatgg gaagattcag   91560
agactaggac attctgacag agttcatgct cctttcaact caccgtctct ctctgatttc   91620
aacaagaatg acttttgaat gagagatcag ttagaagaga tagaatggat ctcttaatgg   91680
tttagggtat agatcatgta aacggacctt tttcgtctca taatcaacag aaacagcctt   91740
tttcaaatga catgtgagag gctcatcacc aggagagaga gtgaatctga ccatacatac   91800
cgagttcttt cagaaatgca tatccattct cctcgtcgaa gagatccatc tcactacctt   91860
tagagcatat ccagactttt gattgatatc tcacaaattc aacacctgga tagacttctc   91920
taaacctttt atcgaaagtc agaatccatg cgaaatgata tagaattcta ctgatggtac   91980
agactggtag tctgactatc tctgatgaaa tgttgaaccc ttcctcatct aagtagggaa   92040
gatgaagtaa atctgagatc agtttatata catctgtctc atttcctact aaatccttca   92100
gatgattcaa aatcagatca tcatcccatc gcatctctaa atcaagacga tagattcgat   92160
tgacctgacc catttcaaga atcgattcat gaaagtgatc aagactctca tctaattcta   92220
gaccaagctt ttcatccaca agatcaatga tgaatgaaac taaaccccttg tagaccacca   92280
catccttgta atctggtcga actacaatcg tatatccttc taatgggctt ggatagcatg   92340
agaattcacc aatcgatttg agataaagag aaccaatctg atcatctcat tcatcatttc   92400
taatgagatg aacacgaaaa ggtgagagac gatatgtgcc tgattcaatc ttcttcttca   92460
atctttcaaa ctgaatctca ctcatacgaa aattcacatc attcatctgg aattcataga   92520
cagactctat acatctagct aactccaaat tgaattcatt ggcagactca agacatctag   92580
ctagcttcaa atccatcttc tctctatcta cacagtatgt tctaagactt gtcaacagat   92640
tgcttgatct tctaaccata tgttctgtat tcttcatgat gttttttcatt ctcttcttca   92700
tattgtattc tttagactat ctgttgatgg gatgattccc atagctagaa agacaccaac   92760
catcaaacct aatccaactg ccactctagc cttcccactt tctgggagac tcatttcaga   92820
gaatggcagc tcattttcaa tggtttgaag tacttcacca gagagagatt ttctttccag   92880
aaaacagacc ttcttgaaca tctctctatg tgattctgct tgaaaaaacg gatcatatga   92940
ttcgattcta ggaaagattt catccggagg ggcgatttca ggtacccctg gcgcaaacaa   93000
gtaccaaaca gtacaactca cacctaagct cacaagtata atgaaacgac catatcgacc   93060
ttgataataa gttagtactt caaccaagat cttatcgtag ttttcatgaa ccaaacttcg   93120
cataccatca cctaaccttg taaatggaaa caattgagga acttaaaaag ggattgcgtt   93180
gtaggataat ccaattgtct gacagatatg tgtcagactt cttctgatct tctttgtgat   93240
gaatagttga tgagtcaagt aggttgtctg acctggcata taacgataga caatctccat   93300
aaaatgacta tcctttctat gatgatttga accttgatca gttgataatg agaatgatct   93360
gagactatga tagagagttc cttccagaaa gcgtggtgac atgcgttgtt cactagccag   93420
actagattcc atagacagat cttcatcact atccagacct attccatgag gaagacgagg   93480
tacatcagat aaacaacctt tacttaacca acctcttta ctgaagcaac ggcaggtcat   93540
ggaatcttct agagattccc aaagtttctt cttcctctcc acgcacaggc agatcttagg   93600
ctttctgttc tttggtcgtt tcattatgcc agctaatcca gttaactgat gcttttttag   93660
aagctaagct gttcacctca gtaacgcgtg ggaatctgcc gaacttcttt gctcagtgaa   93720
ccccgcatct gagggtcggg gcgtgaaggc ctgtcggctt tggaaatctg acgattacct   93780
aaacctaaag gctgcgagta ccgatgctcg agacttcgtc ccttactccg atcccgcctc   93840
gaatgaaatg acagtttggg cacaccatcc tgccgagaga taggctagtt tgctcaaagc   93900
atctggtatg agagcaacat cttttctctc ctcatgcacc gtctttttgtg ttttttggtca   93960
aagggaggag cgttagcaaa ggaaggagga aagcggagga gctttagcga cgatgacgat   94020
aaagggagag ccctagtttt gagtttgatc tttcacttca ttcaatcata aagagctcga   94080
tcatcaacta atagatagaa attctaacac gaggatcatc aacacaccgg cgaataaaaa   94140
gcacgtaagg tatacgcctt ccaattctca tgtcttaaga gatttgtgca actttttgtgg   94200
aatgagatac ttaaccaacg cgcctttagt gctttctatt tctataagta gtacttgatc   94260
ccggaaaaag ggtcaaggga taggcttgat gccagatcca ctttttaggg tgactcagca   94320
gttgaagaag gttgtaattt gactagcttt tctctctttc ctgtgctcgc taactttttc   94380
atccgtgata attgactaaa ctctgtcagg tgctatctac gaacaccaaa agcttcgggt   94440
atcttgagct ttagaaggac agcatccgat cgggagacag acccttcagc ggcatctatt   94500
acctatcttc ttaattcagc ttccgcgcct ggtgaatcga aaaagcctag ttatttatct   94560
tcggagacag tatccgattt agcatttagt ggcaaaaccc cctctcgggc gatcttctta   94620
tacggacttt atatctaata atatctgact tctcggcaaa gacctactcc agataggttg   94680
aggaggcata agtcaatgat gatggcatcg aatgcctctt tgaaaggaaa gaaaaagctc   94740
ttgtcgcaat tattgaatca atagttaacc caaacacaga gtaggctgct tgaaaaaaag   94800
ctctaagcct ttcgctcttc ccttcccaac cccggctaac tttttttctta actaccttat   94860
tcatgaacct tttaccctta aacaacggga gttatgtcct atccccatg gttatgcccg   94920
atttcaattg aggagaatga ttggacctaa ccctttataa aggcttgctt cttttccggt   94980
ccgggctagt tcgcaaaacc tagactccca tggctcgctt ggaaaacgtt cgtacgttgc   95040
taacctctta ttctcctcct acccttgaac tcttcttgaa tcgaggagtt aaagctcagc   95100
tagggctgtt cctctctccg atggatgagc agcattctga tatgatttct taagaaaacc   95160
tcagtggggc gtgccccaac cataatccaa gtgggcccaa tgagaagaga cccgccctcc   95220
cactctctct catttattca gcgaaaaaac tacatgacgg ggccttcc gttcagaggt   95280
aacgaatcta ttttttttctg ttttatgggg gatcccttgc atgcccaagt ccaaagtaga   95340
atatacttgt atagtaaaag taaatacgca aaaaatcgcc attcaatttc attcttttcca   95400
gtcccaatag ttgttaatat tagatcggaa cctttttcgca caactcgcgg attttccttg   95460
ttcgtttaac gcggaaagca tcctttggag atcttccaag gaatactccc gatctttttg   95520
ccgtccctgg aagaatttct ctctaattat ttgagtgaat tcccatgcat cgccgggata   95580
```

-continued

```
aagatttttgc attttaccga tgattttctt ttttagcgaa aagtggttaa tcgctagatc  95640
ccttaatagt gcttgctgct ccgcggtgaa tgtgtttagt ggttttcgaa tggagtcctc  95700
ctgaattacg tcttttagtt ctgccttagg aagtttattt attagagaag ccatttcgtt  95760
ctgcttaagc tcaacggtga taaaatgatt gtctggaatt ggaatctctt gttcatagac  95820
tatggtggga aggtcgttta gactaggaag agacgcttcc cccctttcta gggggcctaa  95880
gtgcaattct agatctacgg gtttgtgagt gcattccgct atttgcgcga actccgtgaa  95940
atacaaataa aaaaaaaaaa atccacgtcg aaatggaaaa agctttcacc aggtccaggt  96000
ccaggaatcg gtattagctc tgttttcgct gttctagagt cggtagtttt aattgctcgt  96060
gttgaatcag ccgggagatt cggatgaaag gttctcgaaa tggaagctct gtaccaaggg  96120
tagaggagaa gagaagcaag ccaccttccc aagctaatca aatcatctct gtcaacaatc  96180
ggtttacatt cattccccgt gaacagagtg actggtggat cggacgctgg ctttgatggt  96240
aacagtgtca attaacattg ccttgcagca caaggtacga gaatcgctgt gatcaagtgc  96300
agggcggcag agtaaatact agtttctttt ttcttccaat tactgctgcg gttgctgttg  96360
ctgggctaaa ccattcatcc ttcatccacc gatcaccaaa tcggcttagc cgagacaaaa  96420
tccactttct tttagagtga ttagctccgt catgccttgc tgctctgccc ctagcccttt  96480
cttagcttcg tagccccatt cttccatcat cttccacttg aggttccttt ggagattcct  96540
cctatcctag gggtgagctt tcttggcttc actctagagt ccaggggac gtcgaagacg  96600
gatacgtatg tttctcctcc agatcctgaa gatgagcatc ttggcctttg aggcctgtct  96660
acctctctcg gaggagaccg tcgtcgatgt gatccagaat gacgttccgg aacgccaagc  96720
agttgaccgt ggagtggttt gtgaaattgt gccacttgct gtattccttc ttaccgattt  96780
attccttttgg ttagcggttt ctgatttact ggcattttgc cgcgatcgcg taatatccaa  96840
ttctcgaatg catgcggcag tctttagctt ttcattctca cgacgcttat atgaccactt  96900
atgcattgat acgtgaatac gatagaatag accgccggta atggctttcc gatgtataag  96960
gatctggtct atccgtgacc gaatgagaat ggaatagcaa atgcaactgc tccattcatt  97020
ttatgaaatc tatcttatct gctgcatcca agcttagcaa gtttttttcc tttattgaat  97080
cctaatctat gctgtgtaag aaagaaggag ctcattccca atgcctcttt tctttactcg  97140
ttctgaaggt agagcaaaga atttcgattc caacaatctg gaaataagaa agcagaccca  97200
cccctagatc ctgttattag tattagacaa cctaggcaag ccaaacaatc agtgagaatt  97260
ccgggggaaca taataagtaa ggcccattac cacccagcac aaaggacttg gtcttctgcc  97320
ctgttggacc ccaacaaaca cttggccttg gctatgttca taggggagcc cttttcccga  97380
tgggaggagc gaacaaacga aggcaaagta gttcaattac aattacatta aaaacagcca  97440
tctttcttct atgtcttaga tcccgtggtt gatagaccgt acttcctttt tgccttgaaa  97500
gcccagtttc atctttcccc tgccgcggga aaggaagtat aagtagggat aacaaagaaa  97560
gtagatcccg ctaaggaggg tagtcccgtt accaccaggc ggaaaagcat cagtcttaat  97620
gctgccgggg tattaactca attgatgttc tgctgcttta aaacgaaagg tgggggaggc  97680
acccgtctaa ggagaaaccc cgggcgccga tatattattt aatagaatag aaaacccccc  97740
aaaaaaggct ttgtcacgag ctggattcga accagcacct ctgctaaagt acaaatatac  97800
gcagcctcac taccttctga tcgcgacttt gtttacccgg ttcccctcgc aaaaggtaca  97860
tccggggccgc tcgcatggac ctacttacct tgcttgtaga ccagctgcag agctaaccct  97920
tgttctattg gtttgatgct accaagacga tttcttt atg cccatcaaaa catcgttaat  97980
gtccattatt tagggcttct tttgtcaact cgccgctgag ttcttcagtc acctgagact  98040
ttcgatgttt gtcccgcata tcactagatc gatcggtatc tttacaaatt gagaaagctt  98100
tcttca                                                              98106
```